United States Patent [19]

Arai et al.

[11] Patent Number: 4,789,396

[45] Date of Patent: Dec. 6, 1988

[54] CERTAIN PYRIDYL THIO OR PHENYL THIO-E THANE-1,3-CYCLOHEXANE DIONE-OXIMINO ESTER HERBICIDES

[75] Inventors: Kenji Arai; Nobuaki Mito, both of Takarazuka; Kouichi Morita, Toyonaka; Naonori Hirata, Sakai, all of Japan

[73] Assignee: Sumitomo Chemical Company, Limited, Osaka, Japan

[21] Appl. No.: 71,662

[22] Filed: Jul. 9, 1987

[30] Foreign Application Priority Data

Jul. 9, 1986 [JP] Japan .................. 61-161582
Dec. 19, 1986 [JP] Japan .................. 61-304821
Dec. 24, 1986 [JP] Japan .................. 61-310456

[51] Int. Cl.⁴ .............. A01N 43/40; A01N 33/02; C07D 213/62; C07C 131/00
[52] U.S. Cl. .................. 71/94; 546/300; 564/256; 564/257; 71/121
[58] Field of Search .......... 546/300; 71/94, 121; 564/256, 257

[56] References Cited

U.S. PATENT DOCUMENTS 4,249,937  2/1981  Iwataki et al. .......... 546/300
4,626,276 12/1986  Luo ..................... 546/300

FOREIGN PATENT DOCUMENTS 0082694   6/1983  European Pat. Off. ..... 546/300
0104876   4/1984  European Pat. Off. ..... 546/300
3230087   2/1984  Fed. Rep. of Germany .. 546/300
2481701  11/1981  France ................. 546/300
2540496   8/1984  France ................. 546/300
54-115349  7/1979  Japan ................. 546/300
54-46749  12/1979  Japan ................. 546/300
55-89203   5/1980  Japan ................. 546/300
1589003    5/1981  United Kingdom ....... 546/300

Primary Examiner—Alan L. Rotman
Assistant Examiner—Robert C. Whittenbauch
Attorney, Agent, or Firm—Stevens, Davis, Miller & Mosher

[57] ABSTRACT

A novel cyclohexane compound represented by the general formula (I),

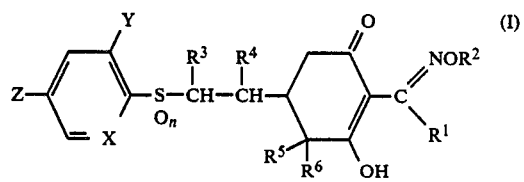

wherein $R^1$ represents a hydrogen atom or a $(C_1-C_6)$alkyl or $(C_1-C_4)$alkoxymethyl group, $R^2$ represents a $(C_1-C_{12})$alkyl, $(C_3-C_6)$alkenyl, $(C_3-C_6)$alkynyl, $(C_3-C_6)$cycloalkylmethyl, halo$(C_3-C_6)$alkenyl, cyano$(C_1-C_4)$alkyl, $(C_1-C_4)$alkoxymethyl, $(C_1-C_4)$alkylthiomethyl or benzyl group, $R^3$ represents a hydrogen atom or a methyl group, $R^4$ represents a hydrogen atom or a methyl group, $R^5$ is a hydrogen atom or a methyl group, and when $R^5$ is a hydrogen atom, $R^6$ is a hydrogen atom or a $(C_1-C_4)$alkoxycarbonyl group,, and when $R^5$ is a methyl group, $R^6$ is a hydrogen atom, X represents a group represented by a formula CH or a nitrogen atom, Y represents a hydrogen or halogen atom, Z represents a trifluoromethyl, trifluoromethoxy or 1,1,2,2-tetrafluoroethoxy group and n is an integer of 0, 1 or 2 and its metal salt, ammonium salt and organic ammonium salt, its production and herbicides containing it as an active ingredient.

21 Claims, No Drawings

CERTAIN PYRIDYL THIO OR PHENYL THIO-ETHANE-1,3-CYCLOHEXANE DIONE-OXIMINO ESTER HERBICIDES

The present invention relates to a novel cyclohexane compound represented by the general formula (I),

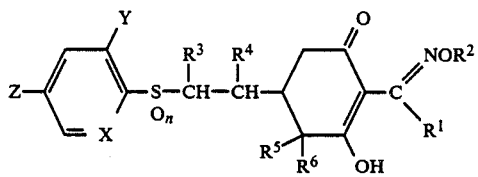

wherein $R^1$ represents a hydrogen atom or a $(C_1-C_6)$alkyl or $(C_1-C_4)$alkoxymethyl group, $R^2$ represents a $(C_1-C_{12})$alkyl, $(C_3-C_6)$alkenyl, $(C_3-C_6)$alkynyl, $(C_3-C_6)$cycloalkylmethyl, halo$(C_3-C_6)$alkenyl, cyano$(C_1-C_4)$alkyl, $(C_1-C_4)$alkoxymethyl, $(C_1-C_4)$alkylthiomethyl or benzyl group, $R^3$ represents a hydrogen atom or a methyl group, $R^4$ represents a hydrogen atom or a methyl group, $R^5$ is a hydrogen atom or a methyl group, and when $R^5$ is a hydrogen atom, $R^6$ is a hydrogen atom or a $(C_1-C_4)$alkoxycarbonyl group, and when $R^5$ is a methyl group, $R^6$ is a hydrogen atom, X represents a group represented by the formula CH or a nitrogen atom, Y represents a hydrogen or halogen atom (fluorine, chlorine, bromine or iodine atom), Z represents a trifluoromethyl, trifluoromethoxy or 1,1,2,2-tetrafluoroethoxy group and n is an integer of 0, 1 or 2 and its metal salt, ammonium salt and organic ammonium salt, its production and herbicides containing it as an active ingredient.

It is described in Japanese Patent Publication Kokai (Laid-open) Nos. 46749/1979 and 115349/1979 that cyclohexane derivatives can be used as an active ingredient for herbicides. These compounds, however, may not always be said to be satisfactory because of their poor herbicidal activity and poor selectivity between crops and weeds.

In view of the situation like this, the present inventors extensively studied to develop a compound having excellent herbicidal activity, and as a result, found a compound having excellent herbicidal activity at low dosage rates and showing no phytotoxicity to crops. The present inventors thus attained to the present invention.

The present compounds exhibit both excellent herbicidal activity and excellent selectivity between crops and weeds, as described below. The present compounds, in foliage treatment and soil treatment in plow field, have a herbicidal activity against various weeds in question, for example, broadleaf weeds such as common purslane (*Portulaca oleracea*), chickweed (*Stellaria media*), common lambsquarters (*Chenopodium album*), redroot pigweed (*Amaranthus retroflexus*), radish (*Raphanus sativus*), velvetleaf (*Abutilon theophrasti*), prickly sida (*Sida spinosa*), black nightshade (*Solanum nigrum*), persian speedwell (*Veronica persica*), common cocklebur (*Xanthium strumarium*), morningglories (Ipomoea spp.), etc.; grassy weeds such as Japanese millet (*Echinochloa frumentacea*), barnyardgrass (*Echinochloa crus-galli*), giant foxtail (*Setaria faberi*), green foxtail (*Setaria viridis*), large crabgrass (*Digitaria sanguinalis*), annual bluegrass (*Poa annua*), blackgrass (*Alopecurus myosuroides*), oat (*Avena sativa*), wild oat (*Avena fatua*), johnsongrass (*Sorghum halepense*), shattercane (*Sorghum bicolor*), downy brome (*Bromus tectorum*), cheat (*Bromus sealinus*), bermudagrass (*Cynodon dactylon*), goosegrass (*Eleusine indica*), quackgrass (*Agropyron repens*), fall panicum (*Panicum dichotomiflorum*), sedge weeds such as purple nutsedge (*Cyperus rotondus*) and yellow nutsedge (*Cyperus esculentus*), etc., and yet, their phytotoxicity to main crops such as corn, wheat, barley, rice, soybean, peanut, cotton, beet, sunflower, etc. is not such a one as to cause a problem.

Further, the present compounds, in treatment under flooded condition in paddy field, show a herbicidal activity against various weeds in question, for example grassy weeds such as barnyardgrass (*Echinochloa oryzicola*), etc., and broadleaf weeds such as common falsepimpernel (*Lindernia procumbens*), long stemmed waterwort (*Elatine triandra*), etc., and yet, their phytotoxicity to rice is not such a one as to cause a problem.

Of the present compounds represented by the general formula (I), those in which $R^1$ is a methyl group, $R^2$ is an ethyl or propyl group, preferably an ethyl group, $R^3$ is a hydrogen atom or a methyl group, $R^4$ is a hydrogen atom or a methyl group, $R^5$ is a hydrogen atom or a methyl group, $R^6$ is a hydrogen atom, X is a group represented by the formula CH, Y is a hydrogen atom, Z is a trifluoromethyl, trifluoromethoxy or 1,1,2,2-tetrafluoroethoxy group and n is an integer of 0, show particularly excellent selectivity between grassy crops such as corn, wheat, rice, etc. and grassy weeds such as barnyardgrass (*Echinochloa crus-galli*), green foxtail, giant foxtail, large crabgrass, oat, johnsongrass, barnyardgrass (*Echinochloa oryzicola*), etc., and they are particularly preferred as a herbicide used in corn and wheat fields.

Also, of the present compounds represented by the general formula (I), those in which $R^1$ is an ethyl or propyl group, $R^2$ is a $(C_3-C_6)$alkenyl group or halo$(C_3-C_6)$alkenyl group, preferably an allyl or 2-butenyl group, $R^3$ is a hydrogen atom or a methyl group, $R^4$ is a hydrogen atom or a methyl group, $R^5$ is a hydrogen atom or a methyl group, $R^6$ is a hydrogen atom, X is a group represented by the formula CH or a nitrogen atom, Y is a hydrogen atom, Z is a trifluoromethyl, trifluoromethoxy or 1,1,2,2-tetrafluoroethoxy group and n is an integer of 0, preferably a trifluoromethyl or trifluoromethoxy group, show particularly excellent selectivity between rice and various weeds in paddy field, so that they are preferred as a herbicide for paddy field.

Also, of the present compounds represented by the general formula (I), those in which $R^1$ is an ethyl or propyl group, $R^2$ is a $(C_1-C_6)$alkyl, $(C_3-C_6)$alkenyl or halo$(C_3-C_6)$alkenyl group, $R^3$ is a hydrogen atom or a methyl group, $R^4$ is a hydrogen atom or a methyl group, $R^5$ is a hydrogen atom or a methyl group, and when $R^5$ is a hydrogen atom, $R^6$ is a hydrogen atom or a $(C_1-C_4)$alkoxycarbonyl group and when $R^5$ is a methyl group, $R^6$ is a hydrogen atom, X is a group represented by the formula CH or a nitrogen atom, Y is a hydrogen atom, Z is a trifluoromethyl or trifluoromethoxy group and n is an integer of 0, exhibit particularly excellent selectivity between broadleaf crops such as soybean, cotton, beet, peanut, sunflower, etc. and various grassy weeds, so that they are preferred as a herbicide for broadleaf crops.

Further, of the present compounds represented by the general formula (I), those in which $R^1$ is a methyl group, $R^2$ is a $(C_1-C_6)$alkyl, $(C_3-C_6)$alkenyl or halo$(C_3-C_6)$alkenyl group, $R^3$ is a hydrogen atom or a methyl group, $R^4$ is a hydrogen atom or a methyl group, $R^5$ is a hydrogen atom or a methyl group, $R^6$ is a hydrogen atom, X is a group represented by the formula CH, Y is a hydrogen atom, Z is a trifluoromethyl group and n is an integer of 0, have particularly a broad herbicidal spectrum, so that they are preferred as a herbicide used in orchards, forests, non-crop lands, etc.

Preferred compounds are 2-(1-propoxyaminoethylidene)- or 2-(1-ethoxyaminoethylidene)-5-[2-(4-trifluoromethylphenylthio)ethyl]cyclohexane-1,3-dione, 2-(1-ethoxyaminoethylidene)-5-[2-(4-trifluoromethoxyphenylthio)ethyl]cyclohexane-1,3-dione, 2-(1-allyloxyaminobutylidene)- or 2-[1-(2-butenyl)oxyaminobutylidene]-5-[2-(5-trifluoromethyl-2-pyridylthio)ethyl]cyclohexane-1,3-dione and 2-(1-ethoxyaminopropylidene)- or 2-(1-allyloxyaminopropylidene)-5-[2-(4-trifluoromethylphenylthio)ethyl]-cyclohexane-1,3-dione.

Next, a method for producing the present compounds will be explained in detail.

The present compounds can be produced by reacting acylcyclohexane represented by the general formula (II),

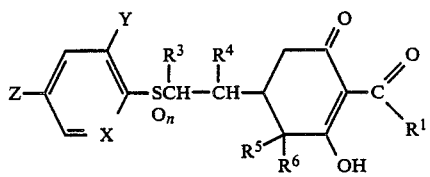
(II)

wherein $R^1$, $R^3$, $R^4$, $R^5$, $R^6$, X, Y, Z and n are as defined above, with hydroxylamine represented by the general formula (III), $NH_2OR^2$ (III)

wherein $R^2$ is as defined above, or its inorganic acid salt.

This reaction is generally carried out with or without a solvent, and as need arises, in the presence of a base, if necessary. The reaction temperature is in a range of from 0° to 100° C., and the reaction time is in a range of from 0.5 to 24 hours. The amount of the reagents used for reaction is from 1 to 2 equivalents for the amine (III) or its inorganic acid salt, and from 1 to 2 equivalents for the dehydrohalogenating agent based on 1 equivalent of acylcyclohexane (II).

The inorganic acid salt of the amine (III) includes hydrochloride, hydrobromide, sulfate, etc.

The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), alcohols (e.g. methanol, ethanol, isopropanol, tert-butanol, octanol, cyclohexanol, methyl cellosolve, diethylene glycol, glycerin), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), water and mixtures thereof.

The base includes organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction solution is poured into water, made neutral to acidic, subjected to the usual after-treatment such as extraction with organic solvents, concentration, etc., and if necessary, purified by chromatography, distillation, recrystallization, etc.

The present compounds represented by the general formula (I) are considered to have the following tautomeric structures:

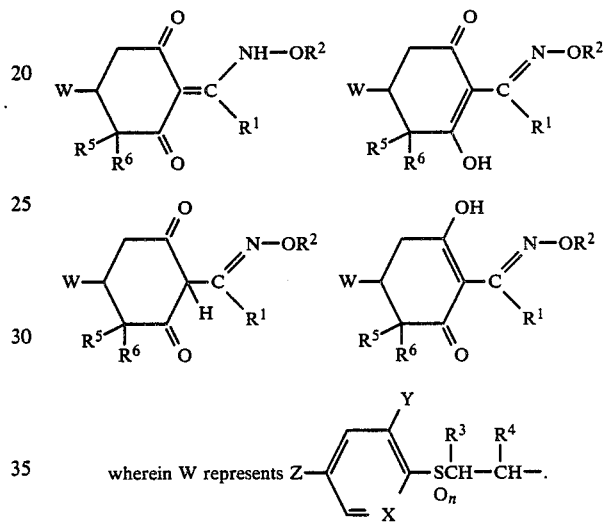

wherein W represents 

Similarly, acylcyclohexane represented by the general formula (II) are also considered to have the following tautomeric structures:

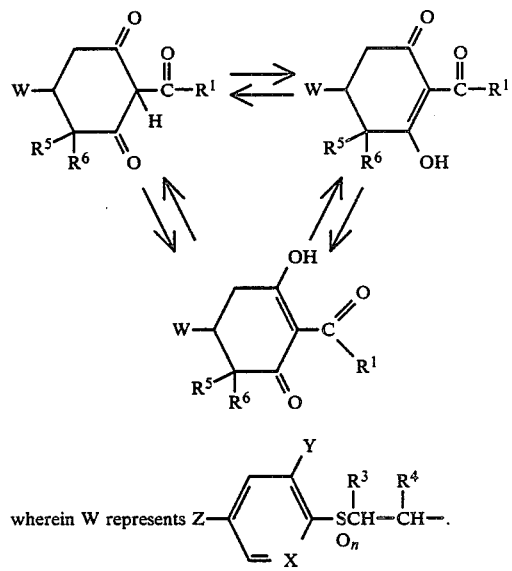

Next, examples of the present compound produced by the method of the present invention will be shown in Table 1.

TABLE 1

Cyclohexanes of the general formula:

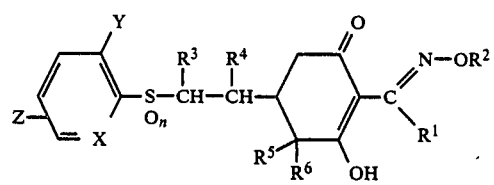

| X | Y | Z | R¹ | R² | R³ | R⁴ | R⁵ | R⁶ | n |
|---|---|---|----|----|----|----|----|----|---|
| CH | H | CF₃ | CH₃ | CH₃ | H | H | H | H | 0 |
| CH | H | CF₃ | CH₃ | CH₂CH₃ | H | H | H | H | 0 |
| CH | H | CF₃ | CH₃ | CH₂CH₂CH₃ | H | H | H | H | 0 |
| CH | H | CF₃ | CH₃ | (CH₂)₃CH₃ | H | H | H | H | 0 |
| CH | H | CF₃ | CH₃ | (CH₂)₄CH₃ | H | H | H | H | 0 |
| CH | H | CF₃ | CH₃ | (CH₂)₁₁CH₃ | H | H | H | H | 0 |
| CH | H | CF₃ | CH₃ | CH(CH₃)₂ | H | H | H | H | 0 |
| CH | H | CF₃ | CH₃ | CH₂CH(CH₃)₂ | H | H | H | H | 0 |
| CH | H | CF₃ | CH₃ | CH₂CH(CH₃)C₂H₅ | H | H | H | H | 0 |
| CH | H | CF₃ | CH₃ | CH₂-cyclopropyl | H | H | H | H | 0 |
| CH | H | CF₃ | CH₃ | CH₂CH=CH₂ | H | H | H | H | 0 |
| CH | H | CF₃ | CH₃ | CH₂CH=CHCH₃ | H | H | H | H | 0 |
| CH | H | CF₃ | CH₃ | CH₂CH=CHCl | H | H | H | H | 0 |
| CH | H | CF₃ | CH₃ | CH₂CH=CCl₂ | H | H | H | H | 0 |
| CH | H | CF₃ | CH₃ | CH₂CH₂CH=CH₂ | H | H | H | H | 0 |
| CH | H | CF₃ | CH₃ | —CH₂C≡CH | H | H | H | H | 0 |
| CH | H | CF₃ | CH₃ | CH₂CN | H | H | H | H | 0 |
| CH | H | CF₃ | CH₃ | CH₂OCH₃ | H | H | H | H | 0 |
| CH | H | CF₃ | CH₃ | CH₂SCH₃ | H | H | H | H | 0 |
| CH | H | CF₃ | CH₃ | CH₂C₆H₅ | H | H | H | H | 0 |
| CH | H | CF₃ | CH₃ | (CH₂)₃CN | H | H | H | H | 0 |
| CH | H | CF₃ | CH₃ | CH₂OCH₂CH₂CH₃ | H | H | H | H | 0 |
| CH | H | CF₃ | CH₃ | CH₂SCH₂CH₂CH₃ | H | H | H | H | 0 |
| CH | H | CF₃ | CH₃ | CH₂C≡CCH₃ | H | H | H | H | 0 |
| CH | H | CF₃ | CH₃ | CH₃ | H | H | CH₃ | H | 0 |
| CH | H | CF₃ | CH₃ | CH₂CH₃ | H | H | CH₃ | H | 0 |
| CH | H | CF₃ | CH₃ | CH₂CH₂CH₃ | H | H | CH₃ | H | 0 |
| CH | H | CF₃ | CH₃ | (CH₂)₃CH₃ | H | H | CH₃ | H | 0 |
| CH | H | CF₃ | CH₃ | (CH₂)₄CH₃ | H | H | CH₃ | H | 0 |
| CH | H | CF₃ | CH₃ | (CH₂)₁₁CH₃ | H | H | CH₃ | H | 0 |
| CH | H | CF₃ | CH₃ | CH(CH₃)₂ | H | H | CH₃ | H | 0 |
| CH | H | CF₃ | CH₃ | CH₂CH(CH₃)₂ | H | H | CH₃ | H | 0 |
| CH | H | CF₃ | CH₃ | CH₂CH(CH₃)C₂H₅ | H | H | CH₃ | H | 0 |
| CH | H | CF₃ | CH₃ | CH₂-cyclopropyl | H | H | CH₃ | H | 0 |
| CH | H | CF₃ | CH₃ | CH₂CH=CH₂ | H | H | CH₃ | H | 0 |
| CH | H | CF₃ | CH₃ | CH₂CH=CHCH₃ | H | H | CH₃ | H | 0 |
| CH | H | CF₃ | CH₃ | CH₂CH=CHCl | H | H | CH₃ | H | 0 |
| CH | H | CF₃ | CH₃ | CH₂CH=CCl₂ | H | H | CH₃ | H | 0 |
| CH | H | CF₃ | CH₃ | CH₂CH₂CH=CH₂ | H | H | CH₃ | H | 0 |
| CH | H | CF₃ | CH₃ | —CH₂C≡CH | H | H | CH₃ | H | 0 |
| CH | H | CF₃ | CH₃ | CH₂CN | H | H | CH₃ | H | 0 |
| CH | H | CF₃ | CH₃ | CH₂OCH₃ | H | H | CH₃ | H | 0 |
| CH | H | CF₃ | CH₃ | CH₂SCH₃ | H | H | CH₃ | H | 0 |
| CH | H | CF₃ | CH₃ | CH₂C₆H₅ | H | H | CH₃ | H | 0 |
| CH | H | CF₃ | CH₃ | CH₃ | H | H | H | H | 1 |
| CH | H | CF₃ | CH₃ | CH₂CH₃ | H | H | H | H | 1 |
| CH | H | CF₃ | CH₃ | CH₂CH₂CH₃ | H | H | H | H | 1 |
| CH | H | CF₃ | CH₃ | (CH₂)₃CH₃ | H | H | H | H | 1 |
| CH | H | CF₃ | CH₃ | (CH₂)₄CH₃ | H | H | H | H | 1 |
| CH | H | CF₃ | CH₃ | (CH₂)₁₁CH₃ | H | H | H | H | 1 |
| CH | H | CF₃ | CH₃ | CH(CH₃)₂ | H | H | H | H | 1 |
| CH | H | CF₃ | CH₃ | CH₂CH(CH₃)₂ | H | H | H | H | 1 |
| CH | H | CF₃ | CH₃ | CH₂CH(CH₃)C₂H₅ | H | H | H | H | 1 |

TABLE 1-continued

| | | | | | | | | | |
|---|---|---|---|---|---|---|---|---|---|
| CH | H | CF$_3$ | CH$_3$ |  | H | H | H | H | 1 |
| CH | H | CF$_3$ | CH$_3$ | CH$_2$CH=CH$_2$ | H | H | H | H | 1 |
| CH | H | CF$_3$ | CH$_3$ | CH$_2$CH=CHCH$_3$ | H | H | H | H | 1 |
| CH | H | CF$_3$ | CH$_3$ | CH$_2$CH=CHCl | H | H | H | H | 1 |
| CH | H | CF$_3$ | CH$_3$ | CH$_2$CH=CCl$_2$ | H | H | H | H | 1 |
| CH | H | CF$_3$ | CH$_3$ | CH$_2$CH$_2$CH=CH$_2$ | H | H | H | H | 1 |
| CH | H | CF$_3$ | CH$_3$ | —CH$_2$C≡CH | H | H | H | H | 1 |
| CH | H | CF$_3$ | CH$_3$ | CH$_2$CN | H | H | H | H | 1 |
| CH | H | CF$_3$ | CH$_3$ | CH$_2$OCH$_3$ | H | H | H | H | 1 |
| CH | H | CF$_3$ | CH$_3$ | CH$_2$SCH$_3$ | H | H | H | H | 1 |
| CH | H | CF$_3$ | CH$_3$ | CH$_2$C$_6$H$_5$ | H | H | H | H | 1 |
| CH | H | CF$_3$ | CH$_3$ | CH$_3$ | H | H | H | H | 2 |
| CH | H | CF$_3$ | CH$_3$ | CH$_2$CH$_3$ | H | H | H | H | 2 |
| CH | H | CF$_3$ | CH$_3$ | CH$_2$CH$_2$CH$_3$ | H | H | H | H | 2 |
| CH | H | CF$_3$ | CH$_3$ | (CH$_2$)$_3$CH$_3$ | H | H | H | H | 2 |
| CH | H | CF$_3$ | CH$_3$ | (CH$_2$)$_4$CH$_3$ | H | H | H | H | 2 |
| CH | H | CF$_3$ | CH$_3$ | (CH$_2$)$_{11}$CH$_3$ | H | H | H | H | 2 |
| CH | H | CF$_3$ | CH$_3$ | CH(CH$_3$)$_2$ | H | H | H | H | 2 |
| CH | H | CF$_3$ | CH$_3$ | CH$_2$CH(CH$_3$)$_2$ | H | H | H | H | 2 |
| CH | H | CF$_3$ | CH$_3$ | CH$_2$CH(CH$_3$)C$_2$H$_5$ | H | H | H | H | 2 |
| CH | H | CF$_3$ | CH$_3$ |  | H | H | H | H | 2 |
| CH | H | CF$_3$ | CH$_3$ | CH$_2$CH=CH$_2$ | H | H | H | H | 2 |
| CH | H | CF$_3$ | CH$_3$ | CH$_2$CH=CHCH$_3$ | H | H | H | H | 2 |
| CH | H | CF$_3$ | CH$_3$ | CH$_2$CH=CHCl | H | H | H | H | 2 |
| CH | H | CF$_3$ | CH$_3$ | CH$_2$CH=CCl$_2$ | H | H | H | H | 2 |
| CH | H | CF$_3$ | CH$_3$ | CH$_2$CH$_2$CH=CH$_2$ | H | H | H | H | 2 |
| CH | H | CF$_3$ | CH$_3$ | —CH$_2$C≡CH | H | H | H | H | 2 |
| CH | H | CF$_3$ | CH$_3$ | CH$_2$CN | H | H | H | H | 2 |
| CH | H | CF$_3$ | CH$_3$ | CH$_2$OCH$_3$ | H | H | H | H | 2 |
| CH | H | CF$_3$ | CH$_3$ | CH$_2$SCH$_3$ | H | H | H | H | 2 |
| CH | H | CF$_3$ | CH$_3$ | CH$_2$C$_6$H$_5$ | H | H | H | H | 2 |
| CH | H | CF$_3$ | CH$_3$ | CH$_3$ | H | CH$_3$ | H | H | 0 |
| CH | H | CF$_3$ | CH$_3$ | CH$_2$CH$_3$ | H | CH$_3$ | H | H | 0 |
| CH | H | CF$_3$ | CH$_3$ | CH$_2$CH$_2$CH$_3$ | H | CH$_3$ | H | H | 0 |
| CH | H | CF$_3$ | CH$_3$ | (CH$_2$)$_3$CH$_3$ | H | CH$_3$ | H | H | 0 |
| CH | H | CF$_3$ | CH$_3$ | (CH$_2$)$_4$CH$_3$ | H | CH$_3$ | H | H | 0 |
| CH | H | CF$_3$ | CH$_3$ | (CH$_2$)$_{11}$CH$_3$ | H | CH$_3$ | H | H | 0 |
| CH | H | CF$_3$ | CH$_3$ | CH(CH$_3$)$_2$ | H | CH$_3$ | H | H | 0 |
| CH | H | CF$_3$ | CH$_3$ | CH$_2$CH(CH$_3$)$_2$ | H | CH$_3$ | H | H | 0 |
| CH | H | CF$_3$ | CH$_3$ | CH$_2$CH(CH$_3$)C$_2$H$_5$ | H | CH$_3$ | H | H | 0 |
| CH | H | CF$_3$ | CH$_3$ |  | H | CH$_3$ | H | H | 0 |
| CH | H | CF$_3$ | CH$_3$ | CH$_2$CH=CH$_2$ | H | CH$_3$ | H | H | 0 |
| CH | H | CF$_3$ | CH$_3$ | CH$_2$CH=CHCH$_3$ | H | CH$_3$ | H | H | 0 |
| CH | H | CF$_3$ | CH$_3$ | CH$_2$CH=CHCl | H | CH$_3$ | H | H | 0 |
| CH | H | CF$_3$ | CH$_3$ | CH$_2$CH=CCl$_2$ | H | CH$_3$ | H | H | 0 |
| CH | H | CF$_3$ | CH$_3$ | CH$_2$CH$_2$CH=CH$_2$ | H | CH$_3$ | H | H | 0 |
| CH | H | CF$_3$ | CH$_3$ | —CH$_2$C≡CH | H | CH$_3$ | H | H | 0 |
| CH | H | CF$_3$ | CH$_3$ | CH$_2$CN | H | CH$_3$ | H | H | 0 |
| CH | H | CF$_3$ | CH$_3$ | CH$_2$OCH$_3$ | H | CH$_3$ | H | H | 0 |
| CH | H | CF$_3$ | CH$_3$ | CH$_2$SCH$_3$ | H | CH$_3$ | H | H | 0 |
| CH | H | CF$_3$ | CH$_3$ | CH$_2$C$_6$H$_5$ | H | CH$_3$ | H | H | 0 |
| CH | H | CF$_3$ | CH$_3$ | CH$_3$ | CH$_3$ | H | H | H | 0 |
| CH | H | CF$_3$ | CH$_3$ | CH$_2$CH$_3$ | CH$_3$ | H | H | H | 0 |
| CH | H | CF$_3$ | CH$_3$ | CH$_2$CH$_2$CH$_3$ | CH$_3$ | H | H | H | 0 |
| CH | H | CF$_3$ | CH$_3$ | (CH$_2$)$_3$CH$_3$ | CH$_3$ | H | H | H | 0 |
| CH | H | CF$_3$ | CH$_3$ | (CH$_2$)$_4$CH$_3$ | CH$_3$ | H | H | H | 0 |
| CH | H | CF$_3$ | CH$_3$ | (CH$_2$)$_{11}$CH$_3$ | CH$_3$ | H | H | H | 0 |
| CH | H | CF$_3$ | CH$_3$ | CH(CH$_3$)$_2$ | CH$_3$ | H | H | H | 0 |
| CH | H | CF$_3$ | CH$_3$ | CH$_2$CH(CH$_3$)$_2$ | CH$_3$ | H | H | H | 0 |
| CH | H | CF$_3$ | CH$_3$ | CH$_2$CH(CH$_3$)C$_2$H$_5$ | CH$_3$ | H | H | H | 0 |

TABLE 1-continued

| | | | | | | | | | |
|---|---|---|---|---|---|---|---|---|---|
| CH | H | CF$_3$ | CH$_3$ | CH$_2$—△ | CH$_3$ | H | H | H | 0 |
| CH | H | CF$_3$ | CH$_3$ | CH$_2$CH=CH$_2$ | CH$_3$ | H | H | H | 0 |
| CH | H | CF$_3$ | CH$_3$ | CH$_2$CH=CHCH$_3$ | CH$_3$ | H | H | H | 0 |
| CH | H | CF$_3$ | CH$_3$ | CH$_2$CH=CHCl | CH$_3$ | H | H | H | 0 |
| CH | H | CF$_3$ | CH$_3$ | CH$_2$CH=CCl$_2$ | CH$_3$ | H | H | H | 0 |
| CH | H | CF$_3$ | CH$_3$ | CH$_2$CH$_2$CH=CH$_2$ | CH$_3$ | H | H | H | 0 |
| CH | H | CF$_3$ | CH$_3$ | —CH$_2$C≡CH | CH$_3$ | H | H | H | 0 |
| CH | H | CF$_3$ | CH$_3$ | CH$_2$CN | CH$_3$ | H | H | H | 0 |
| CH | H | CF$_3$ | CH$_3$ | CH$_2$OCH$_3$ | CH$_3$ | H | H | H | 0 |
| CH | H | CF$_3$ | CH$_3$ | CH$_2$SCH$_3$ | CH$_3$ | H | H | H | 0 |
| CH | H | CF$_3$ | CH$_3$ | CH$_2$C$_6$H$_5$ | CH$_3$ | H | H | H | 0 |
| CH | H | CF$_3$ | C$_2$H$_5$ | CH$_3$ | H | H | H | H | 0 |
| CH | H | CF$_3$ | C$_2$H$_5$ | CH$_2$CH$_3$ | H | H | H | H | 0 |
| CH | H | CF$_3$ | C$_2$H$_5$ | CH$_2$CH$_2$CH$_3$ | H | H | H | H | 0 |
| CH | H | CF$_3$ | C$_2$H$_5$ | (CH$_2$)$_3$CH$_3$ | H | H | H | H | 0 |
| CH | H | CF$_3$ | C$_2$H$_5$ | (CH$_2$)$_4$CH$_3$ | H | H | H | H | 0 |
| CH | H | CF$_3$ | C$_2$H$_5$ | (CH$_2$)$_{11}$CH$_3$ | H | H | H | H | 0 |
| CH | H | CF$_3$ | C$_2$H$_5$ | CH(CH$_3$)$_2$ | H | H | H | H | 0 |
| CH | H | CF$_3$ | C$_2$H$_5$ | CH$_2$CH(CH$_3$)$_2$ | H | H | H | H | 0 |
| CH | H | CF$_3$ | C$_2$H$_5$ | CH$_2$CH(CH$_3$)C$_2$H$_5$ | H | H | H | H | 0 |
| CH | H | CF$_3$ | C$_2$H$_5$ | CH$_2$—△ | H | H | H | H | 0 |
| CH | H | CF$_3$ | C$_2$H$_5$ | CH$_2$CH=CH$_2$ | H | H | H | H | 0 |
| CH | H | CF$_3$ | C$_2$H$_5$ | CH$_2$CH=CHCH$_3$ | H | H | H | H | 0 |
| CH | H | CF$_3$ | C$_2$H$_5$ | CH$_2$CH=CHCl | H | H | H | H | 0 |
| CH | H | CF$_3$ | C$_2$H$_5$ | CH$_2$CH=CCl$_2$ | H | H | H | H | 0 |
| CH | H | CF$_3$ | C$_2$H$_5$ | CH$_2$CH$_2$CH=CH$_2$ | H | H | H | H | 0 |
| CH | H | CF$_3$ | C$_2$H$_5$ | —CH$_2$C≡CH | H | H | H | H | 0 |
| CH | H | CF$_3$ | C$_2$H$_5$ | CH$_2$CN | H | H | H | H | 0 |
| CH | H | CF$_3$ | C$_2$H$_5$ | CH$_2$OCH$_3$ | H | H | H | H | 0 |
| CH | H | CF$_3$ | C$_2$H$_5$ | CH$_2$SCH$_3$ | H | H | H | H | 0 |
| CH | H | CF$_3$ | C$_2$H$_5$ | CH$_2$C$_6$H$_5$ | H | H | H | H | 0 |
| CH | H | CF$_3$ | C$_2$H$_5$ | —CH$_2$—C$_6$H$_{11}$ | H | H | H | H | 0 |
| CH | H | CF$_3$ | C$_2$H$_5$ | CH$_2$C≡CCH$_3$ | H | H | H | H | 0 |
| CH | H | CF$_3$ | C$_2$H$_5$ | CH$_2$OCH$_2$CH$_2$CH$_3$ | H | H | H | H | 0 |
| CH | H | CF$_3$ | C$_2$H$_5$ | CH$_3$ | H | H | H | H | 1 |
| CH | H | CF$_3$ | C$_2$H$_5$ | CH$_2$CH$_3$ | H | H | H | H | 1 |
| CH | H | CF$_3$ | C$_2$H$_5$ | CH$_2$CH$_2$CH$_3$ | H | H | H | H | 1 |
| CH | H | CF$_3$ | C$_2$H$_5$ | (CH$_2$)$_3$CH$_3$ | H | H | H | H | 1 |
| CH | H | CF$_3$ | C$_2$H$_5$ | (CH$_2$)$_4$CH$_3$ | H | H | H | H | 1 |
| CH | H | CF$_3$ | C$_2$H$_5$ | (CH$_2$)$_{11}$CH$_3$ | H | H | H | H | 1 |
| CH | H | CF$_3$ | C$_2$H$_5$ | CH(CH$_3$)$_2$ | H | H | H | H | 1 |
| CH | H | CF$_3$ | C$_2$H$_5$ | CH$_2$CH(CH$_3$)$_2$ | H | H | H | H | 1 |
| CH | H | CF$_3$ | C$_2$H$_5$ | CH$_2$CH(CH$_3$)C$_2$H$_5$ | H | H | H | H | 1 |
| CH | H | CF$_3$ | C$_2$H$_5$ | CH$_2$—△ | H | H | H | H | 1 |
| CH | H | CF$_3$ | C$_2$H$_5$ | CH$_2$CH=CH$_2$ | H | H | H | H | 1 |
| CH | H | CF$_3$ | C$_2$H$_5$ | CH$_2$CH=CHCH$_3$ | H | H | H | H | 1 |
| CH | H | CF$_3$ | C$_2$H$_5$ | CH$_2$CH=CHCl | H | H | H | H | 1 |
| CH | H | CF$_3$ | C$_2$H$_5$ | CH$_2$CH=CCl$_2$ | H | H | H | H | 1 |
| CH | H | CF$_3$ | C$_2$H$_5$ | CH$_2$CH$_2$CH=CH$_2$ | H | H | H | H | 1 |
| CH | H | CF$_3$ | C$_2$H$_5$ | —CH$_2$C≡CH | H | H | H | H | 1 |
| CH | H | CF$_3$ | C$_2$H$_5$ | CH$_2$CN | H | H | H | H | 1 |
| CH | H | CF$_3$ | C$_2$H$_5$ | CH$_2$OCH$_3$ | H | H | H | H | 1 |
| CH | H | CF$_3$ | C$_2$H$_5$ | CH$_2$SCH$_3$ | H | H | H | H | 1 |
| CH | H | CF$_3$ | C$_2$H$_5$ | CH$_2$C$_6$H$_5$ | H | H | H | H | 1 |
| CH | H | CF$_3$ | C$_2$H$_5$ | CH$_3$ | H | H | H | H | 2 |
| CH | H | CF$_3$ | C$_2$H$_5$ | CH$_2$CH$_3$ | H | H | H | H | 2 |
| CH | H | CF$_3$ | C$_2$H$_5$ | CH$_2$CH$_2$CH$_3$ | H | H | H | H | 2 |
| CH | H | CF$_3$ | C$_2$H$_5$ | (CH$_2$)$_3$CH$_3$ | H | H | H | H | 2 |
| CH | H | CF$_3$ | C$_2$H$_5$ | (CH$_2$)$_4$CH$_3$ | H | H | H | H | 2 |

TABLE 1-continued

| | | | | | | | | | |
|---|---|---|---|---|---|---|---|---|---|
| CH | H | CF$_3$ | C$_2$H$_5$ | (CH$_2$)$_{11}$CH$_3$ | H | H | H | H | 2 |
| CH | H | CF$_3$ | C$_2$H$_5$ | CH(CH$_3$)$_2$ | H | H | H | H | 2 |
| CH | H | CF$_3$ | C$_2$H$_5$ | CH$_2$CH(CH$_3$)$_2$ | H | H | H | H | 2 |
| CH | H | CF$_3$ | C$_2$H$_5$ | CH$_2$CHC$_2$H$_5$ with CH$_3$ branch | H | H | H | H | 2 |
| CH | H | CF$_3$ | C$_2$H$_5$ | CH$_2$— | H | H | H | H | 2 |
| CH | H | CF$_3$ | C$_2$H$_5$ | CH$_2$CH=CH$_2$ | H | H | H | H | 2 |
| CH | H | CF$_3$ | C$_2$H$_5$ | CH$_2$CH=CHCH$_3$ | H | H | H | H | 2 |
| CH | H | CF$_3$ | C$_2$H$_5$ | CH$_2$CH=CHCl | H | H | H | H | 2 |
| CH | H | CF$_3$ | C$_2$H$_5$ | CH$_2$CH=CCl$_2$ | H | H | H | H | 2 |
| CH | H | CF$_3$ | C$_2$H$_5$ | CH$_2$CH$_2$CH=CH$_2$ | H | H | H | H | 2 |
| CH | H | CF$_3$ | C$_2$H$_5$ | —CH$_2$C≡CH | H | H | H | H | 2 |
| CH | H | CF$_3$ | C$_2$H$_5$ | CH$_2$CN | H | H | H | H | 2 |
| CH | H | CF$_3$ | C$_2$H$_5$ | CH$_2$OCH$_3$ | H | H | H | H | 2 |
| CH | H | CF$_3$ | C$_2$H$_5$ | CH$_2$SCH$_3$ | H | H | H | H | 2 |
| CH | H | CF$_3$ | C$_2$H$_5$ | CH$_2$C$_6$H$_5$ | H | H | H | H | 2 |
| CH | H | CF$_3$ | C$_2$H$_5$ | CH$_3$ | H | H | CH$_3$ | H | 0 |
| CH | H | CF$_3$ | C$_2$H$_5$ | CH$_2$CH$_3$ | H | H | CH$_3$ | H | 0 |
| CH | H | CF$_3$ | C$_2$H$_5$ | CH$_2$CH$_2$CH$_3$ | H | H | CH$_3$ | H | 0 |
| CH | H | CF$_3$ | C$_2$H$_5$ | (CH$_2$)$_3$CH$_3$ | H | H | CH$_3$ | H | 0 |
| CH | H | CF$_3$ | C$_2$H$_5$ | (CH$_2$)$_4$CH$_3$ | H | H | CH$_3$ | H | 0 |
| CH | H | CF$_3$ | C$_2$H$_5$ | (CH$_2$)$_{11}$CH$_3$ | H | H | CH$_3$ | H | 0 |
| CH | H | CF$_3$ | C$_2$H$_5$ | CH(CH$_3$)$_2$ | H | H | CH$_3$ | H | 0 |
| CH | H | CF$_3$ | C$_2$H$_5$ | CH$_2$CH(CH$_3$)$_2$ | H | H | CH$_3$ | H | 0 |
| CH | H | CF$_3$ | C$_2$H$_5$ | CH$_2$CHC$_2$H$_5$ with CH$_3$ branch | H | H | CH$_3$ | H | 0 |
| CH | H | CF$_3$ | C$_2$H$_5$ | CH$_2$— | H | H | CH$_3$ | H | 0 |
| CH | H | CF$_3$ | C$_2$H$_5$ | CH$_2$CH=CH$_2$ | H | H | CH$_3$ | H | 0 |
| CH | H | CF$_3$ | C$_2$H$_5$ | CH$_2$CH=CHCH$_3$ | H | H | CH$_3$ | H | 0 |
| CH | H | CF$_3$ | C$_2$H$_5$ | CH$_2$CH=CHCl | H | H | CH$_3$ | H | 0 |
| CH | H | CF$_3$ | C$_2$H$_5$ | CH$_2$CH=CCl$_2$ | H | H | CH$_3$ | H | 0 |
| CH | H | CF$_3$ | C$_2$H$_5$ | CH$_2$CH$_2$CH=CH$_2$ | H | H | CH$_3$ | H | 0 |
| CH | H | CF$_3$ | C$_2$H$_5$ | —CH$_2$C≡CH | H | H | CH$_3$ | H | 0 |
| CH | H | CF$_3$ | C$_2$H$_5$ | CH$_2$CN | H | H | CH$_3$ | H | 0 |
| CH | H | CF$_3$ | C$_2$H$_5$ | CH$_2$OCH$_3$ | H | H | CH$_3$ | H | 0 |
| CH | H | CF$_3$ | C$_2$H$_5$ | CH$_2$SCH$_3$ | H | H | CH$_3$ | H | 0 |
| CH | H | CF$_3$ | C$_2$H$_5$ | CH$_2$C$_6$H$_5$ | H | H | CH$_3$ | H | 0 |
| CH | H | CF$_3$ | C$_2$H$_5$ | CH$_3$ | H | CH$_3$ | H | H | 0 |
| CH | H | CF$_3$ | C$_2$H$_5$ | CH$_2$CH$_3$ | H | CH$_3$ | H | H | 0 |
| CH | H | CF$_3$ | C$_2$H$_5$ | CH$_2$CH$_2$CH$_3$ | H | CH$_3$ | H | H | 0 |
| CH | H | CF$_3$ | C$_2$H$_5$ | (CH$_2$)$_3$CH$_3$ | H | CH$_3$ | H | H | 0 |
| CH | H | CF$_3$ | C$_2$H$_5$ | (CH$_2$)$_4$CH$_3$ | H | CH$_3$ | H | H | 0 |
| CH | H | CF$_3$ | C$_2$H$_5$ | (CH$_2$)$_{11}$CH$_3$ | H | CH$_3$ | H | H | 0 |
| CH | H | CF$_3$ | C$_2$H$_5$ | CH(CH$_3$)$_2$ | H | CH$_3$ | H | H | 0 |
| CH | H | CF$_3$ | C$_2$H$_5$ | CH$_2$CH(CH$_3$)$_2$ | H | CH$_3$ | H | H | 0 |
| CH | H | CF$_3$ | C$_2$H$_5$ | CH$_2$CHC$_2$H$_5$ with CH$_3$ branch | H | CH$_3$ | H | H | 0 |
| CH | H | CF$_3$ | C$_2$H$_5$ | CH$_2$—cyclopropyl | H | CH$_3$ | H | H | 0 |
| CH | H | CF$_3$ | C$_2$H$_5$ | CH$_2$CH=CH$_2$ | H | CH$_3$ | H | H | 0 |
| CH | H | CF$_3$ | C$_2$H$_5$ | CH$_2$CH=CHCH$_3$ | H | CH$_3$ | H | H | 0 |
| CH | H | CF$_3$ | C$_2$H$_5$ | CH$_2$CH=CHCl | H | CH$_3$ | H | H | 0 |
| CH | H | CF$_3$ | C$_2$H$_5$ | CH$_2$CH=CCl$_2$ | H | CH$_3$ | H | H | 0 |
| CH | H | CF$_3$ | C$_2$H$_5$ | CH$_2$CH$_2$CH=CH$_2$ | H | CH$_3$ | H | H | 0 |
| CH | H | CF$_3$ | C$_2$H$_5$ | —CH$_2$C≡CH | H | CH$_3$ | H | H | 0 |
| CH | H | CF$_3$ | C$_2$H$_5$ | CH$_2$CN | H | CH$_3$ | H | H | 0 |
| CH | H | CF$_3$ | C$_2$H$_5$ | CH$_2$OCH$_3$ | H | CH$_3$ | H | H | 0 |
| CH | H | CF$_3$ | C$_2$H$_5$ | CH$_2$SCH$_3$ | H | CH$_3$ | H | H | 0 |
| CH | H | CF$_3$ | C$_2$H$_5$ | CH$_2$C$_6$H$_5$ | H | CH$_3$ | H | H | 0 |
| CH | H | CF$_3$ | C$_2$H$_5$ | CH$_3$ | CH$_3$ | H | H | H | 0 |
| CH | H | CF$_3$ | C$_2$H$_5$ | CH$_2$CH$_3$ | CH$_3$ | H | H | H | 0 |
| CH | H | CF$_3$ | C$_2$H$_5$ | CH$_2$CH$_2$CH$_3$ | CH$_3$ | H | H | H | 0 |
| CH | H | CF$_3$ | C$_2$H$_5$ | (CH$_2$)$_3$CH$_3$ | CH$_3$ | H | H | H | 0 |
| CH | H | CF$_3$ | C$_2$H$_5$ | (CH$_2$)$_4$CH$_3$ | CH$_3$ | H | H | H | 0 |
| CH | H | CF$_3$ | C$_2$H$_5$ | (CH$_2$)$_{11}$CH$_3$ | CH$_3$ | H | H | H | 0 |

TABLE 1-continued

| | | | | | | | | | |
|---|---|---|---|---|---|---|---|---|---|
| CH | H | CF$_3$ | C$_2$H$_5$ | CH(CH$_3$)$_2$ | CH$_3$ | H | H | H | 0 |
| CH | H | CF$_3$ | C$_2$H$_5$ | CH$_2$CH(CH$_3$)$_2$ | CH$_3$ | H | H | H | 0 |
| CH | H | CF$_3$ | C$_2$H$_5$ | CH$_2$CH(CH$_3$)C$_2$H$_5$ | CH$_3$ | H | H | H | 0 |
| CH | H | CF$_3$ | C$_2$H$_5$ | CH$_2$-cyclopropyl | CH$_3$ | H | H | H | 0 |
| CH | H | CF$_3$ | C$_2$H$_5$ | CH$_2$CH=CH$_2$ | CH$_3$ | H | H | H | 0 |
| CH | H | CF$_3$ | C$_2$H$_5$ | CH$_2$CH=CHCH$_3$ | CH$_3$ | H | H | H | 0 |
| CH | H | CF$_3$ | C$_2$H$_5$ | CH$_2$CH=CHCl | CH$_3$ | H | H | H | 0 |
| CH | H | CF$_3$ | C$_2$H$_5$ | CH$_2$CH=CCl$_2$ | CH$_3$ | H | H | H | 0 |
| CH | H | CF$_3$ | C$_2$H$_5$ | CH$_2$CH$_2$CH=CH$_2$ | CH$_3$ | H | H | H | 0 |
| CH | H | CF$_3$ | C$_2$H$_5$ | —CH$_2$C≡CH | CH$_3$ | H | H | H | 0 |
| CH | H | CF$_3$ | C$_2$H$_5$ | CH$_2$CN | CH$_3$ | H | H | H | 0 |
| CH | H | CF$_3$ | C$_2$H$_5$ | CH$_2$OCH$_3$ | CH$_3$ | H | H | H | 0 |
| CH | H | CF$_3$ | C$_2$H$_5$ | CH$_2$SCH$_3$ | CH$_3$ | H | H | H | 0 |
| CH | H | CF$_3$ | C$_2$H$_5$ | CH$_2$C$_6$H$_5$ | CH$_3$ | H | H | H | 0 |
| CH | H | CF$_3$ | CH$_2$CH$_2$CH$_3$ | CH$_3$ | H | H | H | H | 0 |
| CH | H | CF$_3$ | CH$_2$CH$_2$CH$_3$ | CH$_2$CH$_3$ | H | H | H | H | 0 |
| CH | H | CF$_3$ | CH$_2$CH$_2$CH$_3$ | CH$_2$CH$_2$CH$_3$ | H | H | H | H | 0 |
| CH | H | CF$_3$ | CH$_2$CH$_2$CH$_3$ | (CH$_2$)$_3$CH$_3$ | H | H | H | H | 0 |
| CH | H | CF$_3$ | CH$_2$CH$_2$CH$_3$ | (CH$_2$)$_4$CH$_3$ | H | H | H | H | 0 |
| CH | H | CF$_3$ | CH$_2$CH$_2$CH$_3$ | (CH$_2$)$_{11}$CH$_3$ | H | H | H | H | 0 |
| CH | H | CF$_3$ | CH$_2$CH$_2$CH$_3$ | CH(CH$_3$)$_2$ | H | H | H | H | 0 |
| CH | H | CF$_3$ | CH$_2$CH$_2$CH$_3$ | CH$_2$CH(CH$_3$)$_2$ | H | H | H | H | 0 |
| CH | H | CF$_3$ | CH$_2$CH$_2$CH$_3$ | CH$_2$CH(CH$_3$)C$_2$H$_5$ | H | H | H | H | 0 |
| CH | H | CF$_3$ | CH$_2$CH$_2$CH$_3$ | CH$_2$-cyclopropyl | H | H | H | H | 0 |
| CH | H | CF$_3$ | CH$_2$CH$_2$CH$_3$ | CH$_2$CH=CH$_2$ | H | H | H | H | 0 |
| CH | H | CF$_3$ | CH$_2$CH$_2$CH$_3$ | CH$_2$CH=CHCH$_3$ | H | H | H | H | 0 |
| CH | H | CF$_3$ | CH$_2$CH$_2$CH$_3$ | CH$_2$CH=CHCl | H | H | H | H | 0 |
| CH | H | CF$_3$ | CH$_2$CH$_2$CH$_3$ | CH$_2$CH=CCl$_2$ | H | H | H | H | 0 |
| CH | H | CF$_3$ | CH$_2$CH$_2$CH$_3$ | CH$_2$CH$_2$CH=CH$_2$ | H | H | H | H | 0 |
| CH | H | CF$_3$ | CH$_2$CH$_2$CH$_3$ | —CH$_2$C≡CH | H | H | H | H | 0 |
| CH | H | CF$_3$ | CH$_2$CH$_2$CH$_3$ | CH$_2$CN | H | H | H | H | 0 |
| CH | H | CF$_3$ | CH$_2$CH$_2$CH$_3$ | CH$_2$OCH$_3$ | H | H | H | H | 0 |
| CH | H | CF$_3$ | CH$_2$CH$_2$CH$_3$ | CH$_2$SCH$_3$ | H | H | H | H | 0 |
| CH | H | CF$_3$ | CH$_2$CH$_2$CH$_3$ | CH$_2$C$_6$H$_5$ | H | H | H | H | 0 |
| CH | H | CF$_3$ | CH$_2$CH$_2$CH$_3$ | CH$_3$ | CH$_3$ | H | H | H | 0 |
| CH | H | CF$_3$ | CH$_2$CH$_2$CH$_3$ | CH$_2$CH$_3$ | CH$_3$ | H | H | H | 0 |
| CH | H | CF$_3$ | CH$_2$CH$_2$CH$_3$ | CH$_2$CH$_2$CH$_3$ | CH$_3$ | H | H | H | 0 |
| CH | H | CF$_3$ | CH$_2$CH$_2$CH$_3$ | (CH$_2$)$_3$CH$_3$ | CH$_3$ | H | H | H | 0 |
| CH | H | CF$_3$ | CH$_2$CH$_2$CH$_3$ | (CH$_2$)$_4$CH$_3$ | CH$_3$ | H | H | H | 0 |
| CH | H | CF$_3$ | CH$_2$CH$_2$CH$_3$ | (CH$_2$)$_{11}$CH$_3$ | CH$_3$ | H | H | H | 0 |
| CH | H | CF$_3$ | CH$_2$CH$_2$CH$_3$ | CH(CH$_3$)$_2$ | CH$_3$ | H | H | H | 0 |
| CH | H | CF$_3$ | CH$_2$CH$_2$CH$_3$ | CH$_2$CH(CH$_3$)$_2$ | CH$_3$ | H | H | H | 0 |
| CH | H | CF$_3$ | CH$_2$CH$_2$CH$_3$ | CH$_2$CH(CH$_3$)C$_2$H$_5$ | CH$_3$ | H | H | H | 0 |
| CH | H | CF$_3$ | CH$_2$CH$_2$CH$_3$ | CH$_2$-cyclopropyl | CH$_3$ | H | H | H | 0 |
| CH | H | CF$_3$ | CH$_2$CH$_2$CH$_3$ | CH$_2$CH=CH$_2$ | CH$_3$ | H | H | H | 0 |
| CH | H | CF$_3$ | CH$_2$CH$_2$CH$_3$ | CH$_2$CH=CHCH$_3$ | CH$_3$ | H | H | H | 0 |
| CH | H | CF$_3$ | CH$_2$CH$_2$CH$_3$ | CH$_2$CH=CHCl | CH$_3$ | H | H | H | 0 |
| CH | H | CF$_3$ | CH$_2$CH$_2$CH$_3$ | CH$_2$CH=CCl$_2$ | CH$_3$ | H | H | H | 0 |
| CH | H | CF$_3$ | CH$_2$CH$_2$CH$_3$ | CH$_2$CH$_2$CH=CH$_2$ | CH$_3$ | H | H | H | 0 |
| CH | H | CF$_3$ | CH$_2$CH$_2$CH$_3$ | —CH$_2$C≡CH | CH$_3$ | H | H | H | 0 |
| CH | H | CF$_3$ | CH$_2$CH$_2$CH$_3$ | CH$_2$CN | CH$_3$ | H | H | H | 0 |
| CH | H | CF$_3$ | CH$_2$CH$_2$CH$_3$ | CH$_2$OCH$_3$ | CH$_3$ | H | H | H | 0 |
| CH | H | CF$_3$ | CH$_2$CH$_2$CH$_3$ | CH$_3$SCH$_3$ | CH$_3$ | H | H | H | 0 |
| CH | H | CF$_3$ | CH$_2$CH$_2$CH$_3$ | CH$_2$C$_6$H$_5$ | CH$_3$ | H | H | H | 0 |
| CH | H | CF$_3$ | CH$_2$CH$_2$CH$_3$ | CH$_3$ | H | CH$_3$ | H | H | 0 |
| CH | H | CF$_3$ | CH$_2$CH$_2$CH$_3$ | CH$_2$CH$_3$ | H | CH$_3$ | H | H | 0 |
| CH | H | CF$_3$ | CH$_2$CH$_2$CH$_3$ | CH$_2$CH$_2$CH$_3$ | H | CH$_3$ | H | H | 0 |
| CH | H | CF$_3$ | CH$_2$CH$_2$CH$_3$ | (CH$_2$)$_3$CH$_3$ | H | CH$_3$ | H | H | 0 |
| CH | H | CF$_3$ | CH$_2$CH$_2$CH$_3$ | (CH$_2$)$_4$CH$_3$ | H | CH$_3$ | H | H | 0 |
| CH | H | CF$_3$ | CH$_2$CH$_2$CH$_3$ | (CH$_2$)$_{11}$CH$_3$ | H | CH$_3$ | H | H | 0 |
| CH | H | CF$_3$ | CH$_2$CH$_2$CH$_3$ | CH(CH$_3$)$_2$ | H | CH$_3$ | H | H | 0 |

TABLE 1-continued

| | | | | | | | | | |
|---|---|---|---|---|---|---|---|---|---|
| CH | H | CF$_3$ | CH$_2$CH$_2$CH$_3$ | CH$_2$CH(CH$_3$)$_2$ | H | CH$_3$ | H | H | 0 |
| CH | H | CF$_3$ | CH$_2$CH$_2$CH$_3$ | CH$_2$CH(CH$_3$)C$_2$H$_5$ | H | CH$_3$ | H | H | 0 |
| CH | H | CF$_3$ | CH$_2$CH$_2$CH$_3$ | CH$_2$-cyclopropyl | H | CH$_3$ | H | H | 0 |
| CH | H | CF$_3$ | CH$_2$CH$_2$CH$_3$ | CH$_2$CH=CH$_2$ | H | CH$_3$ | H | H | 0 |
| CH | H | CF$_3$ | CH$_2$CH$_2$CH$_3$ | CH$_2$CH=CHCH$_3$ | H | CH$_3$ | H | H | 0 |
| CH | H | CF$_3$ | CH$_2$CH$_2$CH$_3$ | CH$_2$CH=CHCl | H | CH$_3$ | H | H | 0 |
| CH | H | CF$_3$ | CH$_2$CH$_2$CH$_3$ | CH$_2$CH=CCl$_2$ | H | CH$_3$ | H | H | 0 |
| CH | H | CF$_3$ | CH$_2$CH$_2$CH$_3$ | CH$_2$CH$_2$CH=CH$_2$ | H | CH$_3$ | H | H | 0 |
| CH | H | CF$_3$ | CH$_2$CH$_2$CH$_3$ | —CH$_2$C≡CH | H | CH$_3$ | H | H | 0 |
| CH | H | CF$_3$ | CH$_2$CH$_2$CH$_3$ | CH$_2$CN | H | CH$_3$ | H | H | 0 |
| CH | H | CF$_3$ | CH$_2$CH$_2$CH$_3$ | CH$_2$OCH$_3$ | H | CH$_3$ | H | H | 0 |
| CH | H | CF$_3$ | CH$_2$CH$_2$CH$_3$ | CH$_2$SCH$_3$ | H | CH$_3$ | H | H | 0 |
| CH | H | CF$_3$ | CH$_2$CH$_2$CH$_3$ | CH$_2$C$_6$H$_5$ | H | CH$_3$ | H | H | 0 |
| CH | H | CF$_3$ | CH(CH$_3$)$_2$ | CH$_3$ | H | H | H | H | 0 |
| CH | H | CF$_3$ | CH(CH$_3$)$_2$ | CH$_2$CH$_3$ | H | H | H | H | 0 |
| CH | H | CF$_3$ | CH(CH$_3$)$_2$ | CH$_2$CH$_2$CH$_3$ | H | H | H | H | 0 |
| CH | H | CF$_3$ | CH(CH$_3$)$_2$ | (CH$_2$)$_3$CH$_3$ | H | H | H | H | 0 |
| CH | H | CF$_3$ | CH(CH$_3$)$_2$ | (CH$_2$)$_4$CH$_3$ | H | H | H | H | 0 |
| CH | H | CF$_3$ | CH(CH$_3$)$_2$ | (CH$_2$)$_{11}$CH$_3$ | H | H | H | H | 0 |
| CH | H | CF$_3$ | CH(CH$_3$)$_2$ | CH(CH$_3$)$_2$ | H | H | H | H | 0 |
| CH | H | CF$_3$ | CH(CH$_3$)$_2$ | CH$_2$CH(CH$_3$)$_2$ | H | H | H | H | 0 |
| CH | H | CF$_3$ | CH(CH$_3$)$_2$ | CH$_2$CH(CH$_3$)C$_2$H$_5$ | H | H | H | H | 0 |
| CH | H | CF$_3$ | CH(CH$_3$)$_2$ | CH$_2$-cyclopropyl | H | H | H | H | 0 |
| CH | H | CF$_3$ | CH(CH$_3$)$_2$ | CH$_2$CH=CH$_2$ | H | H | H | H | 0 |
| CH | H | CF$_3$ | CH(CH$_3$)$_2$ | CH$_2$CH=CHCH$_3$ | H | H | H | H | 0 |
| CH | H | CF$_3$ | CH(CH$_3$)$_2$ | CH$_2$CH=CHCl | H | H | H | H | 0 |
| CH | H | CF$_3$ | CH(CH$_3$)$_2$ | CH$_2$CH=CCl$_2$ | H | H | H | H | 0 |
| CH | H | CF$_3$ | CH(CH$_3$)$_2$ | CH$_2$CH$_2$CH=CH$_2$ | H | H | H | H | 0 |
| CH | H | CF$_3$ | CH(CH$_3$)$_2$ | —CH$_2$C≡CH | H | H | H | H | 0 |
| CH | H | CF$_3$ | CH(CH$_3$)$_2$ | CH$_2$CN | H | H | H | H | 0 |
| CH | H | CF$_3$ | CH(CH$_3$)$_2$ | CH$_2$OCH$_3$ | H | H | H | H | 0 |
| CH | H | CF$_3$ | CH(CH$_3$)$_2$ | CH$_2$SCH$_3$ | H | H | H | H | 0 |
| CH | H | CF$_3$ | CH(CH$_3$)$_2$ | CH$_2$C$_6$H$_5$ | H | H | H | H | 0 |
| CH | H | CF$_3$ | CH$_2$CH(CH$_3$)$_2$ | CH$_3$ | H | H | H | H | 0 |
| CH | H | CF$_3$ | CH$_2$CH(CH$_3$)$_2$ | CH$_2$CH$_3$ | H | H | H | H | 0 |
| CH | H | CF$_3$ | CH$_2$CH(CH$_3$)$_2$ | CH$_2$CH$_2$CH$_3$ | H | H | H | H | 0 |
| CH | H | CF$_3$ | CH$_2$CH(CH$_3$)$_2$ | (CH$_2$)$_3$CH$_3$ | H | H | H | H | 0 |
| CH | H | CF$_3$ | CH$_2$CH(CH$_3$)$_2$ | (CH$_2$)$_4$CH$_3$ | H | H | H | H | 0 |
| CH | H | CF$_3$ | CH$_2$CH(CH$_3$)$_2$ | (CH$_2$)$_{11}$CH$_3$ | H | H | H | H | 0 |
| CH | H | CF$_3$ | CH$_2$CH(CH$_3$)$_2$ | CH(CH$_3$)$_2$ | H | H | H | H | 0 |
| CH | H | CF$_3$ | CH$_2$CH(CH$_3$)$_2$ | CH$_2$CH(CH$_3$)$_2$ | H | H | H | H | 0 |
| CH | H | CF$_3$ | CH$_2$CH(CH$_3$)$_2$ | CH$_2$CH(CH$_3$)C$_2$H$_5$ | H | H | H | H | 0 |
| CH | H | CF$_3$ | CH$_2$CH(CH$_3$)$_2$ | CH$_2$-cyclopropyl | H | H | H | H | 0 |
| CH | H | CF$_3$ | CH$_2$CH(CH$_3$)$_2$ | CH$_2$CH=CH$_2$ | H | H | H | H | 0 |
| CH | H | CF$_3$ | CH$_2$CH(CH$_3$)$_2$ | CH$_2$CH=CHCH$_3$ | H | H | H | H | 0 |
| CH | H | CF$_3$ | CH$_2$CH(CH$_3$)$_2$ | CH$_2$CH=CHCl | H | H | H | H | 0 |
| CH | H | CF$_3$ | CH$_2$CH(CH$_3$)$_2$ | CH$_2$CH=CCl$_2$ | H | H | H | H | 0 |
| CH | H | CF$_3$ | CH$_2$CH(CH$_3$)$_2$ | CH$_2$CH$_2$CH=CH$_2$ | H | H | H | H | 0 |
| CH | H | CF$_3$ | CH$_2$CH(CH$_3$)$_2$ | —CH$_2$C≡CH | H | H | H | H | 0 |
| CH | H | CF$_3$ | CH$_2$CH(CH$_3$)$_2$ | CH$_2$CN | H | H | H | H | 0 |
| CH | H | CF$_3$ | CH$_2$CH(CH$_3$)$_2$ | CH$_2$OCH$_3$ | H | H | H | H | 0 |
| CH | H | CF$_3$ | CH$_2$CH(CH$_3$)$_2$ | CH$_2$SCH$_3$ | H | H | H | H | 0 |
| CH | H | CF$_3$ | CH$_2$CH(CH$_3$)$_2$ | CH$_2$C$_6$H$_5$ | H | H | H | H | 0 |
| CH | H | CF$_3$ | H | CH$_3$ | H | H | H | H | 0 |
| CH | H | CF$_3$ | H | CH$_2$CH$_3$ | H | H | H | H | 0 |
| CH | H | CF$_3$ | H | CH$_2$CH$_2$CH$_3$ | H | H | H | H | 0 |
| CH | H | CF$_3$ | H | (CH$_2$)$_3$CH$_3$ | H | H | H | H | 0 |
| CH | H | CF$_3$ | H | (CH$_2$)$_4$CH$_3$ | H | H | H | H | 0 |
| CH | H | CF$_3$ | H | (CH$_2$)$_{11}$CH$_3$ | H | H | H | H | 0 |
| CH | H | CF$_3$ | H | CH(CH$_3$)$_2$ | H | H | H | H | 0 |
| CH | H | CF$_3$ | H | CH$_2$CH(CH$_3$)$_2$ | H | H | H | H | 0 |

TABLE 1-continued

| | | | | | | | | | |
|---|---|---|---|---|---|---|---|---|---|
| CH | H | CF₃ | H | CH₃\|CH₂CHC₂H₅ | H | H | H | H | O |
| CH | H | CF₃ | H | CH₂—▷ | H | H | H | H | O |
| CH | H | CF₃ | H | CH₂CH=CH₂ | H | H | H | H | O |
| CH | H | CF₃ | H | CH₂CH=CHCH₃ | H | H | H | H | O |
| CH | H | CF₃ | H | CH₂CH=CHCl | H | H | H | H | O |
| CH | H | CF₃ | H | CH₂CH=CCl₂ | H | H | H | H | O |
| CH | H | CF₃ | H | CH₂CH₂CH=CH₂ | H | H | H | H | O |
| CH | H | CF₃ | H | —CH₂C≡CH | H | H | H | H | O |
| CH | H | CF₃ | H | CH₂CN | H | H | H | H | O |
| CH | H | CF₃ | H | CH₂OCH₃ | H | H | H | H | O |
| CH | H | CF₃ | H | CH₂SCH₃ | H | H | H | H | O |
| CH | H | CF₃ | H | CH₂C₆H₅ | H | H | H | H | O |
| CH | H | CF₃ | CH₂OCH₃ | CH₃ | H | H | H | H | O |
| CH | H | CF₃ | CH₂OCH₃ | CH₂CH₃ | H | H | H | H | O |
| CH | H | CF₃ | CH₂OCH₃ | CH₂CH₂CH₃ | H | H | H | H | O |
| CH | H | CF₃ | CH₂OCH₃ | (CH₂)₃CH₃ | H | H | H | H | O |
| CH | H | CF₃ | CH₂OCH₃ | (CH₂)₄CH₃ | H | H | H | H | O |
| CH | H | CF₃ | CH₂OCH₃ | (CH₂)₁₁CH₃ | H | H | H | H | O |
| CH | H | CF₃ | CH₂OCH₃ | CH(CH₃)₂ | H | H | H | H | O |
| CH | H | CF₃ | CH₂OCH₃ | CH₂CH(CH₃)₂ | H | H | H | H | O |
| CH | H | CF₃ | CH₂OCH₃ | CH₃\|CH₂CHC₂H₅ | H | H | H | H | O |
| CH | H | CF₃ | CH₂OCH₃ | CH₂—▷ | H | H | H | H | O |
| CH | H | CF₃ | CH₂OCH₃ | CH₂CH=CH₂ | H | H | H | H | O |
| CH | H | CF₃ | CH₂OCH₃ | CH₂CH=CHCH₃ | H | H | H | H | O |
| CH | H | CF₃ | CH₂OCH₃ | CH₂CH=CHCl | H | H | H | H | O |
| CH | H | CF₃ | CH₂OCH₃ | CH₂CH=CCl₂ | H | H | H | H | O |
| CH | H | CF₃ | CH₂OCH₃ | CH₂CH₂CH=CH₂ | H | H | H | H | O |
| CH | H | CF₃ | CH₂OCH₃ | —CH₂C≡CH | H | H | H | H | O |
| CH | H | CF₃ | CH₂OCH₃ | CH₂CN | H | H | H | H | O |
| CH | H | CF₃ | CH₂OCH₃ | CH₂OCH₃ | H | H | H | H | O |
| CH | H | CF₃ | CH₂OCH₃ | CH₂SCH₃ | H | H | H | H | O |
| CH | H | CF₃ | CH₂OCH₃ | CH₂C₆H₅ | H | H | H | H | O |
| CH | H | OCF₃ | CH₃ | CH₃ | H | H | H | H | O |
| CH | H | OCF₃ | CH₃ | CH₂CH₃ | H | H | H | H | O |
| CH | H | OCF₃ | CH₃ | CH₂CH₂CH₃ | H | H | H | H | O |
| CH | H | OCF₃ | CH₃ | (CH₂)₃CH₃ | H | H | H | H | O |
| CH | H | OCF₃ | CH₃ | (CH₂)₄CH₃ | H | H | H | H | O |
| CH | H | OCF₃ | CH₃ | (CH₂)₁₁CH₃ | H | H | H | H | O |
| CH | H | OCF₃ | CH₃ | CH(CH₃)₂ | H | H | H | H | O |
| CH | H | OCF₃ | CH₃ | CH₂CH(CH₃)₂ | H | H | H | H | O |
| CH | H | OCF₃ | CH₃ | CH₃\|CH₂CHC₂H₅ | H | H | H | H | O |
| CH | H | OCF₃ | CH₃ | CH₂—▷ | H | H | H | H | O |
| CH | H | OCF₃ | CH₃ | CH₂CH=CH₂ | H | H | H | H | O |
| CH | H | OCF₃ | CH₃ | CH₂CH=CHCH₃ | H | H | H | H | O |
| CH | H | OCF₃ | CH₃ | CH₂CH=CHCl | H | H | H | H | O |
| CH | H | OCF₃ | CH₃ | CH₂CH=CCl₂ | H | H | H | H | O |
| CH | H | OCF₃ | CH₃ | CH₂CH₂CH=CH₂ | H | H | H | H | O |
| CH | H | OCF₃ | CH₃ | —CH₂C≡CH | H | H | H | H | O |
| CH | H | OCF₃ | CH₃ | CH₂CN | H | H | H | H | O |
| CH | H | OCF₃ | CH₃ | CH₂OCH₃ | H | H | H | H | O |
| CH | H | OCF₃ | CH₃ | CH₂SCH₃ | H | H | H | H | O |
| CH | H | OCF₃ | CH₃ | CH₂C₆H₅ | H | H | H | H | O |
| CH | H | OCF₃ | C₂H₅ | CH₃ | H | H | H | H | O |
| CH | H | OCF₃ | C₂H₅ | CH₂CH₃ | H | H | H | H | O |
| CH | H | OCF₃ | C₂H₅ | CH₂CH₂CH₃ | H | H | H | H | O |
| CH | H | OCF₃ | C₂H₅ | (CH₂)₃CH₃ | H | H | H | H | O |
| CH | H | OCF₃ | C₂H₅ | (CH₂)₄CH₃ | H | H | H | H | O |
| CH | H | OCF₃ | C₂H₅ | (CH₂)₁₁CH₃ | H | H | H | H | O |

-continued

| | | | | | | | | | |
|---|---|---|---|---|---|---|---|---|---|
| CH | H | OCF₃ | C₂H₅ | CH(CH₃)₂ | H | H | H | H | 0 |
| CH | H | OCF₃ | C₂H₅ | CH₂CH(CH₃)₂ | H | H | H | H | 0 |
| CH | H | OCF₃ | C₂H₅ | CH₂CH(CH₃)C₂H₅ | H | H | H | H | 0 |
| CH | H | OCF₃ | C₂H₅ | CH₂-cyclopropyl | H | H | H | H | 0 |
| CH | H | OCF₃ | C₂H₅ | CH₂CH=CH₂ | H | H | H | H | 0 |
| CH | H | OCF₃ | C₂H₅ | CH₂CH=CHCH₃ | H | H | H | H | 0 |
| CH | H | OCF₃ | C₂H₅ | CH₂CH=CHCl | H | H | H | H | 0 |
| CH | H | OCF₃ | C₂H₅ | CH₂CH=CCl₂ | H | H | H | H | 0 |
| CH | H | OCF₃ | C₂H₅ | CH₂CH₂CH=CH₂ | H | H | H | H | 0 |
| CH | H | OCF₃ | C₂H₅ | —CH₂C≡CH | H | H | H | H | 0 |
| CH | H | OCF₃ | C₂H₅ | CH₂CN | H | H | H | H | 0 |
| CH | H | OCF₃ | C₂H₅ | CH₂OCH₃ | H | H | H | H | 0 |
| CH | H | OCF₃ | C₂H₅ | CH₂SCH₃ | H | H | H | H | 0 |
| CH | H | OCF₃ | C₂H₅ | CH₂C₆H₅ | H | H | H | H | 0 |
| CH | H | OCF₃ | CH₂CH₂CH₃ | CH₃ | H | H | H | H | 0 |
| CH | H | OCF₃ | CH₂CH₂CH₃ | CH₂CH₃ | H | H | H | H | 0 |
| CH | H | OCF₃ | CH₂CH₂CH₃ | CH₂CH₂CH₃ | H | H | H | H | 0 |
| CH | H | OCF₃ | CH₂CH₂CH₃ | (CH₂)₃CH₃ | H | H | H | H | 0 |
| CH | H | OCF₃ | CH₂CH₂CH₃ | (CH₂)₄CH₃ | H | H | H | H | 0 |
| CH | H | OCF₃ | CH₂CH₂CH₃ | (CH₂)₁₁CH₃ | H | H | H | H | 0 |
| CH | H | OCF₃ | CH₂CH₂CH₃ | CH(CH₃)₂ | H | H | H | H | 0 |
| CH | H | OCF₃ | CH₂CH₂CH₃ | CH₂CH(CH₃)₂ | H | H | H | H | 0 |
| CH | H | OCF₃ | CH₂CH₂CH₃ | CH₂CH(CH₃)C₂H₅ | H | H | H | H | 0 |
| CH | H | OCF₃ | CH₂CH₂CH₃ | CH₂-cyclopropyl | H | H | H | H | 0 |
| CH | H | OCF₃ | CH₂CH₂CH₃ | CH₂CH=CH₂ | H | H | H | H | 0 |
| CH | H | OCF₃ | CH₂CH₂CH₃ | CH₂CH=CHCH₃ | H | H | H | H | 0 |
| CH | H | OCF₃ | CH₂CH₂CH₃ | CH₂CH=CHCl | H | H | H | H | 0 |
| CH | H | OCF₃ | CH₂CH₂CH₃ | CH₂CH=CCl₂ | H | H | H | H | 0 |
| CH | H | OCF₃ | CH₂CH₂CH₃ | CH₂CH₂CH=CH₂ | H | H | H | H | 0 |
| CH | H | OCF₃ | CH₂CH₂CH₃ | —CH₂C≡CH | H | H | H | H | 0 |
| CH | H | OCF₃ | CH₂CH₂CH₃ | CH₂CN | H | H | H | H | 0 |
| CH | H | OCF₃ | CH₂CH₂CH₃ | CH₂OCH₃ | H | H | H | H | 0 |
| CH | H | OCF₃ | CH₂CH₂CH₃ | CH₂SCH₃ | H | H | H | H | 0 |
| CH | H | OCF₃ | CH₂CH₂CH₃ | CH₂C₆H₅ | H | H | H | H | 0 |
| CH | H | OCF₂CF₂H | CH₃ | CH₃ | H | H | H | H | 0 |
| CH | H | OCF₂CF₂H | CH₃ | CH₂CH₃ | H | H | H | H | 0 |
| CH | H | OCF₂CF₂H | CH₃ | CH₂CH₂CH₃ | H | H | H | H | 0 |
| CH | H | OCF₂CF₂H | CH₃ | (CH₂)₃CH₃ | H | H | H | H | 0 |
| CH | H | OCF₂CF₂H | CH₃ | (CH₂)₄CH₃ | H | H | H | H | 0 |
| CH | H | OCF₂CF₂H | CH₃ | (CH₂)₁₁CH₃ | H | H | H | H | 0 |
| CH | H | OCF₂CF₂H | CH₃ | CH(CH₃)₂ | H | H | H | H | 0 |
| CH | H | OCF₂CF₂H | CH₃ | CH₂CH(CH₃)₂ | H | H | H | H | 0 |
| CH | H | OCF₂CF₂H | CH₃ | CH₂CH(CH₃)C₂H₅ | H | H | H | H | 0 |
| CH | H | OCF₂CF₂H | CH₃ | CH₂-cyclopropyl | H | H | H | H | 0 |
| CH | H | OCF₂CF₂H | CH₃ | CH₂CH=CH₂ | H | H | H | H | 0 |
| CH | H | OCF₂CF₂H | CH₃ | CH₂CH=CHCH₃ | H | H | H | H | 0 |
| CH | H | OCF₂CF₂H | CH₃ | CH₂CH=CHCl | H | H | H | H | 0 |
| CH | H | OCF₂CF₂H | CH₃ | CH₂CH=CCl₂ | H | H | H | H | 0 |
| CH | H | OCF₂CF₂H | CH₃ | CH₂CH₂CH=CH₂ | H | H | H | H | 0 |
| CH | H | OCF₂CF₂H | CH₃ | —CH₂C≡CH | H | H | H | H | 0 |
| CH | H | OCF₂CF₂H | CH₃ | CH₂CN | H | H | H | H | 0 |
| CH | H | OCF₂CF₂H | CH₃ | CH₂OCH₃ | H | H | H | H | 0 |
| CH | H | OCF₂CF₂H | CH₃ | CH₂SCH₃ | H | H | H | H | 0 |
| CH | H | OCF₂CF₂H | CH₃ | CH₂C₆H₅ | H | H | H | H | 0 |
| CH | H | OCF₂CF₂H | C₂H₅ | CH₃ | H | H | H | H | 0 |
| CH | H | OCF₂CF₂H | C₂H₅ | CH₂CH₃ | H | H | H | H | 0 |
| CH | H | OCF₂CF₂H | C₂H₅ | CH₂CH₂CH₃ | H | H | H | H | 0 |
| CH | H | OCF₂CF₂H | C₂H₅ | (CH₂)₃CH₃ | H | H | H | H | 0 |
| CH | H | OCF₂CF₂H | C₂H₅ | (CH₂)₄CH₃ | H | H | H | H | 0 |
| CH | H | OCF₂CF₂H | C₂H₅ | (CH₂)₁₁CH₃ | H | H | H | H | 0 |
| CH | H | OCF₂CF₂H | C₂H₅ | CH(CH₃)₂ | H | H | H | H | 0 |
| CH | H | OCF₂CF₂H | C₂H₅ | CH₂CH(CH₃)₂ | H | H | H | H | 0 |

-continued

| | | | | | | | | | |
|---|---|---|---|---|---|---|---|---|---|
| CH | H | OCF$_2$CF$_2$H | C$_2$H$_5$ | CH$_2$CH(CH$_3$)C$_2$H$_5$ | H | H | H | H | O |
| CH | H | OCF$_2$CF$_2$H | C$_2$H$_5$ | CH$_2$-cyclopropyl | H | H | H | H | O |
| CH | H | OCF$_2$CF$_2$H | C$_2$H$_5$ | CH$_2$CH=CH$_2$ | H | H | H | H | O |
| CH | H | OCF$_2$CF$_2$H | C$_2$H$_5$ | CH$_2$CH=CHCH$_3$ | H | H | H | H | O |
| CH | H | OCF$_2$CF$_2$H | C$_2$H$_5$ | CH$_2$CH=CHCl | H | H | H | H | O |
| CH | H | OCF$_2$CF$_2$H | C$_2$H$_5$ | CH$_2$CH=CCl$_2$ | H | H | H | H | O |
| CH | H | OCF$_2$CF$_2$H | C$_2$H$_5$ | CH$_2$CH$_2$CH=CH$_2$ | H | H | H | H | O |
| CH | H | OCF$_2$CF$_2$H | C$_2$H$_5$ | —CH$_2$C≡CH | H | H | H | H | O |
| CH | H | OCF$_2$CF$_2$H | C$_2$H$_5$ | CH$_2$CN | H | H | H | H | O |
| CH | H | OCF$_2$CF$_2$H | C$_2$H$_5$ | CH$_2$OCH$_3$ | H | H | H | H | O |
| CH | H | OCF$_2$CF$_2$H | C$_2$H$_5$ | CH$_2$SCH$_3$ | H | H | H | H | O |
| CH | H | OCF$_2$CF$_2$H | C$_2$H$_5$ | CH$_2$C$_6$H$_5$ | H | H | H | H | O |
| CH | H | OCF$_2$CF$_2$H | CH$_2$CH$_2$CH$_3$ | CH$_3$ | H | H | H | H | O |
| CH | H | OCF$_2$CF$_2$H | CH$_2$CH$_2$CH$_3$ | CH$_2$CH$_3$ | H | H | H | H | O |
| CH | H | OCF$_2$CF$_2$H | CH$_2$CH$_2$CH$_3$ | CH$_2$CH$_2$CH$_3$ | H | H | H | H | O |
| CH | H | OCF$_2$CF$_2$H | CH$_2$CH$_2$CH$_3$ | (CH$_2$)$_3$CH$_3$ | H | H | H | H | O |
| CH | H | OCF$_2$CF$_2$H | CH$_2$CH$_2$CH$_3$ | (CH$_2$)$_4$CH$_3$ | H | H | H | H | O |
| CH | H | OCF$_2$CF$_2$H | CH$_2$CH$_2$CH$_3$ | (CH$_2$)$_{11}$CH$_3$ | H | H | H | H | O |
| CH | H | OCF$_2$CF$_2$H | CH$_2$CH$_2$CH$_3$ | CH(CH$_3$)$_2$ | H | H | H | H | O |
| CH | H | OCF$_2$CF$_2$H | CH$_2$CH$_2$CH$_3$ | CH$_2$CH(CH$_3$)$_2$ | H | H | H | H | O |
| CH | H | OCF$_2$CF$_2$H | CH$_2$CH$_2$CH$_3$ | CH$_2$CH(CH$_3$)C$_2$H$_5$ | H | H | H | H | O |
| CH | H | OCF$_2$CF$_2$H | CH$_2$CH$_2$CH$_3$ | CH$_2$-cyclopropyl | H | H | H | H | O |
| CH | H | OCF$_2$CF$_2$H | CH$_2$CH$_2$CH$_3$ | CH$_2$CH=CH$_2$ | H | H | H | H | O |
| CH | H | OCF$_2$CF$_2$H | CH$_2$CH$_2$CH$_3$ | CH$_2$CH=CHCH$_3$ | H | H | H | H | O |
| CH | H | OCF$_2$CF$_2$H | CH$_2$CH$_2$CH$_3$ | CH$_2$CH=CHCl | H | H | H | H | O |
| CH | H | OCF$_2$CF$_2$H | CH$_2$CH$_2$CH$_3$ | CH$_2$CH=CCl$_2$ | H | H | H | H | O |
| CH | H | OCF$_2$CF$_2$H | CH$_2$CH$_2$CH$_3$ | CH$_2$CH$_2$CH=CH$_2$ | H | H | H | H | O |
| CH | H | OCF$_2$CF$_2$H | CH$_2$CH$_2$CH$_3$ | —CH$_2$C≡CH | H | H | H | H | O |
| CH | H | OCF$_2$CF$_2$H | CH$_2$CH$_2$CH$_3$ | CH$_2$CN | H | H | H | H | O |
| CH | H | OCF$_2$CF$_2$H | CH$_2$CH$_2$CH$_3$ | CH$_2$OCH$_3$ | H | H | H | H | O |
| CH | H | OCF$_2$CF$_2$H | CH$_2$CH$_2$CH$_3$ | CH$_2$SCH$_3$ | H | H | H | H | O |
| CH | H | OCF$_2$CF$_2$H | CH$_2$CH$_2$CH$_3$ | CH$_2$C$_6$H$_5$ | H | H | H | H | O |
| N | CH | CF$_3$ | CH$_3$ | CH$_3$ | H | H | H | H | O |
| N | CH | CF$_3$ | CH$_3$ | CH$_2$CH$_3$ | H | H | H | H | O |
| N | CH | CF$_3$ | CH$_3$ | CH$_2$CH$_2$CH$_3$ | H | H | H | H | O |
| N | CH | CF$_3$ | CH$_3$ | (CH$_2$)$_3$CH$_3$ | H | H | H | H | O |
| N | CH | CF$_3$ | CH$_3$ | (CH$_2$)$_4$CH$_3$ | H | H | H | H | O |
| N | CH | CF$_3$ | CH$_3$ | (CH$_2$)$_{11}$CH$_3$ | H | H | H | H | O |
| N | CH | CF$_3$ | CH$_3$ | CH(CH$_3$)$_2$ | H | H | H | H | O |
| N | CH | CF$_3$ | CH$_3$ | CH$_2$CH(CH$_3$)$_2$ | H | H | H | H | O |
| N | CH | CF$_3$ | CH$_3$ | CH$_2$CH(CH$_3$)C$_2$H$_5$ | H | H | H | H | O |
| N | CH | CF$_3$ | CH$_3$ | CH$_2$-cyclopropyl | H | H | H | H | O |
| N | CH | CF$_3$ | CH$_3$ | CH$_2$CH=CH$_2$ | H | H | H | H | O |
| N | CH | CF$_3$ | CH$_3$ | CH$_2$CH=CHCH$_3$ | H | H | H | H | O |
| N | CH | CF$_3$ | CH$_3$ | CH$_2$CH=CHCl | H | H | H | H | O |
| N | CH | CF$_3$ | CH$_3$ | CH$_2$CH=CCl$_2$ | H | H | H | H | O |
| N | CH | CF$_3$ | CH$_3$ | CH$_2$CH$_2$CH=CH$_2$ | H | H | H | H | O |
| N | CH | CF$_3$ | CH$_3$ | —CH$_2$C≡CH | H | H | H | H | O |
| N | CH | CF$_3$ | CH$_3$ | CH$_2$CN | H | H | H | H | O |
| N | CH | CF$_3$ | CH$_3$ | CH$_2$OCH$_3$ | H | H | H | H | O |
| N | CH | CF$_3$ | CH$_3$ | CH$_2$SCH$_3$ | H | H | H | H | O |
| N | CH | CF$_3$ | CH$_3$ | CH$_2$C$_6$H$_5$ | H | H | H | H | O |
| N | H | CF$_3$ | C$_2$H$_5$ | CH$_3$ | H | H | H | H | O |
| N | H | CF$_3$ | C$_2$H$_5$ | CH$_2$CH$_3$ | H | H | H | H | O |
| N | H | CF$_3$ | C$_2$H$_5$ | CH$_2$CH$_2$CH$_3$ | H | H | H | H | O |
| N | H | CF$_3$ | C$_2$H$_5$ | (CH$_2$)$_3$CH$_3$ | H | H | H | H | O |
| N | H | CF$_3$ | C$_2$H$_5$ | (CH$_2$)$_4$CH$_3$ | H | H | H | H | O |
| N | H | CF$_3$ | C$_2$H$_5$ | (CH$_2$)$_{11}$CH$_3$ | H | H | H | H | O |
| N | H | CF$_3$ | C$_2$H$_5$ | CH(CH$_3$)$_2$ | H | H | H | H | O |
| N | H | CF$_3$ | C$_2$H$_5$ | CH$_2$CH(CH$_3$)$_2$ | H | H | H | H | O |

-continued

| | | | | | | | | | |
|---|---|---|---|---|---|---|---|---|---|
| N | H | CF$_3$ | C$_2$H$_5$ | CH$_2$CH(CH$_3$)C$_2$H$_5$ | H | H | H | H | 0 |
| N | H | CF$_3$ | C$_2$H$_5$ | CH$_2$-cyclopropyl | H | H | H | H | 0 |
| N | H | CF$_3$ | C$_2$H$_5$ | CH$_2$CH=CH$_2$ | H | H | H | H | 0 |
| N | H | CF$_3$ | C$_2$H$_5$ | CH$_2$CH=CHCH$_3$ | H | H | H | H | 0 |
| N | H | CF$_3$ | C$_2$H$_5$ | CH$_2$CH=CHCl | H | H | H | H | 0 |
| N | H | CF$_3$ | C$_2$H$_5$ | CH$_2$CH=CCl$_2$ | H | H | H | H | 0 |
| N | H | CF$_3$ | C$_2$H$_5$ | CH$_2$CH$_2$CH=CH$_2$ | H | H | H | H | 0 |
| N | H | CF$_3$ | C$_2$H$_5$ | —CH$_2$C≡CH | H | H | H | H | 0 |
| N | H | CF$_3$ | C$_2$H$_5$ | CH$_2$CN | H | H | H | H | 0 |
| N | H | CF$_3$ | C$_2$H$_5$ | CH$_2$OCH$_3$ | H | H | H | H | 0 |
| N | H | CF$_3$ | C$_2$H$_5$ | CH$_2$SCH$_3$ | H | H | H | H | 0 |
| N | H | CF$_3$ | C$_2$H$_5$ | CH$_2$C$_6$H$_5$ | H | H | H | H | 0 |
| N | H | CF$_3$ | CH$_2$CH$_2$CH$_3$ | CH$_3$ | H | H | H | H | 0 |
| N | H | CF$_3$ | CH$_2$CH$_2$CH$_3$ | CH$_2$CH$_3$ | H | H | H | H | 0 |
| N | H | CF$_3$ | CH$_2$CH$_2$CH$_3$ | CH$_2$CH$_2$CH$_3$ | H | H | H | H | 0 |
| N | H | CF$_3$ | CH$_2$CH$_2$CH$_3$ | (CH$_2$)$_3$CH$_3$ | H | H | H | H | 0 |
| N | H | CF$_3$ | CH$_2$CH$_2$CH$_3$ | (CH$_2$)$_4$CH$_3$ | H | H | H | H | 0 |
| N | H | CF$_3$ | CH$_2$CH$_2$CH$_3$ | (CH$_2$)$_{11}$CH$_3$ | H | H | H | H | 0 |
| N | H | CF$_3$ | CH$_2$CH$_2$CH$_3$ | CH(CH$_3$)$_2$ | H | H | H | H | 0 |
| N | H | CF$_3$ | CH$_2$CH$_2$CH$_3$ | CH$_2$CH(CH$_3$)$_2$ | H | H | H | H | 0 |
| N | H | CF$_3$ | CH$_2$CH$_2$CH$_3$ | CH$_2$CH(CH$_3$)C$_2$H$_5$ | H | H | H | H | 0 |
| N | H | CF$_3$ | CH$_2$CH$_2$CH$_3$ | CH$_2$-cyclopropyl | H | H | H | H | 0 |
| N | H | CF$_3$ | CH$_2$CH$_2$CH$_3$ | CH$_2$CH=CH$_2$ | H | H | H | H | 0 |
| N | H | CF$_3$ | CH$_2$CH$_2$CH$_3$ | CH$_2$CH=CHCH$_3$ | H | H | H | H | 0 |
| N | H | CF$_3$ | CH$_2$CH$_2$CH$_3$ | CH$_2$CH=CHCl | H | H | H | H | 0 |
| N | H | CF$_3$ | CH$_2$CH$_2$CH$_3$ | CH$_2$CH=CCl$_2$ | H | H | H | H | 0 |
| N | H | CF$_3$ | CH$_2$CH$_2$CH$_3$ | CH$_2$CH$_2$CH=CH$_2$ | H | H | H | H | 0 |
| N | H | CF$_3$ | CH$_2$CH$_2$CH$_3$ | —CH$_2$C≡CH | H | H | H | H | 0 |
| N | H | CF$_3$ | CH$_2$CH$_2$CH$_3$ | CH$_2$CN | H | H | H | H | 0 |
| N | H | CF$_3$ | CH$_2$CH$_2$CH$_3$ | CH$_2$OCH$_3$ | H | H | H | H | 0 |
| N | H | CF$_3$ | CH$_2$CH$_2$CH$_3$ | CH$_2$SCH$_3$ | H | H | H | H | 0 |
| N | H | CF$_3$ | CH$_2$CH$_2$CH$_3$ | CH$_2$C$_6$H$_5$ | H | H | H | H | 0 |
| N | Cl | CF$_3$ | CH$_3$ | CH$_3$ | H | H | H | H | 0 |
| N | Cl | CF$_3$ | CH$_3$ | CH$_2$CH$_3$ | H | H | H | H | 0 |
| N | Cl | CF$_3$ | CH$_3$ | CH$_2$CH$_2$CH$_3$ | H | H | H | H | 0 |
| N | Cl | CF$_3$ | CH$_3$ | (CH$_2$)$_3$CH$_3$ | H | H | H | H | 0 |
| N | Cl | CF$_3$ | CH$_3$ | (CH$_2$)$_4$CH$_3$ | H | H | H | H | 0 |
| N | Cl | CF$_3$ | CH$_3$ | (CH$_2$)$_{11}$CH$_3$ | H | H | H | H | 0 |
| N | Cl | CF$_3$ | CH$_3$ | CH(CH$_3$)$_2$ | H | H | H | H | 0 |
| N | Cl | CF$_3$ | CH$_3$ | CH$_2$CH(CH$_3$)$_2$ | H | H | H | H | 0 |
| N | Cl | CF$_3$ | CH$_3$ | CH$_2$CH(CH$_3$)C$_2$H$_5$ | H | H | H | H | 0 |
| N | Cl | CF$_3$ | CH$_3$ | CH$_2$-cyclopropyl | H | H | H | H | 0 |
| N | Cl | CF$_3$ | CH$_3$ | CH$_2$CH=CH$_2$ | H | H | H | H | 0 |
| N | Cl | CF$_3$ | CH$_3$ | CH$_2$CH=CHCH$_3$ | H | H | H | H | 0 |
| N | Cl | CF$_3$ | CH$_3$ | CH$_2$CH=CHCl | H | H | H | H | 0 |
| N | Cl | CF$_3$ | CH$_3$ | CH$_2$CH=CCl$_2$ | H | H | H | H | 0 |
| N | Cl | CF$_3$ | CH$_3$ | CH$_2$CH$_2$CH=CH$_2$ | H | H | H | H | 0 |
| N | Cl | CF$_3$ | CH$_3$ | —CH$_2$C≡CH | H | H | H | H | 0 |
| N | Cl | CF$_3$ | CH$_3$ | CH$_2$CN | H | H | H | H | 0 |
| N | Cl | CF$_3$ | CH$_3$ | CH$_2$OCH$_3$ | H | H | H | H | 0 |
| N | Cl | CF$_3$ | CH$_3$ | CH$_2$SCH$_3$ | H | H | H | H | 0 |
| N | Cl | CF$_3$ | CH$_3$ | CH$_2$C$_6$H$_5$ | H | H | H | H | 0 |
| N | Cl | CF$_3$ | C$_2$H$_5$ | CH$_3$ | H | H | H | H | 0 |
| N | Cl | CF$_3$ | C$_2$H$_5$ | CH$_2$CH$_3$ | H | H | H | H | 0 |
| N | Cl | CF$_3$ | C$_2$H$_5$ | CH$_2$CH$_2$CH$_3$ | H | H | H | H | 0 |
| N | Cl | CF$_3$ | C$_2$H$_5$ | (CH$_2$)$_3$CH$_3$ | H | H | H | H | 0 |
| N | Cl | CF$_3$ | C$_2$H$_5$ | (CH$_2$)$_4$CH$_3$ | H | H | H | H | 0 |
| N | Cl | CF$_3$ | C$_2$H$_5$ | (CH$_2$)$_{11}$CH$_3$ | H | H | H | H | 0 |
| N | Cl | CF$_3$ | C$_2$H$_5$ | CH(CH$_3$)$_2$ | H | H | H | H | 0 |
| N | Cl | CF$_3$ | C$_2$H$_5$ | CH$_2$CH(CH$_3$)$_2$ | H | H | H | H | 0 |

| | | | | | | | | | |
|---|---|---|---|---|---|---|---|---|---|
| N | Cl | CF$_3$ | C$_2$H$_5$ | CH$_2$CH(CH$_3$)C$_2$H$_5$ | H | H | H | H | 0 |
| N | Cl | CF$_3$ | C$_2$H$_5$ | CH$_2$-cyclopropyl | H | H | H | H | 0 |
| N | Cl | CF$_3$ | C$_2$H$_5$ | CH$_2$CH=CH$_2$ | H | H | H | H | 0 |
| N | Cl | CF$_3$ | C$_2$H$_5$ | CH$_2$CH=CHCH$_3$ | H | H | H | H | 0 |
| N | Cl | CF$_3$ | C$_2$H$_5$ | CH$_2$CH=CHCl | H | H | H | H | 0 |
| N | Cl | CF$_3$ | C$_2$H$_5$ | CH$_2$CH=CCl$_2$ | H | H | H | H | 0 |
| N | Cl | CF$_3$ | C$_2$H$_5$ | CH$_2$CH$_2$CH=CH$_2$ | H | H | H | H | 0 |
| N | Cl | CF$_3$ | C$_2$H$_5$ | —CH$_2$C≡CH | H | H | H | H | 0 |
| N | Cl | CF$_3$ | C$_2$H$_5$ | CH$_2$CN | H | H | H | H | 0 |
| N | Cl | CF$_3$ | C$_2$H$_5$ | CH$_2$OCH$_3$ | H | H | H | H | 0 |
| N | Cl | CF$_3$ | C$_2$H$_5$ | CH$_2$SCH$_3$ | H | H | H | H | 0 |
| N | Cl | CF$_3$ | C$_2$H$_5$ | CH$_2$C$_6$H$_5$ | H | H | H | H | 0 |
| N | Cl | CF$_3$ | CH$_2$CH$_2$CH$_3$ | CH$_3$ | H | H | H | H | 0 |
| N | Cl | CF$_3$ | CH$_2$CH$_2$CH$_3$ | CH$_2$CH$_3$ | H | H | H | H | 0 |
| N | Cl | CF$_3$ | CH$_2$CH$_2$CH$_3$ | CH$_2$CH$_2$CH$_3$ | H | H | H | H | 0 |
| N | Cl | CF$_3$ | CH$_2$CH$_2$CH$_3$ | (CH$_2$)$_3$CH$_3$ | H | H | H | H | 0 |
| N | Cl | CF$_3$ | CH$_2$CH$_2$CH$_3$ | (CH$_2$)$_4$CH$_3$ | H | H | H | H | 0 |
| N | Cl | CF$_3$ | CH$_2$CH$_2$CH$_3$ | (CH$_2$)$_{11}$CH$_3$ | H | H | H | H | 0 |
| N | Cl | CF$_3$ | CH$_2$CH$_2$CH$_3$ | CH(CH$_3$)$_2$ | H | H | H | H | 0 |
| N | Cl | CF$_3$ | CH$_2$CH$_2$CH$_3$ | CH$_2$CH(CH$_3$)$_2$ | H | H | H | H | 0 |
| N | Cl | CF$_3$ | CH$_2$CH$_2$CH$_3$ | CH$_2$CH(CH$_3$)C$_2$H$_5$ | H | H | H | H | 0 |
| N | Cl | CF$_3$ | CH$_2$CH$_2$CH$_3$ | CH$_2$-cyclopropyl | H | H | H | H | 0 |
| N | Cl | CF$_3$ | CH$_2$CH$_2$CH$_3$ | CH$_2$CH=CH$_2$ | H | H | H | H | 0 |
| N | Cl | CF$_3$ | CH$_2$CH$_2$CH$_3$ | CH$_2$CH=CHCH$_3$ | H | H | H | H | 0 |
| N | Cl | CF$_3$ | CH$_2$CH$_2$CH$_3$ | CH$_2$CH=CHCl | H | H | H | H | 0 |
| N | Cl | CF$_3$ | CH$_2$CH$_2$CH$_3$ | CH$_2$CH=CCl$_2$ | H | H | H | H | 0 |
| N | Cl | CF$_3$ | CH$_2$CH$_2$CH$_3$ | CH$_2$CH$_2$CH=CH$_2$ | H | H | H | H | 0 |
| N | Cl | CF$_3$ | CH$_2$CH$_2$CH$_3$ | —CH$_2$C≡CH | H | H | H | H | 0 |
| N | Cl | CF$_3$ | CH$_2$CH$_2$CH$_3$ | CH$_2$CN | H | H | H | H | 0 |
| N | Cl | CF$_3$ | CH$_2$CH$_2$CH$_3$ | CH$_2$OCH$_3$ | H | H | H | H | 0 |
| N | Cl | CF$_3$ | CH$_2$CH$_2$CH$_3$ | CH$_2$SCH$_3$ | H | H | H | H | 0 |
| N | Cl | CF$_3$ | CH$_2$CH$_2$CH$_3$ | CH$_2$C$_6$H$_5$ | H | H | H | H | 0 |
| H | H | CF$_3$ | CH$_2$OCH$_3$ | CH$_3$ | H | H | H | H | 0 |
| H | H | CF$_3$ | CH$_2$OCH$_3$ | CH$_2$CH$_3$ | H | H | H | H | 0 |
| H | H | CF$_3$ | CH$_2$OCH$_3$ | CH$_2$CH$_2$CH$_3$ | H | H | H | H | 0 |
| H | H | CF$_3$ | CH$_2$OCH$_3$ | (CH$_2$)$_3$CH$_3$ | H | H | H | H | 0 |
| H | H | CF$_3$ | CH$_2$OCH$_3$ | (CH$_2$)$_4$CH$_3$ | H | H | H | H | 0 |
| H | H | CF$_3$ | CH$_2$OCH$_3$ | (CH$_2$)$_{11}$CH$_3$ | H | H | H | H | 0 |
| H | H | CF$_3$ | CH$_2$OCH$_3$ | CH(CH$_3$)$_2$ | H | H | H | H | 0 |
| H | H | CF$_3$ | CH$_2$OCH$_3$ | CH$_2$CH(CH$_3$)$_2$ | H | H | H | H | 0 |
| H | H | CF$_3$ | CH$_2$OCH$_3$ | CH$_2$CH(CH$_3$)C$_2$H$_5$ | H | H | H | H | 0 |
| H | H | CF$_3$ | CH$_2$OCH$_3$ | CH$_2$-cyclopropyl | H | H | H | H | 0 |
| H | H | CF$_3$ | CH$_2$OCH$_3$ | CH$_2$CH=CH$_2$ | H | H | H | H | 0 |
| H | H | CF$_3$ | CH$_2$OCH$_3$ | CH$_2$CH=CHCH$_3$ | H | H | H | H | 0 |
| H | H | CF$_3$ | CH$_2$OCH$_3$ | CH$_2$CH=CHCl | H | H | H | H | 0 |
| N | H | CF$_3$ | CH$_2$OCH$_3$ | CH$_2$CH=CCl$_2$ | H | H | H | H | 0 |
| N | H | CF$_3$ | CH$_2$OCH$_3$ | CH$_2$CH$_2$CH=CH$_2$ | H | H | H | H | 0 |
| N | H | CF$_3$ | CH$_2$OCH$_3$ | —CH$_2$C≡CH | H | H | H | H | 0 |
| N | H | CF$_3$ | CH$_2$OCH$_3$ | CH$_2$CN | H | H | H | H | 0 |
| N | H | CF$_3$ | CH$_2$OCH$_3$ | CH$_2$OCH$_3$ | H | H | H | H | 0 |
| N | H | CF$_3$ | CH$_2$OCH$_3$ | CH$_2$SCH$_3$ | H | H | H | H | 0 |
| N | H | CF$_3$ | CH$_2$OCH$_3$ | CH$_2$C$_6$H$_5$ | H | H | H | H | 0 |
| N | H | CF$_3$ | H | CH$_3$ | H | H | H | H | 0 |
| N | H | CF$_3$ | H | CH$_2$CH$_3$ | H | H | H | H | 0 |
| N | H | CF$_3$ | H | CH$_2$CH$_2$CH$_3$ | H | H | H | H | 0 |
| N | H | CF$_3$ | H | (CH$_2$)$_3$CH$_3$ | H | H | H | H | 0 |
| N | H | CF$_3$ | H | (CH$_2$)$_4$CH$_3$ | H | H | H | H | 0 |
| N | H | CF$_3$ | H | (CH$_2$)$_{11}$CH$_3$ | H | H | H | H | 0 |
| N | H | CF$_3$ | H | CH(CH$_3$)$_2$ | H | H | H | H | 0 |
| N | H | CF$_3$ | H | CH$_2$CH(CH$_3$)$_2$ | H | H | H | H | 0 |

-continued

| | | | | | | | | | |
|---|---|---|---|---|---|---|---|---|---|
| N | H | CF₃ | H | CH₂CH(CH₃)C₂H₅ | H | H | H | H | 0 |
| N | H | CF₃ | H | CH₂-cyclopropyl | H | H | H | H | 0 |
| N | H | CF₃ | H | CH₂CH=CH₂ | H | H | H | H | 0 |
| N | H | CF₃ | H | CH₂CH=CHCH₃ | H | H | H | H | 0 |
| N | H | CF₃ | H | CH₂CH=CHCl | H | H | H | H | 0 |
| N | H | CF₃ | H | CH₂CH=CCl₂ | H | H | H | H | 0 |
| N | H | CF₃ | H | CH₂CH₂CH=CH₂ | H | H | H | H | 0 |
| N | H | CF₃ | H | —CH₂C≡CH | H | H | H | H | 0 |
| N | H | CF₃ | H | CH₂CN | H | H | H | H | 0 |
| N | H | CF₃ | H | CH₂OCH₃ | H | H | H | H | 0 |
| N | H | CF₃ | H | CH₂SCH₃ | H | H | H | H | 0 |
| N | H | CF₃ | H | CH₂C₆H₅ | H | H | H | H | 0 |
| CH | H | CF₃ | CH₃ | CH₃ | H | H | H | COOCH₃ | 0 |
| CH | H | CF₃ | CH₃ | CH₂CH₃ | H | H | H | COOCH₃ | 0 |
| CH | H | CF₃ | CH₃ | CH₂CH₂CH₃ | H | H | H | COOCH₃ | 0 |
| CH | H | CF₃ | CH₃ | (CH₂)₃CH₃ | H | H | H | COOCH₃ | 0 |
| CH | H | CF₃ | CH₃ | (CH₂)₄CH₃ | H | H | H | COOCH₃ | 0 |
| CH | H | CF₃ | CH₃ | (CH₂)₁₁CH₃ | H | H | H | COOCH₃ | 0 |
| CH | H | CF₃ | CH₃ | CH(CH₃)₂ | H | H | H | COOCH₃ | 0 |
| CH | H | CF₃ | CH₃ | CH₂CH(CH₃)₂ | H | H | H | COOCH₃ | 0 |
| CH | H | CF₃ | CH₃ | CH₂CH(CH₃)C₂H₅ | H | H | H | COOCH₃ | 0 |
| CH | H | CF₃ | CH₃ | CH₂-cyclopropyl | H | H | H | COOCH₃ | 0 |
| CH | H | CF₃ | CH₃ | CH₂CH=CH₂ | H | H | H | COOCH₃ | 0 |
| CH | H | CF₃ | CH₃ | CH₂CH=CHCH₃ | H | H | H | COOCH₃ | 0 |
| CH | H | CF₃ | CH₃ | CH₂CH=CHCl | H | H | H | COOCH₃ | 0 |
| CH | H | CF₃ | CH₃ | CH₂CH=CCl₂ | H | H | H | COOCH₃ | 0 |
| CH | H | CF₃ | CH₃ | CH₂CH₂CH=CH₂ | H | H | H | COOCH₃ | 0 |
| CH | H | CF₃ | CH₃ | —CH₂C≡CH | H | H | H | COOCH₃ | 0 |
| CH | H | CF₃ | CH₃ | CH₂CN | H | H | H | COOCH₃ | 0 |
| CH | H | CF₃ | CH₃ | CH₂OCH₃ | H | H | H | COOCH₃ | 0 |
| CH | H | CF₃ | CH₃ | CH₂SCH₃ | H | H | H | COOCH₃ | 0 |
| CH | H | CF₃ | CH₃ | CH₂C₆H₅ | H | H | H | COOCH₃ | 0 |
| CH | H | CF₃ | CH₃ | CH₃ | H | H | H | COOCH₃ | 1 |
| CH | H | CF₃ | CH₃ | CH₂CH₃ | H | H | H | COOCH₃ | 1 |
| CH | H | CF₃ | CH₃ | CH₂CH₂CH₃ | H | H | H | COOCH₃ | 1 |
| CH | H | CF₃ | CH₃ | (CH₂)₃CH₃ | H | H | H | COOCH₃ | 1 |
| CH | H | CF₃ | CH₃ | (CH₂)₄CH₃ | H | H | H | COOCH₃ | 1 |
| CH | H | CF₃ | CH₃ | (CH₂)₁₁CH₃ | H | H | H | COOCH₃ | 1 |
| CH | H | CF₃ | CH₃ | CH(CH₃)₂ | H | H | H | COOCH₃ | 1 |
| CH | H | CF₃ | CH₃ | CH₂CH(CH₃)₂ | H | H | H | COOCH₃ | 1 |
| CH | H | CF₃ | CH₃ | CH₂CH(CH₃)C₂H₅ | H | H | H | COOCH₃ | 1 |
| CH | H | CF₃ | CH₃ | CH₂-cyclopropyl | H | H | H | COOCH₃ | 1 |
| CH | H | CF₃ | CH₃ | CH₂CH=CH₂ | H | H | H | COOCH₃ | 1 |
| CH | H | CF₃ | CH₃ | CH₂CH=CHCH₃ | H | H | H | COOCH₃ | 1 |
| CH | H | CF₃ | CH₃ | CH₂CH=CHCl | H | H | H | COOCH₃ | 1 |
| CH | H | CF₃ | CH₃ | CH₂CH=CCl₂ | H | H | H | COOCH₃ | 1 |
| CH | H | CF₃ | CH₃ | CH₂CH₂CH=CH₂ | H | H | H | COOCH₃ | 1 |
| CH | H | CF₃ | CH₃ | —CH₂C≡CH | H | H | H | COOCH₃ | 1 |
| CH | H | CF₃ | CH₃ | CH₂CN | H | H | H | COOCH₃ | 1 |
| CH | H | CF₃ | CH₃ | CH₂OCH₃ | H | H | H | COOCH₃ | 1 |
| CH | H | CF₃ | CH₃ | CH₂SCH₃ | H | H | H | COOCH₃ | 1 |
| CH | H | CF₃ | CH₃ | CH₂C₆H₅ | H | H | H | COOCH₃ | 1 |
| CH | H | CF₃ | CH₃ | CH₃ | H | H | H | COOCH₃ | 2 |
| CH | H | CF₃ | CH₃ | CH₂CH₃ | H | H | H | COOCH₃ | 2 |
| CH | H | CF₃ | CH₃ | CH₂CH₂CH₃ | H | H | H | COOCH₃ | 2 |
| CH | H | CF₃ | CH₃ | (CH₂)₃CH₃ | H | H | H | COOCH₃ | 2 |
| CH | H | CF₃ | CH₃ | (CH₂)₄CH₃ | H | H | H | COOCH₃ | 2 |
| CH | H | CF₃ | CH₃ | (CH₂)₁₁CH₃ | H | H | H | COOCH₃ | 2 |
| CH | H | CF₃ | CH₃ | CH(CH₃)₂ | H | H | H | COOCH₃ | 2 |
| CH | H | CF₃ | CH₃ | CH₂CH(CH₃)₂ | H | H | H | COOCH₃ | 2 |

-continued

| | | | | | | | | | |
|---|---|---|---|---|---|---|---|---|---|
| CH | H | CF$_3$ | CH$_3$ | CH$_3$<br>\|<br>CH$_2$CHC$_2$H$_5$ | H | H | H | COOCH$_3$ | 2 |
| CH | H | CF$_3$ | CH$_3$ | CH$_2$—△ | H | H | H | COOCH$_3$ | 2 |
| CH | H | CF$_3$ | CH$_3$ | CH$_2$CH=CH$_2$ | H | H | H | COOCH$_3$ | 2 |
| CH | H | CF$_3$ | CH$_3$ | CH$_2$CH=CHCH$_3$ | H | H | H | COOCH$_3$ | 2 |
| CH | H | CF$_3$ | CH$_3$ | CH$_2$CH=CHCl | H | H | H | COOCH$_3$ | 2 |
| CH | H | CF$_3$ | CH$_3$ | CH$_2$CH=CCl$_2$ | H | H | H | COOCH$_3$ | 2 |
| CH | H | CF$_3$ | CH$_3$ | CH$_2$CH$_2$CH=CH$_2$ | H | H | H | COOCH$_3$ | 2 |
| CH | H | CF$_3$ | CH$_3$ | —CH$_2$C≡CH | H | H | H | COOCH$_3$ | 2 |
| CH | H | CF$_3$ | CH$_3$ | CH$_2$CN | H | H | H | COOCH$_3$ | 2 |
| CH | H | CF$_3$ | CH$_3$ | CH$_2$OCH$_3$ | H | H | H | COOCH$_3$ | 2 |
| CH | H | CF$_3$ | CH$_3$ | CH$_2$SCH$_3$ | H | H | H | COOCH$_3$ | 2 |
| CH | H | CF$_3$ | CH$_3$ | CH$_2$C$_6$H$_5$ | H | H | H | COOCH$_3$ | 2 |
| CH | H | CF$_3$ | CH$_3$ | CH$_3$ | CH$_3$ | H | H | COOCH$_3$ | 0 |
| CH | H | CF$_3$ | CH$_3$ | CH$_2$CH$_3$ | CH$_3$ | H | H | COOCH$_3$ | 0 |
| CH | H | CF$_3$ | CH$_3$ | CH$_2$CH$_2$CH$_3$ | CH$_3$ | H | H | COOCH$_3$ | 0 |
| CH | H | CF$_3$ | CH$_3$ | (CH$_2$)$_3$CH$_3$ | CH$_3$ | H | H | COOCH$_3$ | 0 |
| CH | H | CF$_3$ | CH$_3$ | (CH$_2$)$_4$CH$_3$ | CH$_3$ | H | H | COOCH$_3$ | 0 |
| CH | H | CF$_3$ | CH$_3$ | (CH$_2$)$_{11}$CH$_3$ | CH$_3$ | H | H | COOCH$_3$ | 0 |
| CH | H | CF$_3$ | CH$_3$ | CH(CH$_3$)$_2$ | CH$_3$ | H | H | COOCH$_3$ | 0 |
| CH | H | CF$_3$ | CH$_3$ | CH$_2$CH(CH$_3$)$_2$ | CH$_3$ | H | H | COOCH$_3$ | 0 |
| CH | H | CF$_3$ | CH$_3$ | CH$_3$<br>\|<br>CH$_2$CHC$_2$H$_5$ | CH$_3$ | H | H | COOCH$_3$ | 0 |
| CH | H | CF$_3$ | CH$_3$ | CH$_2$—△ | CH$_3$ | H | H | COOCH$_3$ | 0 |
| CH | H | CF$_3$ | CH$_3$ | CH$_2$CH=CH$_2$ | CH$_3$ | H | H | COOCH$_3$ | 0 |
| CH | H | CF$_3$ | CH$_3$ | CH$_2$CH=CHCH$_3$ | CH$_3$ | H | H | COOCH$_3$ | 0 |
| CH | H | CF$_3$ | CH$_3$ | CH$_2$CH=CHCl | CH$_3$ | H | H | COOCH$_3$ | 0 |
| CH | H | CF$_3$ | CH$_3$ | CH$_2$CH=CCl$_2$ | CH$_3$ | H | H | COOCH$_3$ | 0 |
| CH | H | CF$_3$ | CH$_3$ | CH$_2$CH$_2$CH=CH$_2$ | CH$_3$ | H | H | COOCH$_3$ | 0 |
| CH | H | CF$_3$ | CH$_3$ | —CH$_2$C≡CH | CH$_3$ | H | H | COOCH$_3$ | 0 |
| CH | H | CF$_3$ | CH$_3$ | CH$_2$CN | CH$_3$ | H | H | COOCH$_3$ | 0 |
| CH | H | CF$_3$ | CH$_3$ | CH$_2$OCH$_3$ | CH$_3$ | H | H | COOCH$_3$ | 0 |
| CH | H | CF$_3$ | CH$_3$ | CH$_2$SCH$_3$ | CH$_3$ | H | H | COOCH$_3$ | 0 |
| CH | H | CF$_3$ | CH$_3$ | CH$_2$C$_6$H$_5$ | CH$_3$ | H | H | COOCH$_3$ | 0 |
| CH | H | CF$_3$ | CH$_3$ | CH$_3$ | H | CH$_3$ | H | COOCH$_3$ | 0 |
| CH | H | CF$_3$ | CH$_3$ | CH$_2$CH$_3$ | H | CH$_3$ | H | COOCH$_3$ | 0 |
| CH | H | CF$_3$ | CH$_3$ | CH$_2$CH$_2$CH$_3$ | H | CH$_3$ | H | COOCH$_3$ | 0 |
| CH | H | CF$_3$ | CH$_3$ | (CH$_2$)$_3$CH$_3$ | H | CH$_3$ | H | COOCH$_3$ | 0 |
| CH | H | CF$_3$ | CH$_3$ | (CH$_2$)$_4$CH$_3$ | H | CH$_3$ | H | COOCH$_3$ | 0 |
| CH | H | CF$_3$ | CH$_3$ | (CH$_2$)$_{11}$CH$_3$ | H | CH$_3$ | H | COOCH$_3$ | 0 |
| CH | H | CF$_3$ | CH$_3$ | CH(CH$_3$)$_2$ | H | CH$_3$ | H | COOCH$_3$ | 0 |
| CH | H | CF$_3$ | CH$_3$ | CH$_2$CH(CH$_3$)$_2$ | H | CH$_3$ | H | COOCH$_3$ | 0 |
| CH | H | CF$_3$ | CH$_3$ | CH$_3$<br>\|<br>CH$_2$CHC$_2$H$_5$ | H | CH$_3$ | H | COOCH$_3$ | 0 |
| CH | H | CF$_3$ | CH$_3$ | CH$_2$—△ | H | CH$_3$ | H | COOCH$_3$ | 0 |
| CH | H | CF$_3$ | CH$_3$ | CH$_2$CH=CH$_2$ | H | CH$_3$ | H | COOCH$_3$ | 0 |
| CH | H | CF$_3$ | CH$_3$ | CH$_2$CH=CHCH$_3$ | H | CH$_3$ | H | COOCH$_3$ | 0 |
| CH | H | CF$_3$ | CH$_3$ | CH$_2$CH=CHCl | H | CH$_3$ | H | COOCH$_3$ | 0 |
| CH | H | CF$_3$ | CH$_3$ | CH$_2$CH=CCl$_2$ | H | CH$_3$ | H | COOCH$_3$ | 0 |
| CH | H | CF$_3$ | CH$_3$ | CH$_2$CH$_2$CH=CH$_2$ | H | CH$_3$ | H | COOCH$_3$ | 0 |
| CH | H | CF$_3$ | CH$_3$ | —CH$_2$C≡CH | H | CH$_3$ | H | COOCH$_3$ | 0 |
| CH | H | CF$_3$ | CH$_3$ | CH$_2$CN | H | CH$_3$ | H | COOCH$_3$ | 0 |
| CH | H | CF$_3$ | CH$_3$ | CH$_2$OCH$_3$ | H | CH$_3$ | H | COOCH$_3$ | 0 |
| CH | H | CF$_3$ | CH$_3$ | CH$_2$SCH$_3$ | H | CH$_3$ | H | COOCH$_3$ | 0 |
| CH | H | CF$_3$ | CH$_3$ | CH$_2$C$_6$H$_5$ | H | CH$_3$ | H | COOCH$_3$ | 0 |
| CH | H | CF$_3$ | C$_2$H$_5$ | CH$_3$ | H | H | H | COOCH$_3$ | 0 |
| CH | H | CF$_3$ | C$_2$H$_5$ | CH$_2$CH$_3$ | H | H | H | COOCH$_3$ | 0 |
| CH | H | CF$_3$ | C$_2$H$_5$ | CH$_2$CH$_2$CH$_3$ | H | H | H | COOCH$_3$ | 0 |
| CH | H | CF$_3$ | C$_2$H$_5$ | (CH$_2$)$_3$CH$_3$ | H | H | H | COOCH$_3$ | 0 |
| CH | H | CF$_3$ | C$_2$H$_5$ | (CH$_2$)$_4$CH$_3$ | H | H | H | COOCH$_3$ | 0 |
| CH | H | CF$_3$ | C$_2$H$_5$ | (CH$_2$)$_{11}$CH$_3$ | H | H | H | COOCH$_3$ | 0 |
| CH | H | CF$_3$ | C$_2$H$_5$ | CH(CH$_3$)$_2$ | H | H | H | COOCH$_3$ | 0 |
| CH | H | CF$_3$ | C$_2$H$_5$ | CH$_2$CH(CH$_3$)$_2$ | H | H | H | COOCH$_3$ | 0 |

-continued

| | | | | | | | | | |
|---|---|---|---|---|---|---|---|---|---|
| CH | H | CF₃ | C₂H₅ | CH₂CHC₂H₅ (with CH₃ branch) | H | H | H | COOCH₃ | 0 |
| CH | H | CF₃ | C₂H₅ | CH₂-cyclopropyl | H | H | H | COOCH₃ | 0 |
| CH | H | CF₃ | C₂H₅ | CH₂CH=CH₂ | H | H | H | COOCH₃ | 0 |
| CH | H | CF₃ | C₂H₅ | CH₂CH=CHCH₃ | H | H | H | COOCH₃ | 0 |
| CH | H | CF₃ | C₂H₅ | CH₂CH=CHCl | H | H | H | COOCH₃ | 0 |
| CH | H | CF₃ | C₂H₅ | CH₂CH=CCl₂ | H | H | H | COOCH₃ | 0 |
| CH | H | CF₃ | C₂H₅ | CH₂CH₂CH=CH₂ | H | H | H | COOCH₃ | 0 |
| CH | H | CF₃ | C₂H₅ | —CH₂C≡CH | H | H | H | COOCH₃ | 0 |
| CH | H | CF₃ | C₂H₅ | CH₂CN | H | H | H | COOCH₃ | 0 |
| CH | H | CF₃ | C₂H₅ | CH₂OCH₃ | H | H | H | COOCH₃ | 0 |
| CH | H | CF₃ | C₂H₅ | CH₂SCH₃ | H | H | H | COOCH₃ | 0 |
| CH | H | CF₃ | C₂H₅ | CH₂C₆H₅ | H | H | H | COOCH₃ | 0 |
| CH | H | CF₃ | C₂H₅ | CH₃ | H | CH₃ | H | COOCH₃ | 0 |
| CH | H | CF₃ | C₂H₅ | CH₂CH₃ | H | CH₃ | H | COOCH₃ | 0 |
| CH | H | CF₃ | C₂H₅ | CH₂CH₂CH₃ | H | CH₃ | H | COOCH₃ | 0 |
| CH | H | CF₃ | C₂H₅ | (CH₂)₃CH₃ | H | CH₃ | H | COOCH₃ | 0 |
| CH | H | CF₃ | C₂H₅ | (CH₂)₄CH₃ | H | CH₃ | H | COOCH₃ | 0 |
| CH | H | CF₃ | C₂H₅ | (CH₂)₁₁CH₃ | H | CH₃ | H | COOCH₃ | 0 |
| CH | H | CF₃ | C₂H₅ | CH(CH₃)₂ | H | CH₃ | H | COOCH₃ | 0 |
| CH | H | CF₃ | C₂H₅ | CH₂CH(CH₃)₂ | H | CH₃ | H | COOCH₃ | 0 |
| CH | H | CF₃ | C₂H₅ | CH₂CHC₂H₅ (with CH₃ branch) | H | CH₃ | H | COOCH₃ | 0 |
| CH | H | CF₃ | C₂H₅ | CH₂-cyclopropyl | H | CH₃ | H | COOCH₃ | 0 |
| CH | H | CF₃ | C₂H₅ | CH₂CH=CH₂ | H | CH₃ | H | COOCH₃ | 0 |
| CH | H | CF₃ | C₂H₅ | CH₂CH=CHCH₃ | H | CH₃ | H | COOCH₃ | 0 |
| CH | H | CF₃ | C₂H₅ | CH₂CH=CHCl | H | CH₃ | H | COOCH₃ | 0 |
| CH | H | CF₃ | C₂H₅ | CH₂CH=CCl₂ | H | CH₃ | H | COOCH₃ | 0 |
| CH | H | CF₃ | C₂H₅ | CH₂CH₂CH=CH₂ | H | CH₃ | H | COOCH₃ | 0 |
| CH | H | CF₃ | C₂H₅ | —CH₂C≡CH | H | CH₃ | H | COOCH₃ | 0 |
| CH | H | CF₃ | C₂H₅ | CH₂CN | H | CH₃ | H | COOCH₃ | 0 |
| CH | H | CF₃ | C₂H₅ | CH₂OCH₃ | H | CH₃ | H | COOCH₃ | 0 |
| CH | H | CF₃ | C₂H₅ | CH₂SCH₃ | H | CH₃ | H | COOCH₃ | 0 |
| CH | H | CF₃ | C₂H₅ | CH₂C₆H₅ | H | CH₃ | H | COOCH₃ | 0 |
| CH | H | CF₃ | C₂H₅ | CH₃ | CH₃ | CH₃ | H | COOCH₃ | 0 |
| CH | H | CF₃ | C₂H₅ | CH₂CH₃ | CH₃ | CH₃ | H | COOCH₃ | 0 |
| CH | H | CF₃ | C₂H₅ | CH₂CH₂CH₃ | CH₃ | CH₃ | H | COOCH₃ | 0 |
| CH | H | CF₃ | C₂H₅ | (CH₂)₃CH₃ | CH₃ | CH₃ | H | COOCH₃ | 0 |
| CH | H | CF₃ | C₂H₅ | (CH₂)₄CH₃ | CH₃ | CH₃ | H | COOCH₃ | 0 |
| CH | H | CF₃ | C₂H₅ | (CH₂)₁₁CH₃ | CH₃ | CH₃ | H | COOCH₃ | 0 |
| CH | H | CF₃ | C₂H₅ | CH(CH₃)₂ | CH₃ | CH₃ | H | COOCH₃ | 0 |
| CH | H | CF₃ | C₂H₅ | CH₂CH(CH₃)₂ | CH₃ | CH₃ | H | COOCH₃ | 0 |
| CH | H | CF₃ | C₂H₅ | CH₂CHC₂H₅ (with CH₃ branch) | CH₃ | H | H | COOCH₃ | 0 |
| CH | H | CF₃ | C₂H₅ | CH₂-cyclopropyl | CH₃ | H | H | COOCH₃ | 0 |
| CH | H | CF₃ | C₂H₅ | CH₂CH=CH₂ | CH₃ | H | H | COOCH₃ | 0 |
| CH | H | CF₃ | C₂H₅ | CH₂CH=CHCH₃ | CH₃ | H | H | COOCH₃ | 0 |
| CH | H | CF₃ | C₂H₅ | CH₂CH=CHCl | CH₃ | H | H | COOCH₃ | 0 |
| CH | H | CF₃ | C₂H₅ | CH₂CH=CCl₂ | CH₃ | H | H | COOCH₃ | 0 |
| CH | H | CF₃ | C₂H₅ | CH₂CH₂CH=CH₂ | CH₃ | H | H | COOCH₃ | 0 |
| CH | H | CF₃ | C₂H₅ | —CH₂C≡CH | CH₃ | H | H | COOCH₃ | 0 |
| CH | H | CF₃ | C₂H₅ | CH₂CN | CH₃ | H | H | COOCH₃ | 0 |
| CH | H | CF₃ | C₂H₅ | CH₂OCH₃ | CH₃ | H | H | COOCH₃ | 0 |
| CH | H | CF₃ | C₂H₅ | CH₂SCH₃ | CH₃ | H | H | COOCH₃ | 0 |
| CH | H | CF₃ | C₂H₅ | CH₂C₆H₅ | CH₃ | H | H | COOCH₃ | 0 |
| CH | H | CF₃ | CH₂CH₂CH₃ | CH₃ | H | H | H | COOCH₃ | 0 |
| CH | H | CF₃ | CH₂CH₂CH₃ | CH₂CH₃ | H | H | H | COOCH₃ | 0 |
| CH | H | CF₃ | CH₂CH₂CH₃ | CH₂CH₂CH₃ | H | H | H | COOCH₃ | 0 |
| CH | H | CF₃ | CH₂CH₂CH₃ | (CH₂)₃CH₃ | H | H | H | COOCH₃ | 0 |
| CH | H | CF₃ | CH₂CH₂CH₃ | (CH₂)₄CH₃ | H | H | H | COOCH₃ | 0 |
| CH | H | CF₃ | CH₂CH₂CH₃ | (CH₂)₁₁CH₃ | H | H | H | COOCH₃ | 0 |
| CH | H | CF₃ | CH₂CH₂CH₃ | CH(CH₃)₂ | H | H | H | COOCH₃ | 0 |
| CH | H | CF₃ | CH₂CH₂CH₃ | CH₂CH(CH₃)₂ | H | H | H | COOCH₃ | 0 |

-continued

| | | | | | | | | | |
|---|---|---|---|---|---|---|---|---|---|
| CH | H | CF$_3$ | CH$_2$CH$_2$CH$_3$ | CH$_2$CH(CH$_3$)C$_2$H$_5$ | H | H | H | COOCH$_3$ | 0 |
| CH | H | CF$_3$ | CH$_2$CH$_2$CH$_3$ | CH$_2$-cyclopropyl | H | H | H | COOCH$_3$ | 0 |
| CH | H | CF$_3$ | CH$_2$CH$_2$CH$_3$ | CH$_2$CH=CH$_2$ | H | H | H | COOCH$_3$ | 0 |
| CH | H | CF$_3$ | CH$_2$CH$_2$CH$_3$ | CH$_2$CH=CHCH$_3$ | H | H | H | COOCH$_3$ | 0 |
| CH | H | CF$_3$ | CH$_2$CH$_2$CH$_3$ | CH$_2$CH=CHCl | H | H | H | COOCH$_3$ | 0 |
| CH | H | CF$_3$ | CH$_2$CH$_2$CH$_3$ | CH$_2$CH=CCl$_2$ | H | H | H | COOCH$_3$ | 0 |
| CH | H | CF$_3$ | CH$_2$CH$_2$CH$_3$ | CH$_2$CH$_2$CH=CH$_2$ | H | H | H | COOCH$_3$ | 0 |
| CH | H | CF$_3$ | CH$_2$CH$_2$CH$_3$ | —CH$_2$C≡CH | H | H | H | COOCH$_3$ | 0 |
| CH | H | CF$_3$ | CH$_2$CH$_2$CH$_3$ | CH$_2$CN | H | H | H | COOCH$_3$ | 0 |
| CH | H | CF$_3$ | CH$_2$CH$_2$CH$_3$ | CH$_2$OCH$_3$ | H | H | H | COOCH$_3$ | 0 |
| CH | H | CF$_3$ | CH$_2$CH$_2$CH$_3$ | CH$_2$SCH$_3$ | H | H | H | COOCH$_3$ | 0 |
| CH | H | CF$_3$ | CH$_2$CH$_2$CH$_3$ | CH$_2$C$_6$H$_5$ | H | H | H | COOCH$_3$ | 0 |
| CH | H | CF$_3$ | CH$_2$CH$_2$CH$_3$ | CH$_3$ | CH$_3$ | H | H | COOCH$_3$ | 0 |
| CH | H | CF$_3$ | CH$_2$CH$_2$CH$_3$ | CH$_2$CH$_3$ | CH$_3$ | H | H | COOCH$_3$ | 0 |
| CH | H | CF$_3$ | CH$_2$CH$_2$CH$_3$ | CH$_2$CH$_2$CH$_3$ | CH$_3$ | H | H | COOCH$_3$ | 0 |
| CH | H | CF$_3$ | CH$_2$CH$_2$CH$_3$ | (CH$_2$)$_3$CH$_3$ | CH$_3$ | H | H | COOCH$_3$ | 0 |
| CH | H | CF$_3$ | CH$_2$CH$_2$CH$_3$ | (CH$_2$)$_4$CH$_3$ | CH$_3$ | H | H | COOCH$_3$ | 0 |
| CH | H | CF$_3$ | CH$_2$CH$_2$CH$_3$ | (CH$_2$)$_{11}$CH$_3$ | CH$_3$ | H | H | COOCH$_3$ | 0 |
| CH | H | CF$_3$ | CH$_2$CH$_2$CH$_3$ | CH(CH$_3$)$_2$ | CH$_3$ | H | H | COOCH$_3$ | 0 |
| CH | H | CF$_3$ | CH$_2$CH$_2$CH$_3$ | CH$_2$CH(CH$_3$)$_2$ | CH$_3$ | H | H | COOCH$_3$ | 0 |
| CH | H | CF$_3$ | CH$_2$CH$_2$CH$_3$ | CH$_2$CH(CH$_3$)C$_2$H$_5$ | CH$_3$ | H | H | COOCH$_3$ | 0 |
| CH | H | CF$_3$ | CH$_2$CH$_2$CH$_3$ | CH$_2$-cyclopropyl | CH$_3$ | H | H | COOCH$_3$ | 0 |
| CH | H | CF$_3$ | CH$_2$CH$_2$CH$_3$ | CH$_2$CH=CH$_2$ | CH$_3$ | H | H | COOCH$_3$ | 0 |
| CH | H | CF$_3$ | CH$_2$CH$_2$CH$_3$ | CH$_2$CH=CHCH$_3$ | CH$_3$ | H | H | COOCH$_3$ | 0 |
| CH | H | CF$_3$ | CH$_2$CH$_2$CH$_3$ | CH$_2$CH=CHCl | CH$_3$ | H | H | COOCH$_3$ | 0 |
| CH | H | CF$_3$ | CH$_2$CH$_2$CH$_3$ | CH$_2$CH=CCl$_2$ | CH$_3$ | H | H | COOCH$_3$ | 0 |
| CH | H | CF$_3$ | CH$_2$CH$_2$CH$_3$ | CH$_2$CH$_2$CH=CH$_2$ | CH$_3$ | H | H | COOCH$_3$ | 0 |
| CH | H | CF$_3$ | CH$_2$CH$_2$CH$_3$ | —CH$_2$C≡CH | CH$_3$ | H | H | COOCH$_3$ | 0 |
| CH | H | CF$_3$ | CH$_2$CH$_2$CH$_3$ | CH$_2$CN | CH$_3$ | H | H | COOCH$_3$ | 0 |
| CH | H | CF$_3$ | CH$_2$CH$_2$CH$_3$ | CH$_2$OCH$_3$ | CH$_3$ | H | H | COOCH$_3$ | 0 |
| CH | H | CF$_3$ | CH$_2$CH$_2$CH$_3$ | CH$_2$SCH$_3$ | CH$_3$ | H | H | COOCH$_3$ | 0 |
| CH | H | CF$_3$ | CH$_2$CH$_2$CH$_3$ | CH$_2$C$_6$H$_5$ | CH$_3$ | H | H | COOCH$_3$ | 0 |
| CH | H | CF$_3$ | CH$_2$CH$_2$CH$_3$ | CH$_3$ | H | CH$_3$ | H | COOCH$_3$ | 0 |
| CH | H | CF$_3$ | CH$_2$CH$_2$CH$_3$ | CH$_2$CH$_3$ | H | CH$_3$ | H | COOCH$_3$ | 0 |
| CH | H | CF$_3$ | CH$_2$CH$_2$CH$_3$ | CH$_2$CH$_2$CH$_3$ | H | CH$_3$ | H | COOCH$_3$ | 0 |
| CH | H | CF$_3$ | CH$_2$CH$_2$CH$_3$ | (CH$_2$)$_3$CH$_3$ | H | CH$_3$ | H | COOCH$_3$ | 0 |
| CH | H | CF$_3$ | CH$_2$CH$_2$CH$_3$ | (CH$_2$)$_4$CH$_3$ | H | CH$_3$ | H | COOCH$_3$ | 0 |
| CH | H | CF$_3$ | CH$_2$CH$_2$CH$_3$ | (CH$_2$)$_{11}$CH$_3$ | H | CH$_3$ | H | COOCH$_3$ | 0 |
| CH | H | CF$_3$ | CH$_2$CH$_2$CH$_3$ | CH(CH$_3$)$_2$ | H | CH$_3$ | H | COOCH$_3$ | 0 |
| CH | H | CF$_3$ | CH$_2$CH$_2$CH$_3$ | CH$_2$CH(CH$_3$)$_2$ | H | CH$_3$ | H | COOCH$_3$ | 0 |
| CH | H | CF$_3$ | CH$_2$CH$_2$CH$_3$ | CH$_2$CH(CH$_3$)C$_2$H$_5$ | H | CH$_3$ | H | COOCH$_3$ | 0 |
| CH | H | CF$_3$ | CH$_2$CH$_2$CH$_3$ | CH$_2$-cyclopropyl | H | CH$_3$ | H | COOCH$_3$ | 0 |
| CH | H | CF$_3$ | CH$_2$CH$_2$CH$_3$ | CH$_2$CH=CH$_2$ | H | CH$_3$ | H | COOCH$_3$ | 0 |
| CH | H | CF$_3$ | CH$_2$CH$_2$CH$_3$ | CH$_2$CH=CHCH$_3$ | H | CH$_3$ | H | COOCH$_3$ | 0 |
| CH | H | CF$_3$ | CH$_2$CH$_2$CH$_3$ | CH$_2$CH=CHCl | H | CH$_3$ | H | COOCH$_3$ | 0 |
| CH | H | CF$_3$ | CH$_2$CH$_2$CH$_3$ | CH$_2$CH=CCl$_2$ | H | CH$_3$ | H | COOCH$_3$ | 0 |
| CH | H | CF$_3$ | CH$_2$CH$_2$CH$_3$ | CH$_2$CH$_2$CH=CH$_2$ | H | CH$_3$ | H | COOCH$_3$ | 0 |
| CH | H | CF$_3$ | CH$_2$CH$_2$CH$_3$ | —CH$_2$C≡CH | H | CH$_3$ | H | COOCH$_3$ | 0 |
| CH | H | CF$_3$ | CH$_2$CH$_2$CH$_3$ | CH$_2$CN | H | CH$_3$ | H | COOCH$_3$ | 0 |
| CH | H | CF$_3$ | CH$_2$CH$_2$CH$_3$ | CH$_2$OCH$_3$ | H | CH$_3$ | H | COOCH$_3$ | 0 |
| CH | H | CF$_3$ | CH$_2$CH$_2$CH$_3$ | CH$_2$SCH$_3$ | H | CH$_3$ | H | COOCH$_3$ | 0 |
| CH | H | CF$_3$ | CH$_2$CH$_2$CH$_3$ | CH$_2$C$_6$H$_5$ | H | CH$_3$ | H | COOCH$_3$ | 0 |
| CH | H | CF$_3$ | CH(CH$_3$)$_2$ | CH$_3$ | H | H | H | COOCH$_3$ | 0 |
| CH | H | CF$_3$ | CH(CH$_3$)$_2$ | CH$_2$CH$_3$ | H | H | H | COOCH$_3$ | 0 |
| CH | H | CF$_3$ | CH(CH$_3$)$_2$ | CH$_2$CH$_2$CH$_3$ | H | H | H | COOCH$_3$ | 0 |
| CH | H | CF$_3$ | CH(CH$_3$)$_2$ | (CH$_2$)$_3$CH$_3$ | H | H | H | COOCH$_3$ | 0 |
| CH | H | CF$_3$ | CH(CH$_3$)$_2$ | (CH$_2$)$_4$CH$_3$ | H | H | H | COOCH$_3$ | 0 |
| CH | H | CF$_3$ | CH(CH$_3$)$_2$ | (CH$_2$)$_{11}$CH$_3$ | H | H | H | COOCH$_3$ | 0 |
| CH | H | CF$_3$ | CH(CH$_3$)$_2$ | CH(CH$_3$)$_2$ | H | H | H | COOCH$_3$ | 0 |
| CH | H | CF$_3$ | CH(CH$_3$)$_2$ | CH$_2$CH(CH$_3$)$_2$ | H | H | H | COOCH$_3$ | 0 |

-continued

| | | | | | | | | | |
|---|---|---|---|---|---|---|---|---|---|
| CH | H | CF₃ | CH(CH₃)₂ | CH₃<br>│<br>CH₂CHC₂H₅ | H | H | H | COOCH₃ | 0 |
| CH | H | CF₃ | CH(CH₃)₂ | CH₂— | H | H | H | COOCH₃ | 0 |
| CH | H | CF₃ | CH(CH₃)₂ | CH₂CH=CH₂ | H | H | H | COOCH₃ | 0 |
| CH | H | CF₃ | CH(CH₃)₂ | CH₂CH=CHCH₃ | H | H | H | COOCH₃ | 0 |
| CH | H | CF₃ | CH(CH₃)₂ | CH₂CH=CHCl | H | H | H | COOCH₃ | 0 |
| CH | H | CF₃ | CH(CH₃)₂ | CH₂CH=CCl₂ | H | H | H | COOCH₃ | 0 |
| CH | H | CF₃ | CH(CH₃)₂ | CH₂CH₂CH=CH₂ | H | H | H | COOCH₃ | 0 |
| CH | H | CF₃ | CH(CH₃)₂ | —CH₂C≡CH | H | H | H | COOCH₃ | 0 |
| CH | H | CF₃ | CH(CH₃)₂ | CH₂CN | H | H | H | COOCH₃ | 0 |
| CH | H | CF₃ | CH(CH₃)₂ | CH₂OCH₃ | H | H | H | COOCH₃ | 0 |
| CH | H | CF₃ | CH(CH₃)₂ | CH₂SCH₃ | H | H | H | COOCH₃ | 0 |
| CH | H | CF₃ | CH(CH₃)₂ | CH₂C₆H₅ | H | H | H | COOCH₃ | 0 |
| CH | H | CF₃ | H | CH₃ | H | H | H | COOCH₃ | 0 |
| CH | H | CF₃ | H | CH₂CH₃ | H | H | H | COOCH₃ | 0 |
| CH | H | CF₃ | H | CH₂CH₂CH₃ | H | H | H | COOCH₃ | 0 |
| CH | H | CF₃ | H | (CH₂)₃CH₃ | H | H | H | COOCH₃ | 0 |
| CH | H | CF₃ | H | (CH₂)₄CH₃ | H | H | H | COOCH₃ | 0 |
| CH | H | CF₃ | H | (CH₂)₁₁CH₃ | H | H | H | COOCH₃ | 0 |
| CH | H | CF₃ | H | CH(CH₃)₂ | H | H | H | COOCH₃ | 0 |
| CH | H | CF₃ | H | CH₂CH(CH₃)₂ | H | H | H | COOCH₃ | 0 |
| CH | H | CF₃ | H | CH₃<br>│<br>CH₂CHC₂H₅ | H | H | H | COOCH₃ | 0 |
| CH | H | CF₃ | H | CH₂— | H | H | H | COOCH₃ | 0 |
| CH | H | CF₃ | H | CH₂CH=CH₂ | H | H | H | COOCH₃ | 0 |
| CH | H | CF₃ | H | CH₂CH=CHCH₃ | H | H | H | COOCH₃ | 0 |
| CH | H | CF₃ | H | CH₂CH=CHCl | H | H | H | COOCH₃ | 0 |
| CH | H | CF₃ | H | CH₂CH=CCl₂ | H | H | H | COOCH₃ | 0 |
| CH | H | CF₃ | H | CH₂CH₂CH=CH₂ | H | H | H | COOCH₃ | 0 |
| CH | H | CF₃ | H | —CH₂C≡CH | H | H | H | COOCH₃ | 0 |
| CH | H | CF₃ | H | CH₂CN | H | H | H | COOCH₃ | 0 |
| CH | H | CF₃ | H | CH₂OCH₃ | H | H | H | COOCH₃ | 0 |
| CH | H | CF₃ | H | CH₂SCH₃ | H | H | H | COOCH₃ | 0 |
| CH | H | CF₃ | H | CH₂C₆H₅ | H | H | H | COOCH₃ | 0 |
| CH | H | OCF₃ | CH₃ | CH₃ | H | H | H | COOCH₃ | 0 |
| CH | H | OCF₃ | CH₃ | CH₂CH₃ | H | H | H | COOCH₃ | 0 |
| CH | H | OCF₃ | CH₃ | CH₂CH₂CH₃ | H | H | H | COOCH₃ | 0 |
| CH | H | OCF₃ | CH₃ | (CH₂)₃CH₃ | H | H | H | COOCH₃ | 0 |
| CH | H | OCF₃ | CH₃ | (CH₂)₄CH₃ | H | H | H | COOCH₃ | 0 |
| CH | H | OCF₃ | CH₃ | (CH₂)₁₁CH₃ | H | H | H | COOCH₃ | 0 |
| CH | H | OCF₃ | CH₃ | CH(CH₃)₂ | H | H | H | COOCH₃ | 0 |
| CH | H | OCF₃ | CH₀ | CH₂CH(CH₃)₂ | H | H | H | COOCH₃ | 0 |
| CH | H | OCF₃ | CH₃ | CH₃<br>│<br>CH₂lCHC₂H₅ | H | H | H | COOCH₃ | 0 |
| CH | H | OCF₃ | CH₃ | CH₂— | H | H | H | COOCH₃ | 0 |
| CH | H | OCF₃ | CH₃ | CH₂CH=CH₂ | H | H | H | COOCH₃ | 0 |
| CH | H | OCF₃ | CH₃ | CH₂CH=CHCH₃ | H | H | H | COOCH₃ | 0 |
| CH | H | OCF₃ | CH₃ | CH₂CH=CHCl | H | H | H | COOCH₃ | 0 |
| CH | H | OCF₃ | CH₃ | CH₂CH=CCl₂ | H | H | H | COOCH₃ | 0 |
| CH | H | OCF₃ | CH₃ | CH₂CH₂CH=CH₂ | H | H | H | COOCH₃ | 0 |
| CH | H | OCF₃ | CH₃ | —CH₂C≡CH | H | H | H | COOCH₃ | 0 |
| CH | H | OCF₃ | CH₃ | CH₂CN | H | H | H | COOCH₃ | 0 |
| CH | H | OCF₃ | CH₃ | CH₂OCH₃ | H | H | H | COOCH₃ | 0 |
| CH | H | OCF₃ | CH₃ | CH₂SCH₃ | H | H | H | COOCH₃ | 0 |
| CH | H | OCF₃ | CH₃ | CH₂C₆H₅ | H | H | H | COOCH₃ | 0 |
| CH | H | OCF₃ | C₂H₅ | CH₃ | H | H | H | COOCH₃ | 0 |
| CH | H | OCF₃ | C₂H₅ | CH₂CH₃ | H | H | H | COOCH₃ | 0 |
| CH | H | OCF₃ | C₂H₅ | CH₂CH₂CH₃ | H | H | H | COOCH₃ | 0 |
| CH | H | OCF₃ | C₂H₅ | (CH₂)₃CH₃ | H | H | H | COOCH₃ | 0 |
| CH | H | OCF₃ | C₂H₅ | (CH₂)₄CH₃ | H | H | H | COOCH₃ | 0 |
| CH | H | OCF₃ | C₂H₅ | (CH₂)₁₁CH₃ | H | H | H | COOCH₃ | 0 |
| CH | H | OCF₃ | C₂H₅ | CH(CH₃)₂ | H | H | H | COOCH₃ | 0 |
| CH | H | OCF₃ | C₂H₅ | CH₂CH(CH₃)₂ | H | H | H | COOCH₃ | 0 |
| CH | H | OCF₃ | C₂H₅ | CH₃<br>│<br>CH₂CHC₂H₅ | H | H | H | COOCH₃ | 0 |

-continued

| | | | | | | | | | |
|---|---|---|---|---|---|---|---|---|---|
| CH | H | OCF₃ | C₂H₅ | CH₂-△ | H | H | H | COOCH₃ | 0 |
| CH | H | OCF₃ | C₂H₅ | CH₂CH=CH₂ | H | H | H | COOCH₃ | 0 |
| CH | H | OCF₃ | C₂H₅ | CH₂CH=CHCH₃ | H | H | H | COOCH₃ | 0 |
| CH | H | OCF₃ | C₂H₅ | CH₂CH=CHCl | H | H | H | COOCH₃ | 0 |
| CH | H | OCF₃ | C₂H₅ | CH₂CH=CCl₂ | H | H | H | COOCH₃ | 0 |
| CH | H | OCF₃ | C₂H₅ | CH₂CH₂CH=CH₂ | H | H | H | COOCH₃ | 0 |
| CH | H | OCF₃ | C₂H₅ | —CH₂C≡CH | H | H | H | COOCH₃ | 0 |
| CH | H | OCF₃ | C₂H₅ | CH₂CN | H | H | H | COOCH₃ | 0 |
| CH | H | OCF₃ | C₂H₅ | CH₂OCH₃ | H | H | H | COOCH₃ | 0 |
| CH | H | OCF₃ | C₂H₅ | CH₂SCH₃ | H | H | H | COOCH₃ | 0 |
| CH | H | OCF₃ | C₂H₅ | CH₂C₆H₅ | H | H | H | COOCH₃ | 0 |
| CH | H | OCF₃ | CH₂CH₂CH₃ | CH₃ | H | H | H | COOCH₃ | 0 |
| CH | H | OCF₃ | CH₂CH₂CH₃ | CH₂CH₃ | H | H | H | COOCH₃ | 0 |
| CH | H | OCF₃ | CH₂CH₂CH₃ | CH₂CH₂CH₃ | H | H | H | COOCH₃ | 0 |
| CH | H | OCF₃ | CH₂CH₂CH₃ | (CH₂)₃CH₃ | H | H | H | COOCH₃ | 0 |
| CH | H | OCF₃ | CH₂CH₂CH₃ | (CH₂)₄CH₃ | H | H | H | COOCH₃ | 0 |
| CH | H | OCF₃ | CH₂CH₂CH₃ | (CH₂)₁₁CH₃ | H | H | H | COOCH₃ | 0 |
| CH | H | OCF₃ | CH₂CH₂CH₃ | CH(CH₃)₂ | H | H | H | COOCH₃ | 0 |
| CH | H | OCF₃ | CH₂CH₂CH₃ | CH₂CH(CH₃)₂ | H | H | H | COOCH₃ | 0 |
| CH | H | OCF₃ | CH₂CH₂CH₃ | CH₂CH(CH₃)C₂H₅ | H | H | H | COOCH₃ | 0 |
| CH | H | OCF₃ | CH₂CH₂CH₃ | CH₂-△ | H | H | H | COOCH₃ | 0 |
| CH | H | OCF₃ | CH₂CH₂CH₃ | CH₂CH=CH₂ | H | H | H | COOCH₃ | 0 |
| CH | H | OCF₃ | CH₂CH₂CH₃ | CH₂CH=CHCH₃ | H | H | H | COOCH₃ | 0 |
| CH | H | OCF₃ | CH₂CH₂CH₃ | CH₂CH=CHCl | H | H | H | COOCH₃ | 0 |
| CH | H | OCF₃ | CH₂CH₂CH₃ | CH₂CH=CCl₂ | H | H | H | COOCH₃ | 0 |
| CH | H | OCF₃ | CH₂CH₂CH₃ | CH₂CH₂CH=CH₂ | H | H | H | COOCH₃ | 0 |
| CH | H | OCF₃ | CH₂CH₂CH₃ | —CH₂C≡CH | H | H | H | COOCH₃ | 0 |
| CH | H | OCF₃ | CH₂CH₂CH₃ | CH₂CN | H | H | H | COOCH₃ | 0 |
| CH | H | OCF₃ | CH₂CH₂CH₃ | CH₂OCH₃ | H | H | H | COOCH₃ | 0 |
| CH | H | OCF₃ | CH₂CH₂CH₃ | CH₂SCH₃ | H | H | H | COOCH₃ | 0 |
| CH | H | OCF₃ | CH₂CH₂CH₃ | CH₂C₆H₅ | H | H | H | COOCH₃ | 0 |
| CH | H | OCF₂CF₂H | CH₃ | CH₃ | H | H | H | COOCH₃ | 0 |
| CH | H | OCF₂CF₂H | CH₃ | CH₂CH₃ | H | H | H | COOCH₃ | 0 |
| CH | H | OCF₂CF₂H | CH₃ | CH₂CH₂CH₃ | H | H | H | COOCH₃ | 0 |
| CH | H | OCF₂CF₂H | CH₃ | (CH₂)₃CH₃ | H | H | H | COOCH₃ | 0 |
| CH | H | OCF₂CF₂H | CH₃ | (CH₂)₄CH₃ | H | H | H | COOCH₃ | 0 |
| CH | H | OCF₂CF₂H | CH₃ | (CH₂)₁₁CH₃ | H | H | H | COOCH₃ | 0 |
| CH | H | OCF₂CF₂H | CH₃ | CH(CH₃)₂ | H | H | H | COOCH₃ | 0 |
| CH | H | OCF₂CF₂H | CH₃ | CH₂CH(CH₃)₂ | H | H | H | COOCH₃ | 0 |
| CH | H | OCF₂CF₂H | CH₃ | CH₂CH(CH₃)C₂H₅ | H | H | H | COOCH₃ | 0 |
| CH | H | OCF₂CF₂H | CH₃ | CH₂-△ | H | H | H | COOCH₃ | 0 |
| CH | H | OCF₂CF₂H | CH₃ | CH₂CH=CH₂ | H | H | H | COOCH₃ | 0 |
| CH | H | OCF₂CF₂H | CH₃ | CH₂CH=CHCH₃ | H | H | H | COOCH₃ | 0 |
| CH | H | OCF₂CF₂H | CH₃ | CH₂CH=CHCl | H | H | H | COOCH₃ | 0 |
| CH | H | OCF₂CF₂H | CH₃ | CH₂CH=CCl₂ | H | H | H | COOCH₃ | 0 |
| CH | H | OCF₂CF₂H | CH₃ | CH₂CH₂CH=CH₂ | H | H | H | COOCH₃ | 0 |
| CH | H | OCF₂CF₂H | CH₃ | —CH₂C≡CH | H | H | H | COOCH₃ | 0 |
| CH | H | OCF₂CF₂H | CH₃ | CH₂CN | H | H | H | COOCH₃ | 0 |
| CH | H | OCF₂CF₂H | CH₃ | CH₂OCH₃ | H | H | H | COOCH₃ | 0 |
| CH | H | OCF₂CF₂H | CH₃ | CH₂SCH₃ | H | H | H | COOCH₃ | 0 |
| CH | H | OCF₂CF₂H | CH₃ | CH₂C₆H₅ | H | H | H | COOCH₃ | 0 |
| CH | H | OCF₂CF₂H | C₂H₅ | CH₃ | H | H | H | COOCH₃ | 0 |
| CH | H | OCF₂CF₂H | C₂H₅ | CH₂CH₃ | H | H | H | COOCH₃ | 0 |
| CH | H | OCF₂CF₂H | C₂H₅ | CH₂CH₂CH₃ | H | H | H | COOCH₃ | 0 |
| CH | H | OCF₂CF₂H | C₂H₅ | (CH₂)₃CH₃ | H | H | H | COOCH₃ | 0 |
| CH | H | OCF₂CF₂H | C₂H₅ | (CH₂)₄CH₃ | H | H | H | COOCH₃ | 0 |
| CH | H | OCF₂CF₂H | C₂H₅ | (CH₂)₁₁CH₃ | H | H | H | COOCH₃ | 0 |
| CH | H | OCF₂CF₂H | C₂H₅ | CH(CH₃)₂ | H | H | H | COOCH₃ | 0 |
| CH | H | OCF₂CF₂H | C₂H₅ | CH₂CH(CH₃)₂ | H | H | H | COOCH₃ | 0 |
| CH | H | OCF₂CF₂H | C₂H₅ | CH₂CH(CH₃)C₂H₅ | H | H | H | COOCH₃ | 0 |

-continued

| | | | | | | | | | |
|---|---|---|---|---|---|---|---|---|---|
| CH | H | OCF$_2$CF$_2$H | C$_2$H$_5$ | CH$_2$-△ | H | H | H | COOCH$_3$ | 0 |
| CH | H | OCF$_2$CF$_2$H | C$_2$H$_5$ | CH$_2$CH=CH$_2$ | H | H | H | COOCH$_3$ | 0 |
| CH | H | OCF$_2$CF$_2$H | C$_2$H$_5$ | CH$_2$CH=CHCH$_3$ | H | H | H | COOCH$_3$ | 0 |
| CH | H | OCF$_2$CF$_2$H | C$_2$H$_5$ | CH$_2$CH=CHCl | H | H | H | COOCH$_3$ | 0 |
| CH | H | OCF$_2$CF$_2$H | C$_2$H$_5$ | CH$_2$CH=CCl$_2$ | H | H | H | COOCH$_3$ | 0 |
| CH | H | OCF$_2$CF$_2$H | C$_2$H$_5$ | CH$_2$CH$_2$CH=CH$_2$ | H | H | H | COOCH$_3$ | 0 |
| CH | H | OCF$_2$CF$_2$H | C$_2$H$_5$ | —CH$_2$C≡CH | H | H | H | COOCH$_3$ | 0 |
| CH | H | OCF$_2$CF$_2$H | C$_2$H$_5$ | CH$_2$CN | H | H | H | COOCH$_3$ | 0 |
| CH | H | OCF$_2$CF$_2$H | C$_2$H$_5$ | CH$_2$OCH$_3$ | H | H | H | COOCH$_3$ | 0 |
| CH | H | OCF$_2$CF$_2$H | C$_2$H$_5$ | CH$_2$SCH$_3$ | H | H | H | COOCH$_3$ | 0 |
| CH | H | OCF$_2$CF$_2$H | C$_2$H$_5$ | CH$_2$C$_6$H$_5$ | H | H | H | COOCH$_3$ | 0 |
| CH | H | OCF$_2$CF$_2$H | CH$_2$CH$_2$CH$_3$ | CH$_3$ | H | H | H | COOCH$_3$ | 0 |
| CH | H | OCF$_2$CF$_2$H | CH$_2$CH$_2$CH$_3$ | CH$_2$CH$_3$ | H | H | H | COOCH$_3$ | 0 |
| CH | H | OCF$_2$CF$_2$H | CH$_2$CH$_2$CH$_3$ | CH$_2$CH$_2$CH$_3$ | H | H | H | COOCH$_3$ | 0 |
| CH | H | OCF$_2$CF$_2$H | CH$_2$CH$_2$CH$_3$ | (CH$_2$)$_3$CH$_3$ | H | H | H | COOCH$_3$ | 0 |
| CH | H | OCF$_2$CF$_2$H | CH$_2$CH$_2$CH$_3$ | (CH$_2$)$_4$CH$_3$ | H | H | H | COOCH$_3$ | 0 |
| CH | H | OCF$_2$CF$_2$H | CH$_2$CH$_2$CH$_3$ | (CH$_2$)$_{11}$CH$_3$ | H | H | H | COOCH$_3$ | 0 |
| CH | H | OCF$_2$CF$_2$H | CH$_2$CH$_2$CH$_3$ | CH(CH$_3$)$_2$ | H | H | H | COOCH$_3$ | 0 |
| CH | H | OCF$_2$CF$_2$H | CH$_2$CH$_2$CH$_3$ | CH$_2$CH(CH$_3$)$_2$ | H | H | H | COOCH$_3$ | 0 |
| CH | H | OCF$_2$CF$_2$H | CH$_2$CH$_2$CH$_3$ | CH$_2$CHC$_2$H$_5$ with CH$_3$ branch | H | H | H | COOCH$_3$ | 0 |
| CH | H | OCF$_2$CF$_2$H | CH$_2$CH$_2$CH$_3$ | CH$_2$-△ | H | H | H | COOCH$_3$ | 0 |
| CH | H | OCF$_2$CF$_2$H | CH$_2$CH$_2$CH$_3$ | CH$_2$CH=CH$_2$ | H | H | H | COOCH$_3$ | 0 |
| CH | H | OCF$_2$CF$_2$H | CH$_2$CH$_2$CH$_3$ | CH$_2$CH=CHCH$_3$ | H | H | H | COOCH$_3$ | 0 |
| CH | H | OCF$_2$CF$_2$H | CH$_2$CH$_2$CH$_3$ | CH$_2$CH=CHCl | H | H | H | COOCH$_3$ | 0 |
| CH | H | OCF$_2$CF$_2$H | CH$_2$CH$_2$CH$_3$ | CH$_2$CH=CCl$_2$ | H | H | H | COOCH$_3$ | 0 |
| CH | H | OCF$_2$CF$_2$H | CH$_2$CH$_2$CH$_3$ | CH$_2$CH$_2$CH=CH$_2$ | H | H | H | COOCH$_3$ | 0 |
| CH | H | OCF$_2$CF$_2$H | CH$_2$CH$_2$CH$_3$ | —CH$_2$C≡CH | H | H | H | COOCH$_3$ | 0 |
| CH | H | OCF$_2$CF$_2$H | CH$_2$CH$_2$CH$_3$ | CH$_2$CN | H | H | H | COOCH$_3$ | 0 |
| CH | H | OCF$_2$CF$_2$H | CH$_2$CH$_2$CH$_3$ | CH$_2$OCH$_3$ | H | H | H | COOCH$_3$ | 0 |
| CH | H | OCF$_2$CF$_2$H | CH$_2$CH$_2$CH$_3$ | CH$_2$SCH$_3$ | H | H | H | COOCH$_3$ | 0 |
| CH | H | OCF$_2$CF$_2$H | CH$_2$CH$_2$CH$_3$ | CH$_2$C$_6$H$_5$ | H | H | H | COOCH$_3$ | 0 |
| N | H | CF$_3$ | CH$_3$ | CH$_3$ | H | H | H | COOC$_2$H$_5$ | 0 |
| N | H | CF$_3$ | CH$_3$ | CH$_2$CH$_3$ | H | H | H | COOC$_2$H$_5$ | 0 |
| N | H | CF$_3$ | CH$_3$ | CH$_2$CH$_2$CH$_3$ | H | H | H | COOC$_2$H$_5$ | 0 |
| N | H | CF$_3$ | CH$_3$ | (CH$_2$)$_3$CH$_3$ | H | H | H | COOC$_2$H$_5$ | 0 |
| N | H | CF$_3$ | CH$_3$ | (CH$_2$)$_4$CH$_3$ | H | H | H | COOC$_2$H$_5$ | 0 |
| N | H | CF$_3$ | CH$_3$ | (CH$_2$)$_{11}$CH$_3$ | H | H | H | COOC$_2$H$_5$ | 0 |
| N | H | CF$_3$ | CH$_3$ | CH(CH$_3$)$_2$ | H | H | H | COOC$_2$H$_5$ | 0 |
| N | H | CF$_3$ | CH$_3$ | CH$_2$CH(CH$_3$)$_2$ | H | H | H | COOC$_2$H$_5$ | 0 |
| N | H | CF$_3$ | CH$_3$ | CH$_2$CHC$_2$H$_5$ with CH$_3$ branch | H | H | H | COOC$_2$H$_5$ | 0 |
| N | H | CF$_3$ | CH$_3$ | CH$_2$-△ | H | H | H | COOC$_2$H$_5$ | 0 |
| N | H | CF$_3$ | CH$_3$ | CH$_2$CH=CH$_2$ | H | H | H | COOC$_2$H$_5$ | 0 |
| N | H | CF$_3$ | CH$_3$ | CH$_2$CH=CHCH$_3$ | H | H | H | COOC$_2$H$_5$ | 0 |
| N | H | CF$_3$ | CH$_3$ | CH$_2$CH=CHCl | H | H | H | COOC$_2$H$_5$ | 0 |
| N | H | CF$_3$ | CH$_3$ | CH$_2$CH=CCl$_2$ | H | H | H | COOC$_2$H$_5$ | 0 |
| N | H | CF$_3$ | CH$_3$ | CH$_2$CH$_2$CH=CH$_2$ | H | H | H | COOC$_2$H$_5$ | 0 |
| N | H | CF$_3$ | CH$_3$ | —CH$_2$C≡CH | H | H | H | COOC$_2$H$_5$ | 0 |
| N | H | CF$_3$ | CH$_3$ | CH$_2$CN | H | H | H | COOC$_2$H$_5$ | 0 |
| N | H | CF$_3$ | CH$_3$ | CH$_2$OCH$_3$ | H | H | H | COOC$_2$H$_5$ | 0 |
| N | H | CF$_3$ | CH$_3$ | CH$_2$SCH$_3$ | H | H | H | COOC$_2$H$_5$ | 0 |
| N | H | CF$_3$ | CH$_3$ | CH$_2$C$_6$H$_5$ | H | H | H | COOC$_2$H$_5$ | 0 |
| N | H | CF$_3$ | C$_2$H$_5$ | CH$_3$ | H | H | H | COOC$_2$H$_5$ | 0 |
| N | H | CF$_3$ | C$_2$H$_5$ | CH$_2$CH$_3$ | H | H | H | COOC$_2$H$_5$ | 0 |
| N | H | CF$_3$ | C$_2$H$_5$ | CH$_2$CH$_2$CH$_3$ | H | H | H | COOC$_2$H$_5$ | 0 |
| N | H | CF$_3$ | C$_2$H$_5$ | (CH$_2$)$_3$CH$_3$ | H | H | H | COOC$_2$H$_5$ | 0 |
| N | H | CF$_3$ | C$_2$H$_5$ | (CH$_2$)$_4$CH$_3$ | H | H | H | COOC$_2$H$_5$ | 0 |
| N | H | CF$_3$ | C$_2$H$_5$ | (CH$_2$)$_{11}$CH$_3$ | H | H | H | COOC$_2$H$_5$ | 0 |
| N | H | CF$_3$ | C$_2$H$_5$ | CH(CH$_3$)$_2$ | H | H | H | COOC$_2$H$_5$ | 0 |
| N | H | CF$_3$ | C$_2$H$_5$ | CH$_2$CH(CH$_3$)$_2$ | H | H | H | COOC$_2$H$_5$ | 0 |
| N | H | CF$_3$ | C$_2$H$_5$ | CH$_2$CHC$_2$H$_5$ with CH$_3$ branch | H | H | H | COOC$_2$H$_5$ | 0 |

-continued

| | | | | | | | | | |
|---|---|---|---|---|---|---|---|---|---|
| N | H | CF₃ | C₂H₅ | CH₂—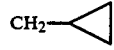 | H | H | H | COOC₂H₅ | O |
| N | H | CF₃ | C₂H₅ | CH₂CH=CH₂ | H | H | H | COOC₂H₅ | O |
| N | H | CF₃ | C₂H₅ | CH₂CH=CHCH₃ | H | H | H | COOC₂H₅ | O |
| N | H | CF₃ | C₂H₅ | CH₂CH=CHCl | H | H | H | COOC₂H₅ | O |
| N | H | CF₃ | C₂H₅ | CH₂CH=CCl₂ | H | H | H | COOC₂H₅ | O |
| N | H | CF₃ | C₂H₅ | CH₂CH₂CH=CH₂ | H | H | H | COOC₂H₅ | O |
| N | H | CF₃ | C₂H₅ | —CH₂C≡CH | H | H | H | COOC₂H₅ | O |
| N | H | CF₃ | C₂H₅ | CH₂CN | H | H | H | COOC₂H₅ | O |
| N | H | CF₃ | C₂H₅ | CH₂OCH₃ | H | H | H | COOC₂H₅ | O |
| N | H | CF₃ | C₂H₅ | CH₂SCH₃ | H | H | H | COOC₂H₅ | O |
| N | H | CF₃ | C₂H₅ | CH₂C₆H₅ | H | H | H | COOC₂H₅ | O |
| N | H | CF₃ | CH₂CH₂CH₃ | CH₃ | H | H | H | COOC₂H₅ | O |
| N | H | CF₃ | CH₂CH₂CH₃ | CH₂CH₃ | H | H | H | COOC₂H₅ | O |
| N | H | CF₃ | CH₂CH₂CH₃ | CH₂CH₂CH₃ | H | H | H | COOC₂H₅ | O |
| N | H | CF₃ | CH₂CH₂CH₃ | (CH₂)₃CH₃ | H | H | H | COOC₂H₅ | O |
| N | H | CF₃ | CH₂CH₂CH₃ | (CH₂)₄CH₃ | H | H | H | COOC₂H₅ | O |
| N | H | CF₃ | CH₂CH₂CH₃ | (CH₂)₁₁CH₃ | H | H | H | COOC₂H₅ | O |
| N | H | CF₃ | CH₂CH₂CH₃ | CH(CH₃)₂ | H | H | H | COOC₂H₅ | O |
| N | H | CF₃ | CH₂CH₂CH₃ | CH₂CH(CH₃)₂ | H | H | H | COOC₂H₅ | O |
| N | H | CF₃ | CH₂CH₂CH₃ | CH₂CH(CH₃)C₂H₅ | H | H | H | COOC₂H₅ | O |
| N | H | CF₃ | CH₂CH₂CH₃ | CH₂—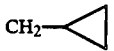 | H | H | H | COOC₂H₅ | O |
| N | H | CF₃ | CH₂CH₂CH₃ | CH₂CH=CH₂ | H | H | H | COOC₂H₅ | O |
| N | H | CF₃ | CH₂CH₂CH₃ | CH₂CH=CHCH₃ | H | H | H | COOC₂H₅ | O |
| N | H | CF₃ | CH₂CH₂CH₃ | CH₂CH=CHCl | H | H | H | COOC₂H₅ | O |
| N | H | CF₃ | CH₂CH₂CH₃ | CH₂CH=CCl₂ | H | H | H | COOC₂H₅ | O |
| N | H | CF₃ | CH₂CH₂CH₃ | CH₂CH₂CH=CH₂ | H | H | H | COOC₂H₅ | O |
| N | H | CF₃ | CH₂CH₂CH₃ | —CH₂C≡CH | H | H | H | COOC₂H₅ | O |
| N | H | CF₃ | CH₂CH₂CH₃ | CH₂CN | H | H | H | COOC₂H₅ | O |
| N | H | CF₃ | CH₂CH₂CH₃ | CH₂OCH₃ | H | H | H | COOC₂H₅ | O |
| N | H | CF₃ | CH₂CH₂CH₃ | CH₂SCH₃ | H | H | H | COOC₂H₅ | O |
| N | H | CF₃ | CH₂CH₂CH₃ | CH₂C₆H₅ | H | H | H | COOC₂H₅ | O |
| N | H | CF₃ | H | CH₃ | H | H | H | COOC₂H₅ | O |
| N | H | CF₃ | H | CH₂CH₃ | H | H | H | COOC₂H₅ | O |
| N | H | CF₃ | H | CH₂CH₂CH₃ | H | O | H | COOC₂H₅ | O |
| N | H | CF₃ | H | (CH₂)₃CH₃ | O | H | H | COOC₂H₅ | O |
| N | H | CF₃ | H | (CH₂)₄CH₃ | H | H | H | COOC₂H₅ | O |
| N | H | CF₃ | H | (CH₂)₁₁CH₃ | H | H | H | COOC₂H₅ | O |
| N | H | CF₃ | H | CH(CH₃)₂ | H | H | H | COOC₂H₅ | O |
| N | H | CF₃ | H | CH₂CH(CH₃)₂ | H | H | H | COOC₂H₅ | O |
| N | H | CF₃ | H | CH₂CH(CH₃)C₂H₅ | H | H | H | COOC₂H₅ | O |
| N | H | CF₃ | H | CH₂—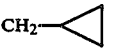 | H | H | H | COOC₂H₅ | O |
| N | H | CF₃ | H | CH₂CH=CH₂ | H | H | H | COOC₂H₅ | O |
| N | H | CF₃ | H | CH₂CH=CHCH₃ | H | H | H | COOC₂H₅ | O |
| N | H | CF₃ | H | CH₂CH=CHCl | H | H | H | COOC₂H₅ | O |
| N | H | CF₃ | H | CH₂CH=CCl₂ | H | H | H | COOC₂H₅ | O |
| N | H | CF₃ | H | CH₂CH₂CH=CH₂ | H | H | H | COOC₂H₅ | O |
| N | H | CF₃ | H | —CH₂C≡CH | H | H | H | COOC₂H₅ | O |
| N | H | CF₃ | H | CH₂CN | H | H | H | COOC₂H₅ | O |
| N | H | CF₃ | H | CH₂OCH₃ | H | H | H | COOC₂H₅ | O |
| N | H | CF₃ | H | CH₂SCH₃ | H | H | H | COOC₂H₅ | O |
| N | H | CF₃ | H | CH₂C₆H₅ | H | H | H | COOC₂H₅ | O |
| N | Cl | CF₃ | CH₃ | CH₃ | H | H | H | COOC₂H₅ | O |
| N | Cl | CF₃ | CH₃ | CH₂CH₃ | H | H | H | COOC₂H₅ | O |
| N | Cl | CF₃ | CH₃ | CH₂CH₂CH₃ | H | H | H | COOC₂H₅ | O |
| N | Cl | CF₃ | CH₃ | (CH₂)₃CH₃ | H | H | H | COOC₂H₅ | O |
| N | Cl | CF₃ | CH₃ | (CH₂)₄CH₃ | H | H | H | COOC₂H₅ | O |
| N | Cl | CF₃ | CH₃ | (CH₂)₁₁CH₃ | H | H | H | COOC₂H₅ | O |
| N | Cl | CF₃ | CH₃ | CH(CH₃)₂ | H | H | H | COOC₂H₅ | O |
| N | Cl | CF₃ | CH₃ | CH₂CH(CH₃)₂ | H | H | H | COOC₂H₅ | O |
| N | Cl | CF₃ | CH₃ | CH₂CH(CH₃)C₂H₅ | H | H | H | COOC₂H₅ | O |

-continued

| | | | | | | | | | |
|---|---|---|---|---|---|---|---|---|---|
| N | Cl | $CF_3$ | $CH_3$ | $CH_2-\triangleleft$ | H | H | H | $COOC_2H_5$ | 0 |
| N | Cl | $CF_3$ | $CH_3$ | $CH_2CH=CH_3$ | H | H | H | $COOC_2H_5$ | 0 |
| N | Cl | $CF_3$ | $CH_3$ | $CH_2CH=CHCH_3$ | H | H | H | $COOC_2H_5$ | 0 |
| N | Cl | $CF_3$ | $CH_3$ | $CH_2CH=CHCl$ | H | H | H | $COOC_2H_5$ | 0 |
| N | Cl | $CF_3$ | $CH_3$ | $CH_2CH=CCl_2$ | H | H | H | $COOC_2H_5$ | 0 |
| N | Cl | $CF_3$ | $CH_3$ | $CH_2CH_2CH=CH_2$ | H | H | H | $COOC_2H_5$ | 0 |
| N | Cl | $CF_3$ | $CH_3$ | $-CH_2C\equiv CH$ | H | H | H | $COOC_2H_5$ | 0 |
| N | Cl | $CF_3$ | $CH_3$ | $CH_2CN$ | H | H | H | $COOC_2H_5$ | 0 |
| N | Cl | $CF_3$ | $CH_3$ | $CH_2OCH_3$ | H | H | H | $COOC_2H_5$ | 0 |
| N | Cl | $CF_3$ | $CH_3$ | $CH_2SCH_3$ | H | H | H | $COOC_2H_5$ | 0 |
| N | Cl | $CF_3$ | $CH_3$ | $CH_2C_6H_5$ | H | H | H | $COOC_2H_5$ | 0 |
| N | Cl | $CF_3$ | $C_2H_5$ | $CH_3$ | H | H | H | $COOC_2H_5$ | 0 |
| N | Cl | $CF_3$ | $C_2H_5$ | $CH_2CH_3$ | H | H | H | $COOC_2H_5$ | 0 |
| N | Cl | $CF_3$ | $C_2H_5$ | $CH_2CH_2CH_3$ | H | H | H | $COOC_2H_5$ | 0 |
| N | Cl | $CF_3$ | $C_2H_5$ | $(CH_2)_3CH_3$ | H | H | H | $COOC_2H_5$ | 0 |
| N | Cl | $CF_3$ | $C_2H_5$ | $(CH_2)_4CH_3$ | H | H | H | $COOC_2H_5$ | 0 |
| N | Cl | $CF_3$ | $C_2H_5$ | $(CH_2)_{11}CH_3$ | H | H | H | $COOC_2H_5$ | 0 |
| N | Cl | $CF_3$ | $C_2H_5$ | $CH(CH_3)_2$ | H | H | H | $COOC_2H_5$ | 0 |
| N | Cl | $CF_3$ | $C_2H_5$ | $CH_2CH(CH_3)_2$ | H | H | H | $COOC_2H_5$ | 0 |
| N | Cl | $CF_3$ | $C_2H_5$ | $CH_2CHC_2H_5$ with $CH_3$ branch | H | H | H | $COOC_2H_5$ | 0 |
| N | Cl | $CF_3$ | $C_2H_5$ | $CH_2-\triangleleft$ | H | H | H | $COOC_2H_5$ | 0 |
| N | Cl | $CF_3$ | $C_2H_5$ | $CH_2CH=CH_2$ | H | H | H | $COOC_2H_5$ | 0 |
| N | Cl | $CF_3$ | $C_2H_5$ | $CH_2CH=CHCH_3$ | H | H | H | $COOC_2H_5$ | 0 |
| N | Cl | $CF_3$ | $C_2H_5$ | $CH_2CH=CHCl$ | H | H | H | $COOC_2H_5$ | 0 |
| N | Cl | $CF_3$ | $C_2H_5$ | $CH_2CH=CCl_2$ | H | H | H | $COOC_2H_5$ | 0 |
| N | Cl | $CF_3$ | $C_2H_5$ | $CH_2CH_2CH=CH_2$ | H | H | H | $COOC_2H_5$ | 0 |
| N | Cl | $CF_3$ | $C_2H_5$ | $-CH_2C\equiv CH$ | H | H | H | $COOC_2H_5$ | 0 |
| N | Cl | $CF_3$ | $C_2H_5$ | $CH_2CN$ | H | H | H | $COOC_2H_5$ | 0 |
| N | Cl | $CF_3$ | $C_2H_5$ | $CH_2OCH_3$ | H | H | H | $COOC_2H_5$ | 0 |
| N | Cl | $CF_3$ | $C_2H_5$ | $CH_2SCH_3$ | H | H | H | $COOC_2H_5$ | 0 |
| N | Cl | $CF_3$ | $C_2H_5$ | $CH_2C_6H_5$ | H | H | H | $COOC_2H_5$ | 0 |
| N | Cl | $CF_3$ | $CH_2CH_2CH_3$ | $CH_3$ | H | H | H | $COOC_2H_5$ | 0 |
| N | Cl | $CF_3$ | $CH_2CH_2CH_3$ | $CH_2CH_3$ | H | H | H | $COOC_2H_5$ | 0 |
| N | Cl | $CF_3$ | $CH_2CH_2CH_3$ | $CH_2CH_2CH_3$ | H | H | H | $COOC_2H_5$ | 0 |
| N | Cl | $CF_3$ | $CH_2CH_2CH_3$ | $(CH_2)_3CH_3$ | H | H | H | $COOC_2H_5$ | 0 |
| N | Cl | $CF_3$ | $CH_2CH_2CH_3$ | $(CH_2)_4CH_3$ | H | H | H | $COOC_2H_5$ | 0 |
| N | Cl | $CF_3$ | $CH_2CH_2CH_3$ | $(CH_2)_{11}CH_3$ | H | H | H | $COOC_2H_5$ | 0 |
| N | Cl | $CF_3$ | $CH_2CH_2CH_3$ | $CH(CH_3)_2$ | H | H | H | $COOC_2H_5$ | 0 |
| N | Cl | $CF_3$ | $CH_2CH_2CH_3$ | $CH_2CH(CH_3)_2$ | H | H | H | $COOC_2H_5$ | 0 |
| N | Cl | $CF_3$ | $CH_2CH_2CH_3$ | $CH_2CHC_2H_5$ with $CH_3$ branch | H | H | H | $COOC_2H_5$ | 0 |
| N | Cl | $CF_3$ | $CH_2CH_2CH_3$ | $CH_2-\triangleleft$ | H | H | H | $COOC_2H_5$ | 0 |
| N | Cl | $CF_3$ | $CH_2CH_2CH_3$ | $CH_2CH=CH_2$ | H | H | H | $COOC_2H_5$ | 0 |
| N | Cl | $CF_3$ | $CH_2CH_2CH_3$ | $CH_2CH=CHCH_3$ | H | H | H | $COOC_2H_5$ | 0 |
| N | Cl | $CF_3$ | $CH_2CH_2CH_3$ | $CH_2CH=CHCl$ | H | H | H | $COOC_2H_5$ | 0 |
| N | Cl | $CF_3$ | $CH_2CH_2CH_3$ | $CH_2CH=CCl_2$ | H | H | H | $COOC_2H_5$ | 0 |
| N | Cl | $CF_3$ | $CH_2CH_2CH_3$ | $CH_2CH_2CH=CH_2$ | H | H | H | $COOC_2H_5$ | 0 |
| N | Cl | $CF_3$ | $CH_2CH_2CH_3$ | $-CH_2C\equiv CH$ | H | H | H | $COOC_2H_5$ | 0 |
| N | Cl | $CF_3$ | $CH_2CH_2CH_3$ | $CH_2CN$ | H | H | H | $COOC_2H_5$ | 0 |
| N | Cl | $CF_3$ | $CH_2CH_2CH_3$ | $CH_2OCH_3$ | H | H | H | $COOC_2H_5$ | 0 |
| N | Cl | $CF_3$ | $CH_2CH_2CH_3$ | $CH_2SCH_3$ | H | H | H | $COOC_2H_5$ | 0 |
| N | Cl | $CF_3$ | $CH_2CH_2CH_3$ | $CH_2C_6H_5$ | H | H | H | $COOC_2H_5$ | 0 |
| CH | F | $CF_3$ | $CH_3$ | $C_2H_5$ | H | H | H | H | 0 |
| CH | F | $CF_3$ | $CH_3$ | $CH_2CH_2CH_3$ | H | H | H | H | 0 |
| CH | F | $CF_3$ | $C_2H_5$ | $C_2H_5$ | H | H | H | H | 0 |
| CH | F | $CF_3$ | $CH_2CH_2CH_3$ | $C_2H_5$ | H | H | H | H | 0 |
| CH | F | $CF_3$ | $CH_2CH_2CH_3$ | $CH_2CH=CH_2$ | H | H | H | H | 0 |
| CH | Br | $CF_3$ | $CH_3$ | $C_2H_5$ | H | H | H | H | 0 |

The compound represented by the general formula (I) can form a salt such as metal, ammonium and organic ammonium salt, which have a herbicidal activity.

The salt can be prepared by reacting a compound represented by the general formula (I) with potassium hydroxide or sodium hydroxide in solvent such as water, acetone and alcohol to form a potassium or sodium salt and following by reacting the potassium or sodium salt with another salt such as metal chloride, hydroxide, sulfate and nitrate.

The organic ammonium salt can be prepared by reacting a compound represented by the general formula (I) with organic ammonium hydroxide in solvent such as water, acetone and alcohol.

The organic ammonium salt includes a tetraalkylammonium salt, benzyltrialkylammonium salt, etc.

PRODUCTION EXAMPLE 1

0.6 Gram of 2-butyryl-5-[2-(5-trifluoromethyl-2-pyridylthio)ethyl]cyclohexane-1,3-dione was dissolved in a mixed solvent of 10 ml of ethanol and 1 ml of water, and 0.2 g of ethoxyamine hydrochloride and 0.07 g of sodium hydroxide were added to the resulting solution which was then stirred at room temperature for 2.5 hours. The reaction solution was poured into water, weakly acidified and extracted with ethyl acetate. After removing ethyl acetate, the residue was purified by thin layer chromatography (eluent, hexane:ethyl acetate=5:1) to obtain 0.45 g of 2-(1-ethoxyaminobutylidene)-5-[2-(5-trifluoromethyl-2-pyridylthio)ethyl]cyclohexane-1,3-dione.

$n_D^{21.5}$: 1.5439.

Nuclear magnetic resonance spectrum (CDCl$_3$): δ (ppm) 14.58 (1H, s), 8.65 (1H, s), 7.65 (1H, dd), 7.23 (1H, d), 4.11 (2H, q), 3.25 (2H, t), 3.1–1.5 (11H, m), 1.29 (3H, t), 0.84 (3H, t).

PRODUCTION EXAMPLE 2

0.19 Gram of 2-propionyl-5-[2-(4-trifluoromethylphenylthio)ethyl]cyclohexane-1,3-dione was dissolved in 5 ml of ethanol, and 0.07 g of allyloxyamine hydrochloride and 0.06 g of triethylamine were added to the resulting solution which was then stirred overnight at room temperature. The reaction solution was poured into water, acidified and extracted with chloroform. After removing chloroform, the residue was purified by thin layer chromatography (eluent, hexane:ethyl acetate=5:1) to obtain 0.13 g of 2-(1-allyloxyaminopropylidene)-5-[2-(4-trifluoromethylphenylthio)ethyl]cyclohexane-1,3-dione.

$n_D^{19.5}$: 1.5624.

Nuclear magnetic resonance spectrum (CDCl$_3$): δ (ppm) 14.63 (1H, s), 7.46 (4H, ABq), 6.35–5.71 (1H, m), 5.45 (2H, bd), 5.23 (1H, m), 4.54 (2H, d), 3.01 (2H, t), 3.0–1.5 (9H, m), 1.14 (3H, t).

PRODUCTION EXAMPLE 3

2.1 Grams of 2-acetyl-5-[2-(4-trifluoromethylphenylthio)ethyl]cyclohexane-1,3-dione was dissolved in 10 ml of ethanol, and 0.71 g of ethoxyamine hydrochloride and 0.68 g of triethylamine were added to the resulting solution which was then stirred overnight at room temperature. The reaction solution was poured into water, acidified with dilute hydrochloric acid and extracted with chloroform. Chloroform was removed and the residue was purified by column chromatography on silica gel (eluent, ethyl acetate:hexane=1:5) to obtain 1.2 g of 2-(1-ethoxyaminoethylidene)-5-[2-(4-trifluoromethylphenylthio)ethyl]cyclohexane-1,3-dione as white crystals.

m.p., 92°–93° C.

Nuclear magnetic resonance spectrum (CDCl$_3$): δ (ppm) 14.63 (1H, bs), 7.41 (4H, ABq), 4.09 (2H, q), 3.02 (2H, t), 2.36 (3H, s), 2.8–1.5 (7H, m), 1.31 (3H, t).

PRODUCTION EXAMPLE 4

0.19 Gram of 2-acetyl-5-[2-(4-trifluoromethoxyphenylthio)ethyl]cyclohexane-1,3-dione was dissolved in 10 ml of ethanol, and 0.07 g of ethoxyamine hydrochloride and 0.06 g of triethylamine were added to the resulting solution which was then stirred overnight at room temperature. The reaction solution was poured into water, acidified with dilute hydrochloric acid and extracted with chloroform. Chloroform was removed and the residue was purified by thin layer chromatography (eluent, hexane:ethyl acetate=5:1) to obtain 0.12 g of 2-(1-ethoxyaminoethylidene)-5-[2-(4-trifluoromethoxyphenylthio)ethyl]cyclohexane-1,3-dione.

$n_D^{26}$: 1.5329.

Nuclear magnetic resonance spectrum (CDCl$_3$): δ (ppm) 7.22 (4H, ABq), 4.11 (2H, q), 3.05 (2H, t), 2.35 (3H, s), 2.8–1.5 (7H, m), 1.30 (3H, t), 15–14 (1H, br).

PRODUCTION EXAMPLE 5

0.21 Gram of 2-propionyl-5-[2-(4-α,α,β,β-tetrafluoroethoxyphenylthio)ethyl]cyclohexane-1,3-dione was dissolved in 10 ml of ethanol, and 0.06 g of ethoxyamine hydrochloride and 0.06 g of triethylamine were added to the resulting solution which was then stirred overnight at room temperature. The reaction solution was poured into water, acidified with dilute hydrochloric acid and extracted with chloroform. Chloroform was removed and the residue was purified by thin layer chromatography (developing solvent, hexane:ethyl acetate=5:1) to obtain 0.07 g of 2-(1-ethoxyaminopropylidene)-5-[2-(4-α,α,β,β-tetrafluoroethoxyphenylthio)ethyl]cyclohexane-1,3-dione.

$n_D^{24}$: 1.5119.

Nuclear magnetic resonance spectrum (CDCl$_3$): δ (ppm) 7.28 (4H, ABq), 5.92 (1H, tt, J=54 Hz, 3 Hz), 4.13 (2H, q), 3.1–1.5 (9H, m), 1.31 (3H, t), 1.13 (3H, t), 15–14 (1H, br).

PRODUCTION EXAMPLE 6

0.27 Gram of 2-propionyl-5-[2-(4-trifluoromethylphenylthio)propyl]cyclohexane-1,3-dione was dissolved in 10 ml of ethyl acetate, and 0.08 g of ethoxyamine hydrochloride and 0.1 g of N,N-diethylaniline were added to the resulting solution which was then refluxed for 5 hours. The reaction solution was cooled to room temperature, poured into water, weakly acidified and extracted with ethyl acetate. The ethyl acetate layer was washed with dilute hydrochloric acid and water subsequently and dried over anhydrous magnesium sulfate. After removing ethyl acetate, the residue was purified by thin layer chromatography (eluent, hexane:ethyl acetate=5:1) to obtain 0.13 g of 2-(1-ethoxyaminopropylidene)-5-[2-(4-trifluoromethylphenylthio)propyl]cyclohexane-1,3-dione.

$n_D^{24}$: 1.5293.

Nuclear magnetic resonance spectrum (CDCl$_3$): δ (ppm) 15–14 (1H, br), 7.45 (4H, brs), 4.10 (2H, q), 3.32 (1H, m), 2.7–1.5 (9H, m), 1.35 (3H, d), 1.31 (3H, t), 1.14 (3H, t).

PRODUCTION EXAMPLE 7

0.4 Gram of 2-acetyl-5-[1-methyl-2-(4-trifluoromethylphenylthio)ethyl]cyclohexane-1,3-dione and 0.1 g of ethoxyamine hydrochloride were dissolved in 10 ml of methanol and 0.15 g of potassium carbonate was added to the resulting solution which was then refluxed for 3 hours. The reaction solution was poured into water and extracted with chloroform. After removing chloroform, the residue was purified by thin layer chromatography (eluent, hexane:ethyl acetate=5:1) to obtain 0.3 g of 2-(1-ethoxyaminoethylidene)-5-[1-methyl-2-(4-trifluoromethylphenylthio)ethyl]cyclohexane-1,3-dione.

$n_D^{25.5}$: 1.5145.

Nuclear magnetic resonance spectrum (CDCl$_3$): δ (ppm) 15-14 (1H, br), 7.39 (4H, ABq), 4.11 (2H, q), 3.0-1.5 (6H, m), 2.93 (2H, t), 2.34 (3H, s), 1.30 (3H, t), 1.12 (3H, d).

PRODUCTION EXAMPLE 8

To the suspension of 0.3 g of sodium hydride (60% oil dispersion) in 10 ml of dimethylformamide, 0.09 g of 2-butenyloxyamine hydrochloride was added under cooling with ice-water bath and then stirred. After 30 minutes, 0.21 g of 2-acetyl-5-[2-(4-trifluoromethylphenylthio)ethyl]cyclohexane-1,3-dione was added to the resulting solution which was then stirred for 7 hours under cooling with ice-water bath. The reaction solution was poured into water, acidified with dilute hydrochloric acid and extracted with ether. After removing ether, the residue was purified by thin layer chromatography (eluent, hexane:ethyl acetate=5:1) to obtain 0.22 g of 2-[1-(2-butenyloxyamino)ethylidene]5-[2-(4-trifluoromethylphenylthio)ethyl]cyclohexane-1,3-dione.
m.p. 72°-73° C.

Nuclear magnetic resonance (CDCl$_3$): δ (ppm) 15-14 (1H, br), 7.35 (4H, ABq), 5.55 (2H, m), 4.35 (2H, d), 2.91 (2H, t), 2.5-1.5 (7H, m), 2.34 (3H, s), 1.7 (3H, brd).

PRODUCTION EXAMPLE 9

0.2 Gram of 2-propionyl-5-[2-(4-trifluoromethylphenylthio)ethyl]cyclohexane-1,3-dione was dissolved in 10 ml of chloroform and 0.07 g of propoxyamine hydrochloride and 0.5 ml of pyridine were added to the resulting solution which was then stirred at 50°-60° C. for 5 hours. The reaction solution was poured into water, acidified with dilute hydrochloric acid and extracted with chloroform. After removing chloroform, the residue was purified by thin layer chromatography (eluent, hexane:ethyl acetate=5:1) to obtain 0.11 g of 2-(1-propoxyaminopropylidene)-5-[2-(4-trifluoromethylphenylthio)ethyl]cyclohexane-1,3-dione.
$n_D^{24}$: 1.5376.

Nuclear magnetic resonance spectrum (CDCl$_3$): δ (ppm) 15-14 (1H, br), 7.43 (4H, ABq), 4.00 (2H, t), 3.2-1.5 (13H, m), 1.15 (3H, t), 0.99 (3H, t).

Some of the present compounds produced by the methods described above will be shown in Table 2.

TABLE 2

General formula:

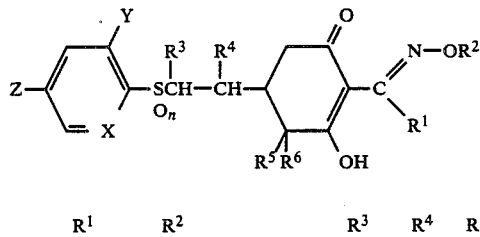

| Compound No. | X | Y | Z | R$^1$ | R$^2$ | R$^3$ | R$^4$ | R$^5$ | R$^6$ | n | Physical properties |
|---|---|---|---|---|---|---|---|---|---|---|---|
| 1 | CH | H | CF$_3$ | CH$_3$ | CH$_3$ | H | H | H | H | 0 | mp 76-77° C. |
| 2 | CH | H | CF$_3$ | CH$_3$ | C$_2$H$_5$ | H | H | H | H | 0 | mp 92-93° C. |
| 3 | CH | H | CF$_3$ | CH$_3$ | n-C$_3$H$_7$ | H | H | H | H | 0 | mp 91-92° C. |
| 4 | CH | H | CF$_3$ | CH$_3$ | n-C$_4$H$_9$ | H | H | H | H | 0 | $n_D^{24}$ 1.5092 |
| 5 | CH | H | CF$_3$ | CH$_3$ | n-C$_5$H$_{11}$ | H | H | H | H | 0 | $n_D^{24}$ 1.5265 |
| 6 | CH | H | CF$_3$ | CH$_3$ | (CH$_2$)$_{11}$CH$_3$ | H | H | H | H | 0 | $n_D^{23}$ 1.5322 |
| 7 | CH | H | CF$_3$ | CH$_3$ | CH(CH$_3$)$_2$ | H | H | H | H | 0 | mp 94-95° C. |
| 8 | CH | H | CF$_3$ | CH$_3$ | CH$_2$CH(CH$_3$)$_2$ | H | H | H | H | 0 | mp 76-77° C. |
| 9 | CH | H | CF$_3$ | CH$_3$ | —CH$_2$—◁ | H | H | H | H | 0 | mp 86-87° C. |
| 10 | CH | H | CF$_3$ | CH$_3$ | CH$_2$CH=CH$_2$ | H | H | H | H | 0 | $n_D^{24}$ 1.5165 |
| 11 | CH | H | CF$_3$ | CH$_3$ | CH$_2$CH=CHCH$_3$ | H | H | H | H | 0 | mp 72-73° C. |
| 12 | CH | H | CF$_3$ | CH$_3$ | CH$_2$CH=CHCl | H | H | H | H | 0 | $n_D^{23.5}$ 1.5572 |
| 13 | CH | H | CF$_3$ | CH$_3$ | CH$_2$CH=CCl$_2$ | H | H | H | H | 0 | $n_D^{24.5}$ 1.5519 |
| 14 | CH | H | CF$_3$ | CH$_3$ | CH$_2$CH$_2$CH=CH$_2$ | H | H | H | H | 0 | $n_D^{22.5}$ 1.5450 |
| 15 | CH | H | CF$_3$ | CH$_3$ | CH$_2$C≡CH | H | H | H | H | 0 | $n_D^{24}$ 1.5516 |
| 16 | CH | H | CF$_3$ | CH$_3$ | CH$_2$CN | H | H | H | H | 0 | $n_D^{24}$ 1.5276 |
| 17 | CH | H | CF$_3$ | CH$_3$ | CH$_2$OCH$_3$ | H | H | H | H | 0 | mp 86.5-87.5° C. |
| 18 | CH | H | CF$_3$ | CH$_3$ | CH$_2$SCH$_3$ | H | H | H | H | 0 | mp 80-81°C. |
| 19 | CH | H | CF$_3$ | CH$_3$ | CH$_2$C$_6$H$_5$ | H | H | H | H | 0 | mp 72-73° C. |
| 20 | CH | H | CF$_3$ | CH$_3$ | C$_2$H$_5$ | H | H | CH$_3$ | H | 0 | $n_D^{23}$ 1.5181 |
| 21 | CH | H | CF$_3$ | CH$_3$ | CH$_2$CH=CH$_2$ | H | H | CH$_3$ | H | 0 | $n_D^{23}$ 1.5276 |
| 22 | CH | H | CF$_3$ | CH$_3$ | C$_2$H$_5$ | H | H | H | H | 1 | mp 103-104° C. |
| 23 | CH | H | CF$_3$ | CH$_3$ | CH$_2$CH=CH$_2$ | H | H | H | H | 1 | $n_D^{22.5}$ 1.5384 |
| 24 | CH | H | CF$_3$ | CH$_3$ | C$_2$H$_5$ | H | H | H | H | 2 | mp 120-121° C. |
| 25 | CH | H | CF$_3$ | CH$_3$ | CH$_2$CH=CH$_2$ | H | H | H | H | 2 | mp 117-118° C. |
| 26 | CH | H | CF$_3$ | CH$_3$ | C$_2$H$_5$ | CH$_3$ | H | H | H | 0 | $n_D^{24}$ 1.5347 |
| 27 | CH | H | CF$_3$ | CH$_3$ | n-C$_3$H$_7$ | CH$_3$ | H | H | H | 0 | $n_D^{24}$ 1.5336 |
| 28 | CH | H | CF$_3$ | CH$_3$ | CH$_2$CH=CH$_2$ | CH$_3$ | H | H | H | 0 | $n_D^{24}$ 1.5372 |
| 29 | CH | H | CF$_3$ | CH$_3$ | CH$_2$CH=CHCl | CH$_3$ | H | H | H | 0 | $n_D^{24}$ 1.5461 |
| 30 | CH | H | CF$_3$ | CH$_3$ | C$_2$H$_5$ | H | CH$_3$ | H | H | 0 | $n_D^{25.5}$ 1.5371 |
| 31 | CH | H | CF$_3$ | CH$_3$ | n-C$_3$H$_7$ | H | CH$_3$ | H | H | 0 | $n_D^{25.5}$ 1.5145 |
| 32 | CH | H | CF$_3$ | C$_2$H$_5$ | CH$_3$ | H | H | H | H | 0 | $n_D^{24}$ 15426 |
| 33 | CH | H | CF$_3$ | C$_2$H$_5$ | C$_2$H$_5$ | H | H | H | H | 0 | $n_D^{22}$ 1.5333 |
| 34 | CH | H | CF$_3$ | C$_2$H$_5$ | n-C$_3$H$_7$ | H | H | H | H | 0 | $n_D^{24}$ 1.5376 |
| 35 | CH | H | CF$_3$ | C$_2$H$_5$ | n-C$_4$H$_9$ | H | H | H | H | 0 | $n_D^{24}$ 1.5058 |
| 36 | CH | H | CF$_3$ | C$_2$H$_5$ | n-C$_5$H$_{11}$ | H | H | H | H | 0 | $n_D^{24}$ 1.5251 |

TABLE 2-continued

General formula:

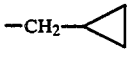

| Compound No. | X | Y | Z | R¹ | R² | R³ | R⁴ | R⁵ | R⁶ | n | Physical properties |
|---|---|---|---|---|---|---|---|---|---|---|---|
| 37 | CH | H | $CF_3$ | $C_2H_5$ | $(CH_2)_{11}CH_3$ | H | H | H | H | 0 | $n_D^{23}$ 1.5325 |
| 38 | CH | H | $CF_3$ | $C_2H_5$ | $CH(CH_3)_2$ | H | H | H | H | 0 | $n_D^{23}$ 1.5328 |
| 39 | CH | H | $CF_3$ | $C_2H_5$ | $CH_2CH(CH_3)_2$ | H | H | H | H | 0 | $n_D^{23}$ 1.5465 |
| 40 | CH | H | $CF_3$ | $C_2H_5$ | $-CH_2-\triangleleft$ | H | H | H | H | 0 | $n_D^{24}$ 1.5456 |
| 41 | CH | H | $CF_3$ | $C_2H_5$ | $CH_2CH=CH_2$ | H | H | H | H | 0 | $n_D^{19.5}$ 1.5399 |
| 42 | CH | H | $CF_3$ | $C_2H_5$ | $CH_2CH=CHCH_3$ | H | H | H | H | 0 | $n_D^{21.5}$ 1.5344 |
| 43 | CH | H | $CF_3$ | $C_2H_5$ | $CH_2CH=CHCl$ | H | H | H | H | 0 | $n_D^{24}$ 1.5416 |
| 44 | CH | H | $CF_3$ | $C_2H_5$ | $CH_2CH=CCl_2$ | H | H | H | H | 0 | $n_D^{24}$ 1.5549 |
| 45 | CH | H | $CF_3$ | $C_2H_5$ | $CH_2CH_2CH=CH_2$ | H | H | H | H | 0 | $n_D^{23}$ 1.5365 |
| 46 | CH | H | $CF_3$ | $C_2H_5$ | $CH_2C\equiv CH$ | H | H | H | H | 0 | $n_D^{24}$ 1.5499 |
| 47 | CH | H | $CF_3$ | $C_2H_5$ | $CH_2CN$ | H | H | H | H | 0 | $n_D^{24}$ 1.5276 |
| 48 | CH | H | $CF_3$ | $C_2H_5$ | $CH_2OCH_3$ | H | H | H | H | 0 | $n_D^{21.5}$ 1.5352 |
| 49 | CH | H | $CF_3$ | $C_2H_5$ | $CH_2SCH_3$ | H | H | H | H | 0 | $n_D^{24}$ 1.5616 |
| 50 | CH | H | $CF_3$ | $C_2H_5$ | $CH_2C_6H_5$ | H | H | H | H | 0 | $n_D^{24}$ 1.5697 |
| 51 | CH | H | $CF_3$ | $C_2H_5$ | $C_2H_5$ | $CH_3$ | H | H | H | 0 | $n_D^{24}$ 1.5293 |
| 52 | CH | H | $CF_3$ | $C_2H_5$ | $CH_2CH=CH_2$ | $CH_3$ | H | H | H | 0 | $n_D^{24}$ 1.5249 |
| 53 | CH | H | $CF_3$ | $n-C_3H_7$ | $CH_3$ | H | H | H | H | 0 | $n_D^{24}$ 1.5391 |
| 54 | CH | H | $CF_3$ | $n-C_3H_7$ | $C_2H_5$ | H | H | H | H | 0 | $n_D^{24}$ 1.5345 |
| 55 | CH | H | $CF_3$ | $n-C_3H_7$ | $n-C_3H_7$ | H | H | H | H | 0 | $n_D^{24}$ 1.5320 |
| 56 | CH | H | $CF_3$ | $n-C_3H_7$ | $CH_2CH=CH_2$ | H | H | H | H | 0 | $n_D^{19.5}$ 1.5402 |
| 57 | CH | H | $CF_3$ | $n-C_3H_7$ | $C_2CH=CHCl$ | H | H | H | H | 0 | $n_D^{25.5}$ 1.5152 |
| 58 | CH | H | $CF_3$ | $n-C_3H_7$ | $CH_2CH=CCl_2$ | H | H | H | H | 0 | $n_D^{24}$ 1.5605 |
| 59 | CH | H | $CF_3$ | $n-C_3H_7$ | $C_2H_5$ | $CH_3$ | H | H | H | 0 | $n_D^{24}$ 1.5229 |
| 60 | CH | H | $CF_3$ | $n-C_3H_7$ | $CH_2CH=CH_2$ | $CH_3$ | H | H | H | 0 | $n_D^{24}$ 1.5298 |
| 61 | CH | H | $CF_3$ | $n-C_3H_7$ | $CH_2CH=CHCH_3$ | $CH_3$ | H | H | H | 0 | $n_D^{24}$ 1.5263 |
| 62 | CH | H | $CF_3$ | $CH(CH_3)_2$ | $C_2H_5$ | H | H | H | H | 0 | $n_D^{24}$ 1.5278 |
| 63 | CH | H | $CF_3$ | $CH(CH_3)_2$ | $CH_2CH=CHCH_3$ | H | H | H | H | 0 | $n_D^{24}$ 1.5282 |
| 64 | CH | H | $CF_3$ | $CH_2CH(CH_3)_2$ | $CH_3$ | H | H | H | H | 0 | $n_D^{24}$ 1.5295 |
| 65 | CH | H | $CF_3$ | $CH_2CH(CH_3)_2$ | $C_2H_5$ | H | H | H | H | 0 | $n_D^{24}$ 1.5351 |
| 66 | CH | H | $CF_3$ | $CH_2CH(CH_3)_2$ | $CH_2CH=CHCH_3$ | H | H | H | H | 0 | $n_D^{24}$ 1.5306 |
| 67 | CH | H | $CF_3$ | $CH_2OCH_3$ | $C_2H_5$ | H | H | H | H | 0 | $n_D^{22}$ 1.5286 |
| 68 | CH | H | $CF_3$ | $CH_2OCH_3$ | $CH_2CH=CH_2$ | H | H | H | H | 0 | $n_D^{22}$ 1.5461 |
| 69 | CH | H | $OCF_3$ | $CH_3$ | $CH_3$ | H | H | H | H | 0 | $n_D^{26}$ 1.5376 |
| 70 | CH | H | $OCF_3$ | $CH_3$ | $C_2H_5$ | H | H | H | H | 0 | $n_D^{26}$ 1.5329 |
| 71 | CH | H | $OCF_3$ | $CH_3$ | $n-C_3H_7$ | H | H | H | H | 0 | mp 57–58° C. |
| 72 | CH | H | $OCF_3$ | $CH_3$ | $CH_2CH=CH_2$ | H | H | H | H | 0 | $n_D^{26}$ 1.5406 |
| 73 | CH | H | $OCF_3$ | $C_2H_5$ | $CH_3$ | H | H | H | H | 0 | $n_D^{27.5}$ 1.5337 |
| 74 | CH | H | $OCF_3$ | $C_2H_5$ | $C_2H_5$ | H | H | H | H | 0 | $n_D^{27.5}$ 1.5226 |
| 75 | CH | H | $OCF_3$ | $C_2H_5$ | $CH_2CH=CH_2$ | H | H | H | H | 0 | $n_D^{27.5}$ 1.5308 |
| 76 | CH | H | $OCF_3$ | $n-C_3H_7$ | $CH_3$ | H | H | H | H | 0 | $n_D^{26}$ 1.5059 |
| 77 | CH | H | $OCF_3$ | $n-C_3H_7$ | $C_2H_5$ | H | H | H | H | 0 | $n_D^{26}$ 1.5196 |
| 78 | CH | H | $OCF_3$ | $n-C_3H_7$ | $CH_2CH=CH_2$ | H | H | H | H | 0 | $n_D^{26}$ 1.5283 |
| 79 | CH | H | $OCF_2CF_2H$ | $CH_3$ | $C_2H_5$ | H | H | H | H | 0 | $n_D^{24.5}$ 1.5244 |
| 80 | CH | H | $OCF_2CF_2H$ | $CH_3$ | $CH_2CH=CH_2$ | H | H | H | H | 0 | $n_D^{24.5}$ 1.5213 |
| 81 | CH | H | $OCF_2CF_2H$ | $C_2H_5$ | $C_2H_5$ | H | H | H | H | 0 | $n_D^{24}$ 1.5119 |
| 82 | CH | H | $OCF_2CF_2H$ | $C_2H_5$ | $CH_2CH=CH_2$ | H | H | H | H | 0 | $n_D^{24}$ 1.5286 |
| 83 | CH | H | $OCF_2CF_2H$ | $n-C_3H_7$ | $C_2H_5$ | H | H | H | H | 0 | $n_D^{24}$ 1.5185 |
| 84 | CH | H | $OCF_2CF_2H$ | $n-C_3H_7$ | $CH_2CH=CH_2$ | H | H | H | H | 0 | $n_D^{24}$ 1.5248 |
| 85 | N | H | $CF_3$ | $CH_3$ | $CH_3$ | H | H | H | H | 0 | $n_D^{22}$ 1.5402 |
| 86 | N | H | $CF_3$ | $CH_3$ | $C_2H_5$ | H | H | H | H | 0 | $n_D^{22}$ 1.5518 |
| 87 | N | H | $CF_3$ | $CH_3$ | $CH_2CH=CH_2$ | H | H | H | H | 0 | $n_D^{21}$ 1.5405 |
| 88 | N | H | $CF_3$ | $CH_3$ | $CH_2CH=CHCl$ | H | H | H | H | 0 | $n_D^{22}$ 1.5552 |
| 89 | N | H | $CF_3$ | $C_2H_5$ | $C_2H_5$ | H | H | H | H | 0 | $n_D^{26}$ 1.5374 |
| 90 | N | H | $CF_3$ | $C_2H_5$ | $n-C_3H_7$ | H | H | H | H | 0 | $n_D^{23}$ 1.5302 |
| 91 | N | H | $CF_3$ | $C_2H_5$ | $CH_2CH=CH_2$ | H | H | H | H | 0 | $n_D^{20}$ 1.5298 |
| 92 | N | H | $CF_3$ | $C_2H_5$ | $CH_2CH=CHCH_3$ | H | H | H | H | 0 | $n_D^{20}$ 1.5271 |
| 93 | N | H | $CF_3$ | $C_2H_5$ | $CH_2CH=CHCl$ | H | H | H | H | 0 | $n_D^{20}$ 1.5386 |
| 94 | N | H | $CF_3$ | $C_2H_5$ | $CH_2CH=CCl_2$ | H | H | H | H | 0 | $n_D^{23}$ 1.5175 |
| 95 | N | H | $CF_3$ | $C_2H_5$ | $CH_2\equiv CH$ | H | H | H | H | 0 | $n_D^{21}$ 1.5378 |
| 96 | N | H | $CF_3$ | $C_2H_5$ | $CH_2OCH_3$ | H | H | H | H | 0 | $n_D^{21}$ 1.5172 |
| 97 | N | H | $CF_3$ | $n-C_3H_7$ | $CH_3$ | H | H | H | H | 0 | $n_D^{21}$ 1.5372 |
| 98 | N | H | $CF_3$ | $n-C_3H_7$ | $C_25$ | H | H | H | H | 0 | $n_D^{21.5}$ 1.5239 |
| 99 | N | H | $CF_3$ | $n-C_3H_7$ | $CH_2CH=CH_2$ | H | H | H | H | 0 | $n_D^{21.5}$ 1.5331 |
| 100 | N | H | $CF_3$ | $n-C_3H_7$ | $CH_2CH=CHCH_3$ | H | H | H | H | 0 | $n_D^{21}$ 1.5361 |
| 101 | N | H | $CF_3$ | $n-C_3H_7$ | $CH_2CH=CHCl$ | H | H | H | H | 0 | $n_D^{20}$ 1.5432 |

TABLE 2-continued

General formula:

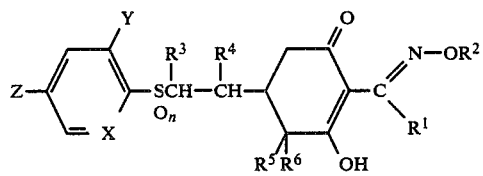

| Compound No. | X | Y | Z | $R^1$ | $R^2$ | $R^3$ | $R^4$ | $R^5$ | $R^6$ | n | Physical properties |
|---|---|---|---|---|---|---|---|---|---|---|---|
| 102 | N | H | $CF_3$ | $n\text{-}C_3H_7$ | $CH_2C{\equiv}CH$ | H | H | H | H | 0 | $n_D^{20}$ 1.5517 |
| 103 | N | H | $CF_3$ | $n\text{-}C_3H_7$ | $CH_2CN$ | H | H | H | H | 0 | $n_D^{20}$ 1.5192 |
| 104 | N | H | $CF_3$ | $n\text{-}C_3H_7$ | $CH_2OCH_3$ | H | H | H | H | 0 | $n_D^{21}$ 1.5212 |
| 105 | N | Cl | $CF_3$ | $C_2H_5$ | $CH_2CH{=}CH_2$ | H | H | H | H | 0 | mp 64–65° C. |
| 106 | N | Cl | $CF_3$ | $C_2H_5$ | $CH_2CH{=}CHCH_3$ | H | H | H | H | 0 | mp 58–59° C. |
| 107 | N | Cl | $CF_3$ | $C_2H_5$ | $CH_2CH{=}CHCl$ | H | H | H | H | 0 | $n_D^{20}$ 1.5472 |
| 108 | N | Cl | $CF_3$ | $n\text{-}C_3H_7$ | $CH_2CH{=}CH_2$ | H | H | H | H | 0 | $n_D^{19}$ 1.5287 |
| 109 | N | H | $CF_3$ | $CH_2OCH_3$ | $CH_2CH{=}CH_2$ | H | H | H | H | 0 | $n_D^{20}$ 1.5397 |
| 110 | N | H | $CF_3$ | $CH_2OCH_3$ | $CH_2CH{=}CHCl$ | H | H | H | H | 0 | $n_D^{26}$ 1.5269 |
| 111* | CH | H | $CF_3$ | $CH_3$ | $C_2H_5$ | H | H | H | H | 0 | mp 175–178° C. (dec.) |
| 112* | CH | H | $CF_3$ | $CH_3$ | $C_2H_5$ | H | H | H | H | 0 | mp 144–146° C. (dec.) |
| 113* | CH | H | $CF_3$ | $CH_3$ | $C_2H_5$ | H | H | H | H | 0 | mp 182–185° C. (dec.) |
| 114* | CH | H | $CF_3$ | $CH_3$ | $C_2H_5$ | H | H | H | H | 0 | mp 72–73° C. |
| 115* | CH | H | $CF_3$ | $CH_3$ | $C_2H_5$ | H | H | H | H | 0 | mp 232–235° C. (dec.) |
| 116* | CH | H | $CF_3$ | $CH_3$ | $C_2H_5$ | H | H | H | H | 0 | mp 58–61° C. |
| 117 | CH | H | $CF_3$ | $CH_3$ | $C_2H_5$ | H | H | H | $COOCH_3$ | 0 | $n_D^{23.5}$ 1.5376 |
| 118 | CH | H | $CF_3$ | $C_2H_5$ | $C_2H_5$ | H | H | H | $COOCH_3$ | 0 | $n_D^{24}$ 1.5339 |
| 119 | CH | H | $CF_3$ | $n\text{-}C_3H_7$ | $C_2H_5$ | H | H | H | $COOCH_3$ | 0 | $n_D^{24}$ 1.5186 |
| 120 | CH | H | $OCF_3$ | $CH_3$ | $C_2H_5$ | H | H | H | $COOCH_3$ | 0 | $n_D^{20.5}$ 1.5291 |
| 121 | CH | H | $OCF_3$ | $CH_3$ | $n\text{-}C_3H_7$ | H | H | H | $COOCH_3$ | 0 | $n_D^{20.5}$ 1.5283 |
| 122 | CH | H | $OCF_3$ | $C_2H_5$ | $C_2H_5$ | H | H | H | $COOCH_3$ | 0 | $n_D^{20.5}$ 1.5301 |
| 123 | CH | H | $CF_3$ | $C_2H_5$ | $C_2H_5$ | $CH_3$ | H | H | $COOCH_3$ | 0 | $n_D^{25}$ 1.5212 |
| 124 | CH | H | $CF_3$ | $C_2H_5$ | $C_2H_5$ | $CH_3$ | H | H | $COOCH_3$ | 0 | $n_D^{25}$ 1.5087 |
| 125 | CH | H | $CF_3$ | $CH_3$ | $C_2H_5$ | H | $CH_3$ | H | $COOCH_3$ | 0 | $n_D^{25.5}$ 1.5209 |
| 126 | CH | H | $CF_3$ | $C_2H_5$ | $C_2H_5$ | H | $CH_3$ | H | $COOCH_3$ | 0 | $n_D^{25.5}$ 1.5198 |
| 127 | CH | H | $CF_3$ | $CH_3$ | $CH_2CH{=}CH_2$ | H | H | H | $COOCH_3$ | 0 | $n_D^{23.5}$ 1.5347 |
| 128 | CH | H | $CF_3$ | $C_2H_5$ | $CH_2CH{=}CH_3$ | H | H | H | $COOCH_3$ | 0 | $n_D^{24}$ 1.5315 |
| 129 | CH | H | $CF_3$ | $n\text{-}C_3H_7$ | $CH_2CH{=}CH_3$ | H | H | H | $COOCH_3$ | 0 | $n_D^{24}$ 1.5291 |
| 130 | CH | H | $OCF_3$ | $CH_3$ | $CH_2CH{=}CH_3$ | H | H | H | $COOCH_3$ | 0 | $n_D^{20.5}$ 1.5341 |
| 131 | CH | H | $OCF_3$ | $C_2H_5$ | $CH_2CH{=}CH_3$ | H | H | H | $COOCH_3$ | 0 | $n_D^{20.5}$ 1.5329 |
| 132 | CH | H | $CF_3$ | $CH_3$ | $CH_2CH{=}CH_3$ | $CH_3$ | H | H | $COOCH_3$ | 0 | $n_D^{25}$ 1.5268 |
| 133 | CH | H | $CF_3$ | $C_2H_5$ | $CH_2CH{=}CH_3$ | $CH_3$ | H | H | $COOCH_3$ | 0 | $n_D^{25}$ 1.5208 |
| 134 | N | H | $CF_3$ | $C_2H_5$ | $C_2H_5$ | H | H | H | $COOCH_2H_5$ | 0 | $n_D^{20}$ 1.5423 |
| 135 | CH | F | $CF_3$ | $CH_3$ | $C_2H_5$ | H | H | H | H | 0 | $n_D^{25}$ 1.5311 |

*111 sodium salt
*112 copper salt
*113 calcium salt
*114 tetrapropylammonium salt hydrate
*115 lithium salt
*116 benzyltrimethylammonium salt hydrate Acylcyclohexane, a material, represented by the general formula (II) is produced, for example, by a series of reactions described below:

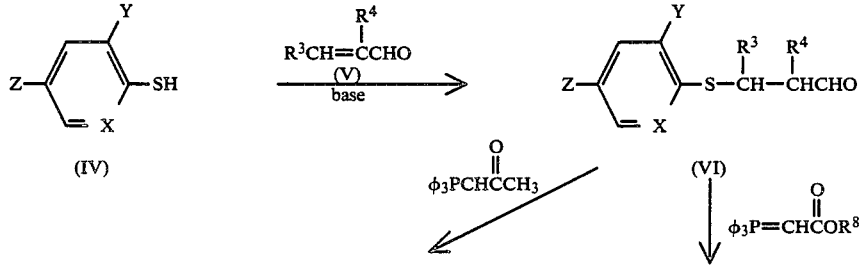

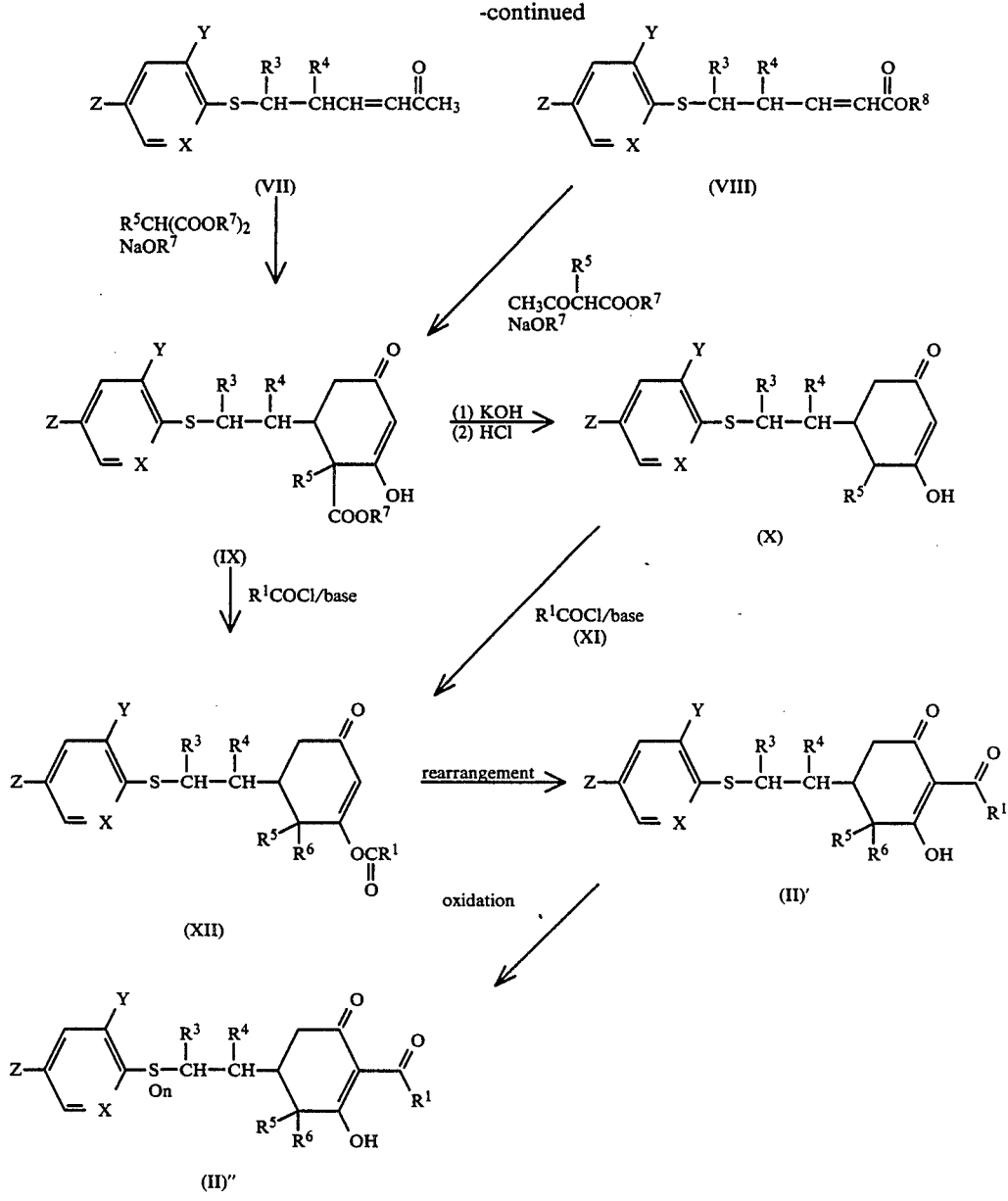

(n = 1 or 2)

wherein $R^1$, $R^2$, $R^3$, $R^4$, $R^5$, $R^6$, X, Y and Z are as defined above, $R^7$ is a ($C_1$-$C_4$)alkyl group and $R^8$ is a ($C_1$-$C_4$)alkyl group.

The compound represented by the general formula (VI) is produced by reacting 1 mole of a thiol (IV) with 1 to 1.2 moles of an α,β-unsaturated aldehyde (V) without a solvent or in an inert solvent and under heating or cooling in the presence of a catalyst. The reaction temperature is from 0° C. to the boiling point of the solvent used, preferably from 0° C. to room temperature in the presence of a catalyst. For the catalyst, bases such as triethylamine, alkoxides, etc. are used in an amount of from 0.05 to 0.005 mole equivalent. The solvent includes organic solvents such as alcohol, diethyl ether, tetrahydrofuran (THF), benzene, toluene, chloroform, ethyl acetate, etc. The reaction time is generally from 30 minutes to several hours, and after completion of the reaction, water is added to the reaction solution which is then extracted with an organic solvent. The desired product obtained may be purified if necessary by recrystallization or column chromatography.

Examples of the compound of the general formula (VI) thus obtained are shown in Table 3.

TABLE 3

Compounds of the general formula (VI):

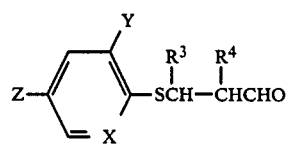

| X | Y | Z | $R^3$ | $R^4$ |
|---|---|---|---|---|
| CH | H | $CF_3$ | H | H |
| CH | H | $CF_3$ | $CH_3$ | H |
| CH | H | $CF_3$ | H | $CH_3$ |
| CH | H | $CF_3$ | $CH_3$ | $CH_3$ |

TABLE 3-continued

Compounds of the general formula (VI):

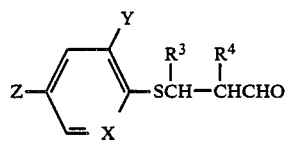

| X | Y | Z | R³ | R⁴ |
|---|---|---|----|----|
| CH | H | OCF₃ | H | H |
| CH | H | OCF₃ | CH₃ | H |
| CH | H | OCF₃ | H | CH₃ |
| CH | H | OCF₃ | CH₃ | CH₃ |
| CH | H | OCF₂CF₂H | H | H |
| CH | H | OCF₂CF₂H | CH₃ | H |
| CH | H | OCF₂CF₂H | H | CH₃ |
| CH | H | OCF₂CF₂H | CH₃ | CH₃ |
| N | H | CF₃ | H | H |
| N | H | CF₃ | CH₃ | H |
| N | H | CF₃ | H | CH₃ |
| N | H | CF₃ | CH₃ | CH₃ |
| N | Cl | CF₃ | H | H |
| N | Cl | CF₃ | CH₃ | H |
| N | Cl | CF₃ | H | CH₃ |
| N | Cl | CF₃ | CH₃ | CH₃ |

The compound represented by the general formula (VII) is produced by reacting 1 mole of the aldehyde compound (VI) with 1 to 1.1 moles of Wittig reagent represented by the formula,

in an inert solvent. The reaction temperature is from 0° C. to the boiling point of the solvent used, preferably from 0° C. to room temperature. The reaction solvent includes organic solvents such as diethyl ether, THF, benzene, toluene, chloroform, dichloromethane, ethyl acetate, etc., and preferably solvents of high solubility such as THF, chloroform, ethyl acetate, etc. are used. The reaction time is generally from 1 to 10 hours, and after completion of the reaction, the solvent is removed and the residue is extracted with a solvent such as hexane, ether, etc. The desired product thus extracted may be purified if necessary by recrystallization or column chromatography.

Examples of the compound of the general formula (VII) thus obtained are shown in Table 4.

TABLE 4

Compounds of the general formula (VII):

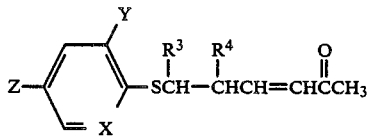

| X | Y | Z | R³ | R⁴ |
|---|---|---|----|----|
| CH | H | CF₃ | H | H |
| CH | H | CF₃ | CH₃ | H |
| CH | H | CF₃ | H | CH₃ |
| CH | H | CF₃ | CH₃ | CH₃ |
| CH | H | OCF₃ | H | H |
| CH | H | OCF₃ | CH₃ | H |
| CH | H | OCF₃ | H | CH₃ |
| CH | H | OCF₃ | CH₃ | CH₃ |
| CH | H | OCF₂CF₂H | H | H |
| CH | H | OCF₂CF₂H | CH₃ | H |

TABLE 4-continued

Compounds of the general formula (VII):

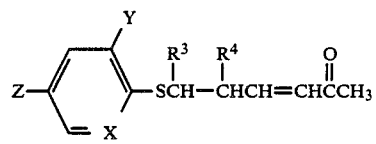

| X | Y | Z | R³ | R⁴ |
|---|---|---|----|----|
| CH | H | OCF₂CF₂H | H | CH₃ |
| CH | H | OCF₂CF₂H | CH₃ | CH₃ |
| N | H | CF₃ | H | H |
| N | H | CF₃ | CH₃ | H |
| N | H | CF₃ | H | CH₃ |
| N | H | CF₃ | CH₃ | CH₃ |
| N | Cl | CF₃ | H | H |
| N | Cl | CF₃ | CH₃ | H |
| N | Cl | CF₃ | H | CH₃ |
| N | Cl | CF₃ | CH₃ | CH₃ |

The compound represented by the general formula (IX) is produced by reacting 1 mole of the α,β-unsaturated ketone (VII) with 1 to 1.1 moles of dialkyl malonate in the presence of 1 mole of a metal alkoxide and in alcohol or a mixed solvent of alcohol and an inert solvent. The reaction temperature is generally the boiling point of the solvent used. The reaction solvent includes a mixed solvent of an alcohol (e.g. methanol, ethanol) with THF or dioxane and a mixed solvent of an alcohol with benzene or toluene, among which a mixed solvent of methanol with THF is preferably used. The reaction time is generally from 30 minutes to several hours. After completion of the reaction, the precipitated crystals are collected by filtration to obtain the desired compound as a metal salt.

Examples of the compound of the general formula (IX) thus obtained are shown in Table 5.

TABLE 5

Compounds of the general formula (IX):

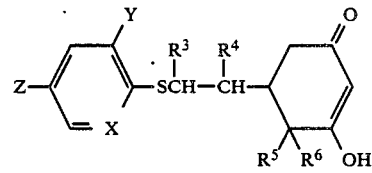

| X | Y | Z | R³ | R⁴ | R⁵ | R⁶ |
|---|---|---|----|----|----|----|
| CH | H | CF₃ | H | H | H | COOCH₃ |
| CH | H | CF₃ | H | CH₃ | H | COOC₂H₅ |
| CH | H | CF₃ | CH₃ | H | H | COOC₂H₅ |
| CH | H | CF₃ | CH₃ | CH₃ | H | COOC₂H₅ |
| CH | H | OCF₃ | H | H | H | COOC₂H₅ |
| CH | H | OCF₃ | CH₃ | H | H | COOC₂H₅ |
| CH | H | OCF₃ | H | CH₃ | H | COOCH₃ |
| CH | H | OCF₃ | CH₃ | CH₃ | H | COOCH₃ |
| CH | H | OCF₂CF₂H | H | H | H | COOCH₃ |
| CH | H | OCF₂CF₂H | CH₃ | H | H | COOCH₃ |
| CH | H | OCF₂CF₂H | H | CH₃ | H | COOCH₃ |
| CH | H | OCF₂CF₂H | CH₃ | CH₃ | H | COOCH₃ |
| N | H | CF₃ | H | H | H | COOCH₃ |
| N | H | CF₃ | CH₃ | H | H | COOCH₃ |
| N | H | CF₃ | H | CH₃ | H | COOCH₃ |
| N | H | CF₃ | CH₃ | CH₃ | H | COOCH₃ |
| N | Cl | CF₃ | H | H | H | COOCH₃ |
| N | Cl | CF₃ | CH₃ | H | H | COOC₂H₅ |
| N | Cl | CF₃ | H | CH₃ | H | COOC₂H₅ |
| N | Cl | CF₃ | CH₃ | CH₃ | H | COOC₂H₅ |
| CH | H | CF₃ | H. | H | CH₃ | COOC₂H₅ |
| CH | H | CF₃ | H | CH₃ | CH₃ | COOC₂H₅ |
| CH | H | CF₃ | CH₃ | H | CH₃ | COOC₂H₅ |

TABLE 5-continued

Compounds of the general formula (IX):

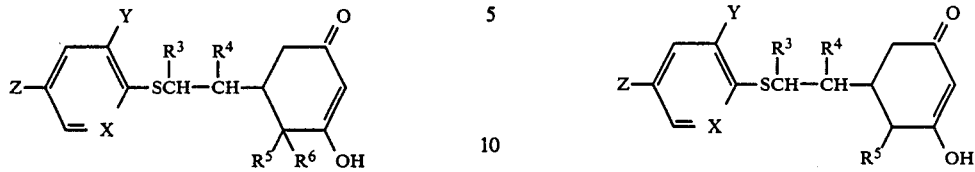

| X | Y | Z | R³ | R⁴ | R⁵ | R⁶ |
|---|---|---|---|---|---|---|
| CH | H | CF₃ | CH₃ | CH₃ | CH₃ | COOCH₃ |
| CH | H | OCF₃ | H | H | CH₃ | COOCH₃ |
| CH | H | OCF₃ | CH₃ | H | CH₃ | COOCH₃ |
| CH | H | OCF₃ | H | CH₃ | CH₃ | COOCH₃ |
| CH | H | OCF₃ | CH₃ | CH₃ | CH₃ | COOCH₃ |
| CH | H | OCF₂CF₂H | H | H | CH₃ | COOCH₃ |
| CH | H | OCF₂CF₂H | CH₃ | H | CH₃ | COOC₂H₅ |
| CH | H | OCF₂CF₂H | H | CH₃ | CH₃ | COOC₂H₅ |
| CH | H | OCF₂CF₂H | CH₃ | CH₃ | CH₃ | COOC₂H₅ |
| N | H | CF₃ | H | H | CH₃ | COOC₂H₅ |
| N | H | CF₃ | CH₃ | H | CH₃ | COOC₂H₅ |
| N | H | CF₃ | H | CH₃ | CH₃ | COOC₂H₅ |
| N | H | CF₃ | CH₃ | CH₃ | CH₃ | COOC₂H₅ |
| N | Cl | CF₃ | H | H | CH₃ | COOC₂H₅ |
| N | Cl | CF₃ | CH₃ | H | CH₃ | COOCH₃ |
| N | Cl | CF₃ | H | CH₃ | CH₃ | COOCH₃ |
| N | Cl | CF₃ | CH₃ | CH₃ | CH₃ | COOCH₃ |

The compound represented by the general formula (X) is obtained by hydrolyzing the metal salt of the compound represented by the general formula (IX) in water using from 1 to 5 equivalents of an alkali, followed by decarboxylation. The reaction temperature is generally from 90° to 100° C. The alkali used includes potassium hydroxide, sodium hydroxide, potassium carbonate, sodium carbonate, etc., and preferably, from 2 to 3 equivalents of sodium carbonate is used. The reaction time is from 1 to several hours. After completion of the reaction, the reaction solution is acidified with hydrochloric acid, and the separated oily product or precipitated crystals are extracted with an organic solvent or filtered off to obtain the desired product. The product may be purified if necessary by recrystallization or column chromatography.

Examples of the compound of the general formula (X) thus obtained are shown in Table 6.

TABLE 6

Compounds of the general formula (X):

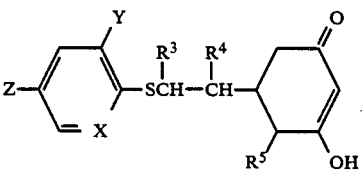

| X | Y | Z | R³ | R⁴ | R⁵ |
|---|---|---|---|---|---|
| CH | H | CF₃ | H | H | H |
| CH | H | CF₃ | CH₃ | H | H |
| CH | H | CF₃ | H | CH₃ | H |
| CH | H | CF₃ | CH₃ | CH₃ | H |

TABLE 6-continued

Compounds of the general formula (X):

| X | Y | Z | R³ | R⁴ | R⁵ |
|---|---|---|---|---|---|
| CH | H | OCF₃ | H | H | H |
| CH | H | OCF₃ | CH₃ | H | H |
| CH | H | OCF₃ | H | CH₃ | H |
| CH | H | OCF₃ | CH₃ | CH₃ | H |
| CH | H | OCF₂CF₂H | H | H | H |
| CH | H | OCF₂CF₂H | CH₃ | H | H |
| CH | H | OCF₂CF₂H | H | CH₃ | H |
| CH | H | OCF₂CF₂H | CH₃ | CH₃ | H |
| N | H | CF₃ | H | H | H |
| N | H | CF₃ | CH₃ | H | H |
| N | H | CF₃ | H | CH₃ | H |
| N | H | CF₃ | CH₃ | CH₃ | H |
| N | Cl | CF₃ | H | H | H |
| N | Cl | CF₃ | CH₃ | H | H |
| N | Cl | CF₃ | H | CH₃ | H |
| N | Cl | CF₃ | CH₃ | CH₃ | H |
| CH | H | CF₃ | H | H | CH₃ |
| CH | H | CF₃ | CH₃ | H | CH₃ |
| CH | H | CF₃ | H | CH₃ | CH₃ |
| CH | H | CF₃ | CH₃ | CH₃ | CH₃ |
| CH | H | OCF₃ | H | H | CH₃ |
| CH | H | OCF₃ | CH₃ | H | CH₃ |
| CH | H | OCF₃ | H | CH₃ | CH₃ |
| CH | H | OCF₃ | CH₃ | CH₃ | CH₃ |
| CH | H | OCF₂CF₂H | H | H | CH₃ |
| CH | H | OCF₂CF₂H | CH₃ | H | CH₃ |
| CH | H | OCF₂CF₂H | H | CH₃ | CH₃ |
| CH | H | OCF₂CF₂H | CH₃ | CH₃ | CH₃ |
| N | H | CF₃ | H | H | CH₃ |
| N | H | CF₃ | CH₃ | H | CH₃ |
| N | H | CF₃ | H | CH₃ | CH₃ |
| N | H | CF₃ | CH₃ | CH₃ | CH₃ |
| N | Cl | CF₃ | H | H | CH₃ |
| N | Cl | CF₃ | CH₃ | H | CH₃ |
| N | Cl | CF₃ | H | CH₃ | CH₃ |
| N | Cl | CF₃ | CH₃ | CH₃ | CH₃ |

The compound represented by the general formula (XII) is produced by reacting 1 mole of the compound represented by the general formula (IX) or (X) with 1 to 1.1 moles of the acid chloride (XI) in an inert solvent in the presence of 1 to 1.1 moles of a base. The reaction temperature is from 0° C. to room temperature, and the solvent includes organic solvents such as ethers (e.g. diethyl ether, THF, dioxane), benzene, toluene, ethyl acetate, acetone, acetonitrile, etc., among which the ethers are preferably used. The base includes organic bases such as triethylamine, pyridine, N,N-diethylaniline, etc. The reaction time is from 30 minutes to several hours. After completion of the reaction, water is added to the reaction solution which is then extracted with an organic solvent to obtain the desired product. The product may be purified if necessary by recrystallization or column chromatography.

Examples of the compound of the general formula (XII) thus obtained are shown in Table 7.

TABLE 7

Compounds of the general formula (XII):

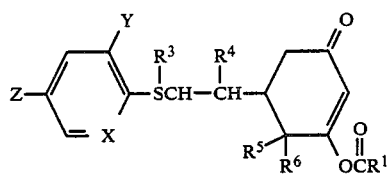

| X | Y | Z | R³ | R⁴ | R¹ | R⁵ | R⁶ |
|---|---|---|---|---|---|---|---|
| CH | H | CF₃ | H | H | H | H | H |
| CH | H | CF₃ | H | H | CH₃ | H | H |
| CH | H | CF₃ | H | H | C₂H₅ | H | H |
| CH | H | CF₃ | H | H | n-C₃H₇ | H | H |
| CH | H | CF₃ | H | H | —CH(CH₃)₂ | H | H |
| CH | H | CF₃ | H | H | —CH₂CH(CH₃)₂ | H | H |
| CH | H | CF₃ | H | H | CH₂OCH₃ | H | H |
| CH | H | CF₃ | CH₃ | H | CH₃ | H | H |
| CH | H | CF₃ | CH₃ | H | C₂H₅ | H | H |
| CH | H | CF₃ | CH₃ | H | n-C₃H₇ | H | H |
| CH | H | CF₃ | CH₃ | H | —CH(CH₃)₂ | H | H |
| CH | H | CF₃ | CH₃ | H | —CH₂CH(CH₃)₂ | H | H |
| CH | H | CF₃ | CH₃ | H | CH₂OCH₃ | H | H |
| CH | H | CF₃ | CH₃ | H | H | H | H |
| CH | H | CF₃ | H | CH₃ | CH₃ | H | H |
| CH | H | CF₃ | H | CH₃ | C₂H₅ | H | H |
| CH | H | CF₃ | H | CH₃ | n-C₃H₇ | H | H |
| CH | H | CF₃ | H | CH₃ | —CH(CH₃)₂ | H | H |
| CH | H | CF₃ | H | CH₃ | —CH₂CH(CH₃)₂ | H | H |
| CH | H | CF₃ | H | CH₃ | CH₂OCH₃ | H | H |
| CH | H | CF₃ | H | CH₃ | H | H | H |
| CH | H | CF₃ | CH₃ | CH₃ | CH₃ | H | H |
| CH | H | OCF₃ | H | H | CH₃ | H | H |
| CH | H | OCF₃ | H | H | C₂H₅ | H | H |
| CH | H | OCF₃ | H | H | n-C₃H₇ | H | H |
| CH | H | OCF₃ | H | H | —CH(CH₃)₂ | H | H |
| CH | H | OCF₃ | H | H | —CH₂CH(CH₃)₂ | H | H |
| CH | H | OCF₃ | H | H | CH₂OCH₃ | H | H |
| CH | H | OCF₃ | CH₃ | H | CH₃ | H | H |
| CH | H | OCF₃ | CH₃ | H | C₂H₅ | H | H |
| CH | H | OCF₃ | CH₃ | H | n-C₃H₇ | H | H |
| CH | H | OCF₃ | CH₃ | H | —CH(CH₃)₂ | H | H |
| CH | H | OCF₃ | CH₃ | H | —CH₂CH(CH₃)₂ | H | H |
| CH | H | OCF₃ | CH₃ | H | CH₂OCH₃ | H | H |
| CH | H | OCF₃ | H | CH₃ | CH₃ | H | H |
| CH | H | OCF₃ | H | CH₃ | C₂H₅ | H | H |
| CH | H | OCF₃ | H | CH₃ | n-C₃H₇ | H | H |
| CH | H | OCF₃ | H | CH₃ | —CH(CH₃)₂ | H | H |
| CH | H | OCF₃ | H | CH₃ | —CH₂CH(CH₃)₂ | H | H |
| CH | H | OCF₃ | H | CH₃ | CH₂OCH₃ | H | H |
| CH | H | OCF₂CF₂H | H | H | CH₃ | H | H |
| CH | H | OCF₂CF₂H | H | H | C₂H₅ | H | H |
| CH | H | OCF₂CF₂H | H | H | n-C₃H₇ | H | H |
| CH | H | OCF₂CF₂H | H | H | —CH(CH₃)₂ | H | H |
| CH | H | OCF₂CF₂H | H | H | —CH₂CH(CH₃)₂ | H | H |
| CH | H | OCF₂CF₂H | H | H | CH₂OCH₃ | H | H |
| CH | H | OCF₂CF₂H | CH₃ | H | CH₃ | H | H |
| CH | H | OCF₂CF₂H | CH₃ | H | C₂H₅ | H | H |
| CH | H | OCF₂CF₂H | CH₃ | H | n-C₃H₇ | H | H |
| CH | H | OCF₂CF₂H | CH₃ | H | —CH(CH₃)₂ | H | H |
| CH | H | OCF₂CF₂H | CH₃ | H | —CH₂CH(CH₃)₂ | H | H |
| CH | H | OCF₂CF₂H | CH₃ | H | CH₂OCH₃ | H | H |
| CH | H | OCF₂CF₂H | H | CH₃ | CH₃ | H | H |
| CH | H | OCF₂CF₂H | H | CH₃ | C₂H₅ | H | H |
| CH | H | OCF₂CF₂H | H | CH₃ | n-C₃H₇ | H | H |
| CH | H | OCF₂CF₂H | H | CH₃ | —CH(CH₃)₂ | H | H |
| CH | H | OCF₂CF₂H | H | CH₃ | —CH₂CH(CH₃)₂ | H | H |
| CH | H | OCF₂CF₂H | H | CH₃ | CH₂OCH₃ | H | H |
| N | H | CF₃ | H | H | CH₃ | H | H |
| N | H | CF₃ | H | H | C₂H₅ | H | H |
| N | H | CF₃ | H | H | n-C₃H₇ | H | H |
| N | H | CF₃ | H | H | —CH(CH₃)₂ | H | H |
| N | H | CF₃ | H | H | —CH₂CH(CH₃)₂ | H | H |
| N | H | CF₃ | H | H | CH₂OCH₃ | H | H |
| N | H | CF₃ | H | H | H | H | H |
| N | H | CF₃ | CH₃ | H | CH₃ | H | H |
| N | H | CF₃ | CH₃ | H | C₂H₅ | H | H |
| N | H | CF₃ | CH₃ | H | n-C₃H₇ | H | H |
| N | H | CF₃ | CH₃ | H | —CH(CH₃)₂ | H | H |
| N | H | CF₃ | CH₃ | H | —CH₂CH(CH₃)₂ | H | H |

TABLE 7-continued

Compounds of the general formula (XII):

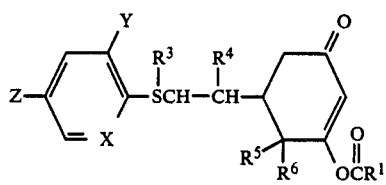

| X | Y | Z | R³ | R⁴ | R¹ | R⁵ | R⁶ |
|---|---|---|---|---|---|---|---|
| N | H | CF₃ | CH₃ | H | CH₂OCH₃ | H | H |
| N | H | CF₃ | H | CH₃ | CH₃ | H | H |
| N | H | CF₃ | H | CH₃ | C₂H₅ | H | H |
| N | H | CF₃ | H | CH₃ | n-C₃H₇ | H | H |
| N | H | CF₃ | H | CH₃ | —CH(CH₃)₂ | H | H |
| N | H | CF₃ | H | CH₃ | —CH₂CH(CH₃)₂ | H | H |
| N | H | CF₃ | H | CH₃ | CH₂OCH₃ | H | H |
| N | Cl | CF₃ | H | H | CH₃ | H | H |
| N | Cl | CF₃ | H | H | C₂H₅ | H | H |
| N | Cl | CF₃ | H | H | n-C₃H₇ | H | H |
| N | Cl | CF₃ | H | H | —CH(CH₃)₂ | H | H |
| N | Cl | CF₃ | H | H | —CH₂CH(CH₃)₂ | H | H |
| N | Cl | CF₃ | H | H | CH₂OCH₃ | H | H |
| N | Cl | CF₃ | CH₃ | H | CH₃ | H | H |
| N | Cl | CF₃ | CH₃ | H | C₂H₅ | H | H |
| N | Cl | CF₃ | CH₃ | H | n-C₃H₇ | H | H |
| N | Cl | CF₃ | CH₃ | H | —CH(CH₃)₂ | H | H |
| N | Cl | CF₃ | CH₃ | H | —CH₂CH(CH₃)₂ | H | H |
| N | Cl | CF₃ | CH₃ | H | CH₂OCH₃ | H | H |
| N | H | CF₃ | CH₃ | CH₃ | CH₃ | H | H |
| N | H | CF₃ | CH₃ | CH₃ | C₂H₅ | H | H |
| CH | H | CF₃ | CH₃ | CH₃ | CH₃ | H | H |
| CH | H | CF₃ | CH₃ | CH₃ | C₂H₅ | H | H |
| N | Cl | CF₃ | H | CH₃ | CH₃ | H | H |
| N | Cl | CF₃ | H | CH₃ | C₂H₅ | H | H |
| N | Cl | CF₃ | H | CH₃ | n-C₃H₇ | H | H |
| N | Cl | CF₃ | H | CH₃ | —CH(CH₃)₂ | H | H |
| N | Cl | CF₃ | H | CH₃ | —CH₂CH(CH₃)₂ | H | H |
| N | Cl | CF₃ | H | CH₃ | CH₂OCH₃ | H | H |
| CH | H | CF₃ | H | H | H | CH₃ | H |
| CH | H | CF₃ | H | H | CH₃ | CH₃ | H |
| CH | H | CF₃ | H | H | C₂H₅ | CH₃ | H |
| CH | H | CF₃ | H | H | n-C₃H₇ | CH₃ | H |
| CH | H | CF₃ | H | H | —CH(CH₃)₂ | CH₃ | H |
| CH | H | CF₃ | H | H | —CH₂CH(CH₃)₂ | CH₃ | H |
| CH | H | CF₃ | H | H | CH₂OCH₃ | CH₃ | H |
| CH | H | CF₃ | CH₃ | H | CH₃ | CH₃ | H |
| CH | H | CF₃ | CH₃ | H | C₂H₅ | CH₃ | H |
| CH | H | CF₃ | CH₃ | H | n-C₃H₇ | CH₃ | H |
| CH | H | CF₃ | CH₃ | H | —CH(CH₃)₂ | CH₃ | H |
| CH | H | CF₃ | CH₃ | H | —CH₂CH(CH₃)₂ | CH₃ | H |
| CH | H | CF₃ | CH₃ | H | CH₂OCH₃ | CH₃ | H |
| CH | H | CF₃ | H | CH₃ | CH₃ | CH₃ | H |
| CH | H | CF₃ | H | CH₃ | C₂H₅ | CH₃ | H |
| CH | H | CF₃ | H | CH₃ | n-C₃H₇ | CH₃ | H |
| CH | H | CF₃ | H | CH₃ | —CH(CH₃)₂ | CH₃ | H |
| CH | H | CF₃ | H | CH₃ | —CH₂CH(CH₃)₂ | CH₃ | H |
| CH | H | CF₃ | H | CH₃ | CH₂OCH₃ | CH₃ | H |
| CH | H | CF₃ | CH₃ | CH₃ | CH₃ | CH₃ | H |
| CH | H | OCF₃ | H | H | CH₃ | CH₃ | H |
| CH | H | OCF₃ | H | H | C₂H₅ | CH₃ | H |
| CH | H | OCF₃ | H | H | n-C₃H₇ | CH₃ | H |
| CH | H | OCF₃ | H | H | —CH(CH₃)₂ | CH₃ | H |
| CH | H | OCF₃ | H | H | —CH₂CH(CH₃)₂ | CH₃ | H |
| CH | H | OCF₃ | H | H | CH₂OCH₃ | CH₃ | H |
| CH | H | OCF₃ | CH₃ | H | CH₃ | CH₃ | H |
| CH | H | OCF₃ | CH₃ | H | C₂H₅ | CH₃ | H |
| CH | H | OCF₃ | CH₃ | H | n-C₃H₇ | CH₃ | H |
| CH | H | OCF₃ | CH₃ | H | —CH(CH₃)₂ | CH₃ | H |
| CH | H | OCF₃ | CH₃ | H | —CH₂CH(CH₃)₂ | CH₃ | H |
| CH | H | OCF₃ | CH₃ | H | CH₂OCH₃ | CH₃ | H |
| CH | H | OCF₃ | H | CH₃ | CH₃ | CH₃ | H |
| CH | H | OCF₃ | H | CH₃ | C₂H₅ | CH₃ | H |
| CH | H | OCF₃ | H | CH₃ | n-C₃H₇ | CH₃ | H |
| CH | H | OCF₃ | H | CH₃ | —CH(CH₃)₂ | CH₃ | H |
| CH | H | OCF₃ | H | CH₃ | —CH₂CH(CH₃)₂ | CH₃ | H |
| CH | H | OCF₃ | H | CH₃ | CH₂OCH₃ | CH₃ | H |
| CH | H | OCF₂CF₂H | H | H | CH₃ | CH₃ | H |
| CH | H | OCF₂CF₂H | H | H | C₂H₅ | CH₃ | H |
| CH | H | OCF₂CF₂H | H | H | n-C₃H₇ | CH₃ | H |

TABLE 7-continued

Compounds of the general formula (XII):

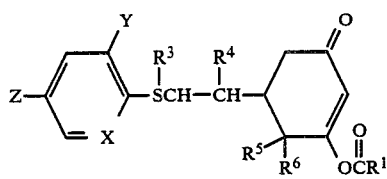

| X | Y | Z | R³ | R⁴ | R¹ | R⁵ | R⁶ |
|---|---|---|---|---|---|---|---|
| CH | H | OCF₂CF₂H | H | H | —CH(CH₃)₂ | CH₃ | H |
| CH | H | OCF₂CF₂H | H | H | —CH₂CH(CH₃)₂ | CH₃ | H |
| CH | H | OCF₂CF₂H | H | H | CH₂OCH₃ | CH₃ | H |
| CH | H | OCF₂CF₂H | CH₃ | H | CH₃ | CH₃ | H |
| CH | H | OCF₂CF₂H | CH₃ | H | C₂H₅ | CH₃ | H |
| CH | H | OCF₂CF₂H | CH₃ | H | n-C₃H₇ | CH₃ | H |
| CH | H | OCF₂CF₂H | CH₃ | H | —CH(CH₃)₂ | CH₃ | H |
| CH | H | OCF₂CF₂H | CH₃ | H | —CH₂CH(CH₃)₂ | CH₃ | H |
| CH | H | OCF₂CF₂H | CH₃ | H | CH₂OCH₃ | CH₃ | H |
| CH | H | OCF₂CF₂H | H | CH₃ | CH₃ | CH₃ | H |
| CH | H | OCF₂CF₂H | H | CH₃ | C₂H₅ | CH₃ | H |
| CH | H | OCF₂CF₂H | H | CH₃ | n-C₃H₇ | CH₃ | H |
| CH | H | OCF₂CF₂H | H | CH₃ | —CH(CH₃)₂ | CH₃ | H |
| CH | H | OCF₂CF₂H | H | CH₃ | —CH₂CH(CH₃)₂ | CH₃ | H |
| CH | H | OCF₂CF₂H | H | CH₃ | CH₂OCH₃ | CH₃ | H |
| N | H | CF₃ | H | H | CH₃ | CH₃ | H |
| N | H | CF₃ | H | H | C₂H₅ | CH₃ | H |
| N | H | CF₃ | H | H | n-C₃H₇ | CH₃ | H |
| N | H | CF₃ | H | H | —CH(CH₃)₂ | CH₃ | H |
| N | H | CF₃ | H | H | —CH₂CH(CH₃)₂ | CH₃ | H |
| N | H | CF₃ | H | H | CH₂OCH₃ | CH₃ | H |
| N | H | CF₃ | H | H | H | CH₃ | H |
| N | H | CF₃ | CH₃ | H | CH₃ | CH₃ | H |
| N | H | CF₃ | CH₃ | H | C₂H₅ | CH₃ | H |
| N | H | CF₃ | CH₃ | H | n-C₃H₇ | CH₃ | H |
| N | H | CF₃ | CH₃ | H | —CH(CH₃)₂ | CH₃ | H |
| N | H | CF₃ | CH₃ | H | —CH₂CH(CH₃)₂ | CH₃ | H |
| N | H | CF₃ | CH₃ | H | CH₂OCH₃ | CH₃ | H |
| N | H | CF₃ | H | CH₃ | CH₃ | CH₃ | H |
| N | H | CF₃ | H | CH₃ | C₂H₅ | CH₃ | H |
| N | H | CF₃ | H | CH₃ | n-C₃H₇ | CH₃ | H |
| N | H | CF₃ | H | CH₃ | —CH(CH₃)₂ | CH₃ | H |
| N | H | CF₃ | H | CH₃ | —CH₂CH(CH₃)₂ | CH₃ | H |
| N | H | CF₃ | H | CH₃ | CH₂OCH₃ | CH₃ | H |
| N | Cl | CF₃ | H | H | CH₃ | CH₃ | H |
| N | Cl | CF₃ | H | H | C₂H₅ | CH₃ | H |
| N | Cl | CF₃ | H | H | n-C₃H₇ | CH₃ | H |
| N | Cl | CF₃ | H | H | —CH(CH₃)₂ | CH₃ | H |
| N | Cl | CF₃ | H | H | —CH₂CH(CH₃)₂ | CH₃ | H |
| N | Cl | CF₃ | H | H | CH₂OCH₃ | CH₃ | H |
| N | Cl | CF₃ | CH₃ | H | CH₃ | CH₃ | H |
| N | Cl | CF₃ | CH₃ | H | C₂H₅ | CH₃ | H |
| N | Cl | CF₃ | CH₃ | H | n-C₃H₇ | CH₃ | H |
| N | Cl | CF₃ | CH₃ | H | —CH(CH₃)₂ | CH₃ | H |
| N | Cl | CF₃ | CH₃ | H | —CH₂CH(CH₃)₂ | CH₃ | H |
| N | Cl | CF₃ | CH₃ | H | CH₂OCH₃ | CH₃ | H |
| N | H | CF₃ | CH₃ | CH₃ | CH₃ | CH₃ | H |
| N | H | CF₃ | CH₃ | CH₃ | C₂H₅ | CH₃ | H |
| CH | H | CF₃ | CH₃ | CH₃ | CH₃ | CH₃ | H |
| CH | H | CF₃ | CH₃ | CH₃ | C₂H₅ | CH₃ | H |
| N | Cl | CF₃ | H | CH₃ | CH₃ | CH₃ | H |
| N | Cl | CF₃ | H | CH₃ | C₂H₅ | CH₃ | H |
| N | Cl | CF₃ | H | CH₃ | n-C₃H₇ | CH₃ | H |
| N | Cl | CF₃ | H | CH₃ | —CH(CH₃)₂ | CH₃ | H |
| N | Cl | CF₃ | H | CH₃ | —CH₂CH(CH₃)₂ | CH₃ | H |
| N | Cl | CF₃ | H | CH₃ | CH₂OCH₃ | CH₃ | H |
| CH | H | CF₃ | H | H | CH₃ | H | COOCH₃ |
| CH | H | CF₃ | H | H | C₂H₅ | H | COOC₂H₅ |
| CH | H | CF₃ | H | H | n-C₃H₇ | H | COOC₂H₅ |
| CH | H | CF₃ | H | H | —CH(CH₃)₂ | H | COOC₂H₅ |
| CH | H | CF₃ | H | H | —CH₂CH(CH₃)₂ | H | COOCH₃ |
| CH | H | CF₃ | H | H | CH₂OCH₃ | H | COOCH₃ |
| CH | H | CF₃ | H | H | H | H | COOCH₃ |
| CH | H | CF₃ | CH₃ | H | CH₃ | H | COOCH₃ |
| CH | H | CF₃ | CH₃ | H | C₂H₅ | H | COOCH₃ |
| CH | H | CF₃ | CH₃ | H | n-C₃H₇ | H | COOCH₃ |
| CH | H | CF₃ | CH₃ | H | —CH(CH₃)₂ | H | COOCH₃ |
| CH | H | CF₃ | CH₃ | H | —CH₂CH(CH₃)₂ | H | COOCH₃ |
| CH | H | CF₃ | CH₃ | H | CH₂OCH₃ | H | COOCH₃ |
| CH | H | CF₃ | H | CH₃ | CH₃ | H | COOCH₃ |

TABLE 7-continued

Compounds of the general formula (XII):

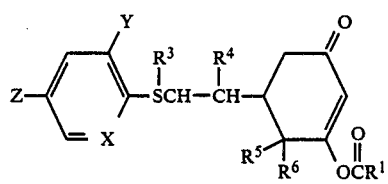

| X | Y | Z | R³ | R⁴ | R¹ | R⁵ | R⁶ |
|---|---|---|---|---|---|---|---|
| CH | H | CF₃ | H | CH₃ | C₂H₅ | H | COOCH₃ |
| CH | H | CF₃ | H | CH₃ | n-C₃H₇ | H | COOCH₃ |
| CH | H | CF₃ | H | CH₃ | —CH(CH₃)₂ | H | COOCH₃ |
| CH | H | CF₃ | H | CH₃ | —CH₂CH(CH₃)₂ | H | COOCH₃ |
| CH | H | CF₃ | H | CH₃ | CH₂OCH₃ | H | COOCH₃ |
| CH | H | OCF₃ | H | H | CH₃ | H | COOCH₃ |
| CH | H | OCF₃ | H | H | C₂H₅ | H | COOCH₃ |
| CH | H | OCF₃ | H | H | n-C₃H₇ | H | COOCH₃ |
| CH | H | OCF₃ | H | H | —CH(CH₃)₂ | H | COOCH₃ |
| CH | H | OCF₃ | H | H | —CH₂CH(CH₃)₂ | H | COOCH₃ |
| CH | H | OCF₃ | H | H | CH₂OCH₃ | H | COOCH₃ |
| CH | H | OCF₃ | CH₃ | H | CH₃ | H | COOCH₃ |
| CH | H | OCF₃ | CH₃ | H | C₂H₅ | H | COOCH₃ |
| CH | H | OCF₃ | CH₃ | H | n-C₃H₇ | H | COOCH₃ |
| CH | H | OCF₃ | CH₃ | H | —CH(CH₃)₂ | H | COOCH₃ |
| CH | H | OCF₃ | CH₃ | H | —CH₂CH(CH₃)₂ | H | COOCH₃ |
| CH | H | OCF₃ | CH₃ | H | CH₂OCH₃ | H | COOCH₃ |
| CH | H | OCF₃ | H | CH₃ | CH₃ | H | COOCH₃ |
| CH | H | OCF₃ | H | CH₃ | C₂H₅ | H | COOCH₃ |
| CH | H | OCF₃ | H | CH₃ | n-C₃H₇ | H | COOCH₃ |
| CH | H | OCF₃ | H | CH₃ | —CH(CH₃)₂ | H | COOCH₃ |
| CH | H | OCF₃ | H | CH₃ | —CH₂CH(CH₃)₂ | H | COOCH₃ |
| CH | H | OCF₃ | H | CH₃ | CH₂OCH₃ | H | COOCH₃ |
| CH | H | OCF₂CF₂H | H | H | CH₃ | H | COOCH₃ |
| CH | H | OCF₂CF₂H | H | H | C₂H₅ | H | COOCH₃ |
| CH | H | OCF₂CF₂H | H | H | n-C₃H₇ | H | COOCH₃ |
| CH | H | OCF₂CF₂H | H | H | —CH(CH₃)₂ | H | COOCH₃ |
| CH | H | OCF₂CF₂H | H | H | —CH₂CH(CH₃)₂ | H | COOCH₃ |
| CH | H | OCF₂CF₂H | H | H | CH₂OCH₃ | H | COOCH₃ |
| CH | H | OCF₂CF₂H | CH₃ | H | CH₃ | H | COOCH₃ |
| CH | H | OCF₂CF₂H | CH₃ | H | C₂H₅ | H | COOCH₃ |
| CH | H | OCF₂CF₂H | CH₃ | H | n-C₃H₇ | H | COOCH₃ |
| CH | H | OCF₂CF₂H | CH₃ | H | —CH(CH₃)₂ | H | COOCH₃ |
| CH | H | OCF₂CF₂H | CH₃ | H | —CH₂CH(CH₃)₂ | H | COOCH₃ |
| CH | H | OCF₂CF₂H | CH₃ | H | CH₂OCH₃ | H | COOCH₃ |
| CH | H | OCF₂CF₂H | H | CH₃ | CH₃ | H | COOCH₃ |
| CH | H | OCF₂CF₂H | H | CH₃ | C₂H₅ | H | COOCH₃ |
| CH | H | OCF₂CF₂H | H | CH₃ | n-C₃H₇ | H | COOCH₃ |
| CH | H | OCF₂CF₂H | H | CH₃ | —CH(CH₃)₂ | H | COOCH₃ |
| CH | H | OCF₂CF₂H | H | CH₃ | —CH₂CH(CH₃)₂ | H | COOCH₃ |
| CH | H | OCF₂CF₂H | H | CH₃ | CH₂OCH₃ | H | COOCH₃ |
| N | H | CF₃ | H | H | CH₃ | H | COOC₂H₅ |
| N | H | CF₃ | H | H | C₂H₅ | H | COOCH₃ |
| N | H | CF₃ | H | H | n-C₃H₇ | H | COOCH₃ |
| N | H | CF₃ | H | H | —CH(CH₃)₂ | H | COOC₂H₅ |
| N | H | CF₃ | H | H | —CH₂CH(CH₃)₂ | H | COOC₂H₅ |
| N | H | CF₃ | H | H | CH₂OCH₃ | H | COOC₂H₅ |
| N | H | CF₃ | CH₃ | H | CH₃ | H | COOC₂H₅ |
| N | H | CF₃ | CH₃ | H | C₂H₅ | H | COOC₂H₅ |
| N | H | CF₃ | CH₃ | H | n-C₃H₇ | H | COOC₂H₅ |
| N | H | CF₃ | CH₃ | H | —CH(CH₃)₂ | H | COOC₂H₅ |
| N | H | CF₃ | CH₃ | H | —CH₂CH(CH₃)₂ | H | COOC₂H₅ |
| N | H | CF₃ | CH₃ | H | CH₂OCH₃ | H | COOC₂H₅ |
| N | H | CF₃ | H | CH₃ | CH₃ | H | COOC₂H₅ |
| N | H | CF₃ | H | CH₃ | C₂H₅ | H | COOC₂H₅ |
| N | H | CF₃ | H | CH₃ | n-C₃H₇ | H | COOC₂H₅ |
| N | H | CF₃ | H | CH₃ | —CH(CH₃)₂ | H | COOC₂H₅ |
| N | H | CF₃ | H | CH₃ | —CH₂CH(CH₃)₂ | H | COOC₂H₅ |
| N | H | CF₃ | H | CH₃ | CH₂OCH₃ | H | COOC₂H₅ |
| N | H | CF₃ | H | H | H | H | COOC₂H₅ |
| N | Cl | CF₃ | H | H | CH₃ | H | COOC₂H₅ |
| N | Cl | CF₃ | H | H | C₂H₅ | H | COOC₂H₅ |
| N | Cl | CF₃ | H | H | n-C₃H₇ | H | COOC₂H₅ |
| N | Cl | CF₃ | H | H | —CH(CH₃)₂ | H | COOC₂H₅ |
| N | Cl | CF₃ | H | H | —CH₂CH(CH₃)₂ | H | COOC₂H₅ |
| N | Cl | CF₃ | H | H | CH₂OCH₃ | H | COOC₂H₅ |
| N | Cl | CF₃ | CH₃ | H | CH₃ | H | COOC₂H₅ |
| N | Cl | CF₃ | CH₃ | H | C₂H₅ | H | COOC₂H₅ |
| N | Cl | CF₃ | CH₃ | H | n-C₃H₇ | H | COOC₂H₅ |
| N | Cl | CF₃ | CH₃ | H | —CH(CH₃)₂ | H | COOC₂H₅ |

TABLE 7-continued

Compounds of the general formula (XII):

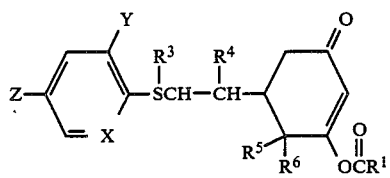

| X | Y | Z | R³ | R⁴ | R¹ | R⁵ | R⁶ |
|---|---|---|----|----|-----|----|----|
| N | Cl | CF₃ | CH₃ | H | —CH₂CH(CH₃)₂ | H | COOC₂H₅ |
| N | Cl | CF₃ | CH₃ | H | CH₂OCH₃ | H | COOC₂H₅ |
| N | H | CF₃ | CH₃ | CH₃ | CH₃ | H | COOC₂H₅ |
| N | H | CF₃ | CH₃ | CH₃ | C₂H₅ | H | COOC₂H₅ |
| CH | H | CF₃ | CH₃ | CH₃ | CH₃ | H | COOC₂H₅ |
| CH | H | CF₃ | CH₃ | CH₃ | C₂H₅ | H | COOC₂H₅ |
| N | Cl | CF₃ | H | CH₃ | CH₃ | H | COOC₂H₅ |
| N | Cl | CF₃ | H | CH₃ | C₂H₅ | H | COOC₂H₅ |
| N | Cl | CF₃ | H | CH₃ | n-C₃H₇ | H | COOC₂H₅ |
| N | Cl | CF₃ | H | CH₃ | —CH(CH₃)₂ | H | COOC₂H₅ |
| N | Cl | CF₃ | H | CH₃ | —CH₂CH(CH₃)₂ | H | COOC₂H₅ |
| N | Cl | CF₃ | H | CH₃ | CH₂OCH₃ | H | COOC₂H₅ |

The compound represented by the general formula (II)′ is obtained by heating the compound represented by the general formula (XII) in the presence of a catalyst. The reaction temperature is from 50° to 150° C., preferably in the vicinity of 100° C. For the solvent, organic solvents such as THF, chloroform, acetonitrile, benzene, toluene, etc. are used. The catalyst includes Lewis acis (e.g. zinc chloride), bases (e.g. 4-dimethylaminopyridine) and acids (e.g. trifluoromethanesulfonic acid), among which the bases are preferably used. The reaction generally comes to an end in several hours. After completion of the reaction, the reaction solution is poured into water, acidified and then extracted with an organic solvent to obtain the desired product. This product may be purified if necessary by recrystallization or column chromatography.

Examples of the compound of the general formula (II)′ thus obtained are shown in Table 8.

TABLE 8

Compounds of the general formula (II)′:

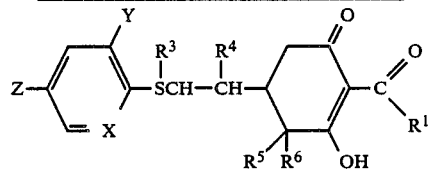

| X | Y | Z | R³ | R⁴ | R¹ | R⁵ | R⁶ |
|---|---|---|----|----|-----|----|----|
| CH | H | CF₃ | H | H | CH₃ | H | H |
| CH | H | CF₃ | H | H | C₂H₅ | H | H |
| CH | H | CF₃ | H | H | n-C₃H₇ | H | H |
| CH | H | CF₃ | H | H | —CH(CH₃)₂ | H | H |
| CH | H | CF₃ | H | H | —CH₂CH(CH₃)₂ | H | H |
| CH | H | CF₃ | H | H | CH₂OCH₃ | H | H |
| CH | H | CF₃ | H | H | H | H | H |
| CH | H | CF₃ | CH₃ | H | CH₃ | H | H |
| CH | H | CF₃ | CH₃ | H | C₂H₅ | H | H |
| CH | H | CF₃ | CH₃ | H | n-C₃H₇ | H | H |
| CH | H | CF₃ | CH₃ | H | —CH(CH₃)₂ | H | H |
| CH | H | CF₃ | CH₃ | H | —CH₂CH(CH₃)₂ | H | H |
| CH | H | CF₃ | CH₃ | H | CH₂OCH₃ | H | H |
| CH | H | CF₃ | CH₃ | H | H | H | H |
| CH | H | CF₃ | H | CH₃ | CH₃ | H | H |
| CH | H | CF₃ | H | CH₃ | C₂H₅ | H | H |
| CH | H | CF₃ | H | CH₃ | n-C₃H₇ | H | H |
| CH | H | CF₃ | H | CH₃ | —CH(CH₃)₂ | H | H |
| CH | H | CF₃ | H | CH₃ | —CH₂CH(CH₃)₂ | H | H |
| CH | H | CF₃ | H | CH₃ | CH₂OCH₃ | H | H |
| CH | H | CF₃ | H | CH₃ | H | H | H |
| CH | H | CF₃ | CH₃ | CH₃ | CH₃ | H | H |
| CH | H | OCF₃ | H | H | CH₃ | H | H |
| CH | H | OCF₃ | H | H | C₂H₅ | H | H |
| CH | H | OCF₃ | H | H | n-C₃H₇ | H | H |
| CH | H | OCF₃ | H | H | —CH(CH₃)₂ | H | H |
| CH | H | OCF₃ | H | H | —CH₂CH(CH₃)₂ | H | H |
| CH | H | OCF₃ | H | H | CH₂OCH₃ | H | H |
| CH | H | OCF₃ | CH₃ | H | CH₃ | H | H |
| CH | H | OCF₃ | CH₃ | H | C₂H₅ | H | H |
| CH | H | OCF₃ | CH₃ | H | n-C₃H₇ | H | H |

TABLE 8-continued

Compounds of the general formula (II)':

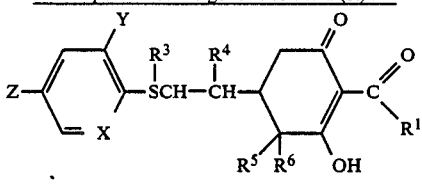

| X | Y | Z | $R^3$ | $R^4$ | $R^1$ | $R^5$ | $R^6$ |
|---|---|---|---|---|---|---|---|
| CH | H | $OCF_3$ | $CH_3$ | H | $-CH(CH_3)_2$ | H | H |
| CH | H | $OCF_3$ | $CH_3$ | H | $-CH_2CH(CH_3)_2$ | H | H |
| CH | H | $OCF_3$ | $CH_3$ | H | $CH_2OCH_3$ | H | H |
| CH | H | $OCF_3$ | H | $CH_3$ | $CH_3$ | H | H |
| CH | H | $OCF_3$ | H | $CH_3$ | $C_2H_5$ | H | H |
| CH | H | $OCF_3$ | H | $CH_3$ | $n-C_3H_7$ | H | H |
| CH | H | $OCF_3$ | H | $CH_3$ | $-CH(CH_3)_2$ | H | H |
| CH | H | $OCF_3$ | H | $CH_3$ | $-CH_2CH(CH_3)_2$ | H | H |
| CH | H | $OCF_3$ | H | $CH_3$ | $CH_2OCH_3$ | H | H |
| CH | H | $OCF_2CF_2H$ | H | H | $CH_3$ | H | H |
| CH | H | $OCF_2CF_2H$ | H | H | $C_2H_5$ | H | H |
| CH | H | $OCF_2CF_2H$ | H | H | $n-C_3H_7$ | H | H |
| CH | H | $OCF_2CF_2H$ | H | H | $-CH(CH_3)_2$ | H | H |
| CH | H | $OCF_2CF_2H$ | H | H | $-CH_2CH(CH_3)_2$ | H | H |
| CH | H | $OCF_2CF_2H$ | H | H | $CH_2OCH_3$ | H | H |
| CH | H | $OCF_2CF_2H$ | $CH_3$ | H | $CH_3$ | H | H |
| CH | H | $OCF_2CF_2H$ | $CH_3$ | H | $C_2H_5$ | H | H |
| CH | H | $OCF_2CF_2H$ | $CH_3$ | H | $n-C_3H_7$ | H | H |
| CH | H | $OCF_2CF_2H$ | $CH_3$ | H | $-CH(CH_3)_2$ | H | H |
| CH | H | $OCF_2CF_2H$ | $CH_3$ | H | $-CH_2CH(CH_3)_2$ | H | H |
| CH | H | $OCF_2CF_2H$ | $CH_3$ | H | $CH_2OCH_3$ | H | H |
| CH | H | $OCF_2CF_2H$ | H | $CH_3$ | $CH_3$ | H | H |
| CH | H | $OCF_2CF_2H$ | H | $CH_3$ | $C_2H_5$ | H | H |
| CH | H | $OCF_2CF_2H$ | H | $CH_3$ | $n-C_3H_7$ | H | H |
| CH | H | $OCF_2CF_2H$ | H | $CH_3$ | $-CH(CH_3)_2$ | H | H |
| CH | H | $OCF_2CF_2H$ | H | $CH_3$ | $-CH_2CH(CH_3)_2$ | H | H |
| CH | H | $OCF_2CF_2H$ | H | $CH_3$ | $CH_2OCH_3$ | H | H |
| N | H | $CF_3$ | H | H | $CH_3$ | H | H |
| N | H | $CF_3$ | H | H | $C_2H_5$ | H | H |
| N | H | $CF_3$ | H | H | $n-C_3H_7$ | H | H |
| N | H | $CF_3$ | H | H | $-CH(CH_3)_2$ | H | H |
| N | H | $CF_3$ | H | H | $-CH_2CH(CH_3)_2$ | H | H |
| N | H | $CF_3$ | H | H | $CH_2OCH_3$ | H | H |
| N | H | $CF_3$ | H | H | $CH_3$ | H | H |
| N | H | $CF_3$ | $CH_3$ | H | $CH_3$ | H | H |
| N | H | $CF_3$ | $CH_3$ | H | $C_2H_5$ | H | H |
| N | H | $CF_3$ | $CH_3$ | H | $n-C_3H_7$ | H | H |
| N | H | $CF_3$ | $CH_3$ | H | $-CH(CH_3)_2$ | H | H |
| N | H | $CF_3$ | $CH_3$ | H | $-CH_2CH(CH_3)_2$ | H | H |
| N | H | $CF_3$ | $CH_3$ | H | $CH_2OCH_3$ | H | H |
| N | H | $CF_3$ | H | $CH_3$ | $CH_3$ | H | H |
| N | H | $CF_3$ | H | $CH_3$ | $C_2H_5$ | H | H |
| N | H | $CF_3$ | H | $CH_3$ | $n-C_3H_7$ | H | H |
| N | H | $CF_3$ | H | $CH_3$ | $-CH(CH_3)_2$ | H | H |
| N | H | $CF_3$ | H | $CH_3$ | $-CH_2CH(CH_3)_2$ | H | H |
| N | H | $CF_3$ | H | $CH_3$ | $CH_2OCH_3$ | H | H |
| N | Cl | $CF_3$ | H | H | $CH_3$ | H | H |
| N | Cl | $CF_3$ | H | H | $C_2H_5$ | H | H |
| N | Cl | $CF_3$ | H | H | $n-C_3H_7$ | H | H |
| N | Cl | $CF_3$ | H | H | $-CH(CH_3)_2$ | H | H |
| N | Cl | $CF_3$ | H | H | $-CH_2CH(CH_3)_2$ | H | H |
| N | Cl | $CF_3$ | H | H | $CH_2OCH_3$ | H | H |
| N | Cl | $CF_3$ | $CH_3$ | H | $CH_3$ | H | H |
| N | Cl | $CF_3$ | $CH_3$ | H | $C_2H_5$ | H | H |
| N | Cl | $CF_3$ | $CH_3$ | H | $n-C_3H_7$ | H | H |
| N | Cl | $CF_3$ | $CH_3$ | H | $-CH(CH_3)_2$ | H | H |
| N | Cl | $CF_3$ | $CH_3$ | H | $-CH_2CH(CH_3)_2$ | H | H |
| N | Cl | $CF_3$ | $CH_3$ | H | $CH_2OCH_3$ | H | H |
| N | H | $CF_3$ | $CH_3$ | $CH_3$ | $CH_3$ | H | H |
| N | H | $CF_3$ | $CH_3$ | $CH_3$ | $C_2H_5$ | H | H |
| CH | H | $CF_3$ | $CH_3$ | $CH_3$ | $CH_3$ | H | H |
| CH | H | $CF_3$ | $CH_3$ | $CH_3$ | $C_2H_5$ | H | H |
| N | Cl | $CF_3$ | H | $CH_3$ | $CH_3$ | H | H |
| N | Cl | $CF_3$ | H | $CH_3$ | $C_2H_5$ | H | H |
| N | Cl | $CF_3$ | H | $CH_3$ | $n-C_3H_7$ | H | H |
| N | Cl | $CF_3$ | H | $CH_3$ | $-CH(CH_3)_2$ | H | H |
| N | Cl | $CF_3$ | H | $CH_3$ | $-CH_2CH(CH_3)_2$ | H | H |
| N | Cl | $CF_3$ | H | $CH_3$ | $CH_2OCH_3$ | H | H |
| CH | H | $CF_3$ | H | H | $CH_3$ | $CH_3$ | H |
| CH | H | $CF_3$ | H | H | $C_2H_5$ | $CH_3$ | H |
| CH | H | $CF_3$ | H | H | $n-C_3H_7$ | $CH_3$ | H |

TABLE 8-continued

Compounds of the general formula (II)':

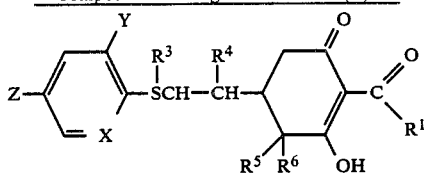

| X | Y | Z | R³ | R⁴ | R¹ | R⁵ | R⁶ |
|---|---|---|---|---|---|---|---|
| CH | H | CF₃ | H | H | —CH(CH₃)₂ | CH₃ | H |
| CH | H | CF₃ | H | H | —CH₂CH(CH₃)₂ | CH₃ | H |
| CH | H | CF₃ | H | H | CH₂OCH₃ | CH₃ | H |
| CH | H | CF₃ | H | H | H | CH₃ | H |
| CH | H | CF₃ | CH₃ | H | CH₃ | CH₃ | H |
| CH | H | CF₃ | CH₃ | H | C₂H₅ | CH₃ | H |
| CH | H | CF₃ | CH₃ | H | n-C₃H₇ | CH₃ | H |
| CH | H | CF₃ | CH₃ | H | —CH(CH₃)₂ | CH₃ | H |
| CH | H | CF₃ | CH₃ | H | —CH₂CH(CH₃)₂ | CH₃ | H |
| CH | H | CF₃ | CH₃ | H | CH₂OCH₃ | CH₃ | H |
| CH | H | CF₃ | H | CH₃ | CH₃ | CH₃ | H |
| CH | H | CF₃ | H | CH₃ | C₂H₅ | CH₃ | H |
| CH | H | CF₃ | H | CH₃ | n-C₃H₇ | CH₃ | H |
| CH | H | CF₃ | H | CH₃ | —CH(CH₃)₂ | CH₃ | H |
| CH | H | CF₃ | H | CH₃ | —CH₂CH(CH₃)₂ | CH₃ | H |
| CH | H | CF₃ | H | CH₃ | CH₂OCH₃ | CH₃ | H |
| CH | H | OCF₃ | H | H | CH₃ | CH₃ | H |
| CH | H | OCF₃ | H | H | C₂H₅ | CH₃ | H |
| CH | H | OCF₃ | H | H | n-C₃H₇ | CH₃ | H |
| CH | H | OCF₃ | H | H | —CH(CH₃)₂ | CH₃ | H |
| CH | H | OCF₃ | H | H | —CH₂CH(CH₃)₂ | CH₃ | H |
| CH | H | OCF₃ | H | H | CH₂OCH₃ | CH₃ | H |
| CH | H | OCF₃ | CH₃ | H | CH₃ | CH₃ | H |
| CH | H | OCF₃ | CH₃ | H | C₂H₅ | CH₃ | H |
| CH | H | OCF₃ | CH₃ | H | n-C₃H₇ | CH₃ | H |
| CH | H | OCF₃ | CH₃ | H | —CH(CH₃)₂ | CH₃ | H |
| CH | H | OCF₃ | CH₃ | H | —CH₂CH(CH₃)₂ | CH₃ | H |
| CH | H | OCF₃ | CH₃ | H | CH₂OCH₃ | CH₃ | H |
| CH | H | OCF₃ | H | CH₃ | CH₃ | CH₃ | H |
| CH | H | OCF₃ | H | CH₃ | C₂H₅ | CH₃ | H |
| CH | H | OCF₃ | H | CH₃ | n-C₃H₇ | CH₃ | H |
| CH | H | OCF₃ | H | CH₃ | —CH(CH₃)₂ | CH₃ | H |
| CH | H | OCF₃ | H | CH₃ | —CH₂CH(CH₃)₂ | CH₃ | H |
| CH | H | OCF₃ | H | CH₃ | CH₂OCH₃ | CH₃ | H |
| CH | H | OCF₂CF₂H | H | H | CH₃ | CH₃ | H |
| CH | H | OCF₂CF₂H | H | H | C₂H₅ | CH₃ | H |
| CH | H | OCF₂CF₂H | H | H | n-C₃H₇ | CH₃ | H |
| CH | H | OCF₂CF₂H | H | H | —CH(CH₃)₂ | CH₃ | H |
| CH | H | OCF₂CF₂H | H | H | —CH₂CH(CH₃)₂ | CH₃ | H |
| CH | H | OCF₂CF₂H | H | H | CH₂OCH₃ | CH₃ | H |
| CH | H | OCF₂CF₂H | CH₃ | H | CH₃ | CH₃ | H |
| CH | H | OCF₂CF₂H | CH₃ | H | C₂H₅ | CH₃ | H |
| CH | H | OCF₂CF₂H | CH₃ | H | n-C₃H₇ | CH₃ | H |
| CH | H | OCF₂CF₂H | CH₃ | H | —CH(CH₃)₂ | CH₃ | H |
| CH | H | OCF₂CF₂H | CH₃ | H | —CH₂CH(CH₃)₂ | CH₃ | H |
| CH | H | OCF₂CF₂H | CH₃ | H | CH₂OCH₃ | CH₃ | H |
| CH | H | OCF₂CF₂H | H | CH₃ | CH₃ | CH₃ | H |
| CH | H | OCF₂CF₂H | H | CH₃ | C₂H₅ | CH₃ | H |
| CH | H | OCF₂CF₂H | H | CH₃ | n-C₃H₇ | CH₃ | H |
| CH | H | OCF₂CF₂H | H | CH₃ | —CH(CH₃)₂ | CH₃ | H |
| CH | H | OCF₂CF₂H | H | CH₃ | —CH₂CH(CH₃)₂ | CH₃ | H |
| CH | H | OCF₂CF₂H | H | CH₃ | CH₂OCH₃ | CH₃ | H |
| N | H | CF₃ | H | H | CH₃ | CH₃ | H |
| N | H | CF₃ | H | H | C₂H₅ | CH₃ | H |
| N | H | CF₃ | H | H | n-C₃H₇ | CH₃ | H |
| N | H | CF₃ | H | H | —CH(CH₃)₂ | CH₃ | H |
| N | H | CF₃ | H | H | —CH₂CH(CH₃)₂ | CH₃ | H |
| N | H | CF₃ | H | H | CH₂OCH₃ | CH₃ | H |
| N | H | CF₃ | H | H | H | CH₃ | H |
| N | H | CF₃ | CH₃ | H | CH₃ | CH₃ | H |
| N | H | CF₃ | CH₃ | H | C₂H₅ | CH₃ | H |
| N | H | CF₃ | CH₃ | H | n-C₃H₇ | CH₃ | H |
| N | H | CF₃ | CH₃ | H | —CH(CH₃)₂ | CH₃ | H |
| N | H | CF₃ | CH₃ | H | —CH₂CH(CH₃)₂ | CH₃ | H |
| N | H | CF₃ | CH₃ | H | CH₂OCH₃ | CH₃ | H |
| N | H | CF₃ | H | CH₃ | CH₃ | CH₃ | H |
| N | H | CF₃ | H | CH₃ | C₂H₅ | CH₃ | H |
| N | H | CF₃ | H | CH₃ | n-C₃H₇ | CH₃ | H |
| N | H | CF₃ | H | CH₃ | —CH(CH₃)₂ | CH₃ | H |
| N | H | CF₃ | H | CH₃ | —CH₂CH(CH₃)₂ | CH₃ | H |
| N | H | CF₃ | H | CH₃ | CH₂OCH₃ | CH₃ | H |

TABLE 8-continued

Compounds of the general formula (II)':

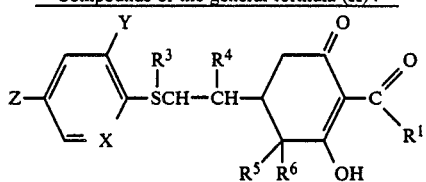

| X | Y | Z | R³ | R⁴ | R¹ | R⁵ | R⁶ |
|---|---|---|---|---|---|---|---|
| N | Cl | CF₃ | H | H | CH₃ | CH₃ | H |
| N | Cl | CF₃ | H | H | C₂H₅ | CH₃ | H |
| N | Cl | CF₃ | H | H | n-C₃H₇ | CH₃ | H |
| N | Cl | CF₃ | H | H | —CH(CH₃)₂ | CH₃ | H |
| N | Cl | CF₃ | H | H | —CH₂CH(CH₃)₂ | CH₃ | H |
| N | Cl | CF₃ | H | H | CH₂OCH₃ | CH₃ | H |
| N | Cl | CF₃ | CH₃ | H | CH₃ | CH₃ | H |
| N | Cl | CF₃ | CH₃ | H | C₂H₅ | CH₃ | H |
| N | Cl | CF₃ | CH₃ | H | n-C₃H₇ | CH₃ | H |
| N | Cl | CF₃ | CH₃ | H | —CH(CH₃)₂ | CH₃ | H |
| N | Cl | CF₃ | CH₃ | H | —CH₂CH(CH₃)₂ | CH₃ | H |
| N | Cl | CF₃ | CH₃ | H | CH₂OCH₃ | CH₃ | H |
| N | H | CF₃ | CH₃ | CH₃ | CH₃ | CH₃ | H |
| N | H | CF₃ | CH₃ | CH₃ | C₂H₅ | CH₃ | H |
| CH | H | CF₃ | CH₃ | CH₃ | CH₃ | CH₃ | H |
| CH | H | CF₃ | CH₃ | CH₃ | C₂H₅ | CH₃ | H |
| N | Cl | CF₃ | H | CH₃ | CH₃ | CH₃ | H |
| N | Cl | CF₃ | H | CH₃ | C₂H₅ | CH₃ | H |
| N | Cl | CF₃ | H | CH₃ | n-C₃H₇ | CH₃ | H |
| N | Cl | CF₃ | H | CH₃ | —CH(CH₃)₂ | CH₃ | H |
| N | Cl | CF₃ | H | CH₃ | —CH₂CH(CH₃)₂ | CH₃ | H |
| N | Cl | CF₃ | H | CH₃ | CH₂OCH₃ | CH₃ | H |
| CH | H | CF₃ | H | H | CH₃ | H | COOCH₃ |
| CH | H | CF₃ | H | H | C₂H₅ | H | COOC₂H₅ |
| CH | H | CF₃ | H | H | n-C₃H₇ | H | COOC₂H₅ |
| CH | H | CF₃ | H | H | —CH(CH₃)₂ | H | COOC₂H₅ |
| CH | H | CF₃ | H | H | —CH₂CH(CH₃)₂ | H | COOCH₃ |
| CH | H | CF₃ | H | H | CH₂OCH₃ | H | COOCH₃ |
| CH | H | CF₃ | H | H | H | H | COOCH₃ |
| CH | H | CF₃ | CH₃ | H | CH₃ | H | COOCH₃ |
| CH | H | CF₃ | CH₃ | H | C₂H₅ | H | COOCH₃ |
| CH | H | CF₃ | CH₃ | H | n-C₃H₇ | H | COOCH₃ |
| CH | H | CF₃ | CH₃ | H | —CH(CH₃)₂ | H | COOCH₃ |
| CH | H | CF₃ | CH₃ | H | —CH₂CH(CH₃)₂ | H | COOCH₃ |
| CH | H | CF₃ | CH₃ | H | CH₂OCH₃ | H | COOCH₃ |
| CH | H | CF₃ | H | CH₃ | CH₃ | H | COOCH₃ |
| CH | H | CF₃ | H | CH₃ | C₂H₅ | H | COOCH₃ |
| CH | H | CF₃ | H | CH₃ | n-C₃H₇ | H | COOCH₃ |
| CH | H | CF₃ | H | CH₃ | —CH(CH₃)₂ | H | COOCH₃ |
| CH | H | CF₃ | H | CH₃ | —CH₂CH(CH₃)₂ | H | COOCH₃ |
| CH | H | CF₃ | H | CH₃ | CH₂OCH₃ | H | COOCH₃ |
| CH | H | CF₃ | CH₃ | CH₃ | CH₃ | H | COOCH₃ |
| CH | H | OCF₃ | H | H | CH₃ | H | COOCH₃ |
| CH | H | OCF₃ | H | H | C₂H₅ | H | COOCH₃ |
| CH | H | OCF₃ | H | H | n-C₃H₇ | H | COOCH₃ |
| CH | H | OCF₃ | H | H | —CH(CH₃)₂ | H | COOCH₃ |
| CH | H | OCF₃ | H | H | —CH₂CH(CH₃)₂ | H | COOCH₃ |
| CH | H | OCF₃ | H | H | CH₂OCH₃ | H | COOCH₃ |
| CH | H | OCF₃ | CH₃ | H | CH₃ | H | COOCH₃ |
| CH | H | OCF₃ | CH₃ | H | C₂H₅ | H | COOCH₃ |
| CH | H | OCF₃ | CH₃ | H | n-C₃H₇ | H | COOCH₃ |
| CH | H | OCF₃ | CH₃ | H | —CH(CH₃)₂ | H | COOCH₃ |
| CH | H | OCF₃ | CH₃ | H | —CH₂CH(CH₃)₂ | H | COOCH₃ |
| CH | H | OCF₃ | CH₃ | H | CH₂OCH₃ | H | COOCH₃ |
| CH | H | OCF₃ | H | CH₃ | CH₃ | H | COOCH₃ |
| CH | H | OCF₃ | H | CH₃ | C₂H₅ | H | COOCH₃ |
| CH | H | OCF₃ | H | CH₃ | n-C₃H₇ | H | COOCH₃ |
| CH | H | OCF₃ | H | CH₃ | —CH(CH₃)₂ | H | COOCH₃ |
| CH | H | OCF₃ | H | CH₃ | —CH₂CH(CH₃)₂ | H | COOCH₃ |
| CH | H | OCF₃ | H | CH₃ | CH₂OCH₃ | H | COOCH₃ |
| CH | H | OCF₂CF₂H | H | H | CH₃ | H | COOCH₃ |
| CH | H | OCF₂CF₂H | H | H | C₂H₅ | H | COOCH₃ |
| CH | H | OCF₂CF₂H | H | H | n-C₃H₇ | H | COOCH₃ |
| CH | H | OCF₂CF₂H | H | H | —CH(CH₃)₂ | H | COOCH₃ |
| CH | H | OCF₂CF₂H | H | H | —CH₂CH(CH₃)₂ | H | COOCH₃ |
| CH | H | OCF₂CF₂H | H | H | CH₂OCH₃ | H | COOCH₃ |
| CH | H | OCF₂CF₂H | CH₃ | H | CH₃ | H | COOCH₃ |
| CH | H | OCF₂CF₂H | CH₃ | H | C₂H₅ | H | COOCH₃ |
| CH | H | OCF₂CF₂H | CH₃ | H | n-C₃H₇ | H | COOCH₃ |
| CH | H | OCF₂CF₂H | CH₃ | H | —CH(CH₃)₂ | H | COOCH₃ |
| CH | H | OCF₂CF₂H | CH₃ | H | —CH₂CH(CH₃)₂ | H | COOCH₃ |

TABLE 8-continued

Compounds of the general formula (II)':

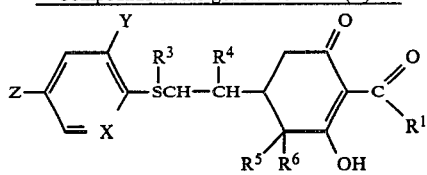

| X | Y | Z | $R^3$ | $R^4$ | $R^1$ | $R^5$ | $R^6$ |
|---|---|---|---|---|---|---|---|
| CH | H | $OCF_2CF_2H$ | $CH_3$ | H | $CH_2OCH_3$ | H | $COOCH_3$ |
| CH | H | $OCF_2CF_2H$ | H | $CH_3$ | $CH_3$ | H | $COOCH_3$ |
| CH | H | $OCF_2CF_2H$ | H | $CH_3$ | $C_2H_5$ | H | $COOCH_3$ |
| CH | H | $OCF_2CF_2H$ | H | $CH_3$ | $n$-$C_3H_7$ | H | $COOCH_3$ |
| CH | H | $OCF_2CF_2H$ | H | $CH_3$ | $-CH(CH_3)_2$ | H | $COOCH_3$ |
| CH | H | $OCF_2CF_2H$ | H | $CH_3$ | $-CH_2CH(CH_3)_2$ | H | $COOCH_3$ |
| CH | H | $OCF_2CF_2H$ | H | $CH_3$ | $CH_2OCH_3$ | H | $COOCH_3$ |
| N | H | $CF_3$ | H | H | $CH_3$ | H | $COOC_2H_5$ |
| N | H | $CF_3$ | H | H | $C_2H_5$ | H | $COOCH_3$ |
| N | H | $CF_3$ | H | H | $n$-$C_3H_7$ | H | $COOCH_3$ |
| N | H | $CF_3$ | H | H | $-CH(CH_3)_2$ | H | $COOC_2H_5$ |
| N | H | $CF_3$ | H | H | $-CH_2CH(CH_3)_2$ | H | $COOC_2H_5$ |
| N | H | $CF_3$ | H | H | $CH_2OCH_3$ | H | $COOC_2H_5$ |
| N | H | $CF_3$ | H | H | H | H | $COOC_2H_5$ |
| N | H | $CF_3$ | $CH_3$ | H | $CH_3$ | H | $COOC_2H_5$ |
| N | H | $CF_3$ | $CH_3$ | H | $C_2H_5$ | H | $COOC_2H_5$ |
| N | H | $CF_3$ | $CH_3$ | H | $n$-$C_3H_7$ | H | $COOC_2H_5$ |
| N | H | $CF_3$ | $CH_3$ | H | $-CH(CH_3)_2$ | H | $COOC_2H_5$ |
| N | H | $CF_3$ | $CH_3$ | H | $-CH_2CH(CH_3)_2$ | H | $COOC_2H_5$ |
| N | H | $CF_3$ | $CH_3$ | H | $CH_2OCH_3$ | H | $COOC_2H_5$ |
| N | H | $CF_3$ | H | $CH_3$ | $CH_3$ | H | $COOC_2H_5$ |
| N | H | $CF_3$ | H | $CH_3$ | $C_2H_5$ | H | $COOC_2H_5$ |
| N | H | $CF_3$ | H | $CH_3$ | $n$-$C_3H_7$ | H | $COOC_2H_5$ |
| N | H | $CF_3$ | H | $CH_3$ | $-CH(CH_3)_2$ | H | $COOC_2H_5$ |
| N | H | $CF_3$ | H | $CH_3$ | $-CH_2CH(CH_3)_2$ | H | $COOC_2H_5$ |
| N | H | $CF_3$ | H | $CH_3$ | $CH_2OCH_3$ | H | $COOC_2H_5$ |
| N | Cl | $CF_3$ | H | H | $C_2H_5$ | H | $COOC_2H_5$ |
| N | Cl | $CF_3$ | H | H | $n$-$C_3H_7$ | H | $COOC_2H_5$ |
| N | Cl | $CF_3$ | H | H | $-CH(CH_3)_2$ | H | $COOC_2H_5$ |
| N | Cl | $CF_3$ | H | H | $-CH_2CH(CH_3)_2$ | H | $COOC_2H_5$ |
| N | Cl | $CF_3$ | H | H | $CH_2OCH_3$ | H | $COOC_2H_5$ |
| N | Cl | $CF_3$ | $CH_3$ | H | $CH_3$ | H | $COOC_2H_5$ |
| N | Cl | $CF_3$ | $CH_3$ | H | $C_2H_5$ | H | $COOC_2H_5$ |
| N | Cl | $CF_3$ | $CH_3$ | H | $n$-$C_3H_7$ | H | $COOC_2H_5$ |
| N | Cl | $CF_3$ | $CH_3$ | H | $-CH(CH_3)_2$ | H | $COOC_2H_5$ |
| N | Cl | $CF_3$ | $CH_3$ | H | $-CH_2CH(CH_{32}$ | H | $COOC_2H_5$ |
| N | Cl | $CF_3$ | $CH_3$ | H | $CH_2OCH_3$ | H | $COOC_2H_5$ |
| N | H | $CF_3$ | $CH_3$ | $CH_3$ | $CH_3$ | H | $COOC_2H_5$ |
| N | H | $CF_3$ | $CH_3$ | $CH_3$ | $C_2H_5$ | H | $COOC_2H_5$ |
| CH | H | $CF_3$ | $CH_3$ | $CH_3$ | $CH_3$ | H | $COOC_2H_5$ |
| CH | H | $CF_3$ | $CH_3$ | $CH_3$ | $C_2H_5$ | H | $COOC_2H_5$ |
| N | Cl | $CF_3$ | H | $CH_3$ | $CH_3$ | H | $COOC_2H_5$ |
| N | Cl | $CF_3$ | H | $CH_3$ | $C_2H_5$ | H | $COOC_2H_5$ |
| N | Cl | $CF_3$ | H | $CH_3$ | $n$-$C_3H_7$ | H | $COOC_2H_5$ |
| N | Cl | $CF_3$ | H | $CH_3$ | $-CH(CH_3)_2$ | H | $COOC_2H_5$ |
| N | Cl | $CF_3$ | H | $CH_3$ | $-CH(CH_3)_2$ | H | $COOC_2H_5$ |
| N | Cl | $CF_3$ | H | $CH_3$ | $CH_2OCH_3$ | H | $COOC_2H_5$ |

The compound represented by the formula (II)" is produced by oxidation of the acylcyclohexane represented by the general formula (II)'. The oxidation reaction can be performed by using a usual method, for example, m-chloroperbenzoic acid in chloroform, hydrogen peroxide in acetic acid, etc.

The number of n is controlled by amount of the oxidant used and the reaction temperature. After completion of the reaction, which is generally required one to several hours, the reaction solution is poured into water, extracted with an organic solvent to obtain the desired product. This product may be purified, if necessary, by recrystallization or column chromatography.

Examples of the compound of the general formula (II)" thus obtained are shown in Tables 9 and 10.

TABLE 9

Compounds of the general formula (II)'':

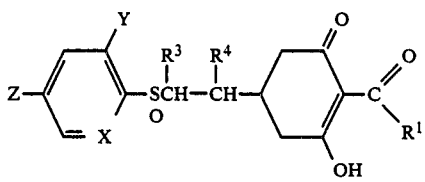

| X | Y | Z | R³ | R⁴ | R¹ | R⁵ | R⁶ |
|---|---|---|---|---|---|---|---|
| CH | H | CF₃ | H | H | CH₃ | H | H |
| CH | H | CF₃ | H | H | C₂H₅ | H | H |
| CH | H | CF₃ | H | H | n-C₃H₇ | H | H |
| CH | H | CF₃ | H | H | —CH(CH₃)₂ | H | H |
| CH | H | CF₃ | H | H | H | H | H |
| CH | H | CF₃ | CH₃ | H | CH₃ | H | H |
| CH | H | CF₃ | CH₃ | H | C₂H₅ | H | H |
| CH | H | CF₃ | CH₃ | H | n-C₃H₇ | H | H |
| CH | H | CF₃ | CH₃ | H | —CH₂CH(CH₃)₂ | H | H |
| CH | H | CF₃ | CH₃ | H | H | H | H |
| CH | H | CF₃ | H | CH₃ | CH₃ | H | H |
| CH | H | CF₃ | H | CH₃ | C₂H₅ | H | H |
| CH | H | CF₃ | H | CH₃ | n-C₃H₇ | H | H |
| CH | H | CF₃ | H | CH₃ | —CH(CH₃)₂ | H | H |
| CH | H | CF₃ | H | CH₃ | —CH₂CH(CH₃)₂ | H | H |
| CH | H | CF₃ | H | CH₃ | H | H | H |
| CH | H | CF₃ | CH₃ | CH₃ | CH₃ | H | H |
| CH | H | OCF₃ | H | H | CH₃ | H | H |
| CH | H | OCF₃ | H | H | C₂H₅ | H | H |
| CH | H | OCF₃ | H | H | n-C₃H₇ | H | H |
| CH | H | OCF₃ | H | H | —CH₂CH(CH₃)₂ | H | H |
| CH | H | OCF₃ | CH₃ | H | CH₃ | H | H |
| CH | H | OCF₃ | CH₃ | H | C₂H₅ | H | H |
| CH | H | OCF₃ | CH₃ | H | n-C₃H₇ | H | H |
| CH | H | OCF₃ | H | CH₃ | CH₃ | H | H |
| CH | H | OCF₃ | H | CH₃ | C₂H₅ | H | H |
| CH | H | OCF₃ | H | CH₃ | n-C₃H₇ | H | H |
| CH | H | OCF₃ | H | CH₃ | —CH(CH₃)₂ | H | H |
| CH | H | OCF₃ | H | CH₃ | —CH₂CH(CH₃)₂ | H | H |
| CH | H | OCF₂CF₂H | H | H | CH₃ | H | H |
| CH | H | OCF₂CF₂H | H | H | C₂H₅ | H | H |
| CH | H | OCF₂CF₂H | H | H | n-C₃H₇ | H | H |
| CH | H | OCF₂CF₂H | H | H | —CH(CH₃)₂ | H | H |
| CH | H | OCF₂CF₂H | CH₃ | H | CH₃ | H | H |
| CH | H | OCF₂CF₂H | CH₃ | H | C₂H₅ | H | H |
| CH | H | OCF₂CF₂H | CH₃ | H | n-C₃H₇ | H | H |
| CH | H | OCF₂CF₂H | CH₃ | H | —H(CH₃)₂ | H | H |
| CH | H | OCF₂CF₂H | CH₃ | H | —CH₂CH(CH₃)₂ | H | H |
| CH | H | OCF₂CF₂H | H | CH₃ | CH₃ | H | H |
| CH | H | OCF₂CF₂H | H | CH₃ | C₂H₅ | H | H |
| CH | H | OCF₂CF₂H | H | CH₃ | n-C₃H₇ | H | H |
| CH | H | OCF₂CF₂H | H | CH₃ | —CH(CH₃)₂ | H | H |
| CH | H | OCF₂CF₂H | H | CH₃ | —CH₂CH(CH₃)₂ | H | H |
| N | H | CF₃ | H | H | CH₃ | H | H |
| N | H | CF₃ | H | H | C₂H₅ | H | H |
| N | H | CF₃ | H | H | n-C₃H₇ | H | H |
| N | H | CF₃ | H | H | —CH(CH₃)₂ | H | H |
| N | H | CF₃ | H | H | —CH₂CH(CH₃)₂ | H | H |
| N | H | CF₃ | CH₃ | H | CH₃ | H | H |
| N | H | CF₃ | CH₃ | H | C₂H₅ | H | H |
| N | H | CF₃ | CH₃ | H | n-C₃H₇ | H | H |
| N | H | CF₃ | CH₃ | H | —CH(CH₃)₂ | H | H |
| N | H | CF₃ | CH₃ | H | —CH₂CH(CH₃)₂ | H | H |
| N | H | CF₃ | H | CH₃ | CH₃ | H | H |
| N | H | CF₃ | H | CH₃ | C₂H₅ | H | H |
| N | H | CF₃ | H | CH₃ | n-C₃H₇ | H | H |
| N | H | CF₃ | H | CH₃ | —CH(CH₃)₂ | H | H |
| N | H | CF₃ | H | CH₃ | —CH₂CH(CH₃)₂ | H | H |
| N | Cl | CF₃ | H | H | CH₃ | H | H |
| N | Cl | CF₃ | H | H | C₂H₅ | H | H |
| N | Cl | CF₃ | H | H | n-C₃H₇ | H | H |
| N | Cl | CF₃ | H | H | —CH(CH₃)₂ | H | H |
| N | Cl | CF₃ | H | H | —CH₂CH(CH₃)₂ | H | H |
| N | Cl | CF₃ | CH₃ | H | CH₃ | H | H |
| N | Cl | CF₃ | CH₃ | H | C₂H₅ | H | H |
| N | Cl | CF₃ | CH₃ | H | n-C₃H₇ | H | H |
| N | H | CF₃ | CH₃ | CH₃ | CH₃ | H | H |
| N | H | CF₃ | CH₃ | CH₃ | C₂H₅ | H | H |
| CH | H | CF₃ | CH₃ | CH₃ | CH₃ | H | H |
| CH | H | CF₃ | CH₃ | CH₃ | C₂H₅ | H | H |

TABLE 9-continued

Compounds of the general formula (II)'':

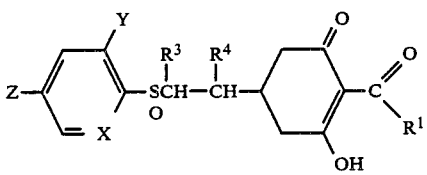

| X | Y | Z | $R^3$ | $R^4$ | $R^1$ | $R^5$ | $R^6$ |
|---|---|---|---|---|---|---|---|
| N | Cl | $CF_3$ | H | $CH_3$ | $CH_3$ | H | H |
| N | Cl | $CF_3$ | H | $CH_3$ | $C_2H_5$ | H | H |
| N | Cl | $CF_3$ | H | $CH_3$ | n-$C_3H_7$ | H | H |
| N | Cl | $CF_3$ | H | $CH_3$ | —$CH(CH_3)_2$ | H | H |
| N | Cl | $CF_3$ | H | $CH_3$ | —$CH_2CH(CH_3)_2$ | H | H |
| CH | H | $CF_3$ | H | H | H | $CH_3$ | H |
| CH | H | $CF_3$ | H | H | $CH_3$ | $CH_3$ | H |
| CH | H | $CF_3$ | H | H | $C_2H_5$ | $CH_3$ | H |
| CH | H | $CF_3$ | H | H | n-$C_3H_7$ | $CH_3$ | H |
| CH | H | $CF_3$ | H | H | —$CH(CH_3)_2$ | $CH_3$ | H |
| CH | H | $CF_3$ | H | H | —$CH_2CH(CH_3)_2$ | $CH_3$ | H |
| CH | H | $CF_3$ | $CH_3$ | H | $CH_3$ | $CH_3$ | H |
| CH | H | $CF_3$ | $CH_3$ | H | $C_2H_5$ | $CH_3$ | H |
| CH | H | $CF_3$ | $CH_3$ | H | n-$C_3H_7$ | $CH_3$ | H |
| CH | H | $CF_3$ | H | $CH_3$ | $CH_3$ | $CH_3$ | H |
| CH | H | $CF_3$ | H | $CH_3$ | $C_2H_5$ | $CH_3$ | H |
| CH | H | $CF_3$ | H | $CH_3$ | n-$C_3H_7$ | $CH_3$ | H |
| CH | H | $CF_3$ | H | $CH_3$ | —$CH(CH_3)_2$ | $CH_3$ | H |
| CH | H | $CF_3$ | H | $CH_3$ | —$CH_2CH(CH_3)_2$ | $CH_3$ | H |
| CH | H | $CF_3$ | $CH_3$ | $CH_3$ | $CH_3$ | $CH_3$ | H |
| CH | H | $OCF_3$ | H | H | $CH_3$ | $CH_3$ | H |
| CH | H | $OCF_3$ | H | H | $C_2H_5$ | $CH_3$ | H |
| CH | H | $OCF_3$ | H | H | n-$C_3H_7$ | $CH_3$ | H |
| CH | H | $OCF_3$ | $CH_3$ | H | $CH_3$ | $CH_3$ | H |
| CH | H | $OCF_3$ | $CH_3$ | H | $C_2H_5$ | $CH_3$ | H |
| CH | H | $OCF_3$ | $CH_3$ | H | n-$C_3H_7$ | $CH_3$ | H |
| CH | H | $OCF_3$ | H | $CH_3$ | $CH_3$ | $CH_3$ | H |
| CH | H | $OCF_3$ | H | $CH_3$ | $C_2H_5$ | $CH_3$ | H |
| CH | H | $OCF_3$ | H | $CH_3$ | n-$C_3H_7$ | $CH_3$ | H |
| CH | H | $OCF_2CF_2H$ | H | H | $CH_3$ | $CH_3$ | H |
| CH | H | $OCF_2CF_2H$ | H | H | $C_2H_5$ | $CH_3$ | H |
| CH | H | $OCF_2CF_2H$ | H | H | n-$C_3H_7$ | $CH_3$ | H |
| CH | H | $OCF_2CF_2H$ | $CH_3$ | H | $CH_3$ | $CH_3$ | H |
| CH | H | $OCF_2CF_2H$ | $CH_3$ | H | $C_2H_5$ | $CH_3$ | H |
| CH | H | $OCF_2CF_2H$ | $CH_3$ | H | n-$C_3H_7$ | $CH_3$ | H |
| CH | H | $OCF_2CF_2H$ | H | $CH_3$ | $CH_3$ | $CH_3$ | H |
| CH | H | $OCF_2CF_2H$ | H | $CH_3$ | $C_2H_5$ | $CH_3$ | H |
| CH | H | $OCF_2CF_2H$ | H | $CH_3$ | n-$C_3H_7$ | $CH_3$ | H |
| N | H | $CF_3$ | H | H | $CH_3$ | $CH_3$ | H |
| N | H | $CF_3$ | H | H | $C_2H_5$ | $CH_3$ | H |
| N | H | $CF_3$ | H | H | n-$C_3H_7$ | $CH_3$ | H |
| N | H | $CF_3$ | $CH_3$ | H | $CH_3$ | $CH_3$ | H |
| N | H | $CF_3$ | $CH_3$ | H | $C_2H_5$ | $CH_3$ | H |
| N | H | $CF_3$ | $CH_3$ | H | n-$C_3H_7$ | $CH_3$ | H |
| N | H | $CF_3$ | H | $CH_3$ | $CH_3$ | $CH_3$ | H |
| N | H | $CF_3$ | H | $CH_3$ | $C_2H_5$ | $CH_3$ | H |
| N | H | $CF_3$ | H | $CH_3$ | n-$C_3H_7$ | $CH_3$ | H |
| N | Cl | $CF_3$ | H | H | $CH_3$ | $CH_3$ | H |
| N | Cl | $CF_3$ | H | H | $C_2H_5$ | $CH_3$ | H |
| N | Cl | $CF_3$ | H | H | n-$C_3H_7$ | $CH_3$ | H |
| N | Cl | $CF_3$ | $CH_3$ | H | $CH_3$ | $CH_3$ | H |
| N | Cl | $CF_3$ | $CH_3$ | H | $C_2H_5$ | $CH_3$ | H |
| N | Cl | $CF_3$ | $CH_3$ | H | n-$C_3H_7$ | $CH_3$ | H |
| N | H | $CF_3$ | $CH_3$ | $CH_3$ | $CH_3$ | $CH_3$ | H |
| N | H | $CF_3$ | $CH_3$ | $CH_3$ | $C_2H_5$ | $CH_3$ | H |
| CH | H | $CF_3$ | $CH_3$ | $CH_3$ | $CH_3$ | $CH_3$ | H |
| CH | H | $CF_3$ | $CH_3$ | $CH_3$ | $C_2H_5$ | $CH_3$ | H |
| N | Cl | $CF_3$ | H | $CH_3$ | $CH_3$ | $CH_3$ | H |
| N | Cl | $CF_3$ | H | $CH_3$ | $C_2H_5$ | $CH_3$ | H |
| N | Cl | $CF_3$ | H | $CH_3$ | n-$C_3H_7$ | $CH_3$ | H |
| CH | H | $CF_3$ | H | H | $CH_3$ | H | $COOCH_3$ |
| CH | H | $CF_3$ | H | H | $C_2H_5$ | H | $COOC_2H_5$ |
| CH | H | $CF_3$ | H | H | n-$C_3H_7$ | H | $COOC_2H_5$ |
| CH | H | $CF_3$ | $CH_3$ | H | $CH_3$ | H | $COOCH_3$ |
| CH | H | $CF_3$ | $CH_3$ | H | $C_2H_5$ | H | $COOCH_3$ |
| CH | H | $CF_3$ | $CH_3$ | H | n-$C_3H_7$ | H | $COOCH_3$ |
| CH | H | $CF_3$ | H | $CH_3$ | $CH_3$ | H | $COOCH_3$ |
| CH | H | $CF_3$ | H | $CH_3$ | $C_2H_5$ | H | $COOCH_3$ |
| CH | H | $CF_3$ | H | $CH_3$ | n-$C_3H_7$ | H | $COOCH_3$ |
| CH | H | $CF_3$ | $CH_3$ | $CH_3$ | $CH_3$ | H | $COOCH_3$ |

TABLE 9-continued

Compounds of the general formula (II)'':

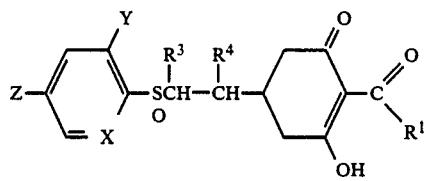

| X | Y | Z | $R^3$ | $R^4$ | $R^1$ | $R^5$ | $R^6$ |
|---|---|---|---|---|---|---|---|
| CH | H | $OCF_3$ | H | H | $CH_3$ | H | $COOCH_3$ |
| CH | H | $OCF_3$ | H | H | $C_2H_5$ | H | $COOCH_3$ |
| CH | H | $OCF_3$ | H | H | $n-C_3H_7$ | H | $COOCH_3$ |
| CH | H | $OCF_3$ | $CH_3$ | H | $CH_3$ | H | $COOCH_3$ |
| CH | H | $OCF_3$ | $CH_3$ | H | $C_2H_5$ | H | $COOCH_3$ |
| CH | H | $OCF_3$ | $CH_3$ | H | $n-C_3H_7$ | H | $COOCH_3$ |
| CH | H | $OCF_3$ | H | $CH_3$ | $CH_3$ | H | $COOCH_3$ |
| CH | H | $OCF_3$ | H | $CH_3$ | $C_2H_5$ | H | $COOCH_3$ |
| CH | H | $OCF_3$ | H | $CH_3$ | $n-C_3H_7$ | H | $COOCH_3$ |
| CH | H | $OCF_2CF_2H$ | H | H | $CH_3$ | H | $COOCH_3$ |
| CH | H | $OCF_2CF_2H$ | H | H | $C_2H_5$ | H | $COOCH_3$ |
| CH | H | $OCF_2CF_2H$ | H | H | $n-C_3H_7$ | H | $COOCH_3$ |
| CH | H | $OCF_2CF_2H$ | $CH_3$ | H | $CH_3$ | H | $COOCH_3$ |
| CH | H | $OCF_2CF_2H$ | $CH_3$ | H | $C_2H_5$ | H | $COOCH_3$ |
| CH | H | $OCF_2CF_2H$ | $CH_3$ | H | $n-C_3H_7$ | H | $COOCH_3$ |
| CH | H | $OCF_2CF_2H$ | H | $CH_3$ | $CH_3$ | H | $COOCH_3$ |
| CH | H | $OCF_2CF_2H$ | H | $CH_3$ | $C_2H_5$ | H | $COOCH_3$ |
| CH | H | $OCF_2CF_2H$ | H | $CH_3$ | $n-C_3H_7$ | H | $COOCH_3$ |
| N | H | $CF_3$ | H | H | $CH_3$ | H | $COOC_2H_5$ |
| N | H | $CF_3$ | H | H | $C_2H_5$ | H | $COOCH_3$ |
| N | H | $CF_3$ | H | H | $n-C_3H_7$ | H | $COOCH_3$ |
| N | H | $CF_3$ | $CH_3$ | H | $CH_3$ | H | $COOC_2H_5$ |
| N | H | $CF_3$ | $CH_3$ | H | $C_2H_5$ | H | $COOC_2H_5$ |
| N | H | $CF_3$ | $CH_3$ | H | $n-C_3H_7$ | H | $COOC_2H_5$ |
| N | H | $CF_3$ | H | $CH_3$ | $CH_3$ | H | $COOC_2H_5$ |
| N | H | $CF_3$ | H | $CH_3$ | $C_2H_5$ | H | $COOC_2H_5$ |
| N | H | $CF_3$ | H | $CH_3$ | $n-C_3H_7$ | H | $COOC_2H_5$ |
| N | Cl | $CF_3$ | H | H | $CH_3$ | H | $COOC_2H_5$ |
| N | Cl | $CF_3$ | H | H | $C_2H_5$ | H | $COOC_2H_5$ |
| N | Cl | $CF_3$ | H | H | $n-C_3H_7$ | H | $COOC_2H_5$ |
| N | Cl | $CF_3$ | $CH_3$ | H | $CH_3$ | H | $COOC_2H_5$ |
| N | Cl | $CF_3$ | $CH_3$ | H | $C_2H_5$ | H | $COOC_2H_5$ |
| N | Cl | $CF_3$ | $CH_3$ | H | $n-C_3H_7$ | H | $COOC_2H_5$ |
| N | H | $CF_3$ | $CH_3$ | $CH_3$ | $CH_3$ | H | $COOC_2H_5$ |
| N | H | $CF_3$ | $CH_3$ | $CH_3$ | $C_2H_5$ | H | $COOC_2H_5$ |
| CH | H | $CF_3$ | $CH_3$ | $CH_3$ | $CH_3$ | H | $COOC_2H_5$ |
| CH | H | $CF_3$ | $CH_3$ | $CH_3$ | $C_2H_5$ | H | $COOC_2H_5$ |
| N | Cl | $CF_3$ | H | $CH_3$ | $CH_3$ | H | $COOC_2H_5$ |
| N | Cl | $CF_3$ | H | $CH_3$ | $C_2H_5$ | H | $COOC_2H_5$ |
| N | Cl | $CF_3$ | H | $CH_3$ | $n-C_3H_7$ | H | $COOC_2H_5$ |

TABLE 10

Compounds of the general formula (II)'':

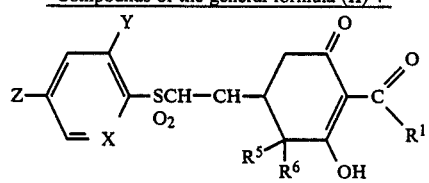

| X | Y | Z | $R^3$ | $R^4$ | $R^1$ | $R^5$ | $R^6$ |
|---|---|---|---|---|---|---|---|
| CH | H | $CF_3$ | H | H | $CH_3$ | H | H |
| CH | H | $CF_3$ | H | H | $C_2H_5$ | H | H |
| CH | H | $CF_3$ | H | H | $n-C_3H_7$ | H | H |
| CH | H | $CF_3$ | H | H | $-CH(CH_3)_2$ | H | H |
| CH | H | $CF_3$ | H | H | $-CH_2CH(CH_3)_2$ | H | H |
| CH | H | $CF_3$ | H | H | H | H | H |
| CH | H | $CF_3$ | $CH_3$ | H | $CH_3$ | H | H |
| CH | H | $CF_3$ | $CH_3$ | H | $C_2H_5$ | H | H |
| CH | H | $CF_3$ | $CH_3$ | H | $n-C_3H_7$ | H | H |
| CH | H | $CF_3$ | H | $CH_3$ | $CH_3$ | H | H |
| CH | H | $CF_3$ | H | $CH_3$ | $C_2H_5$ | H | H |
| CH | H | $CF_3$ | H | $CH_3$ | $n-C_3H_7$ | H | H |
| CH | H | $OCF_3$ | H | H | $CH_3$ | H | H |
| CH | H | $OCF_3$ | H | H | $C_2H_5$ | H | H |

TABLE 10-continued

Compounds of the general formula (II)'':

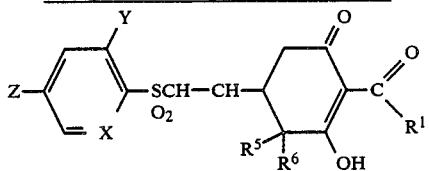

| X | Y | Z | R³ | R⁴ | R¹ | R⁵ | R⁶ |
|---|---|---|---|---|---|---|---|
| CH | H | OCF₃ | H | H | n-C₃H₇ | H | H |
| CH | H | OCF₃ | CH₃ | H | CH₃ | H | H |
| CH | H | OCF₃ | CH₃ | H | C₂H₅ | H | H |
| CH | H | OCF₃ | CH₃ | H | n-C₃H₇ | H | H |
| CH | H | OCF₃ | H | CH₃ | CH₃ | H | H |
| CH | H | OCF₃ | H | CH₃ | C₂H₅ | H | H |
| CH | H | OCF₃ | H | CH₃ | n-C₃H₇ | H | H |
| CH | H | OCF₂CF₂H | H | H | CH₃ | H | H |
| CH | H | OCF₂CF₂H | H | H | C₂H₅ | H | H |
| CH | H | OCF₂CF₂H | H | H | n-C₃H₇ | H | H |
| CH | H | OCF₂CF₂H | CH₃ | H | CH₃ | H | H |
| CH | H | OCF₂CF₂H | CH₃ | H | C₂H₅ | H | H |
| CH | H | OCF₂CF₂H | CH₃ | H | n-C₃H₇ | H | H |
| CH | H | OCF₂CF₂H | H | CH₃ | CH₃ | H | H |
| CH | H | OCF₂CF₂H | H | CH₃ | C₂H₅ | H | H |
| CH | H | OCF₂CF₂H | H | CH₃ | n-C₃H₇ | H | H |
| N | H | CF₃ | H | H | CH₃ | H | H |
| N | H | CF₃ | H | H | C₂H₅ | H | H |
| N | H | CF₃ | H | H | n-C₃H₇ | H | H |
| N | H | CF₃ | CH₃ | H | CH₃ | H | H |
| N | H | CF₃ | CH₃ | H | C₂H₅ | H | H |
| N | H | CF₃ | CH₃ | H | n-C₃H₇ | H | H |
| N | H | CF₃ | H | CH₃ | CH₃ | H | H |
| N | H | CF₃ | H | CH₃ | C₂H₅ | H | H |
| N | H | CF₃ | H | CH₃ | n-C₃H₇ | H | H |
| N | Cl | CF₃ | H | H | CH₃ | H | H |
| N | Cl | CF₃ | H | H | C₂H₅ | H | H |
| N | Cl | CF₃ | H | H | n-C₃H₇ | H | H |
| N | Cl | CF₃ | CH₃ | H | CH₃ | H | H |
| N | Cl | CF₃ | CH₃ | H | C₂H₅ | H | H |
| N | Cl | CF₃ | CH₃ | H | n-C₃H₇ | H | H |
| N | H | CF₃ | CH₃ | CH₃ | CH₃ | H | H |
| N | H | CF₃ | CH₃ | CH₃ | C₂H₅ | H | H |
| CH | H | CF₃ | CH₃ | CH₃ | CH₃ | H | H |
| CH | N | CF₃ | CH₃ | CH₃ | C₂H₅ | H | H |
| N | Cl | CF₃ | H | CH₃ | CH₃ | H | H |
| N | Cl | CF₃ | H | CH₃ | C₂H₅ | H | H |
| N | Cl | CF₃ | H | CH₃ | n-C₃H₇ | H | H |
| CH | H | CF₃ | H | H | CH₃ | CH₃ | H |
| CH | H | CF₃ | H | H | C₂H₅ | CH₃ | H |
| CH | H | CF₃ | H | H | n-C₃H₇ | CH₃ | H |
| CH | H | CF₃ | CH₃ | H | CH₃ | CH₃ | H |
| CH | H | CF₃ | CH₃ | H | C₂H₅ | CH₃ | H |
| CH | H | CF₃ | CH₃ | H | n-C₃H₇ | CH₃ | H |
| CH | H | CF₃ | H | CH₃ | CH₃ | CH₃ | H |
| CH | H | CF₃ | H | CH₃ | C₂H₅ | CH₃ | H |
| CH | H | CF₃ | H | CH₃ | n-C₃H₇ | CH₃ | H |
| CH | H | CF₃ | CH₃ | CH₃ | CH₃ | CH₃ | H |
| CH | H | OCF₃ | H | H | CH₃ | CH₃ | H |
| CH | H | OCF₃ | H | H | C₂H₅ | CH₃ | H |
| CH | H | OCF₃ | H | H | n-C₃H₇ | CH₃ | H |
| CH | H | OCF₃ | CH₃ | H | CH₃ | CH₃ | H |
| CH | H | OCF₃ | CH₃ | H | C₂H₅ | CH₃ | H |
| CH | H | OCF₃ | CH₃ | H | n-C₃H₇ | CH₃ | H |
| CH | H | OCF₃ | H | CH₃ | CH₃ | CH₃ | H |
| CH | H | OCF₃ | H | CH₃ | C₂H₅ | CH₃ | H |
| CH | H | OCF₃ | H | CH₃ | n-C₃H₇ | CH₃ | H |
| CH | H | OCF₂CF₂H | H | H | CH₃ | CH₃ | H |
| CH | H | OCF₂CF₂H | H | H | C₂H₅ | CH₃ | H |
| CH | H | OCF₂CF₂H | H | H | n-C₃H₇ | CH₃ | H |
| CH | H | OCF₂CF₂H | CH₃ | H | CH₃ | CH₃ | H |
| CH | H | OCF₂CF₂H | CH₃ | H | C₂H₅ | CH₃ | H |
| CH | H | OCF₂CF₂H | CH₃ | H | n-C₃H₇ | CH₃ | H |
| CH | H | OCF₂CF₂H | H | CH₃ | CH₃ | CH₃ | H |
| CH | H | OCF₂CF₂H | H | CH₃ | C₂H₅ | CH₃ | H |
| CH | H | OCF₂CF₂H | H | CH₃ | n-C₃H₇ | CH₃ | H |
| N | H | CF₃ | H | H | CH₃ | CH₃ | H |
| N | H | CF₃ | H | H | C₂H₅ | CH₃ | H |
| N | H | CF₃ | H | H | n-C₃H₇ | CH₃ | H |
| N | H | CF₃ | CH₃ | H | CH₃ | CH₃ | H |
| N | H | CF₃ | CH₃ | H | C₂H₅ | CH₃ | H |

TABLE 10-continued

Compounds of the general formula (II)'':

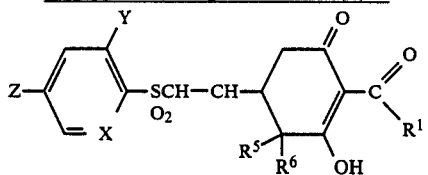

| X | Y | Z | $R^3$ | $R^4$ | $R^1$ | $R^5$ | $R^6$ |
|---|---|---|---|---|---|---|---|
| N | H | $CF_3$ | $CH_3$ | H | $n\text{-}C_3H_7$ | $CH_3$ | H |
| N | H | $CF_3$ | H | $CH_3$ | $CH_3$ | $CH_3$ | H |
| N | H | $CF_3$ | H | $CH_3$ | $C_2H_5$ | $CH_3$ | H |
| N | H | $CF_3$ | H | $CH_3$ | $n\text{-}C_3H_7$ | $CH_3$ | H |
| N | Cl | $CF_3$ | H | H | $CH_3$ | $CH_3$ | H |
| N | Cl | $CF_3$ | H | H | $C_2H_5$ | $CH_3$ | H |
| N | Cl | $CF_3$ | H | H | $n\text{-}C_3H_7$ | $CH_3$ | H |
| N | Cl | $CF_3$ | $CH_3$ | H | $CH_3$ | $CH_3$ | H |
| N | Cl | $CF_3$ | $CH_3$ | H | $C_2H_5$ | $CH_3$ | H |
| N | Cl | $CF_3$ | $CH_3$ | H | $n\text{-}C_3H_7$ | $CH_3$ | H |
| N | H | $CF_3$ | $CH_3$ | $CH_3$ | $CH_3$ | $CH_3$ | H |
| N | H | $CF_3$ | $CH_3$ | $CH_3$ | $C_2H_5$ | $CH_3$ | H |
| CH | H | $CF_3$ | $CH_3$ | $CH_3$ | $CH_3$ | $CH_3$ | H |
| CH | H | $CF_3$ | $CH_3$ | $CH_3$ | $C_2H_5$ | $CH_3$ | H |
| N | Cl | $CF_3$ | H | $CH_3$ | $CH_3$ | $CH_3$ | H |
| N | Cl | $CF_3$ | H | $CH_3$ | $C_2H_5$ | $CH_3$ | H |
| N | Cl | $CF_3$ | H | $CH_3$ | $n\text{-}C_3H_7$ | $CH_3$ | H |
| CH | H | $CF_3$ | H | H | $CH_3$ | H | $COOCH_3$ |
| CH | H | $CF_3$ | H | H | $C_2H_5$ | H | $COOC_2H_5$ |
| CH | H | $CF_3$ | H | H | $n\text{-}C_3H_7$ | H | $COOC_2H_5$ |
| CH | H | $CF_3$ | $CH_3$ | H | $CH_3$ | H | $COOCH_3$ |
| CH | H | $CF_3$ | $CH_3$ | H | $C_2H_5$ | H | $COOCH_3$ |
| CH | H | $CF_3$ | $CH_3$ | H | $n\text{-}C_3H_7$ | H | $COOCH_3$ |
| CH | H | $CF_3$ | H | $CH_3$ | $CH_3$ | H | $COOCH_3$ |
| CH | H | $CF_3$ | H | $CH_3$ | $C_2H_5$ | H | $COOCH_3$ |
| CH | H | $CF_3$ | H | $CH_3$ | $n\text{-}C_3H_7$ | H | $COOCH_3$ |
| CH | H | $OCF_3$ | H | H | $CH_3$ | H | $COOCH_3$ |
| CH | H | $OCF_3$ | H | H | $C_2H_5$ | H | $COOCH_3$ |
| CH | H | $OCF_3$ | H | H | $n\text{-}C_3H_7$ | H | $COOCH_3$ |
| CH | H | $OCF_3$ | $CH_3$ | H | $CH_3$ | H | $COOCH_3$ |
| CH | H | $OCF_3$ | $CH_3$ | H | $C_2H_5$ | H | $COOCH_3$ |
| CH | H | $OCF_3$ | $CH_3$ | H | $n\text{-}C_3H_7$ | H | $COOCH_3$ |
| CH | H | $OCF_3$ | H | $CH_3$ | $CH_3$ | H | $COOCH_3$ |
| CH | H | $OCF_3$ | H | $CH_3$ | $C_2H_5$ | H | $COOCH_3$ |
| CH | H | $OCF_3$ | H | $CH_3$ | $n\text{-}C_3H_7$ | H | $COOCH_3$ |
| CH | H | $OCF_2CF_2H$ | H | H | $CH_3$ | H | $COOCH_3$ |
| CH | H | $OCF_2CF_2H$ | H | H | $C_2H_5$ | H | $COOCH_3$ |
| CH | H | $OCF_2CF_2H$ | H | H | $n\text{-}C_3H_7$ | H | $COOCH_3$ |
| CH | H | $OCF_2CF_2H$ | $CH_3$ | H | $CH_3$ | H | $COOCH_3$ |
| CH | H | $OCF_2CF_2H$ | $CH_3$ | H | $C_2H_5$ | H | $COOCH_3$ |
| CH | H | $OCF_2CF_2H$ | $CH_3$ | H | $n\text{-}C_3H_7$ | H | $COOCH_3$ |
| CH | H | $OCF_2CF_2H$ | H | $CH_3$ | $CH_3$ | H | $COOCH_3$ |
| CH | H | $OCF_2CF_2H$ | H | $CH_3$ | $C_2H_5$ | H | $COOCH_3$ |
| CH | H | $OCF_2CF_2H$ | H | $CH_3$ | $n\text{-}C_3H_7$ | H | $COOCH_3$ |
| N | H | $CF_3$ | H | H | $CH_3$ | H | $COOC_2H_5$ |
| N | H | $CF_3$ | H | H | $C_2H_5$ | H | $COOCH_3$ |
| N | H | $CF_3$ | H | H | $n\text{-}C_3H_7$ | H | $COOCH_3$ |
| N | H | $CF_3$ | $CH_3$ | H | $CH_3$ | H | $COOC_2H_5$ |
| N | H | $CF_3$ | $CH_3$ | H | $C_2H_5$ | H | $COOC_2H_5$ |
| N | H | $CF_3$ | $CH_3$ | H | $n\text{-}C_3H_7$ | H | $COOC_2H_5$ |
| N | H | $CF_3$ | H | $CH_3$ | $CH_3$ | H | $COOC_2H_5$ |
| N | H | $CF_3$ | H | $CH_3$ | $C_2H_5$ | H | $COOC_2H_5$ |
| N | H | $CF_3$ | H | $CH_3$ | $n\text{-}C_3H_7$ | H | $COOC_2H_5$ |
| N | Cl | $CF_3$ | H | H | $CH_3$ | H | $COOC_2H_5$ |
| N | Cl | $CF_3$ | H | H | $C_2H_5$ | H | $COOC_2H_5$ |
| N | Cl | $CF_3$ | H | H | $n\text{-}C_3H_7$ | H | $COOC_2H_5$ |
| N | Cl | $CF_3$ | $CH_3$ | H | $CH_3$ | H | $COOC_2H_5$ |
| N | Cl | $CF_3$ | $CH_3$ | H | $C_2H_5$ | H | $COOC_2H_5$ |
| N | Cl | $CF_3$ | $CH_3$ | H | $n\text{-}C_3H_7$ | H | $COOC_2H_5$ |
| N | H | $CF_3$ | $CH_3$ | $CH_3$ | $CH_3$ | H | $COOC_2H_5$ |
| N | H | $CF_3$ | $CH_3$ | $CH_3$ | $C_2H_5$ | H | $COOC_2H_5$ |
| CH | H | $CF_3$ | $CH_3$ | $CH_3$ | $CH_3$ | H | $COOC_2H_5$ |
| CH | H | $CF_3$ | $CH_3$ | $CH_3$ | $C_2H_5$ | H | $COOC_2H_5$ |
| N | Cl | $CF_3$ | H | $CH_3$ | $CH_3$ | H | $COOC_2H_5$ |
| N | Cl | $CF_3$ | H | $CH_3$ | $C_2H_5$ | H | $COOC_2H_5$ |
| N | Cl | $CF_3$ | H | $CH_3$ | $n\text{-}C_3H_7$ | H | $COOC_2H_5$ |

PRODUCTION EXAMPLE 10

Production of the compound (VI)

Production of 3-(4-trifluoromethylphenylthio)propionaldehyde

Ten grams of 4-trifluoromethylthiophenol was dissolved in 15 ml of THF, and after adding 4.0 g of 95% acrolein under ice-cooling, 0.1 g of triethylamine was added while thoroughly stirring the reaction solution. After stirring for 1.5 hours under ice-cooling, the reaction solution was poured into water and extracted with ether. The ether layer was washed with water and dried over anhydrous magnesium sulfate. The solvent was removed under reduced pressure to obtain 13.1 g of 3-(4-trifluoromethylphenylthio)propionaldehyde.

$^1$H-NMR (CDCl$_3$): δ (ppm) 9.81 (1H, s), 7.47 (4H, ABq), 3.25 (2H, t), 2.84 (2H, t).

Examples of the compound of the general formula (VI) thus produced are shown in Table 11.

TABLE 11

Compounds of the general formula (VI):

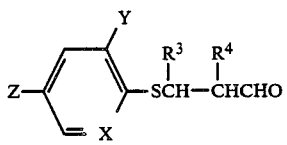

| X | Y | Z | R$^3$ | R$^4$ | Physical property |
|---|---|---|---|---|---|
| CH | H | CF$_3$ | CH$_3$ | H | n$_D^{21}$ 1.5043 |
| CH | H | CF$_3$ | H | CH$_3$ | n$_D^{22}$ 1.5020 |
| CH | H | OCF$_3$ | H | H | n$_D^{29}$ 1.4886 |
| CH | H | OCF$_2$CF$_2$H | H | H | n$_D^{23}$ 1.4771 |
| N | H | CF$_3$ | H | H | n$_D^{22}$ 1.5228 |
| N | Cl | CF$_3$ | H | H | n$_D^{19}$ 1.5262 |

PRODUCTION EXAMPLE 11

Production of the compound (VII)

Production of 6-(4-trifluoromethylphenylthio)-3-hexene-2-one

Ten grams of 3-(4-trifluoromethylphenylthio)propionaldehyde and 15 g of triphenylphosphine acetylmethylene were dissolved in 50 ml of chloroform, followed by stirring for 8 hours under ice-cooling. After removing chloroform, ether was added to the residue, and ether-insoluble products were removed by filtration. The ether-soluble product were purified by column chromatography (eluent; ethyl acetate:hexane=1:3) to obtain 9.9 g of 6-(4-trifluoromethylphenylthio)-3-hexene-2-one.

$^1$H-NMR (CDCl$_3$): δ (ppm) 7.46 (4H, ABq), 6.79 (1H, dt), 6.11 (1H, d), 3.3–2.5 (4H, m), 2.22 (3H, s).

Examples of the compound of the general formula (VII) thus produced are shown in Table 12.

TABLE 12

Compounds of the general formula (VII):

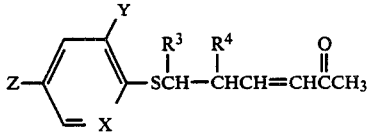

| X | Y | Z | R$^3$ | R$^4$ | Physical property |
|---|---|---|---|---|---|
| CH | H | CF$_3$ | CH$_3$ | H | n$_D^{21}$ 1.5101 |
| CH | H | CF$_3$ | H | CH$_3$ | n$_D^{23}$ 1.5077 |
| CH | H | OCF$_3$ | H | H | n$_D^{26}$ 1.5011 |
| CH | H | OCF$_2$CF$_2$H | H | H | n$_D^{23}$ 1.5002 |
| N | H | CF$_3$ | H | H | n$_D^{22}$ 1.5162 |
| N | Cl | CF$_3$ | H | H | n$_D^{19}$ 1.5332 |

PRODUCTION EXAMPLE 12

Production of the compound (IX)

Production of the sodium salt of 6-methoxycarbonyl-5-[2-(4-trifluoromethylphenylthio)ethyl]cyclohexane-1,3-dione 2.32 Grams of sodium was dissolved in 30 ml of methanol, and 300 ml of THF and 13.5 g of dimethyl malonate were added in this order. Heating under reflux was then carried out for 15 minutes, removed oil bath, and after adding 27.42 g of 6-(4-trifluoromethylphenylthio)-3-hexene-2-one, heating under reflux was again carried out for 30 minutes. The reaction solution was cooled to room temperature, and the precipitated crystals were filtered off and thoroughly washed with ether and hexane to obtain 34.3 g of the sodium salt of 6-methoxycarbonyl-5-[2-(4-trifluoromethylphenylthio)ethyl]cyclohexane-1,3-dione.

$^1$H-NMR (D$_2$O): δ (ppm) 7.45 (4H, ABq), 5.35 (1H, s), 3.88 (3H, s), 3.01 (2H, t), 2.5–1.5 (6H, m).

Examples of the compound of the general formula (IX) thus produced are shown in Table 13.

TABLE 13

Sodium salt of the compounds of the general formula (IX):

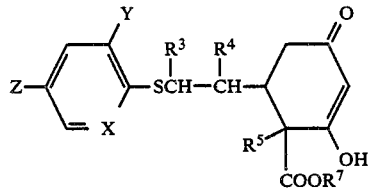

| X | Y | Z | R$^3$ | R$^4$ | R$^5$ | R$^7$ | Physical property ($^1$H—NMR) |
|---|---|---|---|---|---|---|---|
| CH | H | CF$_3$ | H | H | H | CH$_3$ | 7.45 (4H, ABq), 5.35 (1H, s), 3.88 (3H, s), 3.01 (2H, t), 2.5–1.5 (6H, m) |
| CH | H | CF$_3$ | CH$_3$ | H | H | CH$_3$ | 7.43 (4H, brs), 5.21 (1H, s), 3.87 (3H, s), 3.35 (1H, q), |

TABLE 13-continued

Sodium salt of the compounds of the general formula (IX):

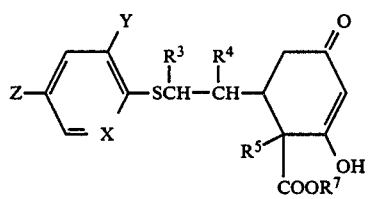

| X | Y | Z | $R^3$ | $R^4$ | $R^5$ | $R^7$ | Physical property ($^1$H—NMR) |
|---|---|---|---|---|---|---|---|
| CH | H | $CF_3$ | H | $CH_3$ | H | $CH_3$ | 1.29 (3H, d), 2.5-1.5 (6H, m) 7.40 (4H, ABq), 5.15 (1H, s), 3.78 (3H, s), 2.90 (2H, d), 1.10 (3H, d), 2.5-1.5 (5H, m) |
| CH | H | $OCF_3$ | H | H | H | $CH_3$ | 7.42 (4H, ABq), 5.11 (1H, s), 3.82 (3H, s), 3.00 (2H, t), 2.5-1.5 (6H, m) |
| CH | H | $OCF_2CF_2H$ | H | H | H | $CH_3$ | 7.40 (4H, ABq), 5.85 (1H, tt), 5.10 (1H, s), 3.79 (3H, s), 3.05 (2H, t), 2.5-1.5 (6H, m). |
| N | H | $CF_3$ | H | H | H | $CH_3$ | 8.62 (1H, s), 7.76 (1H, dd), 7.22 (1H, d), 5.22 (1H, s), 3.81 (3H, s), 3.01 (2H, s), 2.5-1.5 (6H, m) |
| N | Cl | $CF_3$ | H | H | H | $CH_3$ | 8.65 (1H, brs), 7.80 (1H, brs), 5.25 (1H, s), 3.78 (3H, s), 3.02 (2H, t), 2.5-1.5 (6H, m) |
| CH | H | $CF_3$ | H | H | $CH_3$ | $CH_3$ | 7.42 (4H, ABq), 5.34 (1H, s), 3.86 (3H, s), 2.99 (2H, t), 2.5-1.5 (5H, m), 1.10 (3H, s) |

PRODUCTION EXAMPLE 13

Production of the compound (X)

Production of 5-[2-(4-trifluoromethylphenylthio)ethyl]cyclohexane-1,3-dione 2.00 Grams of 6-methoxycarbonyl-5-[2-(4-trifluoromethylphenylthio)ethyl]cyclohexane-1,3-dione was dissolved in 30 ml of water, and 1.6 g of sodium carbonate was added to the resulting solution which was then heated under reflux for 5 hours. After thoroughly cooling the reaction solution, the reaction solution was extracted with ether to remove impurities, and the aqueous layer was acidified with hydrochloric acid and extracted with ethyl acetate to separate the desired product. The ethyl acetate layer was dried over anhydrous magnesium sulfate, and after removing ethyl acetate, the resulting crystals were washed with hexane to obtain 1.5 g of 5-[2-(4-trifluoromethylphenylthio)ethyl]cyclohexane-1,3-dione.

$^1$H-NMR (CDCl$_3$+DMSO-d$_6$): δ (ppm) 7.44 (4H, q), 5.32 (1H, s), 2.99 (2H, t), 2.5-1.5 (7H, m).

Examples of the compound of the general formula (X) thus produced are shown in Table 14.

TABLE 14

Compounds of the general formula (X):

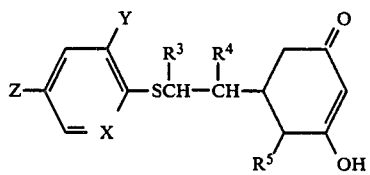

| X | Y | Z | $R^3$ | $R^4$ | $R^5$ | Physical property ($^1$H—NMR) |
|---|---|---|---|---|---|---|
| CH | H | $CF_3$ | H | H | H | 7.44 (4H, ABq), 5.32 (1H, s), |

TABLE 14-continued

Compounds of the general formula (X):

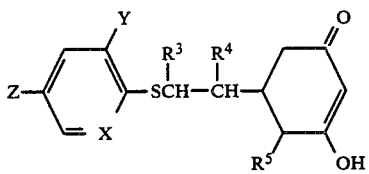

| X | Y | Z | $R^3$ | $R^4$ | $R^5$ | Physical property ($^1$H—NMR) |
|---|---|---|---|---|---|---|
| | | | | | | 2.99 (2H, t), 2.5-1.5 (7H, m) |
| CH | H | $CF_3$ | $CH_3$ | H | H | 7.45 (4H, brs), 5.15 (1H, s), 3.25 (1H, m), 1.17 (3H, d), 2.5-1.5 (7H, m) |
| CH | H | $CF_3$ | H | $CH_3$ | H | 7.42 (4H, ABq), 5.10 (1H, s), 2.95 (2H, d), 1.11 (3H, d), 2.5-1.5 (6H, m) |
| CH | H | $OCF_3$ | H | H | H | 7.40 (4H, ABq), 5.21 (1H, s), 3.03 (2H, t), 2.5-1.5 (7H, m) |
| CH | H | $OCF_2CF_2H$ | H | H | H | 7.41 (3H, s), 5.82 (1H, tt), 5.22 (1H, s), 3.08 (2H, t), 2.5-1.5 (7H, m) |
| N | H | $CF_3$ | H | H | H | 8.60 (1H, s), 7.75 (1H, dd), 7.24 (1H, s), 3.01 (2H, s), 2.5-1.5 (7H, m) |
| N | Cl | $CF_3$ | H | H | H | 8.63 (1H, brs), 7.75 (1H, brs), 3.02 (2H, t), 2.5-1.5 (7H, m) |
| CH | H | $CF_3$ | H | H | $CH_3$ | 7.43 (4H, ABq), 5.31 (1H, s), 2.95 (2H, t), 2.5-1.5 (6H, m), 1.15 (3H, d) |

PRODUCTION EXAMPLE 14

Production of the compound (XII)

Production of 1-acetoxy-5-[2-(4-trifluoromethylphenylthio)ethyl]-1-cyclohexene-3-one 6.32 Grams of 5-[2-(4-trifluoromethylphenylthio)ethyl]cyclohexane-1,3-dione was dissolved in 50 ml of tetrahydrofuran, and 2.12 g of triethylamine was added. Thereafter, 1.73 g of acetyl chloride was added dropwise with thorough stirring under ice-cooling. After continuing stirring for further 2 hours at room temperature, the precipitated solid was filtered off. The solvent was removed from the filtrate, and the residue was dissolved in ether. The ether layer was successively washed with dilute hydrochloric acid, aqueous sodium hydrogencarbonate and water and dried over anhydrous magnesium sulfate. Ether was removed to obtain 7.13 g of 1-acetoxy-5-[2-(4-trifluoromethylphenylthio)ethyl]-1-cyclohexene-3-one.

$^1$H-NMR (CDCl$_3$): δ (ppm) 7.39 (4H, q), 5.86 (1H, s), 3.07 (2H, t), 2.16 (3H, s), 2.5-1.5 (7H, m).

Examples of the compound of the general formula (XII) thus produced are shown in Table 15.

TABLE 15

Compounds of the general formula (XII):

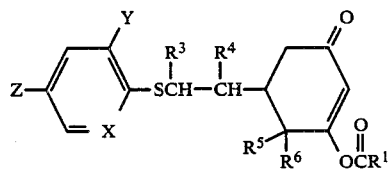

| X | Y | Z | $R^3$ | $R^4$ | $R^5$ | $R^6$ | $R^1$ | Physical property |
|---|---|---|---|---|---|---|---|---|
| CH | H | $CF_3$ | H | H | H | H | $CH_3$ | $n_D^{20}$ 1.5115 |
| CH | H | $CF_3$ | H | H | $CH_3$ | H | $CH_3$ | $n_D^{20}$ 1.5098 |
| CH | H | $CF_3$ | H | H | H | H | $C_2H_5$ | m.p. 47-48° C. |
| CH | H | $CF_3$ | H | H | H | $COOCH_3$ | $CH_3$ | $n_D^{20}$ 1.5058 |
| CH | H | $CF_3$ | H | H | H | H | n-$C_3H_7$ | $n_D^{19}$ 1.4995 |
| CH | H | $CF_3$ | H | H | H | $COOCH_3$ | $C_2H_5$ | $n_D^{19}$ 1.5216 |
| CH | H | $CF_3$ | H | H | H | H | $CH(CH_3)_2$ | $n_D^{20}$ 1.5383 |
| CH | H | $CF_3$ | H | H | H | H | $CH_2CH(CH_3)_2$ | m.p. 64-65° C. |
| CH | H | $CF_3$ | H | H | H | H | $CH_2OCH_3$ | $n_D^{22.5}$ 1.5341 |
| CH | H | $CF_3$ | H | H | H | $COOCH_3$ | n-$C_3H_7$ | $n_D^{20}$ 1.5401 |
| CH | H | $CF_3$ | $CH_3$ | H | H | $COOCH_3$ | $CH_3$ | $n_D^{23}$ 1.5512 |
| CH | H | $CF_2$ | $CH_3$ | H | H | H | $CH_3$ | $n_D^{22.5}$ 1.5326 |
| CH | H | $CF_3$ | $CH_3$ | H | H | $COOCH_3$ | $C_2H_5$ | $n_D^{23}$ 1.5486 |
| CH | H | $CF_3$ | $CH_3$ | H | H | H | $C_2H_5$ | $n_D^{22.5}$ 1.5162 |

TABLE 15-continued

Compounds of the general formula (XII):

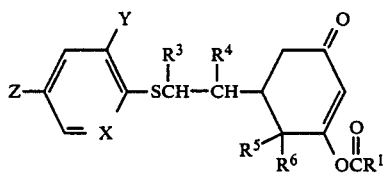

| X | Y | Z | $R^3$ | $R^4$ | $R^5$ | $R^6$ | $R^1$ | Physical property |
|---|---|---|---|---|---|---|---|---|
| CH | H | $CF_3$ | $CH_3$ | H | H | H | n-$C_3H_7$ | $n_D^{23}$ 1.4979 |
| CH | H | $CF_3$ | H | $CH_3$ | H | $COOCH_3$ | $CH_3$ | $n_D^{24}$ 1.5429 |
| CH | H | $CF_3$ | H | $CH_3$ | H | H | $CH_3$ | $n_D^{24}$ 1.5416 |
| CH | H | $CF_3$ | H | $CH_3$ | H | H | $C_2H_5$ | $n_D^{24}$ 1.5326 |
| CH | H | $CF_3$ | H | $CH_3$ | H | $COOCH_3$ | $C_2H_5$ | $n_D^{24}$ 1.5433 |
| CH | H | $CF_3$ | H | $CH_3$ | H | H | n-$C_3H_7$ | $n_D^{22}$ 1.4165 |
| CH | H | $OCF_3$ | H | H | H | $COOCH_3$ | $CH_3$ | $n_D^{26}$ 1.5501 |
| CH | H | $OCF_3$ | H | H | H | H | $CH_3$ | $n_D^{26}$ 1.5385 |
| CH | H | $OCF_3$ | H | H | H | H | $C_2H_5$ | $n_D^{27.5}$ 1.5118 |
| CH | H | $OCF_3$ | H | H | H | H | n-$C_3H_7$ | $n_D^{27.5}$ 1.4911 |
| CH | H | $OCF_3$ | H | H | H | $COOCH_3$ | $C_2H_5$ | $n_D^{25}$ 1.5281 |
| CH | H | $OCF_2CF_2H$ | H | H | H | H | $CH_3$ | $n_D^{24}$ 1.5211 |
| CH | H | $OCF_2CF_2H$ | H | H | H | H | $C_2H_5$ | $n_D^{24}$ 1.5081 |
| CH | H | $OCF_2CF_2H$ | H | H | H | H | n-$C_3H_7$ | $n_D^{24}$ 1.4944 |
| N | H | $CF_3$ | H | H | H | H | $CH_3$ | $n_D^{21}$ 1.5561 |
| N | H | $CF_3$ | H | H | H | H | $C_2H_5$ | $n_D^{21}$ 1.5537 |
| N | H | $CF_3$ | H | H | H | H | n-$C_3H_7$ | $n_D^{21}$ 1.5121 |
| N | Cl | $CF_3$ | H | H | H | H | $CH_3$ | $n_D^{22.5}$ 1.5485 |
| N | Cl | $CF_3$ | H | H | H | H | $C_2H_5$ | $n_D^{22.5}$ 1.5315 |
| N | Cl | $CF_3$ | H | H | H | H | n-$C_3H_7$ | $n_D^{22.5}$ 1.5067 |
| N | H | $CF_3$ | H | H | H | H | $CH_2OCH_3$ | $n_D^{23}$ 1.5135 |
| N | H | $CF_3$ | H | H | H | $COOC_2H_5$ | $C_2H_5$ | $n_D^{24}$ 1.5417 |

PRODUCTION EXAMPLE 15

Production of the compound (II)'

Production of 2-acetyl-5-[2-(4-trifluoromethylphenylthio)ethyl]cyclohexane-1,3-dione 3.3 Grams of 1-acetoxy-5-[2-(4-trifluoromethylphenylthio)ethyl]-1-cyclohexene-3-one and 0.8 g of 4-dimethylaminopyridine were dissolved in acetonitrile, followed by heating under reflux for 2.5 hours. After removing acetonitrile, the residue was dissolved in ethyl acetate, and the ethyl acetate layer was washed with dilute hydrochloric acid and then with water, and dried over anhydrous magnesium sulfate. Ethyl acetate was removed to obtain 3.3 g of 2-acetyl-5-[2-(4-trifluoromethylphenylthio)ethyl]cyclohexane-1,3-dione.

$^1$H-NMR (CDCl$_3$): δ (ppm) 18.16 (1H, s), 7.46 (4H, q), 3.03 (2H, t), 2.58 (3H, s), 2.8–1.6 (7H, m).

Examples of the compound of the general formula (II)' thus produced are shown in Table 16.

TABLE 16

Compounds of the general formula (II)':

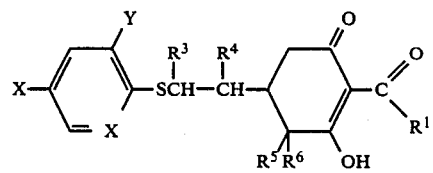

| X | Y | Z | $R^3$ | $R^4$ | $R^5$ | $R^6$ | $R^1$ | Physical property |
|---|---|---|---|---|---|---|---|---|
| CH | H | $CF_3$ | H | H | $CH_3$ | H | $CH_3$ | $n_D^{24}$ 1.5231 |
| CH | H | $CF_3$ | H | H | H | H | $CH_3$ | m.p. 60–61° C. |
| CH | H | $CF_3$ | H | H | H | $COOCH_3$ | $CH_3$ | $n_D^{24}$ 1.5465 |
| CH | H | $CF_3$ | H | H | H | H | $C_2H_5$ | $n_D^{25}$ 1.5161 |
| CH | H | $CF_3$ | H | H | H | $COOCH_3$ | $C_2H_5$ | $n_D^{24}$ 1.5399 |
| CH | H | $CF_3$ | H | H | H | H | n-$C_3H_7$ | $n_D^{25}$ 1.5017 |
| CH | H | $CF_3$ | H | H | H | $COOCH_3$ | n-$C_3H_7$ | $n_D^{23}$ 1.5178 |
| CH | H | $CF_3$ | H | H | H | H | $CH(CH_3)_2$ | $n_D^{23}$ 1.5261 |
| CH | H | $CF_3$ | H | H | H | H | $CH_2CH(CH_3)_2$ | $n_D^{24}$ 1.5362 |
| CH | H | $CF_3$ | H | H | H | H | $CH_2OCH_3$ | $n_D^{23}$ 1.5412 |
| CH | H | $CF_3$ | $CH_3$ | H | H | $COOCH_3$ | $CH_3$ | $n_D^{23}$ 1.5450 |
| CH | H | $CF_3$ | $CH_3$ | H | H | H | $CH_3$ | $n_D^{25.5}$ 1.5288 |
| CH | H | $CF_3$ | $CH_3$ | H | H | $COOCH_3$ | $C_2H_5$ | $n_D^{23}$ 1.5392 |
| CH | H | $CF_3$ | $CH_3$ | H | H | H | $C_2H_5$ | $n_D^{25.5}$ 1.5026 |
| CH | H | $CF_3$ | $CH_3$ | H | H | H | n-$C_3H_7$ | $n_D^{22.5}$ 1.4879 |
| CH | H | $CF_3$ | H | $CH_3$ | H | $COOCH_3$ | $CH_3$ | $n_D^{23}$ 1.5410 |

TABLE 16-continued

Compounds of the general formula (II)':

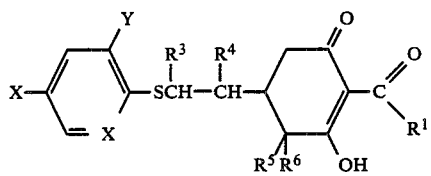

| X | Y | Z | $R^3$ | $R^4$ | $R^5$ | $R^6$ | $R^1$ | Physical property |
|---|---|---|---|---|---|---|---|---|
| CH | H | $CF_3$ | H | $CH_3$ | H | H | $CH_3$ | $n_D^{25.5}$ 1.4852 |
| CH | H | $CF_3$ | H | $CH_3$ | H | H | $C_2H_5$ | $D_D^{25.5}$ 1.4967 |
| CH | H | $CF_3$ | H | $CH_3$ | H | $COOCH_3$ | $C_2H_5$ | $n_D^{23}$ 1.5351 |
| CH | H | $CF_3$ | H | $CH_3$ | H | H | $n-C_3H_7$ | $n_D^{26}$ 1.4801 |
| CH | H | $OCF_3$ | H | H | H | $COOCH_3$ | $CH_3$ | $n_D^{25}$ 1.5320 |
| CH | H | $OCF_3$ | H | H | H | H | $CH_3$ | $n_D^{26}$ 1.5239 |
| CH | H | $OCF_3$ | H | H | H | H | $C_2H_5$ | $n_D^{26.5}$ 1.5113 |
| CH | H | $OCF_3$ | H | H | H | $COOCH_3$ | $C_2H_5$ | $n_D^{25}$ 1.5448 |
| CH | H | $OCF_3$ | H | H | H | H | $n-C_3H_7$ | $n_D^{26.5}$ 1.5099 |
| CH | H | $OCF_2CF_2H$ | H | H | H | H | $CH_3$ | $n_D^{26.5}$ 1.5276 |
| CH | H | $OCF_2CF_2H$ | H | H | H | H | $C_2H_5$ | $n_D^{26.5}$ 1.5146 |
| CH | H | $OCF_2CF_2H$ | H | H | H | H | $n-C_3H_7$ | $n_D^{26.5}$ 1.4878 |
| N | H | $CF_3$ | H | H | H | H | $CH_3$ | $n_D^{25.5}$ 1.5325 |
| N | H | $CF_3$ | H | H | H | H | $C_2H_5$ | $n_D^{25.5}$ 1.5150 |
| N | H | $CF_3$ | H | H | H | H | $n-C_3H_7$ | $n_D^{25.5}$ 1.4949 |
| N | Cl | $CF_3$ | H | H | H | H | $CH_3$ | $n_D^{26}$ 1.5437 |
| N | Cl | $CF_3$ | H | H | H | H | $C_2H_5$ | $n_D^{26}$ 1.5339 |
| N | Cl | $CF_3$ | H | H | H | H | $n-C_3H_7$ | $n_D^{26}$ 1.5201 |
| N | H | $CF_3$ | H | H | H | H | $CH_2OCH_3$ | $n_D^{25}$ 1.5286 |
| N | H | $CF_3$ | H | H | H | $COOC_2H_5$ | $C_2H_5$ | $n_D^{25}$ 1.5472 |

PRODUCTION EXAMPLE 16

Production of the compound (II)"

Production of 2-acetyl-5-[2-(4-trifluoromethylphenylsulfonyl)ethyl]-cyclohexane-1,3-dione To a solution of 2.0 g of 2-acetyl-5-[2-(4-trifluoromethylphenylthio)ethyl]cyclohexane-1,3-dione in 10 ml of acetic acid, 3.2 g of 30% hydrogen peroxide was added. The solution was stirred for 3 hours at 80° C. The solution was poured into water and extracted with ethyl acetate. Removal of solvent afforded 1.6 g of 2-acetyl-5-[2-(4-trifluoromethylphenylsulfonyl)ethyl]cyclohexane-1,3-dione. m.p. 135.5°–136.5° C.

$^1$H-NMR (acetone-$d_6$): δ (ppm) 18–19 (1H, br), 7.75 (4H, ABq), 3.12 (2H, t), 2.20 (3H, s), 2.2–1.4 (7H, m).

Production of 2-acetyl-5-[2-(4-trifluoromethylphenylsulfinyl)ethyl]cyclohexane-1,3-dione To a solution of 2.3 g of 2-acetyl-5-[2-(4-trifluoromethylphenylthio)ethyl]cyclohexane-1,3-dione in 10 ml of acetic acid, 1.8 g of 30% $H_2O_2$ was dropped under cooling with ice-water bath. After stirring for 1 hour at room temperature, the reaction solution was poured into water and extracted with ethyl acetate. Removal of solvent afforded 1.83 g of 2-acetyl-5-[2-(4-trifluoromethylphenylsulfinyl)ethyl]cyclohexane-1,3-dione. m.p. 99°–100° C.

$^1$H-NMR (acetone-$d_6$): δ (ppm) 18.10 (1H, s), 7.84 (4H, s), 2.90 (2H, t), 2.59 (3H, s), 3–1.6 (7H, m).

Examples of the compound of the general formula (II)" thus produced are shown in Table 17.

TABLE 17

Compounds of the General formula (II)":

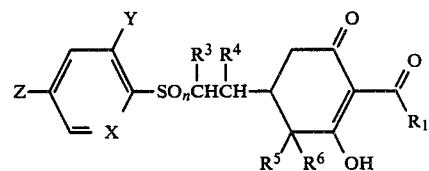

| X | Y | Z | $R_1$ | $R_2$ | $R_3$ | $R_4$ | $R_5$ | $R_6$ | n | Physical properties |
|---|---|---|---|---|---|---|---|---|---|---|
| CH | H | $CF_3$ | $CH_3$ | H | H | H | H | H | 1 | m.p. 99–100° C. |
| CH | H | $CF_3$ | $CH_3$ | H | H | H | H | H | 2 | m.p. 135.5–136.5° C. |
| CH | H | $CF_3$ | $C_2H_5$ | H | H | H | H | H | 1 | m.p. 105–106° C. |
| CH | H | $CF_3$ | $C_2H_5$ | H | H | H | H | H | 2 | m.p. 140–141° C. |

When the present compounds are used as an active ingredient for herbicides, they are generally formulated into emulsifiable concentrates, wettable powders, suspension formulations, granules, etc. by mixing with solid carriers, liquid carriers, surface active agents and other auxiliaries for formulation.

These preparations contain from 0.1 to 90% by weight, preferably from 0.2 to 80% by weight, more preferably from 1 to 80% by weight of the present compounds as an active ingredient.

The solid carriers include fine powders or granules of kaolin clay, attapulgite clay, bentonite, terra abla, pyrophyllite, talc, diatomaceous earth, calcite, walnut powder, urea, ammonium sulfate, synthetic hydrated silicon dioxide, etc. The liquid carriers include aromatic hydrocarbons (e.g. xylene, methylnaphthalene), alcohols (e.g. isopropanol, ethylene glycol, cellosolve), ketones (e.g.

acetone, cyclohexanone, isophorone), vegetable oils (e.g. soybean oil, cotton seed oil), dimethyl sulfoxide, N,N-dimethylformamide, acetontrile, water, etc.

The surface active agents used for emulsification, dispersion, wetting, etc. include anionic surface active agents such as the salt of alkyl sulfates, alkylsulfonates, alkylarylsulfonates, dialkyl sulfosuccinates, the salt of polyoxyethylene alkylaryl ether phosphoric acid ester, etc., and nonionic surface active agents such as polyoxyethylene alkyl ether, polyoxyethylene alkylaryl ether, polyoxyethylene polyoxypropylene block copolymers, sorbitan fatty acid esters, polyoxyethylene sorbitan fatty acid esters, etc.

The auxiliaries for formulation include lignosulfonates, alginates, polyvinyl alcohol, gum arabic, CMC (carboxymethyl cellulose), PAP (isopropyl acid phosphate), etc.

Next, formulation examples will be shown. The present compounds are shown by Compound No. in Table 2. Parts in the examples are by weight.

FORMULATION EXAMPLE 1

Fifty parts of the present compound (4) or (7), 3 parts of calcium lignoinsulfonate, 2 parts of sodium lauryl sulfate and 45 parts of synthetic hydrated silicon dioxide are well pulverized and mixed together to obtain a wettable powder.

FORMULATION EXAMPLE 2

Ten parts of each of the present compound (1)–(134), 14 parts of polyoxyethylene styryl phenyl ether, 6 parts of calcium dodecylbenzenesulfonate, 30 parts of xylene and 40 parts of cyclohexanone are well mixed to obtain an emulsifiable concentrate.

FORMULATION EXAMPLE 3

One part of the present compound (9) or (10), 1 part of synthetic hydrated silicon dioxide, 2 parts of calcium lignosulfonate, 31 parts of bentonite and 65 parts of kaolin clay are well pulverized and mixed together, well kneaded with water, granulated and dried to obtain a granule.

FORMULATION EXAMPLE 4

Twenty-five parts of the present compound (11), 3 parts of polyoxyethylene sorbitan monooleate, 3 parts of CMC and 69 parts of water are mixed and wet-pulverized until the particle size is reduced to 5 microns or less to obtain a suspension formulation.

FORMULATION EXAMPLE 5

Eighty parts of the present compound (1), 3 parts of calcium lignosulfonate, 2 parts of sodium lauryl sulfate and 15 parts of synthetic hydrated silicon dioxide are well pulverized and mixed together to obtain a wettable powder.

FORMULATION EXAMPLE 6

Twenty parts of the present compound (76), 2 parts of calcium lignosulfonate, 3 parts of alkylsulfonate and 10 parts of synthetic hydrated silicon dioxide are well pulverized and mixed together to obtain a wettable powder.

FORMULATION EXAMPLE 7

Two parts of the present compound (82), 1 part of polyoxyethylene sorbitan monooleate, 5 parts of polyvinyl alcohol and 92 parts of water are mixed and wet-pulverized until the particle size is reduced to 5 microns or less to obtain a suspension formulation.

FORMULATION EXAMPLE 8

Twenty parts of the present invention (5), 14 parts of polyoxyethylene styryl phenyl ether, 6 parts of calcium dodecylbenzenesulfonate, 30 parts of xylene and 30 parts of isophorone are well mixed to obtain an emulsifiable concentrate.

Generally, the present compounds are formulated and used in soil treatment, foliage treatment or treatment under flooded condition before or after the emergence of weeds. The soil treatment includes soil surface treatment, soil incorportion treatment, etc., and the foliage treatment includes, in addition to the treatment of plants over the top, directed treatment wherein herbicides are applied to weeds only so as not to attach to crops.

Further, the present compounds can be used as a herbicide for paddy fields, plow fields, orchards, pastures, turfs, forests, non-crop lands, etc., and also an increase in herbicidal activity can be expected by using them in mixture with other herbicides. In addition, they can be used in mixture with insecticides, acaricides, nematocides, plant growth regulators, fertilizers, soil improvers, etc.

When the present compounds are used as an active ingredient for herbicides, their dosage rate varies with weather conditions, preparation forms, when, how and where the treatments are applied, weeds and crops aimed at, etc., but it is generally from 0.05 to 200 g/are, preferably from 0.1 to 100 g/are. The usual dosage is from 0.6 to 10 g/are before the emergence of weeds. It is from 0.1 to 4 g/are after the emergence of weeds and is preferably from 0.2 to 2 g/are especially in corn and wheat fields. It is from 0.1 to 4 g/are in paddy field and is from 10 to 100 g/are in orchards, forests and non-crop lands. In the case of emulsifiable concentrates, wettable powders, suspension formulations, etc., their prescribed amount is generally diluted with water of from 1 to 10 liters/are (if necessary, auxiliaries such as spreading agents are added). Granules, etc. are generally used as such without dilution.

The spreading agents include, in addition to the foregoing surface active agents, polyoxyethylene resin acid (ester), lignosulfonates, abietates, dinaphthylmethanedisulfonates, paraffin, etc.

Next, the usefulness of the present compounds as an active ingredient for herbicides will be illustrated with reference to the following test examples. In the test example, the present compounds are shown by Compound No. in Table 2, and compounds used as a control are shown by Compound symbol in Table 18.

TABLE 18

| Compound symbol | Structural formula | Remark |
|---|---|---|
| (A) | [cyclohexenone with SCH2-phenyl substituent, =NOCH2CH=CH2, C3H7, OH] | Compound described in Japanese Patent Publication Kokai (Laid-open) No. 46749/1979. |
| (B) | [cyclohexenone with Cl-phenyl-SCH2 substituent, =NOCH2CH=CH2, C3H7, OH] | Compound described in Japanese Patent Publication Kokai (Laid-open) No. 115349/1979. |
| (C) | [cyclohexenone with CH3-phenyl-SCH2CH2 substituent, =NOCH2CH=CH2, C3H7, OH] | Compound described in Japanese Patent Publication Kokai (Laid-open) No. 115349/1979. |
| (D) | [triazine structure with Cl, (H3C)2HC-NH, C2H5-NH substituents] | Atrazine |
| (E) | [triazine with SCH3, CH3CH2-NH, C2H5-NH] | Simetryn |
| (F) | [cyclohexenone with C2H5S—CH(CH3)—CH2 substituent, =NOC2H5, C3H7, OH] | Sethoxydim |

The herbicidal activity and phytotoxicity were evaluated in six stages, 0, 1, 2, 3, 4, 5, according to the states of the emergence and growth of test plants (weeds and crops) at the time of examination. A stage "0" means there being little or no difference in the states between the treated test plants and untreated ones; a stage "5" means the complete death of test plants or complete inhibition of the emergence or growth thereof; and the states between "0" and "5" were divided into four stages, 1, 2, 3 and 4.

TEST EXAMPLE 1

Soil surface treatment test in plow field

Plow-field soil was filled in a cylindrical plastic pot (diameter, 10 cm; depth, 10 cm), and the weeds of Japanese millet and oat were sowed and covered with the soil. The prescribed amount of the emulsifiable concentrates of the test compounds prepared according to Formulation example 2 was diluted with water of an amount corresponding to 10 liters/are, and applied to the soil surface by means of a small-sized sprayer. After treatment, the test plants were cultivated for 20 days in a greenhouse to examine the herbicidal activity. The results are shown in Table 19.

TABLE 19

| Compound No. | Dosage (g/are) | Herbicidal activity | |
|---|---|---|---|
| | | Japanese millet | Oat |
| 2 | 40 | 5 | 5 |
| 3 | 40 | 5 | — |
| 10 | 40 | 5 | 5 |
| 11 | 40 | 5 | 5 |
| 12 | 40 | 5 | 5 |
| 13 | 40 | 5 | — |
| 20 | 40 | 5 | 5 |
| 21 | 40 | 5 | 5 |
| 22 | 40 | 5 | 5 |
| 23 | 40 | 5 | 5 |
| 24 | 40 | 5 | — |
| 25 | 40 | 5 | — |
| 26 | 40 | 5 | 5 |
| 27 | 40 | 5 | — |
| 28 | 40 | 5 | — |
| 30 | 40 | 5 | 5 |
| 31 | 40 | 5 | 5 |
| 32 | 40 | 5 | 5 |
| 33 | 40 | 5 | 5 |
| 34 | 40 | 5 | — |

TABLE 19-continued

| Compound No. | Dosage (g/are) | Herbicidal activity Japanese millet | Oat |
|---|---|---|---|
| 41 | 40 | 5 | — |
| 43 | 40 | 5 | — |
| 44 | 40 | 5 | 5 |
| 51 | 40 | 5 | 5 |
| 52 | 40 | 5 | — |
| 53 | 40 | 5 | 5 |
| 54 | 40 | 5 | 5 |
| 55 | 40 | 5 | 5 |
| 56 | 40 | 5 | 5 |
| 57 | 40 | 5 | — |
| 58 | 40 | 5 | — |
| 59 | 40 | 5 | 5 |
| 60 | 40 | 5 | 5 |
| 67 | 40 | 5 | 5 |
| 68 | 40 | 5 | 5 |
| 69 | 40 | 5 | 5 |
| 70 | 40 | 5 | 5 |
| 71 | 40 | 5 | 5 |
| 72 | 40 | 5 | 5 |
| 73 | 40 | 5 | 5 |
| 74 | 40 | 5 | 5 |
| 75 | 40 | 5 | 5 |
| 76 | 40 | 5 | 5 |
| 77 | 40 | 5 | 5 |
| 78 | 40 | 5 | 5 |
| 79 | 40 | 5 | 5 |
| 80 | 40 | 5 | 5 |
| 81 | 40 | 5 | 5 |
| 82 | 40 | 5 | 5 |
| 83 | 40 | 5 | 5 |
| 84 | 40 | 5 | 5 |
| 85 | 40 | 5 | 5 |
| 86 | 40 | 5 | 5 |
| 87 | 40 | 5 | 5 |
| 88 | 40 | 5 | 5 |
| 89 | 40 | 5 | 5 |
| 90 | 40 | 5 | 5 |
| 91 | 40 | 5 | 5 |
| 92 | 40 | 5 | 5 |
| 93 | 40 | 5 | 5 |
| 94 | 40 | 5 | — |
| 95 | 40 | 5 | 5 |
| 97 | 40 | 5 | 5 |
| 98 | 40 | 5 | 5 |
| 99 | 40 | 5 | 5 |
| 100 | 40 | 5 | 5 |
| 101 | 40 | 5 | 5 |
| 102 | 40 | 5 | 5 |
| 103 | 40 | 5 | 5 |
| 104 | 40 | 5 | 5 |
| 105 | 40 | 5 | 5 |
| 106 | 40 | 5 | 5 |
| 107 | 40 | 5 | 5 |
| 108 | 40 | 5 | 5 |
| 109 | 40 | 5 | 5 |
| 110 | 40 | 5 | 5 |
| 111 | 40 | 5 | 5 |
| 112 | 40 | 5 | 5 |
| 114 | 40 | 5 | 5 |

TEST EXAMPLE 2

Foliage treatment test in plow field

Plow-field soil was filled in a cylindrical plastic pot (diameter, 10 cm; depth, 10 cm), and the seeds of Japanese millet and oat were sowed and cultivatied for 10 days in a greenhouse. Thereafter, the prescribed amount of the emulsifiable concentrates of the test compounds prepared according to Formulation example 2 was diluted with a spreading agent-containing water of an amount corresponding to 10 liters/are, and foliage-applied to the test plants over the top by means of a small-sized sprayer. After treatment, the test plants were cultivated for 20 days in a greenhouse to examine the herbicidal activity. The results are shown in Table 20.

TABLE 20

| Compound No. | Dosage (g/are) | Herbicidal activity Japanese millet | Oat |
|---|---|---|---|
| 1 | 40 | 5 | 5 |
| 2 | 40 | 5 | 5 |
| 3 | 40 | 5 | 5 |
| 4 | 40 | 5 | 5 |
| 5 | 40 | 5 | 5 |
| 6 | 40 | 5 | 5 |
| 7 | 40 | 5 | 5 |
| 8 | 40 | 5 | 5 |
| 9 | 40 | 5 | 5 |
| 10 | 40 | 5 | 5 |
| 11 | 40 | 5 | 5 |
| 12 | 40 | 5 | 5 |
| 13 | 40 | 5 | 5 |
| 14 | 40 | 5 | 5 |
| 15 | 40 | 5 | 5 |
| 16 | 40 | 5 | 5 |
| 17 | 40 | 5 | 5 |
| 18 | 40 | 5 | 5 |
| 19 | 40 | 5 | 5 |
| 20 | 40 | 5 | 5 |
| 21 | 40 | 5 | 5 |
| 22 | 40 | 5 | 5 |
| 23 | 40 | 5 | 5 |
| 24 | 40 | 5 | 5 |
| 25 | 40 | 5 | 5 |
| 26 | 40 | 5 | 5 |
| 27 | 40 | 5 | 5 |
| 28 | 40 | 5 | 5 |
| 29 | 40 | 5 | 5 |
| 30 | 40 | 5 | 5 |
| 31 | 40 | 5 | 5 |
| 32 | 40 | 5 | 5 |
| 33 | 40 | 5 | 5 |
| 34 | 40 | 5 | 5 |
| 35 | 40 | 5 | 5 |
| 36 | 40 | 5 | 5 |
| 37 | 40 | 5 | 5 |
| 38 | 40 | 5 | 5 |
| 39 | 40 | 5 | 5 |
| 40 | 40 | 5 | 5 |
| 41 | 40 | 5 | 5 |
| 42 | 40 | 5 | 5 |
| 43 | 40 | 5 | 5 |
| 44 | 40 | 5 | 5 |
| 45 | 40 | 5 | 5 |
| 46 | 40 | 5 | 5 |
| 47 | 40 | 5 | 5 |
| 48 | 40 | 5 | 5 |
| 49 | 40 | 5 | 5 |
| 50 | 40 | 5 | 5 |
| 51 | 40 | 5 | 5 |
| 52 | 40 | 5 | 5 |
| 53 | 40 | 5 | 5 |
| 54 | 40 | 5 | 5 |
| 55 | 40 | 5 | 5 |
| 56 | 40 | 5 | 5 |
| 57 | 40 | 5 | 5 |
| 58 | 40 | 5 | 5 |
| 59 | 40 | 5 | 5 |
| 60 | 40 | 5 | 5 |
| 61 | 40 | 5 | 5 |
| 62 | 40 | 5 | 5 |
| 64 | 40 | 5 | 5 |
| 65 | 40 | 5 | 5 |
| 66 | 40 | 5 | 5 |
| 67 | 40 | 5 | 5 |
| 68 | 40 | 5 | 5 |
| 69 | 40 | 5 | 5 |
| 70 | 40 | 5 | 5 |
| 71 | 40 | 5 | 5 |
| 72 | 40 | 5 | 5 |
| 73 | 40 | 5 | 5 |
| 74 | 40 | 5 | 5 |
| 75 | 40 | 5 | 5 |
| 76 | 40 | 5 | 5 |
| 77 | 40 | 5 | 5 |
| 78 | 40 | 5 | 5 |

TABLE 20-continued

| Compound No. | Dosage (g/are) | Herbicidal activity Japanese millet | Oat |
|---|---|---|---|
| 79 | 40 | 5 | 5 |
| 80 | 40 | 5 | 5 |
| 81 | 40 | 5 | 5 |
| 82 | 40 | 5 | 5 |
| 83 | 40 | 5 | 5 |
| 84 | 40 | 5 | 5 |
| 85 | 40 | 5 | 5 |
| 86 | 40 | 5 | 5 |
| 87 | 40 | 5 | 5 |
| 88 | 40 | 5 | 5 |
| 89 | 40 | 5 | 5 |
| 90 | 40 | 5 | 5 |
| 91 | 40 | 5 | 5 |
| 92 | 40 | 5 | 5 |
| 93 | 40 | 5 | 5 |
| 94 | 40 | 5 | 5 |
| 95 | 40 | 5 | 5 |
| 96 | 40 | 5 | 5 |
| 97 | 40 | 5 | 5 |
| 98 | 40 | 5 | 5 |
| 99 | 40 | 5 | 5 |
| 100 | 40 | 5 | 5 |
| 101 | 40 | 5 | 5 |
| 102 | 40 | 5 | 5 |
| 103 | 40 | 5 | 5 |
| 104 | 40 | 5 | 5 |
| 105 | 40 | 5 | 5 |
| 106 | 40 | 5 | 5 |
| 107 | 40 | 5 | 5 |
| 108 | 40 | 5 | 5 |
| 109 | 40 | 5 | 5 |
| 110 | 40 | 5 | 5 |
| 111 | 40 | 5 | 5 |
| 112 | 40 | 5 | 5 |
| 113 | 40 | 5 | 5 |
| 114 | 40 | 5 | 5 |
| 115 | 40 | 5 | 5 |
| 116 | 40 | 5 | 5 |
| 117 | 40 | 5 | 5 |
| 118 | 40 | 5 | 5 |
| 119 | 40 | 5 | 5 |
| 120 | 40 | 5 | 5 |
| 121 | 40 | 5 | 5 |
| 122 | 40 | 5 | 5 |
| 123 | 40 | 5 | 5 |
| 124 | 40 | 5 | 5 |
| 125 | 40 | 5 | 5 |
| 126 | 40 | 5 | 5 |
| 127 | 40 | 5 | 5 |
| 128 | 40 | 5 | 5 |
| 129 | 40 | 5 | 5 |
| 130 | 40 | 5 | 5 |
| 131 | 40 | 5 | 5 |
| 132 | 40 | 5 | 5 |
| 133 | 40 | 5 | 5 |
| 134 | 40 | 5 | 5 |

TEST EXAMPLE

Foliage treatment test in plow field

Plow-field soil was filled in a cylindrical plastic pot (diameter, 10 cm; depth, 10 cm), and the seeds of Japanese millet, oat, radish and velvetleaf were sowed and cultivated for 10 days in a greenhouse. Thereafter, the prescribed amount of the emulsifiable concentrates of the test compounds prepared according to Formulation example 2 was diluted with a spreading agent-containing water of an amount corresponding to 10 liters/are, and foliage-applied to the test plants over the top by means of a small-sized sprayer. After treatment, the test plants were cultivated for 20 days in a greenhouse to examine the herbicidal activity. The results are shown in Table 21.

TABLE 21

| Compound No. | Dosage (g/are) | Japanese millet | Oat | Radish | Velvetleaf |
|---|---|---|---|---|---|
| 2 | 40 | 5 | 5 | 5 | 5 |
| 3 | 40 | 5 | 5 | 5 | — |
| 11 | 40 | 5 | 5 | 5 | 5 |
| 12 | 40 | 5 | 5 | 5 | 5 |
| 13 | 40 | 5 | 5 | 5 | 5 |
| 20 | 40 | 5 | 5 | 5 | 5 |
| 21 | 40 | 5 | 5 | 5 | 5 |
| 22 | 40 | 5 | 5 | 5 | 5 |
| 23 | 40 | 5 | 5 | 5 | 5 |
| 24 | 40 | 5 | 5 | 5 | 5 |
| 25 | 40 | 5 | 5 | 5 | 5 |
| 26 | 40 | 5 | 5 | 5 | — |
| 28 | 40 | 5 | 5 | 5 | — |
| 29 | 40 | 5 | 5 | 5 | — |
| 30 | 40 | 5 | 5 | 5 | — |
| 33 | 40 | 5 | 5 | 5 | 4 |
| 41 | 40 | 5 | 5 | 5 | — |
| 54 | 40 | 5 | 5 | 5 | 4 |
| 56 | 40 | 5 | 5 | 5 | 4 |
| 86 | 40 | 5 | 5 | 5 | 5 |
| 87 | 40 | 5 | 5 | 5 | 5 |
| 88 | 40 | 5 | 5 | 5 | 5 |
| 89 | 40 | 5 | 5 | 5 | 4 |
| 91 | 40 | 5 | 5 | 5 | — |
| 92 | 40 | 5 | 5 | 5 | 5 |
| 93 | 40 | 5 | 5 | 5 | 4 |
| 95 | 40 | 5 | 5 | 5 | 4 |
| 97 | 40 | 5 | 5 | 4 | — |
| 98 | 40 | 5 | 5 | 5 | — |
| 99 | 40 | 5 | 5 | 5 | — |
| 100 | 40 | 5 | 5 | 5 | — |
| 101 | 40 | 5 | 5 | 5 | 4 |
| 102 | 40 | 5 | 5 | 5 | 4 |
| 103 | 40 | 5 | 5 | — | — |
| 105 | 40 | 5 | 5 | 5 | — |
| 106 | 40 | 5 | 5 | 5 | — |
| 107 | 40 | 5 | 5 | 5 | — |
| 108 | 40 | 5 | 5 | 4 | 4 |
| 109 | 40 | 5 | 5 | — | — |
| 110 | 40 | 5 | 5 | — | — |
| 111 | 40 | 5 | 5 | 5 | 5 |
| 114 | 40 | 5 | 5 | 5 | — |

TEST EXAMPLE 4

Foliage treatment test in plow field

Plow-field soil was filled in a cylindrical plastic pot (diameter, 10 cm; depth, 10 cm), and the seeds of radish and velvetleaf were sowed and cultivated for 10 days in a greenhouse. Thereafter, the prescribed amount of the emulsifiable concentrates of the test compounds prepared according to Formulation example 2 was diluted with a spreading agent-containing water of an amount corresponding to 10 liters/are, and foliage-applied to the test plants over the top by means of a small-sized sprayer. After treatment, the test plants were cultivated for 20 days in a greenhouse to examine the herbicidal activity. The results are shown in Table 22.

TABLE 22

| Compound No. | Dosage (g/are) | Herbicidal activity Radish | Velvetleaf |
|---|---|---|---|
| 11 | 20 | 5 | 5 |
| 12 | 20 | 5 | 5 |
| 13 | 20 | 5 | 5 |
| 20 | 20 | 5 | 5 |
| 21 | 20 | 5 | 5 |
| 22 | 20 | 5 | 5 |
| 23 | 20 | 5 | 5 |
| 24 | 20 | 5 | 5 |
| 25 | 20 | 5 | 5 |

TEST EXAMPLE 5

Treatment test under flooded condition in paddy field

Paddy-field soil was filled in a cylindrical plastic pot (diameter, 8 cm; depth, 12 cm), and a cylindrical plastic pot (diameter, 8 cm; depth, 12 cm), and the seeds of barnyardgrass were incorporated from 1 to 2 cm deep in the soil. After creating the state of paddy field by flooding, the test plants were cultivated in a greenhouse. After 6 days (initial stage of emergence of weeds), the prescribed amount of the emulsifiable concentrates of the test compounds prepared according to Formulation example 2 was diluted with 5 ml of water, and applied to the water surface. After treatment, the test plants were cultivated for 20 days in a greenhouse to examine the herbicidal activity. The results are shown in Table 23.

TABLE 22-continued

| Compound No. | Dosage (g/are) | Herbicidal activity Radish | Velvetleaf |
|---|---|---|---|
| B | 20 | 0 | 0 |

TABLE 23

| Compound No. | Dosage (g/are) | Herbicidal activity Barnyardgrass |
|---|---|---|
| 1 | 40 | 5 |
| 2 | 40 | 5 |
| 3 | 40 | 5 |
| 4 | 40 | 5 |
| 5 | 40 | 5 |
| 6 | 40 | 5 |
| 7 | 40 | 5 |
| 8 | 40 | 5 |
| 9 | 40 | 5 |
| 10 | 40 | 5 |
| 11 | 40 | 5 |
| 12 | 40 | 5 |
| 13 | 40 | 5 |
| 14 | 40 | 5 |
| 15 | 40 | 5 |
| 16 | 40 | 5 |
| 17 | 40 | 5 |
| 18 | 40 | 5 |
| 19 | 40 | 5 |
| 20 | 40 | 5 |
| 21 | 40 | 5 |
| 22 | 40 | 5 |
| 23 | 40 | 5 |
| 24 | 40 | 5 |
| 25 | 40 | 5 |
| 26 | 40 | 5 |
| 27 | 40 | 5 |
| 28 | 40 | 5 |
| 29 | 40 | 5 |
| 30 | 40 | 5 |
| 31 | 40 | 5 |
| 32 | 40 | 5 |
| 33 | 40 | 5 |
| 34 | 40 | 5 |
| 35 | 40 | 5 |
| 36 | 40 | 5 |
| 37 | 40 | 5 |
| 38 | 40 | 5 |
| 39 | 40 | 5 |
| 40 | 40 | 5 |
| 41 | 40 | 5 |
| 42 | 40 | 5 |
| 43 | 40 | 5 |
| 44 | 40 | 5 |
| 45 | 40 | 5 |
| 46 | 40 | 5 |
| 47 | 40 | 5 |
| 48 | 40 | 5 |
| 49 | 40 | 5 |
| 50 | 40 | 5 |
| 51 | 40 | 5 |
| 52 | 40 | 5 |
| 53 | 40 | 5 |
| 54 | 40 | 5 |
| 55 | 40 | 5 |
| 56 | 40 | 5 |
| 57 | 40 | 5 |
| 58 | 40 | 5 |
| 59 | 40 | 5 |
| 60 | 40 | 5 |
| 61 | 40 | 5 |
| 62 | 40 | 5 |
| 64 | 40 | 5 |
| 65 | 40 | 5 |
| 66 | 40 | 5 |
| 67 | 40 | 5 |
| 68 | 40 | 5 |
| 69 | 40 | 5 |
| 70 | 40 | 5 |
| 71 | 40 | 5 |
| 72 | 40 | 5 |
| 73 | 40 | 5 |
| 74 | 40 | 5 |
| 75 | 40 | 5 |
| 76 | 40 | 5 |
| 77 | 40 | 5 |
| 78 | 40 | 5 |
| 79 | 40 | 5 |
| 80 | 40 | 5 |
| 81 | 40 | 5 |
| 82 | 40 | 5 |
| 83 | 40 | 5 |
| 84 | 40 | 5 |
| 85 | 40 | 5 |
| 86 | 40 | 5 |
| 87 | 40 | 5 |
| 88 | 40 | 5 |
| 89 | 40 | 5 |
| 90 | 40 | 5 |
| 91 | 40 | 5 |
| 92 | 40 | 5 |
| 93 | 40 | 5 |
| 94 | 40 | 5 |
| 95 | 40 | 5 |
| 96 | 40 | 5 |
| 97 | 40 | 5 |
| 98 | 40 | 5 |
| 99 | 40 | 5 |
| 100 | 40 | 5 |
| 101 | 40 | 5 |
| 102 | 40 | 5 |
| 103 | 40 | 5 |
| 104 | 40 | 5 |
| 105 | 40 | 5 |
| 106 | 40 | 5 |
| 107 | 40 | 5 |
| 108 | 40 | 5 |
| 109 | 40 | 5 |
| 110 | 40 | 5 |
| 111 | 40 | 5 |
| 112 | 40 | 5 |
| 113 | 40 | 5 |
| 114 | 40 | 5 |
| 115 | 40 | 5 |
| 116 | 40 | 5 |
| 117 | 40 | 5 |
| 118 | 40 | 5 |
| 119 | 40 | 5 |
| 120 | 40 | 5 |
| 121 | 40 | 5 |
| 122 | 40 | 5 |
| 123 | 40 | 5 |
| 124 | 40 | 5 |
| 125 | 40 | 5 |
| 126 | 40 | 5 |
| 127 | 40 | 5 |
| 128 | 40 | 5 |
| 129 | 40 | 5 |
| 130 | 40 | 5 |
| 131 | 40 | 5 |

TABLE 23-continued

| Compound No. | Dosage (g/are) | Herbicidal activity Barnyardgrass |
|---|---|---|
| 132 | 40 | 5 |
| 133 | 40 | 5 |
| 134 | 40 | 5 |

TEST EXAMPLE 6

Soil treatment test in plow field

Plow-field soil was filled in a vat (area, 33×23 cm$^2$; depth, 11 cm), and the seeds of soybean, cotton, barnyardgrass, johnsongrass and green foxtail were sowed and covered from 1 to 2 cm deep with the soil. The prescribed amount of the emulsifiable concentrates of the test compounds prepared according to Formulation example 2 was diluted with water of an amount corresponding to 10 liters/are, and applied to the soil surface by means of a small-sized sprayer. After treatment, the test plants were cultivated for 20 days in a greenhouse to examine the herbicidal activity. The results are shown in Table 24.

TABLE 24

| Compound No. | Dosage (g/are) | Herbicidal activity | | | | |
|---|---|---|---|---|---|---|
| | | Soybean | Cotton | Barnyardgrass | Johnsongrass | Green foxtail |
| 2 | 2.5 | 0 | 0 | 5 | 5 | 5 |
|   | 0.63 | 0 | 0 | 4 | — | 4 |
| 32 | 2.5 | 0 | 0 | 5 | 4 | 5 |
|   | 0.63 | 0 | 0 | — | 3 | 5 |
| 33 | 2.5 | 0 | 0 | 5 | 5 | 5 |
| 41 | 2.5 | 0 | 0 | 5 | 4 | 5 |
|   | 0.63 | 0 | 0 | 4 | — | 5 |
| 59 | 2.5 | 0 | 0 | 5 | 4 | 5 |
| 70 | 2.5 | 0 | 0 | 5 | 5 | 5 |
|   | 0.63 | 0 | 0 | 3 | — | — |
| 74 | 2.5 | 0 | 0 | 5 | 5 | 5 |
|   | 0.63 | 0 | 0 | 3 | 3 | — |
| 77 | 2.5 | 0 | 0 | 5 | 4 | 4 |
| 98 | 2.5 | 0 | 0 | 5 | 5 | 5 |
|   | 0.63 | 0 | 0 | 5 | 4 | 5 |
| 99 | 2.5 | 0 | 0 | 5 | 4 | 5 |
|   | 0.63 | 0 | 0 | 4 | — | 4 |
| 100 | 2.5 | 0 | 0 | 4 | 4 | 5 |
|   | 0.63 | 0 | 0 | — | 3 | 3 |
| A | 2.5 | 0 | 0 | 0 | 1 | 0 |
|   | 0.63 | 0 | 0 | 0 | 0 | 0 |
| B | 2.5 | 0 | 0 | 2 | 1 | 2 |
|   | 0.63 | 0 | 0 | 0 | 0 | 0 |

TEST EXAMPLE 7

Soil treatment test in plow field

Plow-field soil was filled in a vat (area, 33×23 cm$^2$; depth, 11 cm), and the seeds of corn, barnyardgrass, large crabgrass, johnsongrass, green foxtail, oat and fall panicum were sowed and covered from 1 to 2 cm deep with the soil. The prescribed amount of the emulsifiable concentrates of the test compounds prepared according to Formulation example 2 was diluted with water of an amount corresponding to 10 liters/are, and applied to the soil surface by means of a small-sized sprayer. After treatment, the test plants were cultivated for 20 days in a greenhouse to examine the herbicidal activity. The results are shown in Table 25.

TABLE 25

| Compound No. | Dosage (g/are) | Herbicidal activity | | | | | | |
|---|---|---|---|---|---|---|---|---|
| | | Corn | Barnyard-grass | Large crabgrass | Johnson-grass | Green foxtail | Oat | Fall panicum |
| 2 | 2.5 | 0 | 5 | 5 | 4 | 5 | 4 | 5 |
| 26 | 2.5 | 0 | 5 | 5 | 5 | 5 | — | — |
| 70 | 2.5 | 0 | 5 | 4 | 5 | 5 | 5 | 5 |
| A | 2.5 | 0 | 0 | 1 | 1 | 0 | 0 | 1 |
| C | 2.5 | 0 | 3 | 1 | 1 | 1 | 0 | 5 |

TEST EXAMPLE 8

Soil treatment test in plow field

Plow-field soil was filled in a vat (area, 33×23 cm$^2$; depth, 11 cm), and the seeds of wheat, barley, wild oat, blackgrass and annual bluegrass were sowed and covered from 1 to 2 cm deep with the soil. The prescribed amount of the emulsifiable concentrates of the test compounds prepared according to Formulation example 2 was diluted with water of an amount corresponding to 10 liters/are, and applied to the soil surface by means of a small-sized sprayer. After treatment, the test plants were cultivated for 30 days in a greenhouse to examine the herbicidal activity. The results are shown in Table 26.

TABLE 26

| Compound No. | Dosage (g/are) | Herbicidal activity | | | | |
|---|---|---|---|---|---|---|
| | | Wheat | Barley | Wild oat | Black-grass | Annual bluegrass |
| 2 | 2.5 | — | 0 | 5 | 5 | 5 |
|   | 0.63 | 1 | 0 | 4 | 5 | 5 |
| 26 | 2.5 | 0 | 0 | — | 5 | 4 |
| 70 | 2.5 | 1 | 0 | 4 | 4 | 5 |
| B | 2.5 | 1 | 0 | 0 | 2 | 0 |
|   | 0.63 | 0 | 0 | 0 | 0 | 0 |

TEST EXAMPLE 9

Foliage treatment test in plow field

Plow-field soil was filled in a vat (area, 33×23 cm²; depth, 11 cm), and the seeds of soybean, cotton, barnyardgrass, large crabgrass, johnsongrass, green foxtail, oat and annual bluegrass were sowed and cultivated for 18 days. Thereafter, the prescribed amount of the emulsifiable concentrates of the test compounds prepared according to Formulation example 2 was diluted with a spreading agent-containing water of an amount corresponding to 5 liters/are, and uniformly applied to the entire foliage of the test plants over the top by means of a small-sized sprayer. The state of growth of the weeds and crops at that time varied with the kind thereof, but they were in a cotyledonous stage to 3-leaf stage and from 5 to 19 cm in height. Twenty days after treatment, the herbicidal activity was examined. The results are shown in Table 27. These tests were carried out in a greenhouse through the entire period of test.

TABLE 27

| Compound No. | Dosage (g/are) | Herbicidal activity | | | | | | | |
|---|---|---|---|---|---|---|---|---|---|
| | | Soybean | Cotton | Barnyardgrass | Large crabgrass | Johnsongrass | Green foxtail | Oat | Annual bluegrass |
| 32 | 2.5 | 0 | 0 | 5 | 5 | 5 | 5 | 5 | 3 |
| | 0.63 | 0 | 0 | 4 | 4 | 5 | 4 | 4 | — |
| 41 | 2.5 | 0 | 0 | 5 | 5 | 5 | 5 | 5 | 4 |
| | 0.63 | 0 | 0 | 5 | 4 | 4 | 4 | 5 | 3 |
| 51 | 2.5 | 0 | 0 | 5 | 5 | 5 | 5 | 5 | 3 |
| | 0.63 | 0 | 0 | 5 | 4 | — | 5 | 4 | — |
| 54 | 2.5 | 0 | 0 | 5 | 5 | 5 | 5 | 5 | — |
| | 0.63 | 0 | 0 | 5 | 4 | 5 | 5 | 5 | — |
| 59 | 2.5 | 0 | 0 | 5 | 5 | 5 | 5 | 5 | — |
| | 0.63 | 0 | 0 | 5 | 5 | 5 | 4 | 4 | — |
| 70 | 2.5 | 0 | 0 | 5 | 5 | 5 | 5 | 5 | 3 |
| | 0.63 | 0 | 0 | 5 | 4 | 4 | 3 | 4 | — |
| 74 | 2.5 | 0 | 0 | 5 | 5 | 5 | 5 | 4 | 4 |
| | 0.63 | 0 | 0 | 5 | 4 | 5 | 4 | 4 | 3 |
| 75 | 2.5 | 0 | 0 | 5 | 5 | 5 | 5 | 4 | 4 |
| | 0.63 | 0 | 0 | 5 | 4 | 5 | 3 | 4 | 3 |
| 79 | 2.5 | 0 | 0 | 5 | 4 | 4 | 3 | 5 | — |
| | 0.63 | 0 | 0 | 5 | — | 3 | — | 4 | — |
| A | 2.5 | 0 | 0 | 3 | 1 | 2 | 3 | 3 | 2 |
| | 0.63 | 0 | 0 | 1 | 0 | 0 | 1 | 0 | 0 |
| B | 2.5 | 0 | 0 | 3 | 1 | 2 | 3 | 3 | 3 |
| | 0.63 | 0 | 0 | 2 | 0 | 0 | 2 | 0 | 0 |

TEST EXAMPLE 10

Foliage treatment test in plow field

Plow-field soil was filled in a vat (area, 33×23 cm²; depth, 11 cm), and the seeds of soybean, cotton, large crabgrass, johnsongrass, green foxtail, oat and annual bluegrass were sowed and cultivated for 18 days. Thereafter, the prescribed amount of the emulsifiable concentrates of the test compounds prepared according to Formulation example 2 was diluted with a spreading agent-containing water of an amount corresponding to 10 liters/are, and uniformly applied to the entire foliage of the test plants over the top by means of a small-sized sprayer. The state of growth of the weeds and crops at that time varied with the kind thereof, but they were in a cotyledonous stage to 3-leaf stage and from 5 to 19 cm in height. Twenty days after treatment, the herbicidal activity was examined. The results are shown in Table 28. These tests were carried out in a greenhouse through the entire period of test.

TABLE 28

| Compound No. | Dosage (g/are) | Herbicidal activity | | | | | | |
|---|---|---|---|---|---|---|---|---|
| | | Soybean | Cotton | Large crabgrass | Johnsongrass | Green foxtail | Oat | Annual bluegrass |
| 33 | 2.5 | 0 | 0 | 5 | 5 | 5 | 5 | 4 |
| | 0.63 | 0 | 0 | 5 | 5 | 5 | 5 | 4 |
| 56 | 2.5 | 0 | 0 | 5 | 4 | 5 | 5 | 3 |
| | 0.63 | 0 | 0 | — | 4 | 4 | 5 | — |
| C | 2.5 | 0 | 0 | 4 | 3 | 4 | 4 | 0 |
| | 0.63 | 0 | 0 | 3 | 1 | 3 | 3 | 0 |

TEST EXAMPLE 11

Foliage treatment test in plow field

Plow-field soil was filled in a vat (area, 33×23 cm²; depth, 11 cm), and the seeds of soybean, cotton, barnyardgrass, large crabgrass, johnsongrass, green foxtail, oat, annual bluegrass and blackgrass were sowed and cultivated for 18 days. Thereafter, the prescribed amount of the emulsifiable concentrates of the test compounds prepared according to Formulation example 2 was diluted with a spreading agent-containing water of an amount corresponding to 5 liters/are, and uniformly applied to the entire foliage of the test plants over the top by means of a small-sized sprayer. The state of growth of the weeds and crops at that time varied with the kind thereof, but they were in a cotyledonous stage to 3-leaf stage and from 5 to 19 cm in height. Twenty days after treatment, the herbicidal activity was examined. The results are shown in Table 29. These tests were carried out in a greenhouse through the entire period of test.

TABLE 29

| Compound No. | Dosage (g/are) | Herbicidal activity | | | | | | | | |
|---|---|---|---|---|---|---|---|---|---|---|
| | | Soybean | Cotton | Barnyardgrass | Crabgrass | Johnsongrass | Green foxtail | Oat | Annual bluegrass | Blackgrass |
| 89 | 2.5 | 0 | 0 | 5 | 5 | 5 | 5 | 5 | 4 | 5 |
| | 0.63 | 0 | 0 | 5 | 4 | 4 | 4 | 5 | — | 4 |
| 91 | 2.5 | 0 | 0 | 5 | 5 | 5 | 5 | 5 | 4 | 5 |
| | 0.63 | 0 | 0 | 5 | 5 | 4 | 5 | 4 | — | — |
| 92 | 2.5 | 0 | 0 | 5 | 5 | 5 | 5 | 5 | 4 | 5 |
| | 0.63 | 0 | 0 | 5 | 4 | 5 | 5 | 4 | — | 4 |
| 93 | 2.5 | 0 | 0 | 5 | 5 | 5 | 5 | 5 | 4 | 5 |
| | 0.63 | 0 | 0 | 5 | 5 | 5 | 4 | 5 | 4 | 4 |
| 97 | 2.5 | 0 | 0 | 5 | 5 | 5 | 5 | 5 | — | 5 |
| | 0.63 | 0 | 0 | 5 | 4 | 4 | 5 | 4 | — | 4 |
| 98 | 2.5 | 0 | 0 | 5 | 5 | 5 | 5 | 5 | — | 5 |
| | 0.63 | 0 | 0 | 5 | 4 | 5 | 5 | 5 | — | 4 |
| A | 2.5 | 0 | 0 | 3 | 1 | 2 | 3 | 3 | 2 | 2 |
| | 0.63 | 0 | 0 | 1 | 0 | 0 | 1 | 0 | 0 | 0 |
| B | 2.5 | 0 | 0 | 3 | 1 | 2 | 3 | 3 | 3 | 3 |
| | 0.63 | 0 | 0 | 2 | 0 | 0 | 2 | 0 | 0 | 0 |
| D | 2.5 | — | — | 1 | 0 | 0 | 0 | 0 | 0 | 0 |
| | 0.63 | — | — | 0 | 0 | 0 | 0 | 0 | 0 | 0 |

TEST EXAMPLE 12

Foliage treatment test in plow field

Plow-field soil was filled in a vat (area, 33×23 cm$^2$; depth, 11 cm), and the seeds of cotton, barnyardgrass, large crabgrass, johnsongrass, green foxtail, oat, annual bluegrass and blackgrass were sowed and cultivated for 18 days. Thereafter, the prescribed amount of the emulsifiable concentrates of the test compounds prepared according to Formulation example 2 was diluted with a spreading agent-containing water of an amount corresponding to 10 liters/are, and uniformly applied to the entire foliage of the test plants over the top by means of a small-sized sprayer. The state of growth of the weeds and crops at that time varied with the kind thereof, but they were in a cotyledonous stage to 3-leaf stage and from 7 to 15 cm in height. Twenty days after treatment, the herbicidal activity was examined. The results are shown in Table 30. These tests were carried out in a greenhouse through the entire period of test.

TEST EXAMPLE 13

Foliage treatment test in plow field

Plow-field soil was filled in a vat (area, 33×23 cm$^2$; depth, 11 cm), and the seeds of corn, barnyardgrass, large crabgrass, johnsongrass, green foxtail and oat were sowed and cultivated for 18 days. Thereafter, the prescribed amount of the emulsifiable concentrates of the test compounds prepared according to Formulation example 2 was diluted with water of an amount corresponding to 10 liters/are, and uniformly applied to the entire foliage of the test plants over the top by means of a small-sized sprayer. The state of growth of the weeds and crops at that time varied with the kind thereof, but they were in a 1 to 2-leaf stage and from 7 to 15 cm in height. Twenty days after treatment, the herbicidal activity was examined. The results are shown in Table 31. These tests were carried out in a greenhouse through the entire period of test.

TABLE 30

| Compound No. | Dosage (g/are) | Herbicidal activity | | | | | | | |
|---|---|---|---|---|---|---|---|---|---|
| | | Cotton | Barnyardgrass | Large crabgrass | Johnsongrass | Green foxtail | Oat | Annual bluegrass | Blackgrass |
| 2 | 2.5 | 0 | 5 | 5 | 5 | 5 | 5 | 4 | 5 |
| | 0.63 | 0 | 5 | 4 | 5 | 5 | 5 | — | 4 |
| A | 2.5 | 0 | 3 | 1 | 2 | 3 | 3 | 2 | 2 |
| | 0.63 | 0 | 1 | 0 | 0 | 1 | 0 | 0 | 0 |
| B | 2.5 | 0 | 3 | 1 | 2 | 3 | 3 | 3 | 3 |
| | 0.63 | 0 | 2 | 0 | 0 | 2 | 0 | 0 | 0 |
| D | 2.5 | — | 1 | 0 | 0 | 0 | 0 | 0 | 0 |
| | 0.63 | — | 0 | 0 | 0 | 0 | 0 | 0 | 0 |

TABLE 31

| Compound No. | Dosage (g/are) | Herbicidal activity | | | | | |
|---|---|---|---|---|---|---|---|
| | | Corn | Barnyardgrass | Large crabgrass | Johnsongrass | Green foxtail | Oat |
| 2 | 0.63 | 1 | 5 | 4 | 5 | 5 | 4 |
| | 0.16 | 0 | 4 | — | 4 | 4 | 4 |
| 3 | 0.63 | 0 | 5 | 4 | 3 | 4 | 3 |
| 26 | 0.63 | 1 | 5 | 4 | 3 | 5 | 4 |
| 70 | 0.63 | 1 | 5 | 3 | 4 | 5 | 4 |
| 79 | 0.63 | 0 | 5 | 4 | 4 | 4 | 4 |
| C | 0.63 | 3 | 5 | 2 | 1 | 4 | 3 |
| | 0.16 | 1 | 4 | 0 | 1 | 3 | 0 |

TEST EXAMPLE 14

Foliage treatment test in plow field

Plow-field soil was filled in a vat (area, 15×10 cm²; depth, 7 cm), and the seeds of corn, barnyardgrass, large crabgrass, and green foxtail were sowed and cultivated for 14 days. Thereafter, the prescribed amount of the emulsifiable concentrates of the test compounds prepared according to Formulation example 2 was diluted with water of an amount corresponding to 6 liters/are, and uniformly applied to the entire foliage of the test plants over the top by means of a small-sized sprayer. The state of growth of the weeds and crops at that time varied with the kind thereof, but they were in a 1 to 4-leaf stage and from 2 to 42 cm in height. Fifteen days after treatment, the herbicidal activity was examined. The results are shown in Table 32. These tests were carried out in a greenhouse through the entire period of test.

TABLE 32

| Compound No. | Dosage (g/are) | Herbicidal activity | | | |
|---|---|---|---|---|---|
| | | Corn | Barnyardgrass | Large crabgrass | Green foxtail |
| 2 | 0.75 | 0 | 5 | 5 | 5 |
| 70 | 0.75 | 0 | 5 | 4 | 5 |
| A | 0.75 | 1 | 1 | 0 | 0 |
| C | 0.75 | 2 | 5 | 3 | 4 |

TEST EXAMPLE 15

Foliage treatment test in plow field

Plow-field soil was filled in a vat (area, 33×23 cm²; depth, 11 cm), and the seeds of tall morningglory, common cocklebur, velvetleaf, common chickweed, black nightshade and redroot pigweed were sowed and cultivated for 18 days. Thereafter, the prescribed amount of the emulsifiable concentrates of the test compounds prepared according to Formulation example 2 was diluted with a spreading agent-containing water of an amount corresponding to 10 liters/are, and uniformly applied to the entire foliage of the test plants over the top by means of a small-sized sprayer. The state of growth of the weeds and crops at that time varied with the kind thereof, but they were in a 1 to 2-leaf stage and from 3 to 10 cm in height. Twenty days after treatment, the herbicidal activity was examined. The results are shown in Table 33. These tests were carried out in a greenhouse through the entire period of test.

TABLE 33

| Compound No. | Dosage (g/are) | Herbicidal activity | | | | | |
|---|---|---|---|---|---|---|---|
| | | Tall morningglory | Common cocklebur | Velvetleaf | Common chickweed | Black nightshade | Redroot pigweed |
| 2 | 10 | 5 | 4 | 4 | 5 | 4 | 4 |
| B | 10 | 0 | 0 | 0 | 0 | 0 | 0 |

TEST EXAMPLE 16

Treatment test under flooded condition in paddy field

Paddy-field soil was filled in 1/5000 area Wagner's pots, and the seeds of barnyardgrass were incorporated from 1 to 2 cm deep in the soil. After creating the state of paddy field by flooding, rice plants in a 3-leaf stage were transplanted and cultivated in a greenhouse. After 4 days, the prescribed amount of the emulsifiable concentrates of the test compounds prepared according to Formulation example 2 was diluted with 10 ml of water and applied to the water surface, and the depth of water was made 4 cm. After treatment, the test plants were cultivated for 20 days in a greenhouse to examine the herbicidal activity and phytotoxicity. The results are shown in Table 34. In this test, water leakage corresponding to a water level of 3 cm/day was carried out for 2 days from the day subsequent to the treatment.

TABLE 34

| Compound No. | Doasge (g/are) | Herbicidal activity | |
|---|---|---|---|
| | | Rice | Barnyardgrass |
| 2 | 1.25 | 0 | 5 |
| | 0.32 | 0 | 4 |
| 10 | 1.25 | 0 | 5 |
| | 0.32 | 0 | 4 |
| 28 | 1.25 | 1 | 5 |
| | 0.32 | 0 | 4 |
| 29 | 1.25 | 0 | 5 |
| | 0.32 | 0 | 4 |
| 30 | 1.25 | 0 | 5 |
| | 0.32 | 0 | 5 |
| 51 | 1.25 | 1 | 5 |
| | 0.32 | 0 | 4 |
| 70 | 1.25 | 1 | 5 |
| | 0.32 | 0 | 5 |
| 74 | 1.25 | 1 | 5 |
| | 0.32 | 0 | 5 |
| 87 | 1.25 | 0 | 5 |
| | 0.32 | 0 | 5 |
| 98 | 1.25 | 0 | 5 |
| | 0.32 | 0 | 5 |
| 99 | 1.25 | 0 | 5 |
| | 0.32 | 0 | 5 |
| 100 | 1.25 | 0 | 5 |
| | 0.32 | 0 | 5 |
| E | 1.25 | 1 | 2 |
| | 0.32 | 0 | 0 |

TEST EXAMPLE 17

Foliage treatment test in plow field

Plow-field soil was filled in a concrete-pot (area, 40×35 cm²; depth, 35 cm), and the seeds of wheat, annual bluegrass, wild oat and blackgrass were sowed and cultivated for 41 days. Thereafter, the prescribed amount of the emulsifiable concentrates of the test compounds prepared according to Formulation example 2 was diluted with water of an amount corresponding to 7 liters/are, and uniformly applied to the entire foliage of the test plants over the top by means of a small-sized sprayer. The state of growth of the weeds and crops at that time varied with the kind thereof, but they were in a 2 to 3-leaf stage. Twenty-one days after treatment, the herbicidal activity was examined. The results are shown in Table 35. These tests were carried out in outdoors through the entire period of test.

TABLE 35

| Compound No. | Dosage (g/are) | Herbicidal activity | | | |
|---|---|---|---|---|---|
| | | Wheat | Annual bluegrass | Wild oat | Blackgrass |
| 2 | 0.3 | 0 | 4 | 4 | 4 |
| F | 0.3 | 0 | 0 | 1 | 1 |

TEST EXAMPLE 18

Foliage treatment test in plow field

In plow-field wherein ridging was carried out so that the upper row space was 1 meter were sowed the seeds of corn, johnsongrass, green foxtail, large crabgrass and barnyardgrass. When the corn grew to a 4-leaf stage and the weeds grew to a 2 to 4-leaf stage, the rows were partitioned into test plots of 3 m² in area. Thereafter, the prescribed amount of the emulsifiable concentrates of the test compounds prepared according to Formulation example 2 was diluted with water of an amount corresponding to 3 liters/are and foliage-applied to the whole surface of the test plots by means of a small-sized sprayer (three replications). After 30 days, the herbicidal activity was examined. The results are shown in Table 36.

TABLE 36

| Compound No. | Dosage (g/are) | Herbicidal activity | | | | |
|---|---|---|---|---|---|---|
| | | Corn | Johnson-grass | Green foxtail | Large crabgrass | Barnyard-grass |
| 2 | 1 | 0 | 4 | 5 | 5 | 5 |
| D | 20 | 0 | 0 | 4 | 4 | 3 |

What is claimed is:
1. A compound of the formula

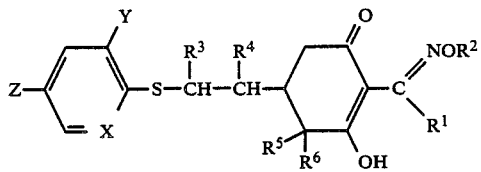

wherein $R^1$ is a methyl group; $R^2$ is an ethyl or propyl group; $R^3$ is a hydrogen atom or a methyl group; $R^4$ is a hydrogen atom or a methyl group; $R^5$ is a hydrogen atom or a methyl group; $R^6$ is a hydrogen atom; X is a CH group; Y is a hydrogen atom; Z is a trifluoromethyl, trifluoromethoxy or 1,1,2,2-tetrafluoroethoxy group; or its alkali, alkaline earth and transition metal, ammonium, tetraalkylammonium or benzyltrialkylammonium salt.

2. The compound according to claim 1, wherein $R^1$ is a methyl group; $R^2$ is an ethyl group; $R^3$ is a hydrogen atom or a methyl group; $R^4$ is a hydrogen atom or a methyl group; $R^5$ is a hydrogen atom or a methyl group; $R^6$ is a hydrogen atom; X is a CH group; Y is a hydrogen atom; and Z is a trifluoromethyl, trifluoromethoxy or 1,1,2,2-tetrafluoroethoxy group.

3. A compound of formula

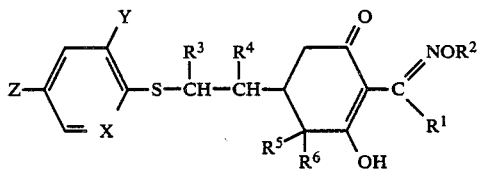

wherein $R^1$ is an ethyl or propyl group; $R^2$ is a (C₃–C₆) alkenyl group or halo(C₃–C₆) alkenyl group; $R^3$ is a hydrogen atom or a methyl group; $R^4$ is a hydrogen atom or a methyl group; $R^5$ is a hydrogen atom or a methyl group; $R^6$ is a hydrogen atom; X is a CH group or a nitrogen atom; Y is a hydrogen atom; Z is a trifluoromethyl, trifluoromethoxy or 1,1,2,2-tetrafluoroethoxy group; or its alkali, alkaline earth and transition metal, ammonium, tetraalkylammonium or benzyltrialkylammonium salt.

4. The compound according to claim 3, wherein $R^1$ is an ethyl or propyl group; $R^2$ is an allyl or 2-butenyl group; $R^3$ is a hydrogen atom or a methyl group; $R^4$ is a hydrogen atom or a methyl group; $R^5$ is a hydrogen atom or a methyl group; $R^6$ is a hydrogen atom; X is a CH group or a nitrogen atom; Y is a hydrogen atom; and Z is a trifluoromethyl, trifluoromethoxy or 1,1,2,2-tetrafluoroethoxy group.

5. A compound of the formula

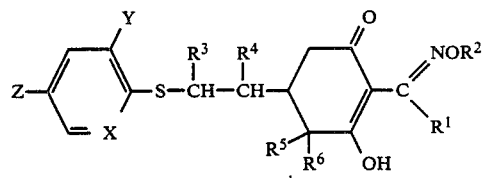

wherein $R^1$ is an ethyl or propyl group; $R^2$ is a (C₁–C₆) alkyl, (C₃–C₆) alkenyl or halo(C₃–C₆) alkenyl group; $R^3$ is a hydrogen atom or a methyl group; $R^4$ is a hydrogen atom or a methyl group; $R^5$ is a hydrogen atom or a methyl group, and when $R^5$ is a hydrogen atom, $R^6$ is a hydrogen atom or a (C₁–C₄) alkoxycarbonyl group, and when $R^5$ is a methyl group, $R^6$ is a hydrogen atom; X is a CH group or a nitrogen atom; Y is a hydrogen atom; Z is a trifluoromethyl or trifluoromethoxy group; or its alkali, alkaline earth, and transition metal, ammonium, tetraalkylammonium or benzyltrialkylammonium salt.

6. A compound of the formula

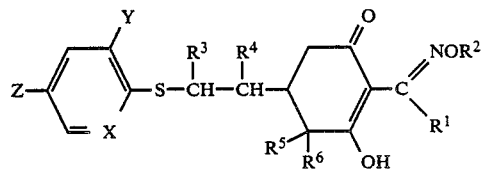

wherein $R^1$ is a methyl group; $R^2$ is a (C₁–C₆) alkyl, (C₃–C₆)alkenyl or halo(C₃–C₆) alkenyl group; $R^3$ is a hydrogen atom or a methyl group; $R^4$ is a hydrogen atom or a methyl group; $R^5$ is a hydrogen atom or a methyl group; $R^6$ is a hydrogen atom; X is a CH group; Y is a hydrogen atom; Z is a trifluoromethyl group; or its metal, ammonium, tetraalkylammonium or benzyltrialkylammonium salt.

7. The compound according to claim 1, of the formula,

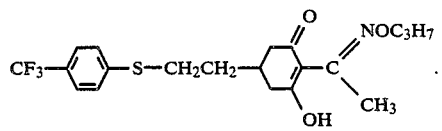

8. The compound according to claim 2, of the formula,

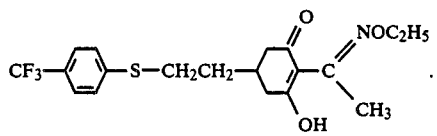

9. The compound according to claim 2, of the formula,

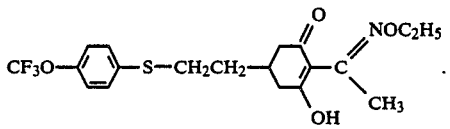

10. The compound according to claim 4, of the formula,

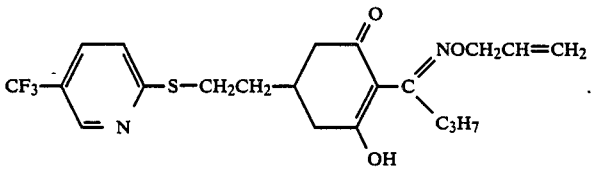

11. The compound according to claim 4, of the formula,

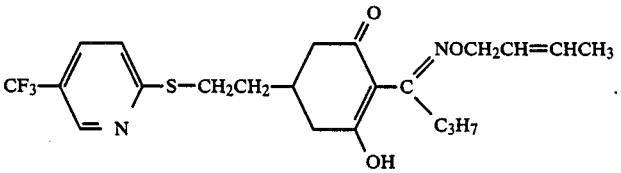

12. The compound according to claim 5, of the formula

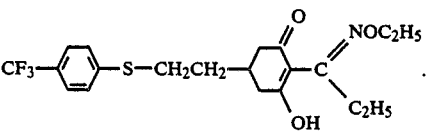

13. The compound according to claim 5, of the formula,

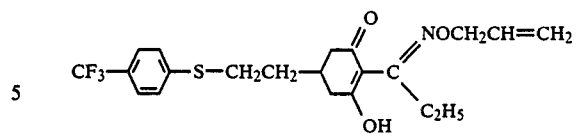

14. A herbicidal composition which comprises as an active ingredient a herbicidally effective amount of the compound according to any one of claims 1-6 and an inert carrier and/or diluent.

15. A method for controlling weeds, which comprises applying a herbicidally effective amount of the compound according to any one of claims 1-6 and an inert carrier and/or diluent to the area where weeds grow.

16. A method for controlling weeds, which comprises applying a herbicidally effective amount of the compound according to claim 1 and an inert carrier and/or diluent to a corn field.

17. A method for controlling weeds, which comprises applying a herbicidally effective amount of the compound according to claim 2 and an inert carrier and/or diluent to a corn field.

18. A method for controlling weeds, which comprises applying a herbicidally effective amount of the compound according to claim 3 and an inert carrier and/or diluent to a rice field.

19. A method for controlling weeds, which comprises applying a herbicidally effective amount of the compound according to claim 4 and an inert carrier and/or diluent to a rice field.

20. A method for controlling weeds, which comprises applying a herbicidally effective amount of the compound according to claim 5 and an inert carrier and/or diluent to broad-leaved crops' field.

21. A method for controlling weeds, which comprises applying a herbicidally effective amount of the compound according to claim 6 and an inert carrier and/or diluent to a non-cropping land.

* * * * *